(12) United States Patent
Brooks et al.

(10) Patent No.: US 9,187,464 B2
(45) Date of Patent: Nov. 17, 2015

(54) TRPV4 ANTAGONISTS

(75) Inventors: Carl Brooks, King of Prussia, PA (US); Mui Cheung, King of Prussia, PA (US); Hilary Schenck Eidam, King of Prussia, PA (US); Krista B. Goodman, King of Prussia, PA (US); Marlys Hammond, Littleton, CO (US); Mark A. Hilfiker, King of Prussia, PA (US); Tram H. Hoang, King of Prussia, PA (US); Jaclyn R. Patterson, King of Prussia, PA (US); Patrick Stoy, King of Prussia, PA (US); Guosen Ye, King of Prussia, PA (US)

(73) Assignee: GlaxoSmithKline Intellectual Property (No. 2) Limited, Brentford, Middlesex (GB)

(*) Notice: Subject to any disclaimer, the term of this patent is extended or adjusted under 35 U.S.C. 154(b) by 0 days.

(21) Appl. No.: 14/125,378

(22) PCT Filed: Jun. 15, 2012

(86) PCT No.: PCT/US2012/042622
§ 371 (c)(1),
(2), (4) Date: Dec. 11, 2013

(87) PCT Pub. No.: WO2013/012500
PCT Pub. Date: Jan. 24, 2013

(65) Prior Publication Data
US 2014/0121206 A1  May 1, 2014

Related U.S. Application Data

(60) Provisional application No. 61/498,110, filed on Jun. 17, 2011.

(51) Int. Cl.
C07D 263/02 (2006.01)
A61K 31/423 (2006.01)
C07D 413/14 (2006.01)
C07D 417/14 (2006.01)
C07D 495/04 (2006.01)
C07F 9/6558 (2006.01)
C07D 419/14 (2006.01)

(52) U.S. Cl.
CPC ............ *C07D 413/14* (2013.01); *C07D 417/14* (2013.01); *C07D 419/14* (2013.01); *C07D 495/04* (2013.01); *C07F 9/65583* (2013.01)

(58) Field of Classification Search
USPC ................. 548/216; 546/271.4; 544/405; 514/255.05, 333, 376
See application file for complete search history.

(56) References Cited

U.S. PATENT DOCUMENTS

2014/0113916 A1* 4/2014 Brooks et al. ............ 514/256
2014/0135369 A1* 5/2014 Brooks et al. ............ 514/376

FOREIGN PATENT DOCUMENTS

| WO | WO 2007/067756 A2 | 6/2007 |
| WO | WO 2008/129007 A1 | 10/2008 |
| WO | WO 2009/095377 A1 | 8/2009 |
| WO | WO 2010/011914 A1 | 1/2010 |
| WO | WO 2012/024183 A1 | 2/2012 |
| WO | WO2012174340 | 12/2012 |
| WO | WO2012174342 | 12/2012 |

OTHER PUBLICATIONS

Fabien Vincent, et al,"Identification and Characterization of novel TRPV4 Modulators", Biochemical and Biophysical Communications, vol. 389 No. 3 2009 pp. 490-494.

* cited by examiner

*Primary Examiner* — Nyeemah A Grazier
(74) *Attorney, Agent, or Firm* — Linda E. Hall; John E. Lemanowicz

(57) ABSTRACT

The present invention relates to spirocarbamate compounds of Formula (I) in which R1, (R2)Y, R3, R4, X and A have the meanings given in the specification. The invention further provides pharmaceutical compositions containing the compounds or pharmaceutically acceptable salts thereof and relates to their use of these compounds as TRPV4 antagonists in treating or preventing conditions associated with TRPV4 imbalance.

20 Claims, No Drawings

TRPV4 ANTAGONISTS

This application is a 371 of International Application No. PCT/US2012/042622, filed 15 Jun. 2012, which claims the benefit of U.S. Provisional Application No. 61/498,110, filed 17 Jun. 2011, which is incorporated herein in its entirety.

FIELD OF THE INVENTION

The present invention relates to spirocarbamate analogs, pharmaceutical compositions containing them and their use as TRPV4 antagonists.

BACKGROUND OF THE INVENTION

TRPV4 is a member of the Transient Receptor Potential (TRP) superfamily of cation channels and is activated by heat, demonstrating spontaneous activity at physiological temperatures (Guler et al., 2002. *J Neurosci* 22: 6408-6414). Consistent with its polymodal activation property TRPV4 is also activated by hypotonicity and physical cell stress/pressure (Strotmann et al., 2000. *Nat Cell Biol* 2: 695-702), through a mechanism involving phospholipase A2 activation, arachidonic acid and epoxyeicosatrienoic acid generation (Vriens et al., 2004. *Proc Natl Acad Sci USA* 101: 396-401), In addition, amongst other mechanisms proposed, tyrosine kinase activity may also regulate TRPV4 (Wegierski et al., 2009. *J Biol Chem*. 284: 2923-33).

Heart failure results in the decreased ability of the left ventricle to pump blood into the peripheral circulation as indicated by a reduced ejection fraction and/or left ventricular dialation. This increases the left ventricular end diastolic pressure resulting in enhanced pulmonary blood pressures. This places the septal barrier, which separates the circulatory aqueous environment and the alveolar airspaces of the lung, at risk. Increased pulmonary pressure results in the flow of fluid from the pulmonary circulation into the alveolar space resulting in lung edema/congestion, as is observed in patients with congestive heart failure.

TRPV4 is expressed in the lung (Delany et al., 2001. *Physiol. Genomics* 4: 165-174) and has been shown to mediate $Ca^{2+}$ entry in isolated endothelial cells and in intact lungs (Jian et al., 2009 *Am J Respir Cell Mol Biol* 38: 386-92). Endothelial cells are responsible for forming the capillary vessels that mediate oxygen/carbon dioxide exchange and contribute to the septal barrier in the lung. Activation of TRPV4 channels results in contraction of endothelial cells in culture and cardiovascular collapse in vivo (Willette et al., 2008 *J Pharmacol Exp Ther* 325: 466-74), at least partially due to the enhanced filtration at the septal barrier evoking lung edema and hemorrage (Alvarez et al., 2006. *Circ Res* 99: 988-95). Indeed filtration at the septal barrier is increased in response to increased vascular and/or airway pressures and this response is dependent on the activity of TRPV4 channels (Jian et al., 2008 *Am J Respir Cell Mol Biol* 38: 386-92). Overall this suggests a clinical benefit of inhibiting TRPV4 function in the treatment of heart failure associated lung congestion.

Additional benefit is suggested in inhibiting TRPV4 function in pulmonary-based pathologies presenting with symptoms including lung edema/congestion, infection, inflammation, pulmonary remodeling and/or altered airway reactivity. A genetic link between TRPV4 and chronic obstructive pulmonary disorder (COPD) has recently been identified (Zhu et al., 2009. *Hum Mol Genetics,* 18: 2053-62) suggesting potential efficacy for TRPV4 modulation in treatment of COPD with or without coincident emphysema. Enhanced TRPV4 activity is also a key driver in ventilator-induced lung injury (Hamanaka et al., 2007. *Am J Physiol* 293: L923-32) and it is suggested that TRPV4 activation may underlie pathologies involved in acute respiratory distress syndrome (ARDS), pulmonary fibrosis and asthma (Liedtke & Simon, 2004. *Am J Physiol* 287: 269-71). A potential clinical benefit for TRPV4 blockers in the treatment of sinusitis, as well as allergic and non-allergic rhinitis is also supported (Bhargave et al., 2008. *Am J Rhinol* 22:7-12).

TRPV4 has been shown to be involved in Acute Lung Injury (ALI). Chemical activation of TRPV4 disrupts the alvelor septal blood barrier potentially leading to pulmonary edema (Alvarez et al, Circ Res. 2006 Oct. 27; 99(9):988-95. TRPV4 is a necessary step in a process known to cause or worsen ALI in humans (Hamanaka et al, Am J Physiol Lung Cell Mol. Physiol. 2007 October; 293(4):L923-32).

Furthermore TRPV4 has in recent years been implicated in a number of other physiological/pathophysiological processes in which TRPV4 antagonists are likely to provide significant clinical benefit. These include various aspects of pain (Todaka et al., 2004. *J Biol Chem* 279: 35133-35138; Grant et al., 2007. *J Physiol* 578: 715-733; Alessandri-Haber et al., 2006. *J Neurosci* 26: 3864-3874), genetic motor neuron disorders (Auer-Grumbach et al., 2009. *Nat. Genet. PMID:* 20037588; Deng et al., 2009. *Nat Genet PMID:* 20037587; Landouré et al., 2009. *Nat Genet PMID:* 20037586), cardiovascular disease (Earley et al., 2005. *Circ Res* 97: 1270-9; Yang et al., 2006. *Am. J. Physiol.* 290:L1267-L1276), and bone related disorders; including osteoarthritis (Muramatsu et al., 2007. *J. Biol. Chem.* 282: 32158-67), genetic gain-of function mutations (Krakow et al., 2009. *Am J Hum Genet.* 84: 307-15; Rock et al., 2008 *Nat Genet.* 40: 999-1003) and osteoclast differentiation (Masuyama et al. 2008. *Cell Metab* 8: 257-65).

SUMMARY OF THE INVENTION

In one aspect this invention provides for spirocarbamate analogs, pharmaceutically acceptable salts thereof, and pharmaceutical compositions containing them.

In a second aspect, this invention provides for the use of the compounds of Formula (I) as TRPV4 antagonists.

In another aspect, this invention provides for the use of the compounds of Formula (I) for treating and preventing conditions associated with TRPV4 imbalance.

In yet another aspect, this invention provides for the use of the compounds of Formula (I) for the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, overactive bladder, pain, motor neuron disorders, genetic gain of function disorders, cardiovascular disease, renal dysfunction, osteoarthritis crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence.

The TRPV4 antagonist may be administered alone or in conjunction with one or more other therapeutic agents, eg. agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonist, HMG-CoA reductase inhibitors, dual non-selective β-adrenoceptor and α₁-adrenoceptor antagonists, type-5 phosphodiesterase inhibitors, and renin inhibitors.

Other aspects and advantages of the present invention are described further in the following detailed description of the preferred embodiments thereof.

DETAILED DESCRIPTION OF THE INVENTION

The present invention provides for compounds of Formula (I):

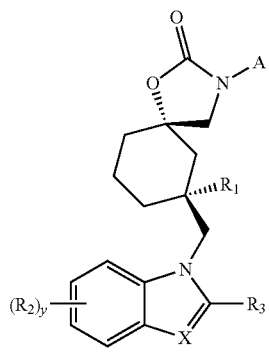

Wherein:

$R_1$ is hydrogen, $C_{1-3}$alkyl, $CH_2OH$, $CH_2$—O—$CH_3$, $CH_2OCH_2Ph$, $CH_2CN$, CN, halo or $C(O)OCH_3$;

$R_2$ is independently hydrogen, CN, $CF_3$, halo, $SO_2C_{1-3}$alkyl, $C_{1-3}$alkyl or C≡CH;

$R_3$ is hydrogen, $C_{1-2}$alkyl, $CF_3$ or OH;

$R_4$ is hydrogen, halo or $C_{1-3}$alkyl;

X is $CR_4$ or N;

A is $(CH_2)_n$-Het;

or A is $(CH_2)_n$—$(CR_aR_b)$—$(CH_2)_m$-Het;

$R_a$ is hydrogen or $C_{1-3}$alkyl, wherein the $C_{1-3}$alkyl may be further substituted with one or more halos;

$R_b$ is $C_{1-3}$alkyl;

or $R_a$ and $R_b$ together with the carbon atom they are attached form a $C_{3-6}$cycloalkyl group;

or one of the carbon atoms in the $C_{3-6}$cycloalkyl group formed by $R_a$ and $R_b$ may be replaced with oxygen to form an oxetane, tetrahydrofuryl or tetrahydropyranyl group;

or one of the carbon atoms in the $C_{3-6}$cycloalkyl group formed by $R_a$ and $R_b$ may be replaced with nitrogen to form a pyrrolidinyl or piperidinyl group;

Het is

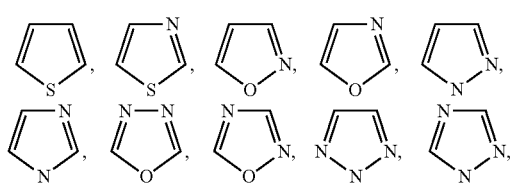

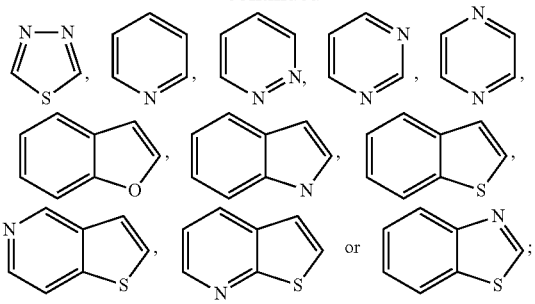

Wherein Het may be substituted by one, two or three substituents chosen from: halo, $C_{1-5}$alkyl, CN, $CH_2F$, $CHF_2$, $CF_3$, $C_{3-6}$cycloalkyl, $(CH_2)_n$—O—$C_{1-3}$alkyl, $(CH_2)_n$-phenyl, $(CH_2)_n$-pyridyl, pyrimidinyl, pyrazinyl, $CH(CH_3)$—O—$C_{1-3}$alkyl, $CH(OH)$—$C_{1-5}$alkyl, $C(CH_3)_2$—$R_5$, $C(O)N(CH_3)_p$, $N(C_{1-3}alkyl)_p$, $NH_2$, $C(O)NH_2$, oxetane, oxetane-$CH_3$, tetrahydrofuryl, tetrahydropyranyl, morpholinyl, or pyrazolyl;

wherein the phenyl, pyrazolyl, and pyridyl substituent on the Het may be further substituted by one or two substituents chosen from: halo, CN, $OCH_3$, $C_{1-3}$alkyl or $CF_3$;

and the $C_{1-6}$alkyl and $C_{3-6}$cycloalkyl substituent on the Het may be further substituted by CN or OH;

$R_5$ is CN, $(CH_2)_m$—OH, $(CH_2)_p$—O—$C(O)$—O—$C_{1-6}$alkyl, or O—$(CH_2)_p$—O—$R_6$;

$R_6$ is $C_{1-4}$alkyl or $P(O)_2(CH_3)_2$;

n is independently 0, 1 or 2;

m is independently 0, 1 or 2;

p is independently 1 or 2; and y is 1, 2 or 3;

or a pharmaceutically acceptable salt thereof.

"Alkyl" refers to a monovalent saturated hydrocarbon chain having the specified number of carbon member atoms. For example, $C_{1-4}$ alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), and butyl (n-butyl, isobutyl, s-butyl, and t-butyl).

"Cycloalkyl" refers to a monovalent saturated or unsaturated hydrocarbon ring having the specified number of carbon member atoms. For example, $C_{3-6}$cycloalkyl refers to a cycloalkyl group having from 3 to 6 carbon member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

With regard to stereoisomers, the compounds of Formula (I) may have one or more asymmetric carbon atom and may occur as racemates, racemic mixtures and as individual enantiomers or diastereomers or diastereomeric mixtures. All such isomeric forms are included within the present invention, including mixtures thereof.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminium, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

REPRESENTATIVE EMBODIMENTS

In one embodiment:
$R_1$ is hydrogen, $C_{1-3}$alkyl, $CH_2OH$, $CH_2$—O—$CH_3$, $CH_2OCH_2Ph$, $CH_2CN$, CN, halo or $C(O)OCH_3$;
$R_2$ is independently hydrogen, CN, $CF_3$, halo, $SO_2C_{1-3}$alkyl, $C_{1-3}$alkyl or C≡CH;
$R_3$ is hydrogen, $C_{1-2}$alkyl, $CF_3$ or OH;
$R_4$ is hydrogen, halo or $C_{1-3}$alkyl;

X is $CR_4$ or N;
A is $(CH_2)_n$-Het;
or A is $(CH_2)_n$—$(CR_aR_b)$—$(CH_2)_m$-Het;
$R_a$ is hydrogen or $C_{1-3}$alkyl, wherein the $C_{1-3}$alkyl may be further substituted with one or more halos;
$R_b$ is $C_{1-3}$alkyl;
or $R_a$ and $R_b$ together with the carbon atom they are attached form a $C_{3-6}$cycloalkyl group;
or one of the carbon atoms in the $C_{3-6}$cycloalkyl group formed by $R_a$ and $R_b$ may be replaced with oxygen to form an oxetane, tetrahydrofuryl or tetrahydropyranyl group;
or one of the carbon atoms in the $C_{3-6}$cycloalkyl group formed by $R_a$ and $R_b$ may be replaced with nitrogen to form a pyrrolidinyl or piperidinyl group;
Het is

[chemical structures]

Wherein Het may be substituted by one, two or three substituents chosen from: halo, $C_{1-5}$alkyl, CN, $CH_2F$, $CHF_2$, $CF_3$, $C_{3-6}$cycloalkyl, $(CH_2)_n$—O—$C_{1-3}$alkyl, $(CH_2)_n$-phenyl, $(CH_2)_n$-pyridyl, pyrimidinyl, pyrazinyl, $CH(CH_3)$—O—$C_{1-3}$alkyl, CH(OH)—$C_{1-5}$alkyl, $C(CH_3)_2$—$R_5$, C(O)N$(CH_3)_p$, $N(C_{1-3}$alkyl$)_p$, $NH_2$, $C(O)NH_2$, oxetane, oxetane-$CH_3$, tetrahydrofuryl, tetrahydropyranyl, morpholinyl, or pyrazolyl;
wherein the phenyl, pyrazolyl, and pyridyl substituent on the Het may be further substituted by one or two substituents chosen from: halo, CN, $OCH_3$, $C_{1-3}$alkyl or $CF_3$;
and the $C_{1-5}$alkyl and $C_{3-6}$cycloalkyl substituent on the Het may be further substituted by CN or OH;
$R_5$ is CN, $(CH_2)_m$—OH, $(CH_2)_p$—O—C(O)—O—$C_{1-5}$alkyl, or O—$(CH_2)_p$—O—$R_6$;
$R_6$ is $C_{1-4}$alkyl or $P(O)_2(CH_3)_2$;
n is independently 0, 1 or 2;
m is independently 0, 1 or 2;
p is independently 1 or 2; and
y is 1, 2 or 3.
In another embodiment:
$R_1$ is hydrogen, $C_{1-3}$alkyl, $CH_2OH$, $CH_2$—O—$CH_3$, $CH_2OCH_2Ph$, $CH_2CN$, CN, halo or $C(O)OCH_3$;
$R_2$ is independently hydrogen, CN, $CF_3$, halo, $SO_2C_{1-3}$alkyl, $C_{1-3}$alkyl or C≡CH;
$R_3$ is hydrogen, $C_{1-2}$alkyl, $CF_3$ or OH;
$R_4$ is hydrogen, halo or $C_{1-3}$alkyl;
X is $CR_4$ or N;
A is $(CH_2)_n$-Het;
or A is $(CH_2)_n$—$(CR_aR_b)$—$(CH_2)_m$-Het;
$R_a$ is hydrogen or $C_{1-3}$alkyl, wherein the $C_{1-3}$alkyl may be further substituted with one or more halos;
$R_b$ is $C_{1-3}$alkyl;
or $R_a$ and $R_b$ together with the carbon atom they are attached form a $C_{3-6}$cycloalkyl group;
or one of the carbon atoms in the $C_{3-6}$cycloalkyl group formed by $R_a$ and $R_b$ may be replaced with oxygen to form an oxetane, tetrahydrofuryl or tetrahydropyranyl group;
or one of the carbon atoms in the $C_{3-6}$cycloalkyl group formed by $R_a$ and $R_b$ may be replaced with nitrogen to form a pyrrolidinyl or piperidinyl group;
Het is

[chemical structures]

Wherein Het may be substituted by one, two or three substituents chosen from: halo, $C_{1-5}$alkyl, CN, $CH_2F$, $CHF_2$, $CF_3$, $C_{3-6}$cycloalkyl, $(CH_2)_n$—O—$C_{1-3}$alkyl, $(CH_2)_n$-phenyl, $(CH_2)_n$-pyridyl, pyrimidinyl, pyrazinyl, $CH(CH_3)$—O—$C_{1-3}$alkyl, $C(CH_3)_2$—OH, $C(CH_3)_2$—O—$CH_3$, $C(CH_3)_2$—CN, $C(CH_3)_2$—$CH_2OH$, $C(CH_3)_2$—$CH_2$—O—C(O)—O—$C_{1-5}$alkyl, $C(O)N(CH_3)_p$, $N(C_{1-3}$alkyl$)_p$, $NH_2$, $C(O)NH_2$, oxetane, oxetane-$CH_3$, tetrahydrofuryl or tetrahydropyranyl;
wherein the phenyl and pyridyl substituent on the Het may be further substituted by one or two substituents chosen from: halo, CN, $OCH_3$, $C_{1-3}$alkyl or $CF_3$;
and the $C_{1-5}$alkyl and $C_{3-6}$cycloalkyl substituent on the Het may be further substituted by CN or OH;
n is independently 0, 1 or 2;
m is independently 0, 1 or 2;
p is independently 1 or 2; and
y is 1, 2 or 3.
In another embodiment:
$R_1$ is hydrogen, $C_{1-3}$ alkyl or $CH_2OH$;
$R_2$ is CN;
$R_3$ is hydrogen;
X is N;
A is $(CH_2)_n$-Het;
or A is $(CH_2)_n$—$(CR_aR_b)$—$(CH_2)_m$-Het;
$R_a$ is hydrogen or $C_{1-3}$alkyl, wherein the $C_{1-3}$alkyl may be further substituted with one or more halos;
$R_b$ is $C_{1-3}$alkyl;
or $R_a$ and $R_b$ together with the carbon atom they are attached form a $C_{3-6}$ cycloalkyl group;
or one of the carbon atoms in the $C_{3-6}$cycloalkyl group formed by $R_a$ and $R_b$ may be replaced with oxygen to form an oxetane, tetrahydrofuryl or tetrahydropyranyl group;

or one of the carbon atoms in the $C_{3-6}$cycloalkyl group formed by $R_a$ and $R_b$ may be replaced with nitrogen to form a pyrrolidinyl or piperidinyl group;

Het is

[Structures: thiophene, thiazole, isoxazole, oxazole, pyrazole, imidazole, oxadiazole, isoxazole variant, triazole, triazole variant, thiadiazole, pyridine, pyridazine, pyrimidine, pyrazine, benzofuran, indole, benzothiophene, azabenzothiophene, thienopyridine, or benzothiazole]

Wherein Het may be substituted by one, two or three substituents chosen from: halo, $C_{1-6}$alkyl, CN, $CH_2F$, $CHF_2$, $CF_3$, $C_{3-6}$cycloalkyl, $(CH_2)_n$—O—$C_{1-3}$alkyl, $(CH_2)_n$-phenyl, $(CH_2)_n$-pyridyl, pyrimidinyl, pyrazinyl, $CH(CH_3)$—O—$C_{1-3}$alkyl, $C(CH_3)_2$—OH, $C(CH_3)_2$—O—$CH_3$, $C(CH_3)_2$—CN, $C(CH_3)_2$—$CH_2OH$, $C(CH_3)_2$—$CH_2$—O—C(O)—O—$C_{1-6}$alkyl, $C(O)N(CH_3)_p$, $N(C_{1-3}alkyl)_p$, $NH_2$, $C(O)NH_2$, oxetane, oxetane-$CH_3$, tetrahydrofuryl or tetrahydropyranyl;
  wherein the phenyl and pyridyl substituent on the Het may be further substituted by one or two substituents chosen from: halo, CN, $OCH_3$, $O_{1-3}$ alkyl or $CF_3$;
  and the $O_{1-6}$ alkyl and $C_{3-6}$cycloalkyl substituent on the Het may be further substituted by CN or OH;

n is independently 0 or 1;
m is independently 0 or 1;
p is independently 1 or 2; and
y is 1 or 2.

In yet another embodiment:
$R_1$ is hydrogen, $C_{1-3}$alkyl or $CH_2OH$;
$R_2$ is CN;
$R_3$ is hydrogen;
X is N;
A is $(CH_2)_n$-Het;
or A is $(CH_2)_n$—$(CR_aR_b)$—$(CH_2)_m$-Het;
$R_a$ is hydrogen or $C_{1-3}$alkyl, wherein the $C_{1-3}$alkyl may be further substituted with one or more halos;
$R_b$ is $C_{1-3}$alkyl;
or $R_a$ and $R_b$ together with the carbon atom they are attached form a $C_{3-6}$ cycloalkyl group;
or one of the carbon atoms in the $C_{3-6}$cycloalkyl group formed by $R_a$ and $R_b$ may be replaced with oxygen to form an oxetane, tetrahydrofuryl or tetrahydropyranyl group;
or one of the carbon atoms in the $C_{3-6}$cycloalkyl group formed by $R_a$ and $R_b$ may be replaced with nitrogen to form a pyrrolidinyl or piperidinyl group;

Het is

[Structures: thiophene, thiazole, isoxazole, oxazole, pyrazole, imidazole, oxadiazole, isoxazole variant, triazole, triazole variant, thiadiazole, pyridine, pyridazine, pyrimidine, or pyrazine]

Wherein Het may be substituted by one, two or three substituents chosen from: halo, $C_{1-5}$alkyl, CN, $CH_2F$, $CHF_2$, $CF_3$, $C_{3-6}$cycloalkyl, $(CH_2)_n$—O—$C_{1-3}$alkyl, $(CH_2)_n$-phenyl, $(CH_2)_n$-pyridyl, pyrimidinyl, pyrazinyl, $CH(CH_3)$—O—$C_{1-3}$alkyl, $C(CH_3)_2$—OH, $C(CH_3)_2$—O—$CH_3$, $C(CH_3)_2$—CN, $C(CH_3)_2$—$CH_2OH$, $C(CH_3)_2$—$CH_2$—O—C(O)—O—$C_{1-5}$alkyl, $C(O)N(CH_3)_p$, $N(C_{1-3}alkyl)_p$, $NH_2$, $C(O)NH_2$, oxetane, oxetane-$CH_3$, tetrahydrofuryl or tetrahydropyranyl;
  wherein the phenyl and pyridyl substituent on the Het may be further substituted by one or two substituents chosen from: halo, CN, $OCH_3$, $C_{1-3}$alkyl, or $CF_3$;
  and the $C_{1-5}$alkyl and $C_{3-6}$cycloalkyl substituent on the Het may be further substituted by CN or OH;

n is independently 0 or 1;
m is independently 0 or 1;
p is independently 1 or 2; and
y is 1 or 2;

In yet another embodiment:
$R_1$ is hydrogen, $C_{1-3}$alkyl or $CH_2OH$;
$R_2$ is CN;
$R_3$ is hydrogen;
X is N;
A is $(CH_2)_n$-Het;
Het is

[Structures: isoxazole, oxazole, pyrazole, imidazole, oxadiazole, isoxazole variant, triazole, triazole variant, pyridine, pyridazine, pyrimidine or pyrazine]

Wherein Het may be substituted by one, two or three substituents chosen from: halo, $C_{1-6}$alkyl, CN, $CH_2F$, $CHF_2$, $CF_3$, $C_{3-6}$cycloalkyl, $(CH_2)_n$—O—$C_{1-3}$alkyl, $(CH_2)_n$-phenyl, $(CH_2)_n$-pyridyl, pyrimidinyl, pyrazinyl, $CH(CH_3)$—O—$C_{1-3}$alkyl, $C(CH_3)_2$—OH, $C(CH_3)_2$—O—$CH_3$, $C(CH_3)_2$—CN, $C(CH_3)_2$—$CH_2OH$, $C(CH_3)_2$—$CH_2$—O—C(O)—O—$C_{1-6}$alkyl, $C(O)N(CH_3)_p$, $N(C_{1-3}alkyl)_p$, $NH_2$, $C(O)NH_2$, oxetane, oxetane-$CH_3$, tetrahydrofuryl or tetrahydropyranyl;
  wherein the phenyl and pyridyl substituent on the Het may be further substituted by one or two substituents chosen from: halo, CN, $OCH_3$, $C_{1-3}$alkyl, or $CF_3$;
  and the $C_{1-6}$alkyl and $C_{3-6}$cycloalkyl substituent on the Het may be further substituted by CN or OH;

n is independently 0 or 1;
p is independently 1 or 2; and
y is 1 or 2.
In yet another embodiment:
R$_1$ is hydrogen, C$_{1-3}$alkyl or CH$_2$OH;
R$_2$ is CN;
R$_3$ is hydrogen;
X is N;
A is (CH$_2$)$_n$-Het;
Het is

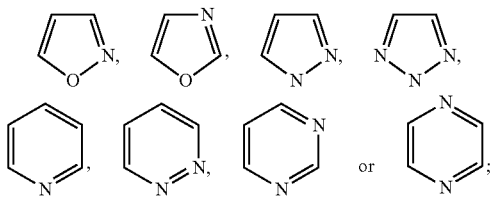

Wherein Het may be substituted by one, two or three substituents chosen from: halo, C$_{1-5}$alkyl, CN, CH$_2$F, CHF$_2$, CF$_3$, C$_{3-6}$cycloalkyl (CH$_2$)$_n$—O—C$_{1-3}$alkyl, (CH$_2$)$_n$-phenyl, (CH$_2$)$_n$-pyridyl, pyrimidinyl, pyrazinyl, CH(CH$_3$)—O—C$_{1-3}$alkyl, C(CH$_3$)$_2$—OH, C(CH$_3$)$_2$—O—CH$_3$, C(CH$_3$)$_2$—CN, C(CH$_3$)$_2$—CH$_2$OH, C(CH$_3$)$_2$—CH$_2$—O—C(O)—O—C$_{1-5}$alkyl, C(O)N(CH$_3$)$_p$, N(C$_{1-3}$alkyl)$_p$, NH$_2$, C(O)NH$_2$, oxetane, oxetane-CH$_3$, tetrahydrofuryl or tetrahydropyranyl;
  wherein the phenyl and pyridyl substituent on the Het may be further substituted by one or two substituents chosen from: halo, CN, OCH$_3$, C$_{1-3}$alkyl, or CF$_3$;
  and the C$_{1-5}$alkyl and C$_{3-6}$cycloalkyl substituent on the Het may be further substituted by CN or OH;
n is 0;
p is independently 1 or 2; and
y is 1 or 2.

It is to be understood that the present invention covers all combinations of particular groups described hereinabove. Specific examples of compounds of the present invention include the following:

1-({(5S,7S)-3-[3-(1,1-dimethylethyl)-5-isoxazolyl]-7-methyl-2-oxo-1-oxa-3-azaspiro[4.5]dec-7-yl}methyl)-1H-benzimidazole-6-carbonitrile;
1-(((5S,7S)-3-(3-(2-cyanopropan-2-yl)isoxazol-5-yl)-7-methyl-2-oxo-1-oxa-3-azaspiro[4.5]decan-7-yl)methyl)-1H-benzo[d]imidazole-6-carbonitrile;
1-({(5S,7S)-3-[5-(1,1-dimethylethyl)-3-isoxazolyl]-7-methyl-2-oxo-1-oxa-3-azaspiro[4.5]dec-7-yl}methyl)-1H-benzimidazole-6-carbonitrile;
1-{[(5S,7S)-7-methyl-2-oxo-3-(2-pyridinylmethyl)-1-oxa-3-azaspiro[4.5]dec-7-yl]methyl}-1H-benzimidazole-6-carbonitrile;
1-({(5S,7S)-3-[2-methyl-2-(5-phenyl-1,3,4-oxadiazol-2-yl)propyl]-2-oxo-1-oxa-3-azaspiro[4.5]dec-7-yl}methyl)-1H-benzimidazole-6-carbonitrile;
1-({(5S,7S)-3-[2-(3-ethyl-1,2,4-oxadiazol-5-yl)-2-methylpropyl]-2-oxo-1-oxa-3-azaspiro[4.5]dec-7-yl}methyl)-1H-benzimidazole-6-carbonitrile;
1-[((5S,7S)-3-{[3-methyl-1-(2-pyrimidinyl)-3-pyrrolidinyl]methyl}-2-oxo-1-oxa-3-azaspiro[4.5]dec-7-yl)methyl]-1H-benzimidazole-6-carbonitrile;
1-({(5S,7S)-7-methyl-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile;
1-{[(5S,7S)-2-oxo-3-({1-[5-(trifluoromethyl)-3-pyridinyl]-1H-1,2,3-triazol-4-yl}methyl)-1-oxa-3-azaspiro[4.5]dec-7-yl]methyl}-1H-benzimidazole-6-carbonitrile;
1-({(5S,7S)-3-[4-chloro-3-(1,1-dimethylethyl)-5-isoxazolyl]-7-methyl-2-oxo-1-oxa-3-azaspiro[4.5]dec-7-yl}methyl)-1H-benzimidazole-6-carbonitrile;
1-({(5S,7S)-7-methyl-2-oxo-3-[5-(trifluoromethyl)-2-pyridinyl]-1-oxa-3-azaspiro[4.5]dec-7-yl}methyl)-1H-benzimidazole-6-carbonitrile;
1-({(5S,7S)-3-[6-(ethyloxy)-3-pyridinyl]-7-methyl-2-oxo-1-oxa-3-azaspiro[4.5]dec-7-yl}methyl)-1H-benzimidazole-6-carbonitrile;
1-(((5S,7S)-3-(6-methoxypyridin-3-yl)-7-methyl-2-oxo-1-oxa-3-azaspiro[4.5]decan-7-ylmethyl)-1H-benzo[d]imidazole-6-carbonitrile;
1-(((5S,7S)-3-(5-ethoxypyrazin-2-yl)-7-methyl-2-oxo-1-oxa-3-azaspiro[4.5]decan-7-yl)methyl)-1H-benzo[d]imidazole-6-carbonitrile;
1-(((5S,7S)-3-(6-methoxy-4-methylpyridin-3-yl)-7-methyl-2-oxo-1-oxa-3-azaspiro[4.5]decan-7-ylmethyl)-1H-benzo[d]imidazole-6-carbonitrile;
1-(((5S,7S)-3-(1-ethyl-5-methyl-1H-pyrazol-4-yl)-7-methyl-2-oxo-1-oxa-3-azaspiro[4.5]decan-7-ylmethyl)-1H-benzo[d]imidazole-6-carbonitrile;
1-(((7S)-3-(5-methoxypyrazin-2-yl)-7-methyl-2-oxo-1-oxa-3-azaspiro[4.5]decan-7-yl)methyl)-1H-benzo[d]imidazole-6-carbonitrile;
1-(((5S,7S)-3-(6-chloropyridin-3-yl)-7-methyl-2-oxo-1-oxa-3-azaspiro[4.5]decan-7-ylmethyl)-1H-benzo[d]imidazole-6-carbonitrile;
1-(((5S,7S)-3-(6-(dimethylamino)pyridin-3-yl)-7-methyl-2-oxo-1-oxa-3-azaspiro[4.5]decan-7-ylmethyl)-1H-benzo[d]imidazole-6-carbonitrile;
tert-butyl (2-(5-((5S,7S)-7-((6-cyano-1H-benzo[d]imidazol-1-yl)methyl)-7-methyl-2-oxo-1-oxa-3-azaspiro[4.5]decan-3-yl)isoxazol-3-yl)-2-methylpropyl)carbonate;
1-(((5S,7S)-3-(3-(1-hydroxy-2-methylpropan-2-yl)isoxazol-5-yl)-7-methyl-2-oxo-1-oxa-3-azaspiro[4.5]decan-7-yl)methyl)-1H-benzo[d]imidazole-6-carbonitrile;
1-(((5S,7S)-3-(4,6-dimethoxypyridin-3-yl)-7-methyl-2-oxo-1-oxa-3-azaspiro[4.5]decan-7-ylmethyl)-1H-benzo[d]imidazole-6-carbonitrile;
1-(((5S,7S)-3-(6-ethoxy-4-methylpyridin-3-yl)-2-oxo-1-oxa-3-azaspiro[4.5]decan-7-yl)methyl)-1H-benzo[d]imidazole-6-carbonitrile;
1-(((5S,7S)-3-(6-ethoxy-4-methylpyridazin-3-yl)-7-methyl-2-oxo-1-oxa-3-azaspiro[4.5]decan-7-ylmethyl)-1H-benzo[d]imidazole-6-carbonitrile;
1-(((5S,7S)-7-methyl-2-oxo-3-(2-(trifluoromethyl)pyrimidin-5-yl)-1-oxa-3-azaspiro[4.5]decan-7-ylmethyl)-1H-benzo[d]imidazole-6-carbonitrile;
1-(((5S,7S)-7-methyl-2-oxo-3-(3-(trifluoromethyl)pyridin-2-yl)-1-oxa-3-azaspiro[4.5]decan-7-ylmethyl)-1H-benzo[d]imidazole-6-carbonitrile;
1-({(5S,7S)-3-[(5-chloro-1-benzothien-3-yl)methyl]-2-oxo-1-oxa-3-azaspiro[4.5]dec-7-yl}methyl)-1H-benzimidazole-6-carbonitrile;
1-{[(5S,7S)-3-(2-{3-[1-(ethyloxy)ethyl]-1,2,4-oxadiazol-5-yl}-2-methylpropyl)-2-oxo-1-oxa-3-azaspiro[4.5]dec-7-yl]methyl}-1H-benzimidazole-6-carbonitrile;
1-{[(5S,7S)-7-methyl-3-(5-methyl-2-pyridinyl)-2-oxo-1-oxa-3-azaspiro[4.5]dec-7-yl]methyl}-1H-benzimidazole-6-carbonitrile;
1-({(5S,7S)-7-methyl-3-[3-(1-methylethyl)-5-isoxazolyl]-2-oxo-1-oxa-3-azaspiro[4.5]dec-7-yl}methyl)-1H-benzimidazole-6-carbonitrile;

1-({(5S,7S)-7-methyl-3-[3-(2-methylpropyl)-5-isoxazolyl]-2-oxo-1-oxa-3-azaspiro[4.5]dec-7-yl}methyl)-1H-benzimidazole-6-carbonitrile;

1-{[(5S,7S)-3-(1-tert-butyl-1H-pyrazol-4-yl)-7-methyl-2-oxo-1-oxa-3-azaspiro[4.5]dec-7-yl]methyl}-1H-benzimidazole-6-carbonitrile;

1-{[(5S,7S)-3-(3-ethyl-5-isoxazolyl)-7-methyl-2-oxo-1-oxa-3-azaspiro[4.5]dec-7-yl]methyl}-1H-benzimidazole-6-carbonitrile;

1-{[(5S,7S)-3-(3-cyclopropyl-5-isoxazolyl)-7-methyl-2-oxo-1-oxa-3-azaspiro[4.5]dec-7-yl]methyl}-1H-benzimidazole-6-carbonitrile;

1-{[(5S,7S)-7-methyl-2-oxo-3-(3-phenyl-5-isoxazolyl)-1-oxa-3-azaspiro[4.5]dec-7-yl]methyl}-1H-benzimidazole-6-carbonitrile;

1-({(5S,7S)-3-[3-(1,1-dimethylethyl)-1-methyl-1H-pyrazol-5-yl]-7-methyl-2-oxo-1-oxa-3-azaspiro[4.5]dec-7-yl}methyl)-1H-benzimidazole-6-carbonitrile;

1-({(5S,7S)-7-methyl-2-oxo-3-[3-(trifluoromethyl)-5-isoxazolyl]-1-oxa-3-azaspiro[4.5]dec-7-yl}methyl)-1H-benzimidazole-6-carbonitrile;

1-({(5S,7S)-3-[3-(1-cyanocyclopropyl)-5-isoxazolyl]-7-methyl-2-oxo-1-oxa-3-azaspiro[4.5]dec-7-yl}methyl)-1H-benzimidazole-6-carbonitrile;

1-(((5S,7S)-3-(3-(2-fluoropropan-2-yl)isoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3-cyclobutylisoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3-(tert-butyl)-4-methylisoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(4-(tert-butyl)oxazol-2-yl)-7-methyl-2-oxo-1-oxa-3-azaspiro[4.5]decan-7-yl)methyl)-1H-benzo[d]imidazole-6-carbonitrile;

1-(((5S,7S)-3-(1-(tert-butyl)-1H-pyrazol-4-yl)-7-methyl-2-oxo-1-oxa-3-azaspiro[4.5]decan-7-yl)methyl)-1H-benzo[d]imidazole-6-carbonitrile;

1-(((5S,7S)-3-(3-(tert-butyl)-4-fluoroisoxazol-5-yl)-7-methyl-2-oxo-1-oxa-3-azaspiro[4.5]decan-7-ylmethyl)-1H-benzo[d]imidazole-6-carbonitrile;

1-(((5S,7S)-3-(3-(1,1-difluoroethyl)isoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3-(tert-butyl)-4-methylisoxazol-5-yl)-2-oxo-1-oxa-3-azaspiro[4.5]decan-7-ylmethyl)-1H-benzo[d]imidazole-6-carbonitrile;

1-(((5S,7S)-3-(3-(tert-butyl)-4-fluoroisoxazol-5-yl)-2-oxo-1-oxa-3-azaspiro[4.5]decan-7-ylmethyl)-1H-benzo[d]imidazole-6-carbonitrile;

1-(((5S,7S)-3-(6-(tert-butyl)pyridazin-3-yl)-7-methyl-2-oxo-1-oxa-3-azaspiro[4.5]decan-7-ylmethyl)-1H-benzo[d]imidazole-6-carbonitrile;

1-(((5S,7S)-3-(5-(tert-butyl)pyrimidin-2-yl)-7-methyl-2-oxo-1-oxa-3-azaspiro[4.5]decan-7-ylmethyl)-1H-benzo[d]imidazole-6-carbonitrile;

1-(((5S,7S)-3-(2-(tert-butyl)-2H-1,2,3-triazol-4-yl)-7-methyl-2-oxo-1-oxa-3-azaspiro[4.5]decan-7-ylmethyl)-1H-benzo[d]imidazole-6-carbonitrile;

1-(((5S,7S)-7-methyl-3-(3-(1-methyl-1H-pyrazol-3-yl)isoxazol-5-yl)-2-oxo-1-oxa-3-azaspiro[4.5]decan-7-ylmethyl)-1H-benzo[d]imidazole-6-carbonitrile;

1-(((5S,7S)-3-(1-(tert-butyl)-1H-1,2,3-triazol-4-yl)-7-methyl-2-oxo-1-oxa-3-azaspiro[4.5]decan-7-ylmethyl)-1H-benzo[d]imidazole-6-carbonitrile;

1-(((5S,7S)-3-(5-(tert-butyl)pyrazin-2-yl)-7-methyl-2-oxo-1-oxa-3-azaspiro[4.5]decan-7-ylmethyl)-1H-benzo[d]imidazole-6-carbonitrile;

1-(((5S,7S)-7-methyl-2-oxo-3-(5-(trifluoromethyl)pyrimidin-2-yl)-1-oxa-3-azaspiro[4.5]decan-7-yl)-1H-benzo[d]imidazole-6-carbonitrile;

1-(((5S,7S)-3-(6-(2-methoxypropan-2-yl)pyridin-3-yl)-7-methyl-2-oxo-1-oxa-3-azaspiro[4.5]decan-7-yl)methyl)-1H-benzo[d]imidazole-6-carbonitrile;

1-(((5S,7S)-7-methyl-2-oxo-3-(3-(prop-1-en-2-yl)isoxazol-5-yl)-1-oxa-3-azaspiro[4.5]decan-7-ylmethyl)-1H-benzo[d]imidazole-6-carbonitrile;

1-(((5S,7S)-3-(3,4-dimethylisoxazol-5-yl)-7-methyl-2-oxo-1-oxa-3-azaspiro[4.5]decan-7-ylmethyl)-1H-benzo[d]imidazole-6-carbonitrile;

1-(((5S,7S)-3-(3,4-dimethylisoxazol-5-yl)-2-oxo-1-oxa-3-azaspiro[4.5]decan-7-yl)methyl)-1H-benzo[d]imidazole-6-carbonitrile;

1-({3-[(5-chloro-1-benzothien-3-yl)methyl]-2-oxo-1-oxa-3-azaspiro[4.5]dec-7-yl}methyl)-1H-indole-6-carbonitrile;

1-({3-[(5-chloro-1-benzothien-3-yl)methyl]-2-oxo-1-oxa-3-azaspiro[4.5]dec-7-yl}methyl)-2-(trifluoromethyl)-1H-benzimidazole-6-carbonitrile;

1-({3-[(5-chloro-1-benzothien-3-yl)methyl]-2-oxo-1-oxa-3-azaspiro[4.5]dec-7-yl}methyl)-1H-benzimidazole-6-carbonitrile;

1-{[3-(1-benzothien-3-ylmethyl)-2-oxo-1-oxa-3-azaspiro[4.5]dec-7-yl]methyl}-1H-benzimidazole-6-carbonitrile;

1-({(5S,7S)-2-oxo-3-[(2-phenyl-1,3-thiazol-4-yl)methyl]-1-oxa-3-azaspiro[4.5]dec-7-yl}methyl)-1H-benzimidazole-6-carbonitrile;

1-({(5S,7S)-2-oxo-3-[(6-phenyl-2-pyridinyl)methyl]-1-oxa-3-azaspiro[4.5]dec-7-yl}methyl)-1H-benzimidazole-6-carbonitrile;

1-[((5S,7S)-3-{2-methyl-2-[3-(tetrahydro-2H-pyran-4-yl)-1,2,4-oxadiazol-5-yl]propyl}-2-oxo-1-oxa-3-azaspiro[4.5]dec-7-yl)methyl]-1H-benzimidazole-6-carbonitrile;

1-({(5S,7S)-2-oxo-3-[(4-phenyl-1,3-thiazol-2-yl)methyl]-1-oxa-3-azaspiro[4.5]dec-7-yl}methyl)-1H-benzimidazole-6-carbonitrile;

1-[((5S,7S)-3-{[3-(4-chlorophenyl)-5-isoxazolyl]methyl}-2-oxo-1-oxa-3-azaspiro[4.5]dec-7-ylmethyl]-1H-benzimidazole-6-carbonitrile;

1-({(5S,7S)-2-oxo-3-[(3-phenyl-5-isoxazolyl)methyl]-1-oxa-3-azaspiro[4.5]dec-7-yl}methyl)-1H-benzimidazole-6-carbonitrile;

1-({(5S,7S)-3-[(1-methyl-5-phenyl-1H-pyrazol-3-yl)methyl]-2-oxo-1-oxa-3-azaspiro[4.5]dec-7-yl}methyl)-1H-benzimidazole-6-carbonitrile;

1-{[(5S,7S)-3-({4-[3-methyl-4-(methyloxy)phenyl]-1,3-thiazol-2-yl}methyl)-2-oxo-1-oxa-3-azaspiro[4.5]dec-7-yl]methyl}-1H-benzimidazole-6-carbonitrile;

1-({(5S,7S)-2-oxo-3-[(3-phenyl-1H-1,2,4-triazol-5-yl)methyl]-1-oxa-3-azaspiro[4.5]dec-7-yl}methyl)-1H-benzimidazole-6-carbonitrile;

1-({(5S,7S)-2-oxo-3-[(5-phenyl-3-pyridinyl)methyl]-1-oxa-3-azaspiro[4.5]dec-7-yl}methyl)-1H-benzimidazole-6-carbonitrile trifluoroacetate;

4-chloro-1-({(5S,7S)-3-[2-methyl-2-(3-phenyl-1,2,4-oxadiazol-5-yl)propyl]-2-oxo-1-oxa-3-azaspiro[4.5]dec-7-yl}methyl)-1H-benzimidazole-6-carbonitrile;

1-({(5S,7S)-3-[2-methyl-2-(3-methyl-1,2,4-oxadiazol-5-yl)propyl]-2-oxo-1-oxa-3-azaspiro[4.5]dec-7-yl}methyl)-1H-benzimidazole-6-carbonitrile;

1-({(5S,7S)-3-[2-methyl-2-(3-phenyl-1,2,4-oxadiazol-5-yl)propyl]-2-oxo-1-oxa-3-azaspiro[4.5]dec-7-yl}methyl)-1H-benzimidazole-6-carbonitrile;

1-[((5S,7S)-3-{2-methyl-2-[3-(1-methylethyl)-1,2,4-oxa-diazol-5-yl]propyl}-2-oxo-1-oxa-3-azaspiro[4.5]dec-7-yl)methyl]-1H-benzimidazole-6-carbonitrile;

1-({(5S,7S)-3-[2-(3-cyclopentyl-1,2,4-oxadiazol-5-yl)-2-methylpropyl]-2-oxo-1-oxa-3-azaspiro[4.5]dec-7-yl}methyl)-1H-benzimidazole-6-carbonitrile;

1-[((5S,7S)-3-{2-methyl-2-[3-(5-pyrimidinyl)-1,2,4-oxadia-zol-5-yl]propyl}-2-oxo-1-oxa-3-azaspiro[4.5]dec-7-yl)methyl]-1H-benzimidazole-6-carbonitrile;

1-[((5S,7S)-3-{2-[3-(1,1-dimethylethyl)-1,2,4-oxadiazol-5-yl]-2-methylpropyl}-2-oxo-1-oxa-3-azaspiro[4.5]dec-7-yl)methyl]-1H-benzimidazole-6-carbonitrile;

1-[((5S,7S)-3-{2-methyl-2-[3-(trifluoromethyl)-1,2,4-oxa-diazol-5-yl]propyl}-2-oxo-1-oxa-3-azaspiro[4.5]dec-7-yl)methyl]-1H-benzimidazole-6-carbonitrile;

1-{[(5S,7S)-3-(2-methyl-2-{3-[(methyloxy)methyl]-1,2,4-oxadiazol-5-yl}propyl)-2-oxo-1-oxa-3-azaspiro[4.5]dec-7-yl]methyl}-1H-benzimidazole-6-carbonitrile;

1-[((5S,7S)-3-{2-methyl-2-[3-(2-methylpropyl)-1,2,4-oxa-diazol-5-yl]propyl}-2-oxo-1-oxa-3-azaspiro[4.5]dec-7-yl)methyl]-1H-benzimidazole-6-carbonitrile;

1-({(5S,7S)-3-[2-methyl-2-(3-{[(1-methylethyl)oxy]me-thyl}-1,2,4-oxadiazol-5-yl)propyl]-2-oxo-1-oxa-3-aza-spiro[4.5]dec-7-yl}methyl)-1H-benzimidazole-6-carbo-nitrile;

4-chloro-1-[((5S,7S)-2-oxo-3-{[4-(3-phenyl-1,2,4-oxadia-zol-5-yl)tetrahydro-2H-pyran-4-yl]methyl}-1-oxa-3-aza-spiro[4.5]dec-7-yl)methyl]-1H-benzimidazole-6-carboni-trile;

4-chloro-1-[((5S,7S)-3-{[4-(3-cyclopentyl-1,2,4-oxadiazol-5-yl)tetrahydro-2H-pyran-4-yl]methyl}-2-oxo-1-oxa-3-azaspiro[4.5]dec-7-yl)methyl]-1H-benzimidazole-6-car-bonitrile;

1-[((5S,7S)-2-oxo-3-{[1-(2-pyridinyl)-3-pyrrolidinyl]me-thyl}-1-oxa-3-azaspiro[4.5]dec-7-yl)methyl]-1H-benz-imidazole-6-carbonitrile;

1-({(5S,7S)-2-oxo-3-[(1-phenyl-1H-1,2,3-triazol-4-yl)me-thyl]-1-oxa-3-azaspiro[4.5]dec-7-yl}methyl)-1H-benz-imidazole-6-carbonitrile;

1-[((5S,7S)-3-{[1-(4-cyanophenyl)-1H-1,2,3-triazol-4-yl]methyl}-2-oxo-1-oxa-3-azaspiro[4.5]dec-7-yl)methyl]-1H-benzimidazole-6-carbonitrile;

1-[((5S,7S)-3-{[1-(4-chlorophenyl)-1H-1,2,3-triazol-4-yl]methyl}-2-oxo-1-oxa-3-azaspiro[4.5]dec-7-yl)methyl]-1H-benzimidazole-6-carbonitrile;

1-[((5S,7S)-3-{[1-(3-chlorophenyl)-1H-1,2,3-triazol-4-yl]methyl}-2-oxo-1-oxa-3-azaspiro[4.5]dec-7-yl)methyl]-1H-benzimidazole-6-carbonitrile;

1-[((5S,7S)-3-{[1-(4-methylphenyl)-1H-1,2,3-triazol-4-yl]methyl}-2-oxo-1-oxa-3-azaspiro[4.5]dec-7-yl)methyl]-1H-benzimidazole-6-carbonitrile;

1-[((5S,7S)-3-{[1-(3-cyanophenyl)-1H-1,2,3-triazol-4-yl]methyl}-2-oxo-1-oxa-3-azaspiro[4.5]dec-7-yl)methyl]-1H-benzimidazole-6-carbonitrile;

1-{[(5S,7S)-2-oxo-3-({1-[3-(trifluoromethyl)phenyl]-1H-1,2,3-triazol-4-yl}methyl)-1-oxa-3-azaspiro[4.5]dec-7-yl]methyl}-1H-benzimidazole-6-carbonitrile;

1-[((5S,7S)-3-{[1-(3-fluorophenyl)-1H-1,2,3-triazol-4-yl]methyl}-2-oxo-1-oxa-3-azaspiro[4.5]dec-7-yl)methyl]-1H-benzimidazole-6-carbonitrile;

1-{[(5S,7S)-3-({1-[3-(methyloxy)phenyl]-1H-1,2,3-triazol-4-yl}methyl)-2-oxo-1-oxa-3-azaspiro[4.5]dec-7-yl]me-thyl}-1H-benzimidazole-6-carbonitrile;

1-[((5S,7S)-3-{[1-(3-methylphenyl)-1H-1,2,3-triazol-4-yl]methyl}-2-oxo-1-oxa-3-azaspiro[4.5]dec-7-yl)methyl]-1H-benzimidazole-6-carbonitrile;

1-({(5S,7S)-3-[(1-cyclohexaneyl-1H-1,2,3-triazol-4-yl)me-thyl]-2-oxo-1-oxa-3-azaspiro[4.5]dec-7-yl}methyl)-1H-benzimidazole-6-carbonitrile;

1-{[(5S,7S)-3-({1-[4-cyano-3-(trifluoromethyl)phenyl]-1H-1,2,3-triazol-4-yl}methyl)-2-oxo-1-oxa-3-azaspiro[4.5]dec-7-yl]methyl}-1H-benzimidazole-6-carbonitrile;

1-[((5S,7S)-3-{[1-(3-chloro-5-cyanophenyl)-1H-1,2,3-tria-zol-4-yl]methyl}-2-oxo-1-oxa-3-azaspiro[4.5]dec-7-yl)methyl]-1H-benzimidazole-6-carbonitrile;

1-{[(5S,7S)-2-oxo-3-({1-[2-(trifluoromethyl)-4-pyridinyl]-1H-1,2,3-triazol-4-yl}methyl)-1-oxa-3-azaspiro[4.5]dec-7-yl]methyl}-1H-benzimidazole-6-carbonitrile;

1-[((5S,7S)-3-{[1-(3,5-difluorophenyl)-1H-1,2,3-triazol-4-yl]methyl}-2-oxo-1-oxa-3-azaspiro[4.5]dec-7-yl)me-thyl]-1H-benzimidazole-6-carbonitrile;

1-{[(5S,7S)-2-oxo-3-({1-[4-(trifluoromethyl)phenyl]-1H-1,2,3-triazol-4-yl}methyl)-1-oxa-3-azaspiro[4.5]dec-7-yl]methyl}-1H-benzimidazole-6-carbonitrile;

1-[((5S,7S)-3-{[1-(3-cyano-5-fluorophenyl)-1H-1,2,3-tria-zol-4-yl]methyl}-2-oxo-1-oxa-3-azaspiro[4.5]dec-7-yl)methyl]-1H-benzimidazole-6-carbonitrile;

1-[((5S,7S)-7-methyl-3-{[1-(1-methylethyl)-1H-1,2,3-tria-zol-4-yl]methyl}-2-oxo-1-oxa-3-azaspiro[4.5]dec-7-yl)methyl]-1H-benzimidazole-6-carbonitrile;

1-({(5R,7S)-7-methyl-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile;

1-[((5S,7S)-3-{[1-(5-chloro-3-pyridinyl)-1H-1,2,3-triazol-4-yl]methyl}-2-oxo-1-oxa-3-azaspiro[4.5]dec-7-yl)me-thyl]-1H-benzimidazole-6-carbonitrile;

1-(((5S,7S)-3-(4-chloro-3-(2-cyanopropan-2-yl)isoxazol-5-yl)-7-methyl-2-oxo-1-oxa-3-azaspiro[4.5]decan-7-yl)me-thyl)-1H-benzo[d]imidazole-6-carbonitrile;

1-({(5S,7S)-3-[4-bromo-3-(1,1-dimethylethyl)-5-isox-azolyl]-7-methyl-2-oxo-1-oxa-3-azaspiro[4.5]dec-7-yl}methyl)-1H-benzimidazole-6-carbonitrile;

1-({(5S,7S)-7-methyl-3-[2-(methyloxy)-3-pyridinyl]-2-oxo-1-oxa-3-azaspiro[4.5]dec-7-yl}methyl)-1H-benzimi-dazole-6-carbonitrile;

1-({(5S,7S)-3-[2,6-bis(methyloxy)-3-pyridinyl]-7-methyl-2-oxo-1-oxa-3-azaspiro[4.5]dec-7-yl}methyl)-1H-benz-imidazole-6-carbonitrile;

1-({(5S,7S)-3-[4-methyl-6-(methyloxy)-3-pyridinyl]-2-oxo-1-oxa-3-azaspiro[4.5]dec-7-yl}methyl)-1H-benzimi-dazole-6-carbonitrile;

1-(((7S)-3-(3,5-dichloropyridin-2-yl)-7-methyl-2-oxo-1-oxa-3-azaspiro[4.5]decan-7-yl)methyl)-1H-benzo[d]imi-dazole-6-carbonitrile;

1-(((5S,7S)-3-(2-ethoxypyrimidin-5-yl)-7-methyl-2-oxo-1-oxa-3-azaspiro[4.5]decan-7-yl)methyl)-1H-benzo[d]imi-dazole-6-carbonitrile;

1-(((5S,7S)-3-(5-chloro-3-fluoropyridin-2-yl)-7-methyl-2-oxo-1-oxa-3-azaspiro[4.5]decan-7-yl)methyl)-1H-benzo[d]imidazole-6-carbonitrile;

1-(((5S,7S)-7-methyl-2-oxo-3-(5-(trifluoromethyl)pyrazin-2-yl)-1-oxa-3-azaspiro[4.5]decan-7-yl)methyl)-1H-benzo[d]imidazole-6-carbonitrile;

1-(((5S,7S)-3-(2-(tert-butyl)pyrimidin-5-yl)-2-oxo-1-oxa-3-azaspiro[4.5]decan-7-yl)methyl)-1H-benzo[d]imidazole-6-carbonitrile;

1-(((5S,7S)-7-methyl-3-(5-methylpyrazin-2-yl)-2-oxo-1-oxa-3-azaspiro[4.5]decan-7-yl)methyl)-1H-benzo[d]imi-dazole-6-carbonitrile;

1-(((5S,7S)-3-(6-ethoxy-4-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methylpyridin-3-yl)-2-oxo-1-oxa-3-azaspiro[4.5]decan-7-yl)methyl)-1H-benzo[d]imidazole-6-carbonitrile;

1-(((5S,7S)-3-(5-chloro-3-methylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methoxypyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methoxypyridin-3-yl)-2-oxo-1-oxa-3-azaspiro[4.5]decan-7-yl)methyl)-1H-benzo[d]imidazole-6-carbonitrile;

1-(((5S,7S)-3-(4-methyl-2-(trifluoromethyl)pyrimidin-5-yl)-2-oxo-1-oxa-3-azaspiro[4.5]decan-7-yl)methyl)-1H-benzo[d]imidazole-6-carbonitrile;

1-(((5S,7S)-3-(6-ethoxy-4-methylpyridin-3-yl)-2-oxo-1-oxa-3-azaspiro[4.5]decan-7-yl)methyl)-5-fluoro-1H-benzo[d]imidazole-6-carbonitrile;

1-(((5S,7S)-3-(2-methoxy-6-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(3-methoxy-5-methylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3-chloro-5-methylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3-ethylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3,5-dimethylpyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3-methyl-5-(trifluoromethyl)pyrazin-2-yl)-2-oxo-1-oxa-3-azaspiro[4.5]decan-7-yl)methyl)-1H-benzo[d]imidazole-6-carbonitrile;

1-(((5S,7S)-3-(6-methoxy-5-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-(2-cyanopropan-2-yl)pyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(2-(tert-butyl)pyrimidin-5-yl)-7-methyl-2-oxo-1-oxa-3-azaspiro[4.5]decan-7-yl)methyl)-1H-benzo[d]imidazole-6-carbonitrile;

1-({(5S,7S)-7-methyl-3-[5-(methyloxy)-2-pyridinyl]-2-oxo-1-oxa-3-azaspiro[4.5]dec-7-yl}methyl)-1H-benzimidazole-6-carbonitrile;

1-({(5S,7S)-3-[6-(ethyloxy)-3-pyridazinyl]-7-methyl-2-oxo-1-oxa-3-azaspiro[4.5]dec-7-yl}methyl)-1H-benzimidazole-6-carbonitrile;

1-{[(5S,7S)-3-(3-chloro-2-pyridinyl)-7-methyl-2-oxo-1-oxa-3-azaspiro[4.5]dec-7-yl]methyl}-1H-benzimidazole-6-carbonitrile;

1-({(5S,7S)-7-methyl-3-[3-(methyloxy)-2-pyridinyl]-2-oxo-1-oxa-3-azaspiro[4.5]dec-7-yl}methyl)-1H-benzimidazole-6-carbonitrile;

1-({(5S,7S)-7-methyl-2-oxo-3-[6-(trifluoromethyl)-3-pyridinyl]-1-oxa-3-azaspiro[4.5]dec-7-yl}methyl)-1H-benzimidazole-6-carbonitrile;

1-(((7S)-7-methyl-3-(6-methylpyridin-3-yl)-2-oxo-1-oxa-3-azaspiro[4.5]decan-7-yl)methyl)-1H-benzo[d]imidazole-6-carbonitrile;

1-({(5S,7S)-3-[4,6-bis(methyloxy)-3-pyridinyl]-2-oxo-1-oxa-3-azaspiro[4.5]dec-7-yl}methyl)-1H-benzimidazole-6-carbonitrile;

1-({(5S,7S)-3-[6-(1-methylethyl)-3-pyridinyl]-2-oxo-1-oxa-3-azaspiro[4.5]dec-7-yl}methyl)-1H-benzimidazole-6-carbonitrile;

1-((7-(hydroxymethyl)-3-(6-methoxy-4-methylpyridin-3-yl)-2-oxo-1-oxa-3-azaspiro[4.5]decan-7-yl)methyl)-1H-benzo[d]imidazole-6-carbonitrile;

1-(((5S,7S)-7-methyl-2-oxo-3-(4-(trifluoromethyl)pyridin-3-yl)-1-oxa-3-azaspiro[4.5]decan-7-yl)methyl)-1H-benzo[d]imidazole-6-carbonitrile;

1-(((5S,7S)-3-(2-(dimethylamino)pyrimidin-5-yl)-7-methyl-2-oxo-1-oxa-3-azaspiro[4.5]decan-7-yl)methyl)-1H-benzo[d]imidazole-6-carbonitrile;

1-(((5S,7S)-7-methyl-3-(4-methylpyridin-3-yl)-2-oxo-1-oxa-3-azaspiro[4.5]decan-7-yl)methyl)-1H-benzo[d]imidazole-6-carbonitrile;

1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(2-(2-hydroxypropan-2-yl)pyrimidin-5-yl)-7-methyl-2-oxo-1-oxa-3-azaspiro[4.5]decan-7-yl)methyl)-1H-benzo[d]imidazole-6-carbonitrile;

1-(((5S,7S)-3-(4-methoxypyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(5-(dimethylamino)pyrazin-2-yl)-7-methyl-2-oxo-1-oxa-3-azaspiro[4.5]decan-7-yl)methyl)-1H-benzo[d]imidazole-6-carbonitrile;

1-{[(5S,7S)-2-oxo-3-(thieno[2,3-b]pyridin-3-ylmethyl)-1-oxa-3-azaspiro[4.5]dec-7-yl]methyl}-1H-benzimidazole-6-carbonitrile;

1-{[(trans)-7-methyl-2-oxo-3-(thieno[2,3-b]pyridin-3-ylmethyl)-1-oxa-3-azaspiro[4.5]dec-7-yl]methyl}-1H-benzimidazole-6-carbonitrile;

1-({(5S,7S)-3-[(3-bromothieno[2,3-b]pyridin-2-yl)methyl]-2-oxo-1-oxa-3-azaspiro[4.5]dec-7-yl}methyl)-1H-benzimidazole-6-carbonitrile; and 1-{[(5S,7S)-3-(2-methyl-2-{3-[1-(methyloxy)ethyl]-1,2,4-oxadiazol-5-yl}propyl)-2-oxo-1-oxa-3-azaspiro[4.5]dec-7-yl]methyl}-1H-benzimidazole-6-carbonitrile;

1-(((5S,7S)-3-((5-ethoxypyrazin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((4-ethoxypyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((5-ethoxypyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((4-fluoropyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((5-fluoropyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-7-methyl-3-((4-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile;

1-(((5S,7S)-7-methyl-3-((6-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile;

1-(((5S,7S)-3-(5-(2-methoxypropan-2-yl)pyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(5-(2-(2-methoxyethoxy)propan-2-yl)
pyrazin-2-yl)-7-methyl-2-oxo-1-oxa-3-azaspiro[4.5]de-
can-7-yl)methyl)-1H-benzo[d]imidazole-6-carbonitrile;

2-((2-(5-((5S,7S)-7-((6-cyano-1H-benzo[d]imidazol-1-yl)
methyl)-7-methyl-2-oxo-1-oxa-3-azaspiro[4.5]decan-3-
yl)pyrazin-2-yl)propan-2-yl)oxy)ethyl dimethylphosphi-
nate;

1-(((5S,7S)-3-(5-fluoro-4-methyl-[2,2'-bipyridin]-5-yl)-7-
methyl-2-oxo-1-oxa-3-azaspiro[4.5]decan-7-yl)methyl)-
1H-benzo[d]imidazole-6-carbonitrile;

1-(((5S,7S)-7-methyl-3-(4-methyl-6-morpholinopyridin-3-
yl)-2-oxo-1-oxa-3-azaspiro[4.5]decan-7-yl)methyl)-1H-
benzo[d]imidazole-6-carbonitrile;

1-(((5S,7S)-3-(5-(2-hydroxypropan-2-yl)pyridin-2-yl)-7-
methyl-2-oxo-1-oxa-3-azaspiro[4.5]decan-7-yl)methyl)-
1H-benzo[d]imidazole-6-carbonitrile;

1-(((5S,7S)-3-(5-(1-hydroxy-2-methylpropan-2-yl)pyrazin-
2-yl)-7-methyl-2-oxo-1-oxa-3-azaspiro[4.5]decan-7-yl)
methyl)-1H-benzo[d]imidazole-6-carbonitrile;

1-(((5S,7S)-3-(6-cyclopropyl-4-methoxypyridin-3-yl)-7-
methyl-2-oxo-1-oxa-3-azaspiro[4.5]decan-7-yl)methyl)-
1H-benzo[d]imidazole-6-carbonitrile;

or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general formula (I) and pharmaceutically acceptable derivatives and salts thereof may be accomplished as outlined below in Schemes 1-8. In the following description, the groups are as defined above for compounds of formula (I) unless otherwise indicated. Abbreviations are as defined in the Examples section. Starting materials are commercially available or are made from commercially available starting materials using methods known to those skilled in the art.

Scheme 1

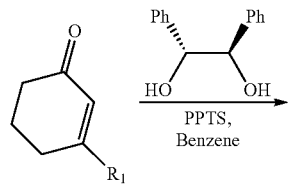

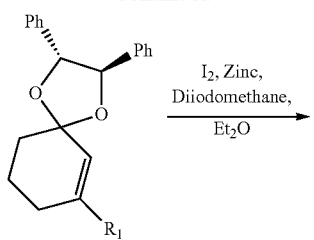

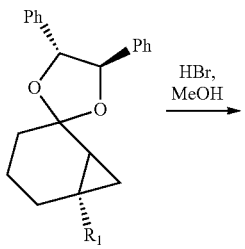

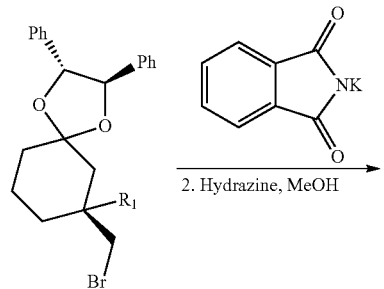

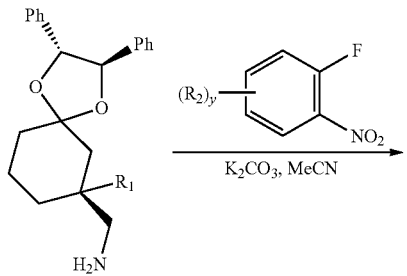

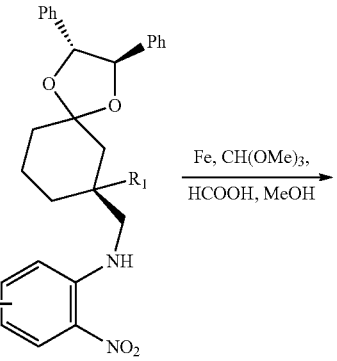

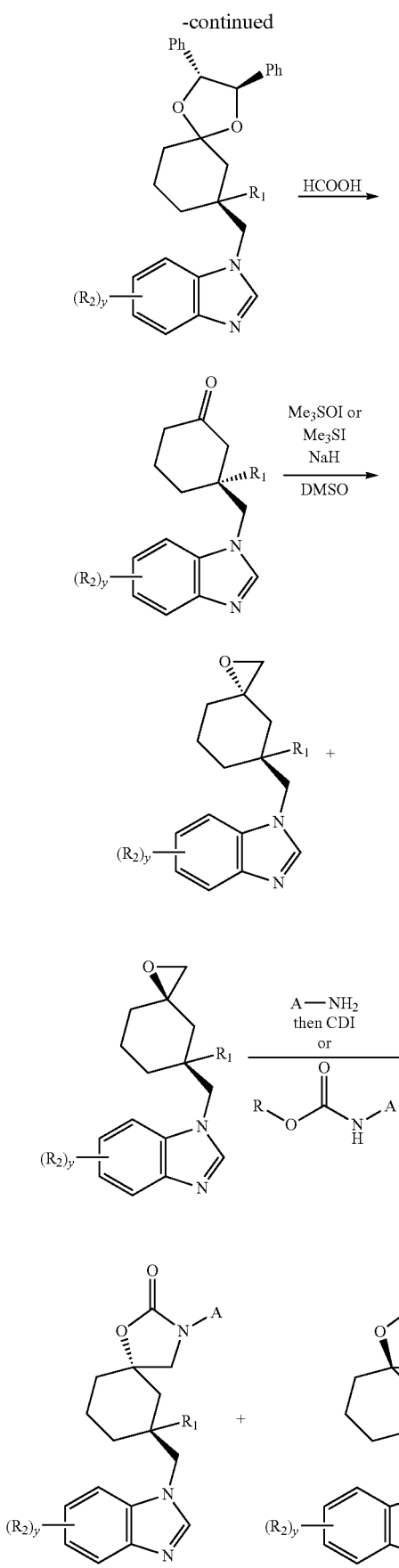

As shown in Scheme 1, the compounds of Formula I can be prepared in a multi-step sequence from 2-cyclohexen-1-one or another substituted cyclohexenone such as 3-methyl-2-cyclohexen-1-one. The cyclohexenone can be protected with (1R,2R)-1,2-diphenyl-1,2-ethanediol in the presence of PPTS in solvent such as benzene under heating conditions to give a dioxaspiro compound which can be treated with Zn/Cu in the presence of di-iodomethane to give a cyclopropane compound. Opening of the cyclopropane with acids such as HBr in solvents such as MeOH provides the bromomethyl intermediate. The bromomethyl intermediate can be displaced by nucleophiles such as potassium phthalimide in the presence of solvents such as NMP under heating conditions to give the phthalimide intermediate which can be removed under standard conditions such as hydrazine in MeOH to give the methylamine compound. The methylamine compound can undergo standard aromatic nucleophilic substitution with appropriately substituted fluoro-nitrobenzene in the presence of bases such as potassium carbonate. The nitro functional group in the resulting intermediate can be reduced and cyclized in the presence of trimethyl orthoformate, formic acid and Fe under heating conditions in a solvent such as methanol to form the benzimidazole compound. Ketal protection can be removed by heating the ketal in the presence of formic acid at high temperature such as 70° C. to form the ketone intermediate. Epoxide formation is accomplished using either trimethylsulfoxonium iodide or trimethylsulfonium iodide in the presence of base such as potassium t-butoxide or sodium hydride to provide a mixture of cis-/trans-epoxides. Enantiopure trans epoxide can be obtained by separation of the cis and trans mixture by separation techniques such as recrystallization or SFC. Two methods for converting the epoxide into the compounds of Formula I are used. In the first method, the epoxide is treated with an appropriately substituted amine (A-NH$_2$) at elevated temperature in an alcohol solvent (i-PrOH, MeOH, or EtOH) or DMF. The crude aminoalcohol is converted to the compound of Formula I by treatment with either CDI or triphosgene/TEA. The second method involves treating the epoxide with an appropriately substituted alkyl carbamate such as ethyl, isobutyl or tert-butyl carbamate in solvents such as THF and/or NMP in the presence of bases such as potassium tert-butoxide or n-BuLi under heating conditions to provide the compound of Formula I in one step.

Scheme 2

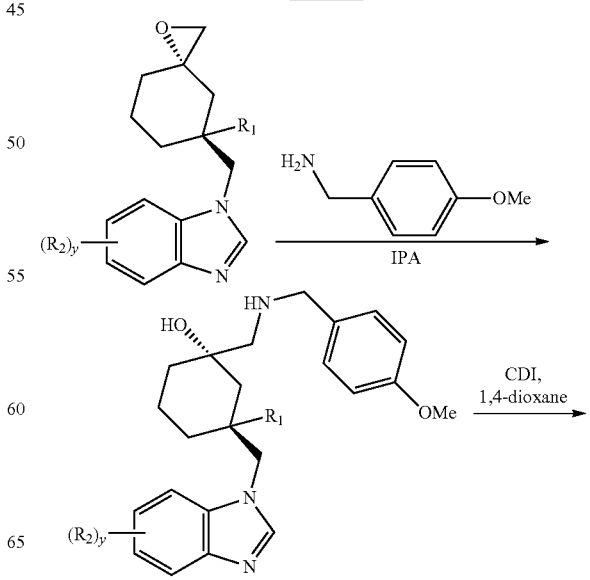

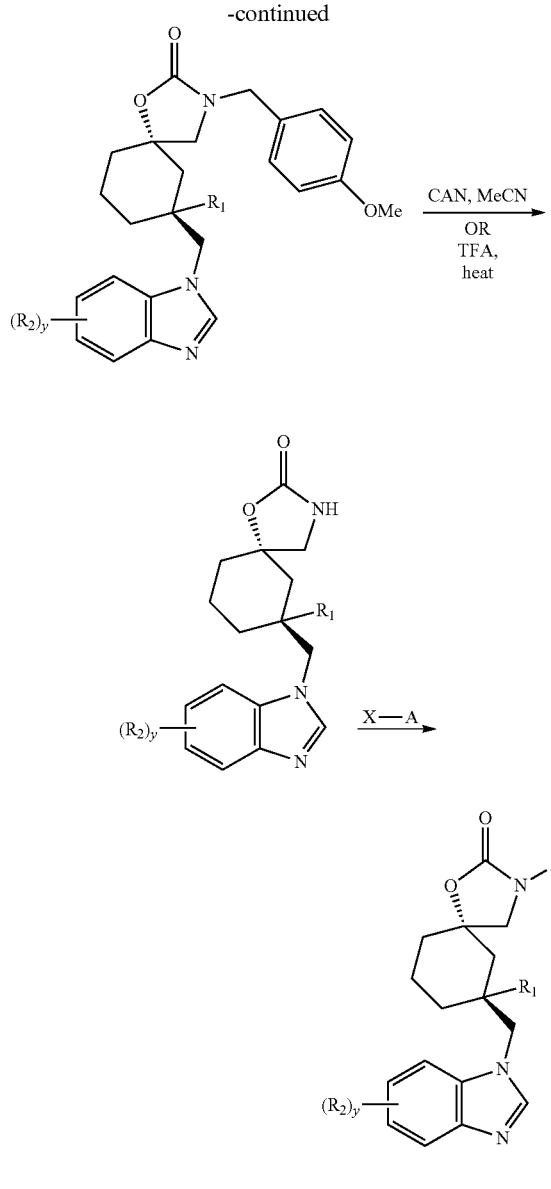

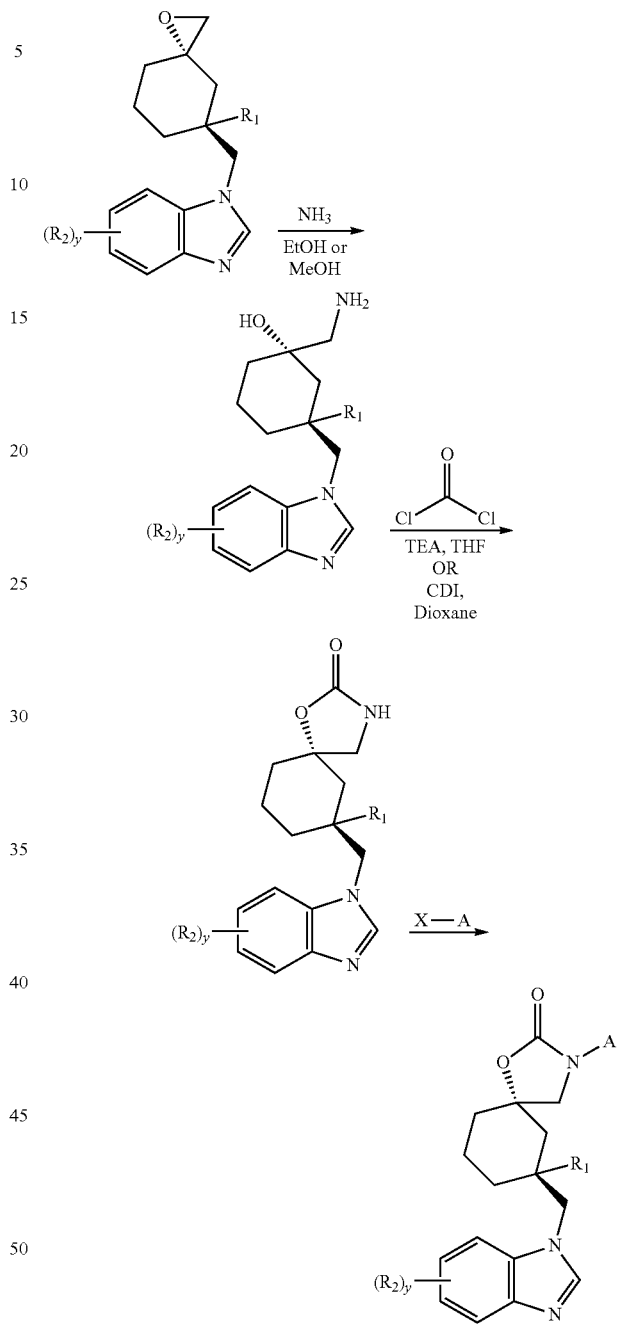

Scheme 3

As shown in Scheme 2, the trans epoxide intermediate can be opened with 1-[4-(methyloxy)phenyl]methanamine to yield the aminoalcohol intermediate which can be cyclized in the presence of CDI or triphosgene/Et$_3$N to give the spirocyclic carbamate. Deprotection of the para-methoxybenzyl group using trifluoroacetic acid or CAN provides the unsubstituted carbamate. Alternatively, the unsubstituted carbamate can be obtained in one-step from the trans epoxide intermediate using Boc-NH$_2$ or NH$_2$CO$_2$Et in the presence of base such as n-BuLi or LiOtBu. Unsubstituted carbamate can be functionalized with heterocyclic groups via a copper-catalyzed N-arylation reaction with an appropriately substituted directed linked heteroaryl halide (X-A=X-Het where X is halo) to give the compound of Formula I. Alternatively, the unsubstituted carbamate can be alkylated with an appropriately substituted alkyl halide or alkyl mesylate (X-A=X—(CH$_2$)$_n$-Het where n is not 0, and X is halo or OMs) in the presence of base such as NaH in solvent such as DMF to give the compound of Formula I.

As shown in Scheme 3, the enantiopure trans epoxide can also be opened with ammonia then cyclized under standard conditions to form the unsubstituted spirocyclic carbamate. The unsubstituted carbamate can be alkylated with an appropriately substituted alkyl halide or alkyl mesylate (XA=X—(CH$_2$)$_n$-Het where n is not 0, and X is halo or OMs) in the presence of NaH/DMF to give the compound of Formula I. Alternatively, the unsubstituted carbamate can be functionalized with heterocyclic groups via a copper-catalyzed N-arylation reaction with an appropriately substituted heteroaryl halide (X-A=X-Het where X is halo) to give the compound of Formula I.

Scheme 4

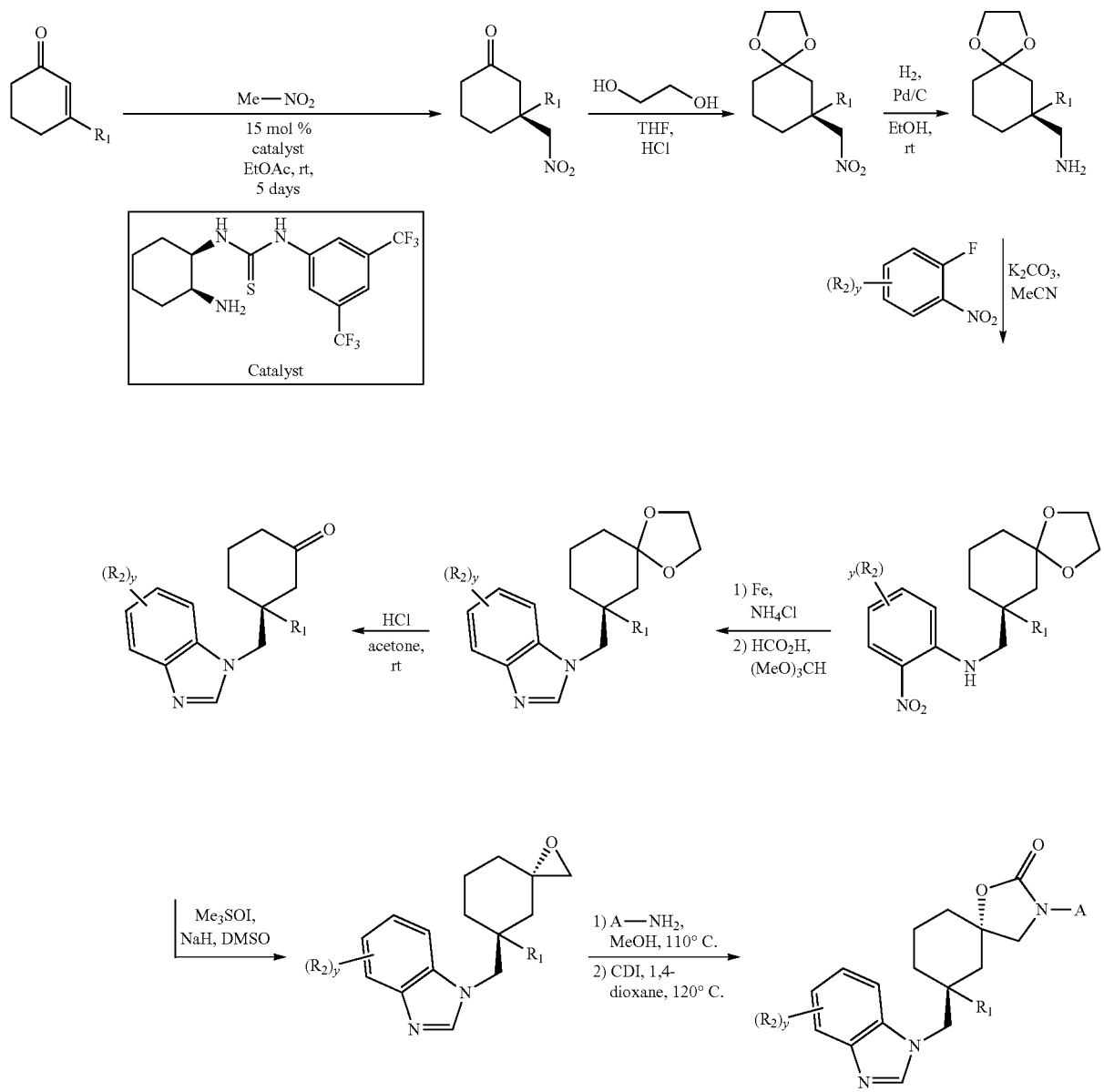

Alternatively, optically-pure compounds of Formula I can be prepared as shown in Scheme 4. Michael addition of nitromethane into the cyclohexenone using a chiral thiourea catalyst can provide an optically-enriched nitromethylcyclohexanone. The ketone can be protected as the acetonide with ethylene glycol, and the nitro group can be reduced to the primary amine using catalytic hydrogenation over palladium on carbon. The requisite benzimidazole moiety can then be installed from the primary amine via $S_{N_{Ar}}2$ addition of the amine into a substituted 2-fluoronitrobenzene followed by reduction of the nitrobenzene to the phenylenediamine. The diamine can be condensed with trimethyl orthoformate under acidic conditions to form the substituted benzimidazole. The acetonide protecting group can then be removed under acidic conditions to form a ketone. The ketone intermediate can be converted to the compound of Formula I via the epoxide opening strategy as described in Schemes 1-3.

Scheme 5

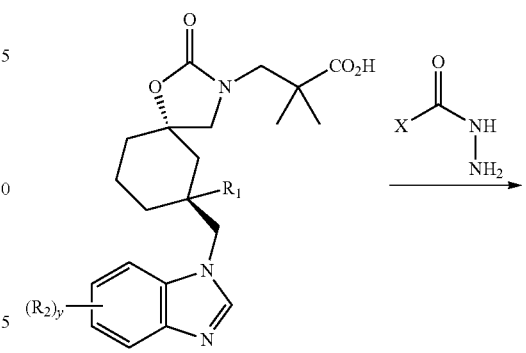

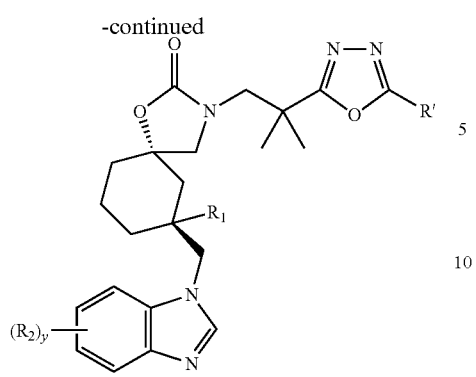
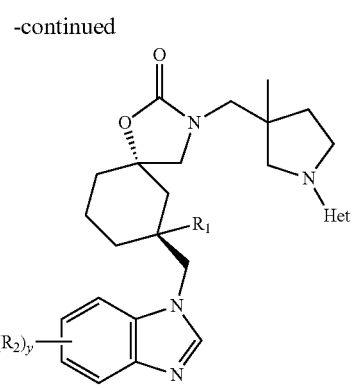

As shown in Scheme 5, a carboxylic acid can be transformed to a 1,3,4-oxadiazole by reacting the acid with an appropriately substituted hydrazine such as benzoyl hydrazine under standard conditions such as triethylamine and 2-chloro-1,3-dimethylimidazolium chloride in DCM to give the compound of Formula I.

As shown in Scheme 7, the spirocyclic carbamate with a cyclic amine like pyrrolidine can displace halo directly from X-Het where X is halo using cesium carbonate in NMP to form the compound of Formula I.

Scheme 6

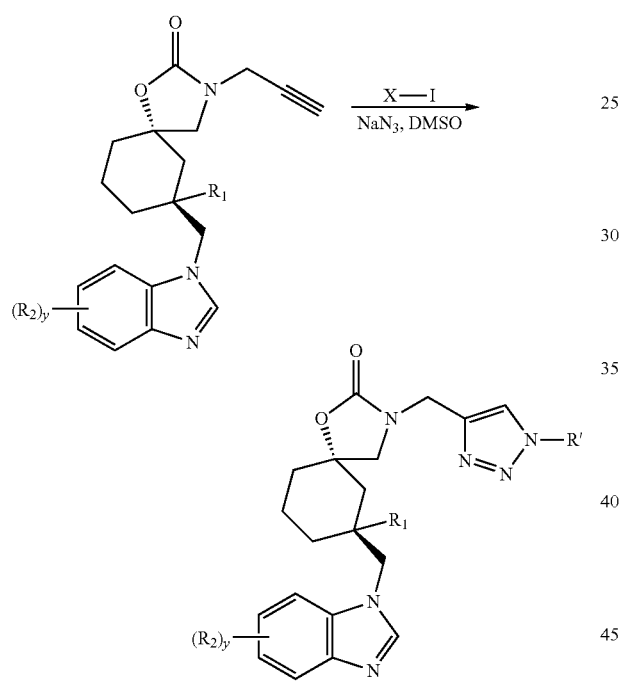

As shown in Scheme 6, the spirocyclic carbamate with a terminal alkyne can be transformed to a substituted 1,2,3-triazole under standard dipolar cycloaddition conditions such as reaction of an aryl iodide and sodium azide in DMSO to provide the compound of Formula I.

Scheme 7

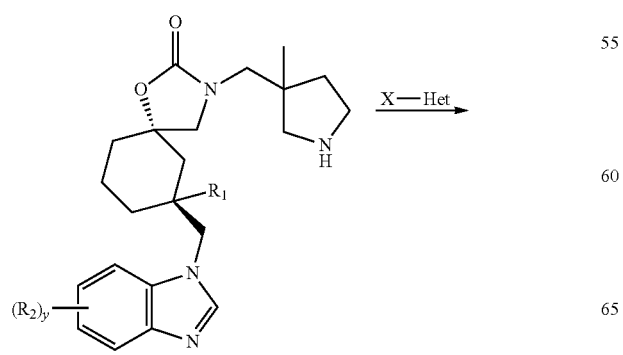

Scheme 8

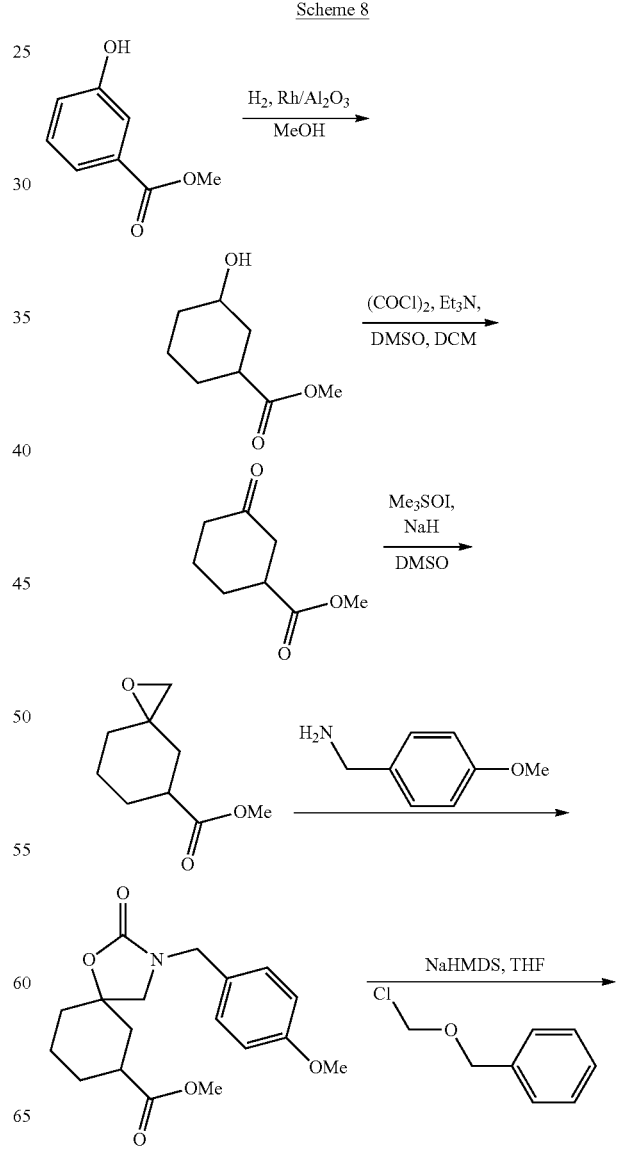

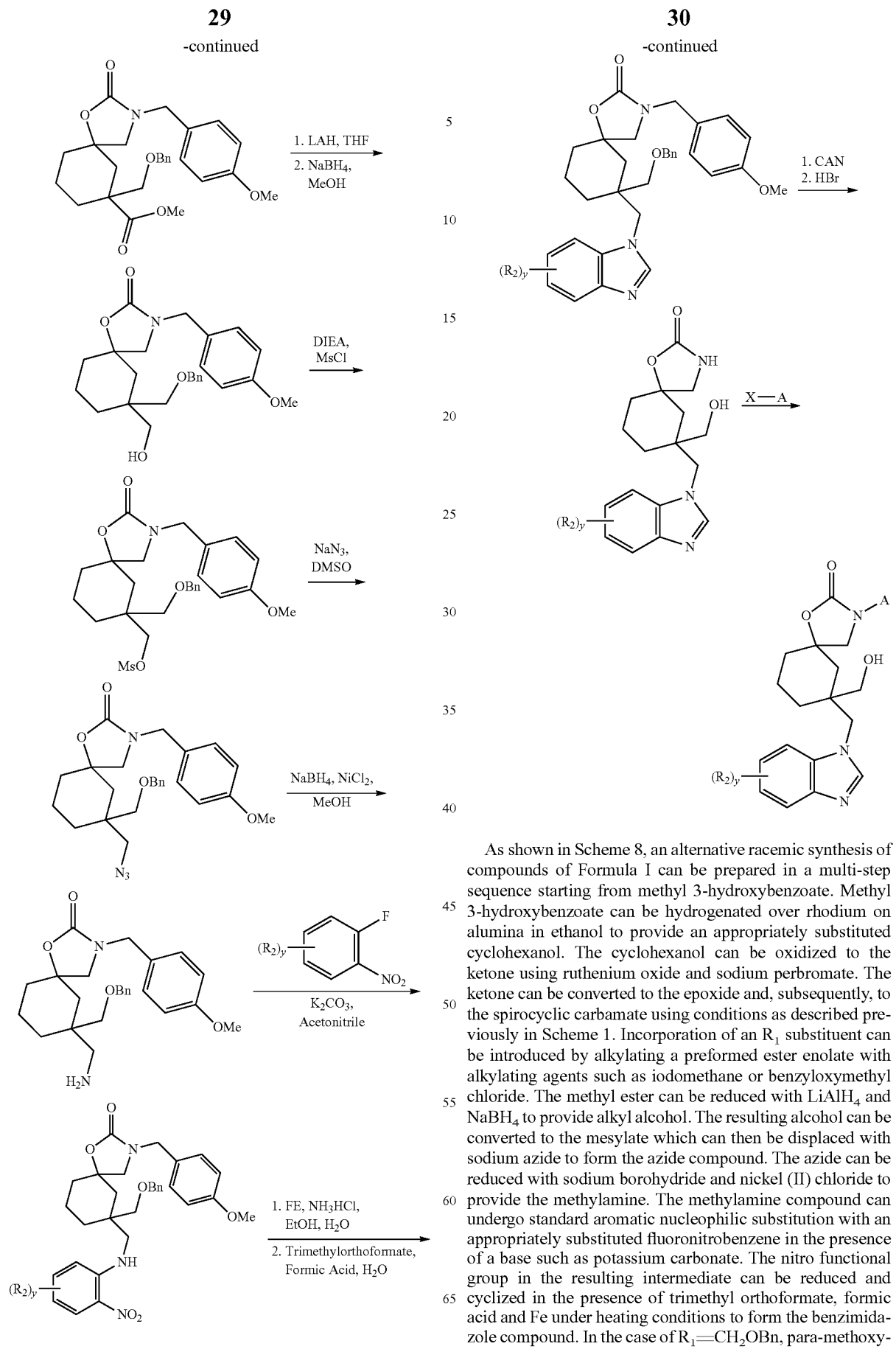

As shown in Scheme 8, an alternative racemic synthesis of compounds of Formula I can be prepared in a multi-step sequence starting from methyl 3-hydroxybenzoate. Methyl 3-hydroxybenzoate can be hydrogenated over rhodium on alumina in ethanol to provide an appropriately substituted cyclohexanol. The cyclohexanol can be oxidized to the ketone using ruthenium oxide and sodium perbromate. The ketone can be converted to the epoxide and, subsequently, to the spirocyclic carbamate using conditions as described previously in Scheme 1. Incorporation of an $R_1$ substituent can be introduced by alkylating a preformed ester enolate with alkylating agents such as iodomethane or benzyloxymethyl chloride. The methyl ester can be reduced with $LiAlH_4$ and $NaBH_4$ to provide alkyl alcohol. The resulting alcohol can be converted to the mesylate which can then be displaced with sodium azide to form the azide compound. The azide can be reduced with sodium borohydride and nickel (II) chloride to provide the methylamine. The methylamine compound can undergo standard aromatic nucleophilic substitution with an appropriately substituted fluoronitrobenzene in the presence of a base such as potassium carbonate. The nitro functional group in the resulting intermediate can be reduced and cyclized in the presence of trimethyl orthoformate, formic acid and Fe under heating conditions to form the benzimidazole compound. In the case of $R_1$=$CH_2OBn$, para-methoxybenzyl group can be deprotected using standard conditions such as CAN to provide the unsubstituted carbamate. In the case of $R_1$=Me, the para-methoxybenzyl group can also be deprotected using TFA at elevated temperature. The benzyl group can be deprotected under standard conditions such as HBr to provide primary alcohol in $R_1$. The resulting compound can be further functionalized with heterocyclic groups via a copper-catalyzed N-arylation reaction with an appropriately substituted directed linked heteroaryl halide (X-A=X-Het where X is halo) to give the compound of Formula I.

Biological Activity

As stated above, the compounds according to Formula I are TRPV4 antagonists, and are useful in the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, motor neuron disorders, genetic gain of function disorders, cardiovascular disease, renal dysfunction and osteoarthritis.

The biological activity of the compounds according to Formula I can be determined using any suitable assay for determining the activity of a candidate compound as a TRPV4 antagonist, as well as tissue and in vivo models.

The biological activity of the compounds of Formula (I) are demonstrated by the following tests.

Ligand-gated Assay:

TRP channel activation/opening results in an influx of divalent and monovalent cations including calcium. The resulting changes in intracellular calcium were monitored using a calcium selective fluorescent dye Fluo4 (MDS Analytical Technologies). Dye loaded cells were initially exposed to test compound to verify a lack of agonist activity. Cells were subsequently activated by addition of an agonist and inhibition of the agonist-induced activation was recorded. Human embryonic kidney 293 cells stably expressing the macrophage scavenger receptor class II (HEK-293-MSR-II) and transduced with 1% BacMam (J. P. Condreay, S. M. Witherspoon, W. C. Clay and T. A. Kost, Proc Natl Acad Sci 96 (1999), pp. 127-132) virus expressing the human TRPV4 gene were plated at 15000 cells/well in a volume of 50 µL in a 384 well poly-D lysine coated plate. Cells were incubated for 24 hours at 37 degrees and 5% $CO_2$. Media was then aspirated using a Tecan Plate-washer and replaced with 20 µL of dye loading buffer: HBSS, 500 uM Brilliant Black (MDS Analytical Technologies), 2 uM Fluo-4. Dye loaded plates were then incubated in the dark at room temperature for 1-1.5 hours. 10 µL of test compound diluted in HBSS (HBSS with 1.5 mM Calcium Chloride, 1.5 mM Magnesium Chloride and 10 mM HEPES. pH 7.4), +0.01% Chaps was added to the plate, incubated for 10 min at room temperature in the dark and then 10 µL of agonist was added at a final concentration equal to the agonist $EC_{80}$. Calcium release was measured using the FLIPRtetra (MDS Analytical Technologies) or FLIPR384 (MDS Analytical Technologies).

All examples described herein possessed TRPV4 biological activity with $IC_{50}$s ranges from 0.1 nM-0.5 µM (see table below). $IC_{50}$ between 0.1-10 nM (+++), >10-50 nM (++), >50-500 nM (+).

| Ex # | $IC_{50}$ |
| --- | --- |
| 1 | (++) |
| 2 | (+++) |
| 3 | (+++) |
| 4 | (+++) |
| 5 | (+++) |
| 6 | (+++) |
| 7 | (+) |
| 8 | (+++) |
| 9 | (+++) |
| 10 | (+++) |
| 11 | (++) |
| 12 | (+++) |
| 13 | (+++) |
| 14 | (+++) |
| 15 | (+++) |
| 16 | (+++) |
| 17 | (++) |
| 18 | (++) |
| 19 | (+++) |
| 20 | (+++) |
| 21 | (+) |
| 22 | (+++) |
| 23 | (++) |
| 24 | (+++) |
| 25 | (+++) |
| 26 | (+) |
| 27 | (+++) |
| 28 | (+++) |
| 29 | (++) |
| 30 | (++) |
| 31 | (+++) |
| 32 | (+) |
| 33 | (++) |
| 34 | (+++) |
| 35 | (++) |
| 36 | (+) |
| 37 | (++) |
| 38 | (++) |
| 39 | (+++) |
| 40 | (++) |
| 41 | (+++) |
| 42 | (++) |
| 43 | (++) |
| 44 | (+++) |
| 45 | (+++) |
| 46 | (+++) |
| 47 | (+++) |
| 48 | (+++) |
| 49 | (+++) |
| 50 | (+++) |
| 51 | (++) |
| 52 | (+) |
| 53 | (+++) |
| 54 | (+) |
| 55 | (+++) |
| 56 | (++) |
| 57 | (+++) |
| 58 | (+) |
| 59 | (+) |
| 60 | (+) |
| 61 | (+++) |
| 62 | (++) |
| 63 | (++) |
| 64 | (+++) |
| 65 | (++) |
| 66 | (++) |
| 67 | (++) |
| 68 | (++) |
| 69 | (+) |
| 70 | (+++) |
| 71 | (+) |
| 72 | (+) |
| 73 | (+++) |
| 74 | (++) |
| 75 | (+++) |
| 76 | (+++) |
| 77 | (+++) |
| 78 | (+++) |
| 79 | (+++) |

| Ex # | IC$_{50}$ |
|---|---|
| 80 | (+++) |
| 81 | (+++) |
| 82 | (+++) |
| 83 | (+++) |
| 84 | (+++) |
| 85 | (+++) |
| 86 | (+) |
| 87 | (++) |
| 88 | (+) |
| 89 | (++) |
| 90 | (+++) |
| 91 | (+) |
| 92 | (++) |
| 93 | (+++) |
| 94 | (++) |
| 95 | (++) |
| 96 | (++) |
| 97 | (++) |
| 98 | (+++) |
| 99 | (+++) |
| 100 | (+++) |
| 101 | (++) |
| 102 | (+++) |
| 103 | (+++) |
| 104 | (+) |
| 105 | (++) |
| 106 | (++) |
| 107 | (+++) |
| 108 | (+++) |
| 109 | (+) |
| 110 | (+++) |
| 111 | (++) |
| 112 | (+++) |
| 113 | (++) |
| 114 | (+++) |
| 115 | (+++) |
| 116 | (++) |
| 117 | (+) |
| 118 | (+++) |
| 119 | (+++) |
| 120 | (+++) |
| 121 | (+++) |
| 122 | (+++) |
| 123 | (+++) |
| 124 | (++) |
| 125 | (+++) |
| 126 | (+++) |
| 127 | (++) |
| 128 | (+++) |
| 129 | (++) |
| 130 | (+) |
| 131 | (+) |
| 132 | (+++) |
| 133 | (+++) |
| 134 | (+++) |
| 135 | (+) |
| 136 | (+) |
| 137 | (++) |
| 138 | (+) |
| 139 | (+++) |
| 140 | (+) |
| 141 | (++) |
| 142 | (++) |
| 143 | (++) |
| 144 | (+++) |
| 145 | (++) |
| 146 | (+++) |
| 147 | (+++) |
| 148 | (++) |
| 149 | (+) |
| 150 | (+) |
| 151 | (+) |
| 152 | (+++) |
| 153 | (+++) |
| 154 | (+++) |
| 155 | (+++) |
| 156 | (+++) |
| 157 | (+++) |
| 158 | (+++) |
| 159 | (+++) |
| 160 | (+++) |
| 161 | (+++) |
| 162 | (+++) |
| 163 | (+++) |
| 164 | (++) |
| 165 | (+++) |
| 166 | (+++) |
| 167 | (+++) |
| 168 | (++) |

Hypotonicity Assay (BHK Cells):

BHK/AC9_DMEM/F12 conditioned (Baby Hamster Kidney) cells were transduced with 2% BacMam virus expressing the human TRPV4 gene and were plated at 10K cells per well in a volume of 50 µL in 384 well poly-D-lysine coated plates. Cells were incubated for 18-24 hours at 37 degrees and 5% $CO_2$. The following day, the media was aspirated using a Tecan Plate-washer and replaced with 20 µL of dye loading buffer: HBSS buffer (HBSS with 1.5 mM Calcium Chloride, 1.5 mM Magnesium Chloride and 10 mM HEPES. pH 7.4), 2.5 mM Probenecid, 500 µM Brilliant Black, 2 µM Fluo-4. The dye loaded cells were incubated for 1-1.5 hours at room temperature in the dark. 10 µL of test compound diluted in HBSS/$H_2O$ (~1:2.3)+0.01% Chaps was added to the plate, incubated for 10 min at room temperature in the dark, and then 10 uL of hypotonic buffer ($H_2O$+1.5 mM $CaCl_2$+~68 mM NaCl; 140 mOsm stock/260 mOsm FAC) was used to test the inhibition of the hypotonicity-induced activation. Reaction was measured on a heated stage (37 degrees) using the FLIPRtetra. (pIC$_{50}$ range 6.3-10.0)

Fluorescent Imaging Plate Reader (FLIPR) Assay

The FLIPR assay detects changes in intracellular $Ca^{2+}$ ($Ca^{2+}_i$) ion concentrations following stimulation of various biochemical pathways that can increase $Ca^{2+}_i$ levels. An increase in $Ca^{2+}_i$ was quantified with the use of dye that becomes activated and subsequently contained within cells, then selectively fluoresces when bound to $Ca^{2+}$. A molecule known to selectively activate human TRPV4 channels, (N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide; GSK1016790A); (Thorneloe, et al., J Pharmacol Exp Ther, 326: 432, August 2008), was applied to cells to trigger TRPV4 channel-dependent influx of $Ca^{2+}$ from the extracellular solution and prevention of the dye accumulation by a molecule was considered as evidence of blockade of native TRPV4 channel activity.

Alveolar macrophages are critical mediators of Acute Lung Injury in multiple animal models and mouse alveolar macrophages display functional changes that are triggered by a prototypical TRPV4 activator (the phorbol ester 4αPDD) and absent in cells where the Trpv4 gene product has been deleted (Hamanaka, et al., 2010). In light of these findings, we obtained primary alveolar macrophages from broncho-alveolar lavage (BAL) solutions obtained from healthy human volunteers. BAL fluid was centrifuged and the resulting cell pellet was washed phosphate-buffered saline (PBS) and resuspended. This solution was then centrifuged and the cell pellet was resuspended in cell culture medium (DMEM with 10% fetal bovine serum supplemented with 1000 units/L penicillin/1000 µg/L streptomycin). In humans and laboratory animals, BAL cells consist largely of alveolar macrophages, although cell populations may be further enriched for alveolar macrophages by adherence to plastic materials such as wells of 96-well plates. We utilized this established principle to enrich for alveolar macrophages by plating human alveolar macrophages at densities of ~40,000 cells/well in 96-well plates, followed by washes with fresh medium after 30-60 minutes of incubation at 37° C. in a 5% $CO_2$ atmosphere and again after 18-24 h of incubation in the same conditions.

After 18 to 24 hours, media was aspirated and replaced with 100 ml load media containing EMEM with Earl's salts and L-Glutamine, 0.1% BSA (Millipore), 4 mM Fluo-4-acetoxymethyl ester fluorescent indicator dye (Fluo-4 AM, Invitrogen) and 2.5 mM probenecid. Cells were then incubated for 1 hour at 37° C. After aspirating off the dye containing media, the cells were washed 3 times with 100 mL of KRH assay buffer (120 mM NaCl, 4.6 mM KCl, 1.03 mM $KH_2PO_4$, 25 mM $NaHCO_3$, 1.0 mM $CaCl_2$, 1.1 mM $MgCl_2$, 11 mM Glucose, 20 mM HEPES, 0.1% gelatin, 2.5 mM probenecid, pH 7.4). To evaluate antagonist effects of a compound, 100 mL KRH assay buffer, containing 0.1% DMSO, 10 & 100 nM of the compound or the precedented, non-selective TRPV channel blocker Ruthenium Red (10 μM), was added to the wells and the plate warmed to 37° C. for 15 minutes before being placed in FLIPR (Molecular Devices, Sunnyvale, Calif.) where dye loaded cells are exposed to excitation light (488 nm) from a 6 watt Argon Laser. After the basal emission fluorescence measurements, the cellular response to a concentration range of TRPV4 opener, GSK1016790A (0.3-1000 nM), was monitored in FLIPR for 10 minutes at 516 nm emission fluorescence intensity. A secondary response to ionomycin (1 μM) was then recorded for all wells for 5 minutes. Peak emission from each well after addition of each stimulant is then exported to an excel spreadsheet. Results from each well were converted to % ionomycin. This data was then transferred to GraphPad Prism version 4.03 for plotting of response to each treatment condition. Shift of receptor EC50 response to GSK1016790A in presence of compound compared to vehicle was utilized to determine compound potency and type of receptor interaction using classical Schild analysis.

Patch Clamp Experiments

Patch clamp experiments can measure cationic currents moving through TRPV4-containing channels in the plasma membrane of cells including human alveolar macrophages. In traditional whole-cell patch-clamp recordings, cells are cultured in a manner such that multiple cells do not directly contact one another to confound the capacitance value of an individual cell's plasma membrane. The membrane of a single cell is contacted by a glass electrode and the membrane is ruptured, resulting in whole-cell configuration, which allows the investigator to fill the cytoplasm of the cell with the contents of the electrode (intracellular) solution and also to evoke membrane currents by manipulating the voltage of the cell membrane. Ionic gradients are established based on the differences in the ions contained within the intracellular solution and those contained within the extracellular solution, which is delivered over the cells via a gravity-fed perfusion system. When applicable, agonists that provoke TRPV4-dependent currents and/or blockers of TRPV4-containing channels can be added to the extracellular solution.

Human primary alveolar macrophages were plated on glass coverslips in growth medium overnight at a low density in order to avoid direct contact between cells. Patch clamp recordings were performed in whole-cell mode. Cells were perfused with standard extracellular solution consisting of (in mM): mM): 140 NaCl, 5 NaCl, 2 $MgCl_2.6H_2O$, 5 $CsCl_2$, 10 HEPES, and 10 D-Glucose, bubbled with 95% $O_2$/5% $CO_2$ gas and adjusted to pH 7.4 with NaOH. The internal solution used to fill the cell via the glass electrode consisted of (in mM: mM) 140 CsCl, 4 $MgCl_2$, 10 N-[2-hydroxyethyl]piperazine-N'-[2-ethanesulfonic acid] (HEPES), and 5 ethylene glycol bis(β-aminoethyl ether)-N,N,N',N'-tetraacetic acid (EGTA), adjusted to pH 7.2 with CsOH. Voltage ramps from −80 to +80 mV over durations of 500 msec were applied and sampled at 500 Hz, and the recordings were filtered at 10 kHz. Data were analyzed using clampfit software and analyzed in Excel spreadsheets or Graphpad Prism 4.

Hypotonic solutions are often used as surrogates for application of mechanical force on cells, as hypotonic extracellular solutions cause cell membranes to stretch. Since hypotonic solutions have been demonstrated to activate TRPV4 and produce TRPV4-dependent currents in cells expressing TRPV4-containing ion channels (Alessandri-Haber, et al., Neuron, 39: 497, July 2003), extracellular solution was replaced with a hypotonic extracellular solution consisting of (in mM): 74 NaCl, 5 KCl, 1.2 $KH_2PO_4$, 1.3 $MgCl_2$, 2.4 $CaCl_2$, and 26 $NaHCO_3$, adjusted to pH 7.4 with NaOH in order to evoke TRPV4-dependent currents. Once the hypotonic solution had evoked changes in currents (quantified at −80 and +80 mV), compound was added to the hypotonic extracellular solution and the reduction in currents was quantified.

Methods of Use

The compounds of the invention are TRPV4 antagonists, and are useful in the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, overactive bladder, pain, motor neuron disorders, genetic gain of function disorders, cardiovascular disease, renal dysfunction, osteoarthritis crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence. Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose. Preferred dosages are 1-500 mg once daily or BID per person.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company) *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

The compounds may be administered alone or in conjunction with one or more other therapeutic agents, said agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonists, HMG-CoA reductase inhibitors, dual non-selective β-adrenoceptor and $α_1$-adrenoceptor antagonists, type-5 phosphodiesterase inhibitors, and renin inhibitors.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

LCMS data was generated on an Agilent 1100 series system using a Sunfire C18, 5 µm column, 3×50 mm, kept at a constant 40° C. A gradient elution of 10 100% MeOH/water/ 0.1% TFA over 2.5 min. was used for each sample with a 1.2 mL/min solvent flow rate.

The naming program used is ACD Name Pro 6.02 or Chem. Draw.

The following abbreviations and terms had the indicated meanings throughout:

| Abbreviation | Meaning |
| --- | --- |
| aq | Aqueous |
| $Boc_2O$ | di-tert-butyl dicarbonate |
| brine | saturated aqueous NaCl |
| CAN | ceric ammonium nitrate |
| CDI | Carbonyldiimidazole |
| $CH_2Cl_2$ or DCM | methylene chloride |
| $CH_3CN$ or MeCN | Acetonitrile |
| $CH_3I$ or MeI | methyl iodide |
| $(COCl)_2$ | oxalyl chloride |
| $Cs_2CO_3$ | cesium carbonate |
| CuCN | copper cyanide |
| $CuSO_4$ | copper sulfate |
| d | Day |
| DCA | dichloroacetic acid |
| DMAP | 4-dimethylaminopyridine |
| DMF | N,N-dimethylformamide |
| DMSO | Dimethylsulfoxide |
| Equiv | Equivalents |
| Et | Ethyl |
| $Et_3N$ or TEA | Triethylamine |
| EtOH | Ethanol |
| $Et_2O$ | diethyl ether |
| EtOAc | ethyl acetate |
| h, hr | Hour |
| HATU | (2-(7-Aza-1H-benzotriazole-1-yl)-1,1,3,3-tetramethyluronium hexafluorophosphate) |
| HBr | hydrobromic acid |
| HCl | hydrochloric acid |
| HPLC | high performance liquid chromatography |
| $H_2SO_4$ | sulfuric acid |
| i-PrOH or IPA | Isopropanol |
| $i-Pr_2NEt$ or DIEA | N',N'-diisopropylethylamine |
| $K_2CO_3$ | potassium carbonate |
| $KNO_3$ | potassium nitrate |
| KOtBu | potassium tert-butoxide |
| LAH | lithium aluminide hydride |
| LCMS | liquid chromatography-mass spectroscopy |
| Me | Methyl |
| MeOH or $CH_3OH$ | Methanol |
| $MgSO_4$ | magnesium sulfate |
| min | Minute |
| MS | mass spectrum |
| MsCl | methanesulfonyl chloride |

| Abbreviation | Meaning |
| --- | --- |
| MTBE | methyl tert-butyl ether |
| μw | Microwave |
| n-BuLi | n-butyllithium |
| $NaBH_4$ | sodium borohydride |
| NaCl | sodium chloride |
| $Na_2CO_3$ | sodium carbonate |
| NaH | sodium hydride |
| $NaHCO_3$ | sodium bicarbonate |
| NaHMDS | sodium hexamethyldisilazane |
| $NaN_3$ | sodium azide |
| NaOH | sodium hydroxide |
| $Na_2SO_4$ | sodium sulfate |
| NCS | N-chlorosuccinimide |
| $NH_3$ | Ammonia |
| $NH_4Cl$ | ammonium chloride |
| $NH_4OH$ | ammonium hydroxide |
| $NiCl_2$ | Nickel (II) chloride |
| NMP | N-methyl pyrrolidone |
| $Pd(PPh_3)_4$ | tetrakis (triphenylphosphine) palladium |
| Ph | Phenyl |
| PPTS | pyridinium p-toluenesulfonate |
| $Rh/Al_2O_3$ | rhodium on aluminum oxide |
| RT, rt | room temperature |
| satd | Saturated |
| SCX | strong cation exchange |
| SFC | supercritical fluid chromatography |
| SPE | solid phase extraction |
| TFA | trifluoroacetic acid |
| THF | Tetrahydrofuran |
| $t_R$ | retention time |

Intermediate 1

1-{[(1S)-1-methyl-3-oxocyclohexaneyl]methyl}-1H-benzimidazole-6-carbonitrile

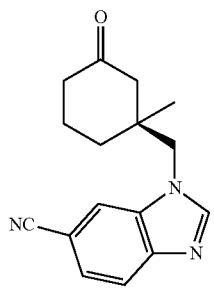 [SMILES: C[C@]1(Cn2cnc3ccc(C#N)cc32)CCCC(=O)C1]

(2R,3R)-7-Methyl-2,3-diphenyl-1,4-dioxaspiro[4.5]dec-6-ene (1R,2R)-1,2-diphenyl-1,2-ethanediol (150 g, 699 mmol) and 3-methyl-2-cyclohexen-1-one (77 g, 699 mmol) were suspended in benzene (1398 mL) and treated with PPTS (4.39 g, 17.48 mmol). The flask was fitted with a Dean-Stark trap filled with benzene and a condenser. The reaction was heated to 115° C. for 3 days, and then the reaction was cooled to ambient temperature and diluted with ether. The mixture was washed with saturated aq $NaHCO_3$. The organic layer was dried over $MgSO_4$, filtered and concentrated to give a red/orange liquid (214 g, 100% yield). The liquid was used without further purification.

(1S,4'R,5'R,6R)-6-Methyl-4',5'-diphenylspiro[bicyclo[4.1.0]heptane-2,2'-1,3]-dioxolane]

Zinc/copper couple was freshly prepared by quickly washing zinc dust with 1N HCl (4×100 mL) in a flask and decanting the supernatant. The solid was then washed in the same manner with distilled water (4×120 mL), 2 mol % $CuSO_4$ solution (2×200 mL), distilled water (4×120 mL), EtOH (4×120 mL) and $Et_2O$ (5×100 mL). The $Et_2O$ suspension of zinc/copper couple was poured onto a funnel and dried by vacuum filtration. The resulting solid was added to a 3 L flask and dried under vacuum at 50° C. for 30 min, then cooled to RT. The flask was fitted with an addition funnel and reflux condenser, then purged with nitrogen and kept under $N_2$ throughout the reaction. Next, 650 mL of $Et_2O$ was added followed by $I_2$ (0.886 g, 3.49 mmol), and the solution was stirred and heated to reflux. Once at reflux, heating was stopped and diiodomethane (150 mL, 1865 mmol) was slowly added making sure to not allow the reaction to reflux out of control. (2R,3R)-7-methyl-2,3-diphenyl-1,4-dioxaspiro[4.5]dec-6-ene (214 g, 698 mmol in 600 mL $Et_2O$) was then added to the reaction mixture, followed by an additional 0.5 eq of diiodomethane. The reaction was heated to reflux, and the reaction was monitored by LCMS. After 1.5 h the reaction was cooled to RT and quenched with saturated aq $Na_2CO_3$ (170 g in 800 mL water). The mixture was stirred for 30 min, then filtered through Celite©. The inorganics were washed with $Et_2O$ (2 L), then the combined organics were washed with saturated $NH_4Cl$ (1 L), saturated $NaHCO_3$ (1 L), brine (1 L), then dried over $MgSO_4$, filtered and concentrated to afford the crude product. Methanol (350 mL) was added to the residue and the suspension was heated to 50° C. The resultant solution was cooled with stirring to RT to crystallize the product. The slurry was stirred overnight at RT, then cooled to 0° C., and stirred for an additional 1 h. The slurry was filtered, washed with a minimal amount of MeOH and dried under reduced pressure to afford the desired product as a white solid (137 g, 61% yield).

(2R,3R,7S)-7-(Bromomethyl)-7-methyl-2,3-diphenyl-1,4-dioxasbiro[4.5]decane (1S,4R,5R,6R)-6-Methyl-4',5'-diphenylspiro[bicyclo[4.1.0]heptane-2,2'-[1,3]dioxolane] (137 g, 428 mmol) was dissolved in MeOH (1993 mL) and treated with hydrobromic acid in water (145 mL, 1283 mmol). The reaction was stirred at RT for 24 h, then concentrated to give a yellow residue. To the residue was added hexane (1 L) and the solution was stirred for 5 min. The hexane was decanted off leaving a yellow liquid behind. This process of adding hexane followed by decanting was repeated. The final volume of yellow liquid was 100 mL. The combined hexane washes were concentrated under reduced pressure to afford the desired product as a light yellow oil (172 g, 100% yield). The oil was used without further purification.

{[(2R,3R,7S)-7-Methyl-2,3-diphenyl-1,4-dioxasbiro[4.5]dec-7-yl]methyl}amine

To a 1 L flask was added (2R,3R,7S)-7-(bromomethyl)-7-methyl-2,3-diphenyl-1,4-dioxaspiro[4.5]decane (172 g, 428 mmol), potassium phthalimide (399 g, 2140 mmol), and NMP (900 mL). The mixture was allowed to stir at 130° C. for 24 h, then 120° C. for 4 days. Next, the mixture was cooled to RT and filtered. The solids were washed with $Et_2O$. The organics were added to a separatory funnel and diluted with $Et_2O$ and water. The ether was separated and washed with saturated aq NaHCO₃, brine and then dried over Na₂SO₄, filtered and concentrated under reduced pressure to afford the desired intermediate as a thick orange/yellow oil which was used directly in the next reaction. To the oil was added methanol (2.25 L) followed by hydrazine (40.3 mL, 1284 mmol). The solution was heated to reflux and the reaction was monitored by LCMS. Following completion (2 h), the solution was then cooled to RT and filtered. The filter cake was washed with MeOH, and the filtrate was then concentrated under reduced pressure. To the residue was added THF and the mixture was stirred. The resulting white solids were collected by filtration and the filtrate concentrated. A third crop was obtained by dissolving the residue in hexane. The solution was stirred with heating, then cooled to RT and filtered. Concentration of the hexane afforded the desired product as a light yellow oil (134.75 g, 93% yield). MS (m/z) 338.2 (M+H⁺).

3-({[(2R,3R,7S)-7-Methyl-2,3-diphenyl-1,4-dioxas-biro[4.5]dec-7-yl]methyl}amino)-4-nitrobenzonitrile A solution of acetonitrile (2049 mL) in a 3 L flask was heated to 40° C. Next, potassium carbonate (198 g, 1434 mmol), 1-[(2R,3R,7S)-7-methyl-2,3-diphenyl-1,4-dioxas-piro[4.5]dec-7-yl]methanamine (242 g, 717 mmol) and 3-fluoro-4-nitrobenzonitrile (119 g, 717 mmol) were added slowly. The mixture was allowed to stir at 40° C. for 2 h, and then cooled to RT. Stirring was continued at RT overnight. The next day, the slurry was filtered and the solids were washed with acetonitrile (500 mL). The filtrate was concentrated to afford the crude product (while keeping the temperature ~60° C. during concentration). To the thick dark residue was added MeOH. The solution was heated to 60° C. on the rotovap and concentrated to a minimal volume. To the residue was added ~500 mL of MeOH slowly with heating to avoid rapid crystallization, and the solution was heated to reflux. Once at reflux, an additional 250 mL MeOH was slowly added. The resulting slurry was allowed to stir at reflux for about 60 min, then heating was stopped and the slurry was allowed to cool to RT and stirring was continued for 3 days. The slurry was cooled to ~10° C. with an ice/water bath. Stirring was continued for ~2 h, and then the slurry was filtered and washed with cold MeOH (100 mL). The solids were dried under reduced pressure to give the desired product as a bright orange solid (245 g, 70.7% yield). This material was used in the next step.

1-{[(2R,3R,7S)-7-Methyl-2,3-diphenyl-1,4-dioxas-piro[4.5]dec-7-yl]methyl}-1H-benzimidazole-6-car-bonitrile A 5 L three neck flask was fitted with a mechanical stirrer and condenser. To the flask was added 3-({[(2R,3R,7S)-7-methyl-2,3-diphenyl-1,4-dioxaspiro[4.5]dec-7-yl]methyl}amino)-4-nitrobenzonitrile (245.5 g, 508 mmol), MeOH (891 mL) and EtOAc (891 mL). Next, trimethyl orthoformate (561 mL, 5077 mmol) and formic acid (195 mL, 5077 mmol) were added. The resulting mixture was heated at 64° C. Next, (2-3 eq) of formic acid, trimethylorthoformate and iron were added every 15 min until the reaction was finished (3.5 h). Next, the mixture was filtered to remove excess iron, and the iron was washed with EtOAc. The filtrate was concentrated and the resulting thick purple residue (residue contained formic acid) was used without further purification (235 g, 100% yield).

1-{[(1S)-1-Methyl-3-oxocyclohexaneyl]methyl}-1H-benzimidazole-6-carbonitrile

A mixture of 1-{[(2R,3R,7S)-7-methyl-2,3-diphenyl-1,4-dioxaspiro[4.5]dec-7-yl]methyl}-1H-benzimidazole-6-carbonitrile (235 g, 508 mmol) in formic acid (1948 mL) was heated to 70° C. for 18 h, then the solution was concentrated under reduced pressure, and diluted with sat. NaHCO₃ until it was basic. The resulting mixture was extracted with DCM (3×), and the combined extracts were washed with brine and then concentrated under reduced pressure. To the residue was added EtOAc (1 L) and then it was concentrated at 60° C. to a volume of approximately 750 mL. The slurry was then allowed to cool. Once solids started to form, the slurry was slowly diluted with 500 mL of hexanes and the temperature was raised to about 60° C. An additional 500 mL of hexanes was slowly added and the temperature was raised to reflux (about 68° C.). Once at reflux, heating was stopped, and the solution was allowed to cool to RT and stir for 5 days. Then the slurry was filtered, the solids were washed with hexanes and dried under reduced pressure to give 105.5 g of product (78% yield). The filtrate was concentrated and loaded onto silica gel and purified on a 220 g column (like a plug of silica) using vacuum to pull solvent through the column, and eluted with 500 mL of DCM, then 1 L of 50% EtOAc/DCM, then 1 L of 100% DCM, then 1 L each of 2.5%, 5%, 7.5%, and 10% MeOH/DCM. Fractions were collected in 1 L portions. Fractions containing product were concentrated to afford an additional 20.4 g (15% yield) of product. MS (m/z) 268.1 (M+H⁺).

Intermediate 2

1-{[(1S)-3-Oxocyclohexaneyl]methyl}-1H-benzimidazole-6-carbonitrile

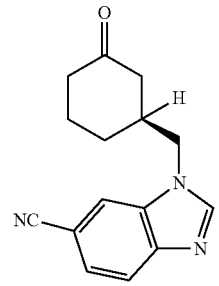 [SMILES: N#Cc1ccc2ncn(C[C@H]3CCCC(=O)C3)c2c1]

(2R,3R)-2,3-Diphenyl-1,4-dioxaspiro[4.5]dec-6-ene

To a 2 L flask was added (1R,2R)-1,2-diphenyl-1,2-ethanediol (200 g, 924 mmol), 2-cyclohexen-1-one (101 g, 1017 mmol), benzene (1232 mL) and PPTS (11.61 g, 46.2 mmol). The flask was fitted with a condenser and a dean-stark trap filled with benzene. The reaction was heated to 115° C. for 18 h (meanwhile trap contained 16.8 mL water indicating reaction completion). The reaction was cooled to RT and diluted with ether. The mixture was washed with saturated aq NaHCO₃. The organic layer was dried over MgSO₄, filtered and concentrated to give an orange liquid. This was passed over a silica gel plug eluting with 100% hexane (500 mL), then 5% EtOAc/Hexane (2 L), then 10% EtOAc/Hexane (500 mL), then 25% EtOAc/Hexane (500 mL). The product eluted in the first ~2.5 L of solvent. Removal of solvent afforded a light yellow oil. To this residue was added ~275 mL of hexane and the solution was let stand and crystals started to rapidly form. After about 1 h at RT, the solution was cooled in the freezer overnight. The next day, the hexane was decanted off, the solids washed with cold hexane. The solids were dried under reduced pressure at 75° C., and 223.75 g of (2R,3R)-2,3-diphenyl-1,4-dioxaspiro[4.5]dec-6-ene was obtained. The hexane solution was concentrated and purified by silica gel (ISCO, 330 g column, 100 mL/min, 0-10% EtOAc/Hexane over 40 min). Concentration of the pure fractions afforded (2R,3R)-2,3-diphenyl-1,4-dioxaspiro[4.5]dec-6-ene as an oil that solidified on sitting (30.47 g).

(1S,4'R,5'R,6R)-4',5'-Diphenylspiro[bicyclo[4.1.0] heptane-2,2'-1,3]-dioxolane]

The zinc/copper couple was freshly prepared by quickly washing zinc dust with 1N HCl (4×100 mL), then washing with distilled water (4×120 mL), 2 mol % $CuSO_4$ solution (2×200 mL), water (4×120 mL), EtOH (4×120 mL) and $Et_2O$ (5×100 mL). The washings were done in a flask with decanting of the liquid. The $Et_2O$ washes were poured onto a funnel and dried by vacuum filtration. The resulting solid was added to a 2 L flask and dried under vacuum at 115° C. for 30 min, then cooled to RT. The flask was fitted with an addition funnel and reflux condenser, then purged with nitrogen and kept under $N_2$ throughout the reaction. Next, 400 mL of $Et_2O$ was added followed by $I_2$ (0.551 g, 2.172 mmol), and the solution was stirred and heated to reflux. Once at reflux, heating was stopped and diiodomethane (87 mL, 1086 mmol) was slowly added making sure to not allow the reaction to reflux out of control. (2R,3R)-2,3-diphenyl-1,4-dioxaspiro[4.5]dec-6-ene (127 g, 434 mmol) was then added in 350 mL ether, followed by an additional 0.5 eq of diiodomethane. The reaction was heated to reflux and the reaction monitored by LCMS. After 1.5 h the reaction was cooled to RT and quenched with saturated aq $Na_2CO_3$ (230 g in 900 mL water). The mixture was stirred for 30 min, then filtered through celite. The inorganics were washed with $Et_2O$ (2 L), then the combined organics were washed with saturated aq $NH_4Cl$ (1 L), saturated aq $NaHCO_3$ (1 L), brine (1 L). The organic layers were dried over $MgSO_4$, filtered and concentrated to afford the crude product (176.45 g). To the residue was added $Et_2O$ (250 mL) and the suspension was heated to reflux, then allowed to cool to RT to crystallize the product. The suspension was put in the freezer for 3 days, then the ether decanted off. Drying of the solids gave (1S,4'R,5'R,6R)-4',5'-diphenylspiro[bicyclo [4.1.0]heptane-2,2'-[1,3]dioxolane] (112.5 g, 85% yield). The material was used as an intermediate without further purification.

(2R,3R,7S)-7-(Bromomethyl)-2,3-diphenyl-1,4-dioxasbiro[4.5]decane

The (4'R,5'R,6R)-4',5'-diphenylspiro[bicyclo[4.1.0]heptane-2,2'-[1,3]dioxolane] (112 g, 366 mmol) was dissolved in MeOH (1704 mL) and treated with hydrobromic acid in water (124 mL, 1097 mmol). The reaction was stirred at RT for 18 h and then concentrated. The residue was dissolved in hexane, then the hexane was decanted off leaving a yellow oil behind (HBr residue). The hexane was concentrated under reduced pressure to afford the (2R,3R,7S)-7-(bromomethyl)-2,3-diphenyl-1,4-dioxaspiro[4.5]decane as a light yellow oil (138.88 g, 98% yield). The oil was used without further purification.

1-[(2R,3R,7S)-2,3-Diphenyl-1,4-dioxasbiro[4.5]dec-7-yl]methanamine

To a 2 L flask was added (2R,3R,7S)-7-(bromomethyl)-2,3-diphenyl-1,4-dioxaspiro[4.5]decane (146 g, 377 mmol), potassium phthalimide (140 g, 754 mmol), and DMF (750 mL). The mixture was allowed to stir at 80° C. for 24 h, then cooled to RT. The mixture was added to a separatory funnel and diluted with $Et_2O$ and water. The ether was separated and the water extracted again with $Et_2O$. The combined ether extracts were washed with saturated aq $NaHCO_3$ and brine. The $Et_2O$ layers were dried over $Na_2SO_4$, filtered and concentrated under reduced pressure to afford the desired intermediate as a pale yellow glassy solid. To the residue was added MeOH (1875 mL) followed by hydrazine (35.5 mL, 1131 mmol). The solution was heated to reflux and the reaction monitored by LCMS. After 2 h, the solution was cooled to RT, filtered and washed with MeOH. The filtrate was concentrated under reduced pressure. To the residue was added THF and the mixture was stirred. The resulting solid was filtered off and the THF concentrated. The residue was dissolved in hexane, stirred with heating, then cooled to RT and filtered. Concentration of the hexane afforded the 1-[(2R,3R,7S)-2,3-diphenyl-1,4-dioxaspiro[4.5]dec-7-yl]methanamine as a light yellow oil (116.28 g, 95% yield). The oil was used without further purification.

3-({[(2R,3R,7S)-2,3-Diphenyl-1,4-dioxaspiro[4.5] dec-7-yl]methyl}amino)-4-nitrobenzonitrile A mixture of 3-fluoro-4-nitrobenzonitrile (55.5 g, 334 mmol), 1-[(2R,3R,7S)-2,3-diphenyl-1,4-dioxaspiro[4.5]dec-7-yl]methanamine (103 g, 318 mmol) and potassium carbonate (88 g, 637 mmol) in acetonitrile (2654 mL) was stirred at RT for 5 days (~200 mL DCM was added to help with solubility). The resulting solution was filtered and the solids washed with MeCN. The resulting solution was concentrated to give the crude product that was dissolved in MeOH (500 mL) and allowed to crystallize with stirring. The slurry was allowed to stir at RT overnight, filtered and the solids dried under reduced pressure to give 3-({[(2R,3R,7S)-2,3-diphenyl-1,4-dioxaspiro[4.5]dec-7-yl]methyl}amino)-4-nitrobenzonitrile (131.41 g, 88% yield). The product was used without further purification.

1-{[(2R,3R,7S)-2,3-Diphenyl-1,4-dioxasbiro[4.5] dec-7-yl]methyl}-1H-benzimidazole-6-carbonitrile To a 3 L flask fitted with an overhead stirrer was added 3-({[(2R,3R,7S)-2,3-diphenyl-1,4-dioxaspiro[4.5]dec-7-yl] methyl}amino)-4-nitrobenzonitrile (131 g, 279 mmol), iron (156 g, 2790 mmol), MeOH (1 L), EtOAc (1 L), trimethyl orthoformate (0.308 L, 2790 mmol) and formic acid (0.107 L, 2790 mmol). The mixture was heated to 64° C. Every 15 min an additional 2-3 eq of iron, formic acid and trimethyl orthoformate was added. After 3 h, the solution was cooled to RT and filtered through Celite© and washed with EtOAc. The filtrate was concentrated to give 1-{[(2R,3R,7S)-2,3-diphenyl-1,4-dioxaspiro[4.5]dec-7-yl]methyl}-1H-benzimidazole-6-carbonitrile (125 g, 100% yield). MS (m/z) 450.2 $(M+H^+)$. The product was used without further purification.

1-{[(1S)-3-Oxocyclohexaneyl]methyl}-1H-benzimidazole-6-carbonitrile

A mixture of 1-{[(2R,3R,7S)-2,3-diphenyl-1,4-dioxaspiro [4.5]dec-7-yl]methyl}-1H-benzimidazole-6-carbonitrile (125 g, 279 mmol) in formic acid (1.5 L) was heated to 70° C. overnight. Then the formic acid was removed via concentration, and the mixture was diluted with DCM and saturated aq NaHCO₃ till basic. The mixture was extracted with DCM (3×). The organic layers were dried over Na₂SO₄, filtered and concentrated and azeotroped with EtOAc. EtOAc (250 mL) was then added and the mixture was stirred at RT which led to solids forming. The slurry was stirred at RT for 15 min and then hexane (500 mL) was added slowly. The slurry was allowed to stir for 3 days at RT and then filtered and washed with hexane. The solids were dried under reduced pressure to give ~61 g product. The filtrate was concentrated and purified via normal phase chromatography (Combiflash Rf, (2×330 g silica column), solid load, 100 mL/min, EtOAc/CH₂Cl₂ 0-100% over 20 min, then 0-10% MeOH/CH₂Cl₂ over 10 min, holding at 10% MeOH/DCM until) all product had eluted from column) to afford the desired product as a tan solid (~7 g). The material was dissolved in EtOAc (15 mL), and heated to reflux. Next, hexane was added until solids started to form. Heating was stopped and the solution was allowed to cool to RT. Stirring was continued overnight at RT. Filtration of the slurry gave the desired product as a light tan powder (3.5 g). MS (m/z) 254.1(M+H⁺).

Intermediate 3

1-{[(3S,5S)-5-Methyl-1-oxasbiro[2,5]oct-5-yl]methyl}-1H-benzimidazole-6-carbonitrile

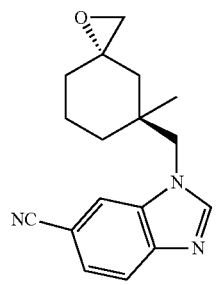 [SMILES: C[C@]1(Cn2cnc3ccc(C#N)cc32)CCC[C@@]2(CO2)C1]

Route 1: To a 2 L flask was added DMSO (604 mL) and 1-{[(1S)-1-methyl-3-oxocyclohexaneyl]methyl}-1H-benzimidazole-6-carbonitrile (121 g, 453 mmol). The solution was stirred and heated to ~35° C. to get all solids to go into solution. Next, trimethylsulfonium iodide (112 g, 543 mmol) was added followed by potassium tert-butoxide (60.9 g, 543 mmol). The mixture was allowed to stir and cool to RT. After 1 h, LCMS indicated the reaction was complete. Next, the DMSO solution was added to a separatory funnel and diluted with 3 L water and 1 L DCM. The DCM was separated, and the water was extracted with DCM (3×500 mL). The combined DCM extracts were washed with brine (2 L) then dried over Na₂SO₄, filtered and concentrated. Half of the residue was purified by prep-SFC (total of 450-injections, 6 min run each) using the following conditions: Column: GreenSep Silica (ES Industries), 25 cm×21.2 mm, Co-solvent: MeOH, % Co-solvent: 25% Isocratic, Flow rate=60 g/min, Temperature: ambient. Following the purification of this material, the pressure on the SFC was too high to continue purification. The remaining dark MeOH solution of material was concentrated (~70 g), dissolved in DCM and purified by silica gel chromatography CISCO): 8×220 g column, 75 mL/min, 0-3.5% MeOH/DCM (0.1% TEA) over 15 min, then holding at 3.5% MeOH until product eluted. Some early fractions contained pure cis product. These were concentrated and combined with the cis product from the SFC purification. The late fractions, which were yellow, were concentrated and re-purified on 3×220 g columns the same way as described above. In this case, some late fractions were pure trans product, and these fractions were isolated and combined with the trans product from the SFC. All mixed fractions were combined and concentrated to give ~36 g of material. This was then purified on the SFC and resulted in no pressure problems. Concentration of the appropriate fractions afforded 42.7 g (33.5% yield) of trans epoxide (1-{[(3S,5S)-5-methyl-1-oxaspiro[2.5]oct-5-yl]methyl}-1H-benzimidazole-6-carbonitrile) and 72.7 g (57% yield) of cis epoxide (1-{[(3R,5S)-5-methyl-1-oxaspiro[2.5]oct-5-yl]methyl}-1H-benzimidazole-6-carbonitrile). MS (m/z) 282.2 (M+H⁺).

Route 2: The cis epoxide can be converted to trans-epoxide using the two step procedure described below.

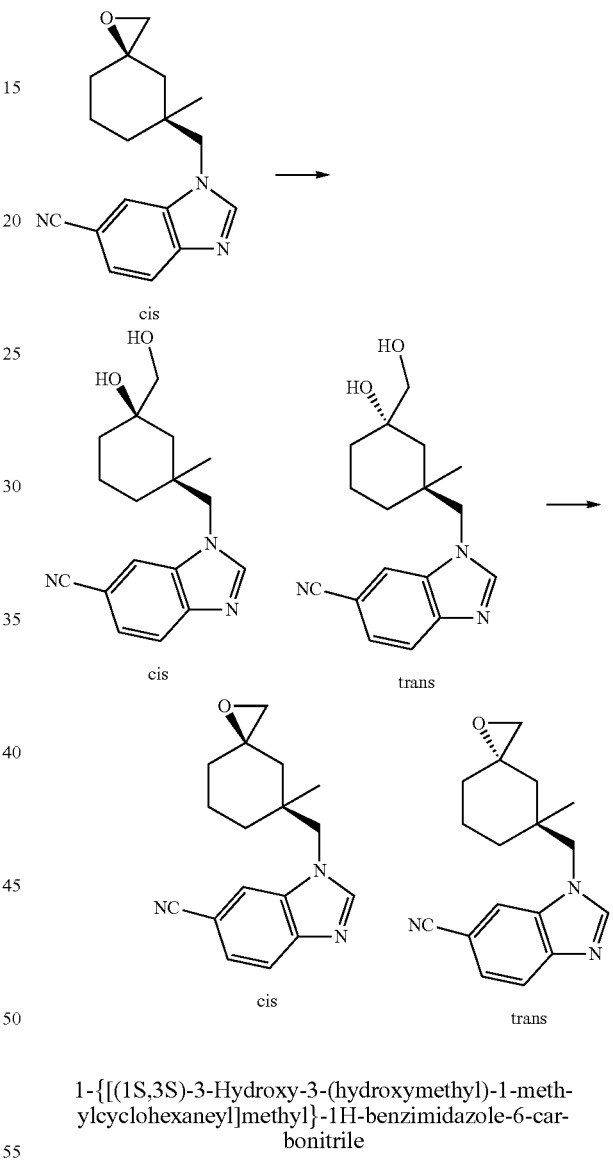

1-{[(1S,3S)-3-Hydroxy-3-(hydroxymethyl)-1-methylcyclohexaneyl]methyl}-1H-benzimidazole-6-carbonitrile To a 3 L flask was added 1-{[(3R,5S)-5-methyl-1-oxaspiro[2.5]oct-5-yl]methyl}-1H-benzimidazole-6-carbonitrile (94.7 g, 337 mmol). The material was azeotroped two times with EtOAc to remove any trace amounts of MeOH from the SFC. Next, to the residue was added DMF (731 mL) and water (731 mL). The solution was cooled to ~18° C. (with an ice water bath). Next, a solution of TFA (51.9 mL, 673 mmol) in water (731 mL) added (pre-cooled to ~10° C.). The entire solution was then cooled with an ice water bath to ~10° C. The temperature was held around 10° C. for about 2.5 h then allowed to warm to RT and stir overnight. The next day, DCM (500 mL) was added, and the solution was made basic by slowly adding 6N NaOH. The mixture was added to a separatory funnel, the DCM separated and the aqueous layer diluted with 6N NaOH (300 mL), and then extracted with DCM (8×250 mL). The combined organic extracts were concentrated under reduced pressure to remove as much DMF as possible. The residue was dissolved in DCM (250 mL) and stirred at RT to crystallize the trans diol. After stirring overnight, the solution was cooled to ~10° C., and the solids were filtered off, washed with DCM and dried under reduced pressure. This yielded 49.15 g of 1-{[(1S,3S)-3-hydroxy-3-(hydroxymethyl)-1-methylcyclohexaneyl]methyl}-1H-benzimidazole-6-carbonitrile (trans diol) as a white solid. The filtrate (~60 g material, a mixture of cis-diol, trans-diol, and elimination side products) was concentrated, loaded onto silica gel and split into 3 equal portions and purified on the ISCO RF (3×330 g column): 0-5% MeOH/DCM over 15 min, hold at 5% for 10 min, then 5-25% over 10 min, then hold at 25%. The trans diol product was combined with the solids from the crystallization and used without further purification. MS (m/z) 300.2 (M+H$^+$).

1-{[(3S,5S)-5-Methyl-1-oxaspiro[2,5]oct-5-yl]methyl}-1H-benzimidazole-6-carbonitrile To a 1 L flask was added 1-{[(1S,3S)-3-hydroxy-3-(hydroxymethyl)-1-methylcyclohexaneyl]methyl}-1H-benzimidazole-6-carbonitrile (21.2 g, 70.8 mmol) and DCM (698 mL) and the temperature was lowered to 5° C. Next DMAP (6.49 g, 53.1 mmol), tosyl-Cl (20.25 g, 106 mmol) and triethylamine (20.23 mL, 145 mmol) were added. The solution was allowed to stir and warm to RT. Stirring was continued for 18 h and then the solution was added to a separatory funnel and diluted with saturated aq NaHCO$_3$ (1 L). The DCM was separated, and washed sequentially with saturated aq NH$_4$Cl, then saturated aq NaHCO$_3$. The DCM was then passed over a phase separator to remove leftover water, concentrated, and taken directly onto the next step. To the yellow residue was added methanol (698 mL) followed by K$_2$CO$_3$ (10.77 g, 78 mmol). The mixture was stirred at RT for 3 h. Following completion, the solution was filtered, and the solids were washed with MeOH. The mixture was then diluted with DCM (500 mL) and saturated aq NaHCO$_3$ (1 L). The solution was added to a 3 L separatory funnel, and the aqueous layer extracted three times with DCM. The combined DCM extracts were washed with brine and then dried over Na$_2$SO$_4$, filtered and concentrated. The crude solid was azeotroped with EtOAc two times to give a yellow residue. The residue was dried under reduced pressure to give 1-{[(3S,5S)-5-methyl-1-oxaspiro[2,5]oct-5-yl]methyl}-1H-benzimidazole-6-carbonitrile as a yellow solid (19.9 g, 95% yield). MS (m/z) 282.2 (M+H$^+$).

Intermediate 4

1-[(3S,5S)-1-Oxaspiro[2.5]oct-5-ylmethyl]-1H-benzimidazole-6-carbonitrile

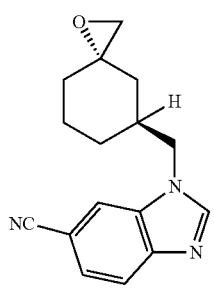 [SMILES: N#Cc1ccc2ncn(C[C@H]3CCC[C@@]4(CO4)C3)c2c1]

A solution of trimethylsulfoxonium iodide (63.1 g, 287 mmol) in DMSO (500 mL) was added sodium hydride (11.46 g, 287 mmol) in portions under nitrogen. The resulting mixture was stirred at RT for 1 h. To the mixture was added a solution of 1-{[(1S)-3-oxocyclohexaneyl]methyl}-1H-benzimidazole-6-carbonitrile (60.5 g, 239 mmol) in DMSO (500 mL) dropwise under nitrogen. The resulting light brown solution was stirred at RT for 1 h. LCMS indicated the mixture was 9:1 trans/cis. Next, the DMSO solution was poured into 2 L water, and then extracted with DCM (3×). The combined DCM extracts were washed with water (2 L) and brine (2 L), and the organic layers were dried over Na$_2$SO$_4$, filtered and concentrated to give 68 g of a tan solid. To the residue was added 500 mL of EtOAc. The mixture was heated to reflux with stirring. Once all solids were in solution, the EtOAc was allowed to evaporate off until the amount of EtOAc was 320 mL, then the heating was stopped and the solution was allowed to cool to RT with stirring. Stirring was continued overnight at RT, then cooled to 5° C. and let stir for 3 h. The slurry was then filtered, washed with minimal amount of cold EtOAc, followed by hexane. The resulting tan solid was dried under reduced pressure to give 1-[(3S,5S)-1-oxaspiro[2.5]oct-5-ylmethyl]-1H-benzimidazole-6-carbonitrile (46 g of a 95:5 trans:cis mixture). The filtrate was concentrated to give 1-[(3S,5S)-1-oxaspiro[2.5]oct-5-ylmethyl]-1H-benzimidazole-6-carbonitrile (22 g, 61:39 trans:cis mixture) and the process repeated. The products were used in subsequent steps as an intermediate. MS (m/z) 268 (M+H$^+$).

Intermediate 5

3-{(5S,7S)-7-[(6-Cyano-1H-benzimidazol-1-ylmethyl]-2-oxo-1-oxa-3-azaspiro[4.5]dec-3-yl}-2,2-dimethylpropanoic acid

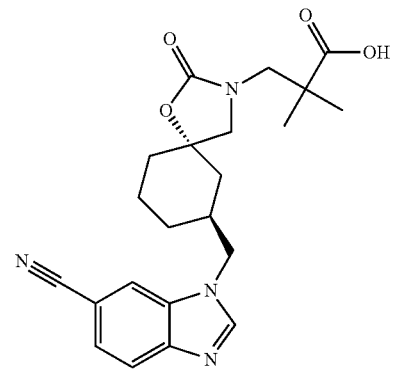 [SMILES: CC(C)(CN1C[C@@]2(CCC[C@H](Cn3cnc4ccc(C#N)cc43)C2)OC1=O)C(=O)O]

3-[({4-[(6-Cyano-1H-benzimidazol-1-yl)methyl]-1-hydroxycyclohexaneyl}methyl)amino]-2,2-dimethylpropanoate A solution of 1-[(5S)-1-oxaspiro[2.5]oct-5-ylmethyl]-1H-benzimidazole-6-carbonitrile (1.064 g, 3.98 mmol) and methyl 3-amino-2,2-dimethylpropanoate (0.679 g, 5.17 mmol) in isopropanol (13.27 mL) was stirred at 100° C. for 1 day. Reaction was concentrated and purified via silica gel chromatography (ISCO, 120 g silica gel column. Solvent A was DCM and solvent B was 0.1M NH$_3$ in MeOH; 0-10% B over 15 min; 10% B over 6 min) to give methyl 3-[({3-[(6-cyano-1H-benzimidazol-1-yl)methyl]-1-hydroxycyclohexaneyl}methyl)amino]-2,2-dimethylpropanoate as a sticky solid (1.05 g, 66.1% yield). MS (m/z) 399.2 (M+H$^+$).

Methyl 3-{(5S,7S)-7-[(6-cyano-1H-benzimidazol-1-ylmethyl]-2-oxo-1-oxa-3-azaspiro[4.5]dec-3-yl}-2,2-dimethylpropanoate A solution of methyl 3-[({3-[(6-cyano-1H-benzimidazol-1-yl)methyl]-1-hydroxycyclohexaneyl}methyl)amino]-2,2-dimethylpropanoate (1.048 g, 2.63 mmol) and CDI (0.853 g, 5.26 mmol) in 1,4-dioxane (15 mL) was stirred at 100° C. for 1 day. The reaction was then concentrated and purified via silica gel chromatography (ISCO, 40 g silica gel column; solvent A=DCM; solvent B=MeOH (0.1M NH$_3$); 0-5% B over 15 min; then 5% B over 5 min) to give methyl 3-{(5S,7S)-7-[(6-cyano-1H-benzimidazol-1-yl)methyl]-2-oxo-1-oxa-3-azaspiro[4.5]dec-3-yl}-2,2-dimethylpropanoate as a beige solid (1.06 g, 95% yield). MS (m/z) 425.2 (M+H$^+$).

3-{(5S,7S)-7-[(6-Cyano-1H-benzimidazol-1-yl)methyl]-2-oxo-1-oxa-3-azasbiro[4.5]dec-3-yl}-2,2-dimethylpropanoic acid A suspension of methyl 3-{(5S,7S)-7-[(6-cyano-1H-benzimidazol-1-yl)methyl]-2-oxo-1-oxa-3-azaspiro[4.5]dec-3-yl}-2,2-dimethylpropanoate (1.06 g, 2.505 mmol) and potassium trimethylsilanolate (0.482 g, 3.76 mmol) in THF (12.5 mL) was stirred at RT overnight. LCMS showed the reaction was not complete. Additional potassium trimethylsilanolate (0.482 g, 3.76 mmol) was then added, and the reaction was stirred for one additional day. The reaction mixture was then concentrated to a light yellow solid. The solid was washed with a mixture of DCM and Et$_2$O and dried under vacuum to give 3-{(5S,7S)-7-[(6-cyano-1H-benzimidazol-1-yl)methyl]-2-oxo-1-oxa-3-azaspiro[4.5]dec-3-yl}-2,2-dimethylpropanoic acid as a light yellow solid. This product was used in the next step without any further purification. MS (m/z) 411.2 (M+H$^+$).

Intermediate 6

1-({(5S,7S)-3-[(3-Methyl-3-pyrrolidinyl)methyl]-2-oxo-1-oxa-3-azasbiro[4.5]dec-7-yl}methyl)-1H-benzimidazole-6-carbonitrile

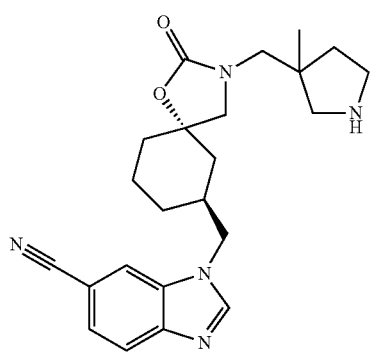 [SMILES: CC1(CN2C[C@@]3(CCC[C@H](Cn4cnc5ccc(C#N)cc54)C3)OC2=O)CCNC1]

1,1-Dimethylethyl 3-{[({(1S,3S)-3-[(6-cyano-1H-benzimidazol-1-yl)methyl]-1-hydroxycyclohexaneyl}methyl)amino]methyl}-3-methyl-1-pyrrolidinecarboxylate A solution of 1,1-dimethylethyl 3-(aminomethyl)-3-methyl-1-pyrrolidinecarboxylate (0.677 g, 3.16 mmol) and 1-[(3S,5S)-1-oxaspiro[2.5]oct-5-ylmethyl]-1H-benzimidazole-6-carbonitrile (0.844 g, 3.16 mmol) in isopropanol (5 mL) was heated at 102° C. overnight. The reaction mixture was concentrated and purified via silica gel chromatography (ISCO, 40 g silica gel column. Solvent A: DCM; B: MeOH; 0-10% B: 15 min; 10% B: 10 min) to give 1,1-dimethylethyl 3-{[({(1S,3S)-3-[(6-cyano-1H-benzimidazol-1-yl)methyl]-1-hydroxycyclohexaneyl}methyl)amino]methyl}-3-methyl-1-pyrrolidinecarboxylate (950 mg, 62.4% yield).

1,1-Dimethylethyl 3-({(5S,7S)-7-[(6-cyano-1H-benzimidazol-1-yl)methyl]-2-oxo-1-oxa-3-azaspiro[4.5]dec-3-yl}methyl)-3-methyl-1-pyrrolidinecarboxylate 1,1-Dimethylethyl3-{[({(1S,3S)-3-[(6-cyano-1H-benzimidazol-1-yl)methyl]-1-hydroxycyclohexaneyl}methyl)amino]methyl}-3-methyl-1-pyrrolidinecarboxylate was treated with CDI (1.537 g, 9.48 mmol) in 1,4-dioxane (5.00 mL) at 103° C. overnight. The reaction mixture was concentrated and purified via silica gel chromatography (ISCO, 40 g silica gel column. Solvent A: DCM; B: MeOH; 0-5% B: 10 min; 5% B: 10 min) to give 1,1-dimethylethyl 3-({(5S,7S)-7-[(6-cyano-1H-benzimidazol-1-yl)methyl]-2-oxo-1-oxa-3-azaspiro[4.5]dec-3-yl}methyl)-3-methyl-1-pyrrolidinecarboxylate as a white foam (752 mg, 46.9% yield). MS (m/z) 508.3 (M+H$^+$).

1-({(5S,7S)-3-[(1,3-Methyl-3-pyrrolidinyl)methyl]-2-oxo-1-oxa-3-azaspiro[4.5]dec-7-yl}methyl)-1H-benzimidazole-6-carbonitrile 1,1-Dimethylethyl 3-({(5S,7S)-7-[(6-cyano-1H-benzimidazol-1-yl)methyl]-2-oxo-1-oxa-3-azaspiro[4.5]dec-3-yl}methyl)-3-methyl-1-pyrrolidinecarboxylate (747 mg, 1.472 mmol) was treated with hydrochloric acid (4M in dioxane) (4 mL, 16.00 mmol) overnight. The rxn was concentrated to 1-({(5S,7S)-3-[(3-methyl-3-pyrrolidinyl)methyl]-2-oxo-1-oxa-3-azaspiro[4.5]dec-7-yl}methyl)-1H-benzimidazole-6-carbonitrile as a crispy foam. MS (m/z) 408.2 (M+H$^+$). The product was used without further purification.

Intermediate 7

1-{[(5S,7S)-7-Methyl-2-oxo-3-(2-propyn-1-yl)-1-oxa-3-azaspiro[4.5]dec-7-yl]methyl}-1H-benzimidazole-6-carbonitrile

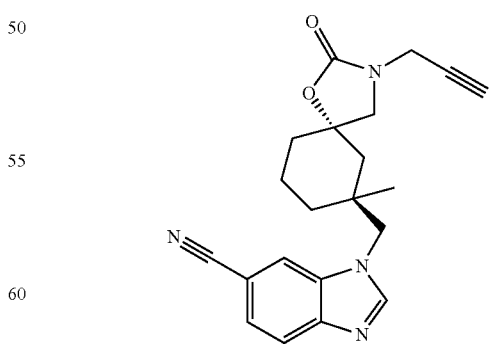

To a 20 mL microwave tube was added 1-{[(3S,5S)-5-methyl-1-oxaspiro[2.5]oct-5-yl]methyl}-1H-benzimidazole-6-carbonitrile (840 mg, 2.99 mmol) and propargyl amine (822 mg, 14.93 mmol) in MeOH (5 mL). The tube was sealed and heated at 100° C. for 2 h on a hotplate. The reaction mixture was then evaporated down directly to a crispy foam, codistilled 2× with DCM, and left on highvac for 3 h to remove any residual MeOH and the volatile amine. The yellow residue was then treated with CDI (2.42 g, 14.93 mmol) and 1,4-dioxane (5 mL) was added. The reaction mixture was stirred and heated at 100° C. for 2 h, then left at RT overnight. LCMS then indicated the reaction was not complete. The reaction mixture was then heated at 120° C. for 6 h. The mixture (dark orange oil) was loaded onto florisil and purified using silica gel chromatography CISCO): 0.5-5% MeOH/DCM (30 min), 5% (10 min), 120 g silica. The desired product eluted at 18 min. The product was dried under vacuum at RT overnight to yield 1-{[(5S,7S)-7-methyl-2-oxo-3-(2-propyn-1-yl)-1-oxa-3-azaspiro[4.5]dec-7-yl]methyl}-1H-benzimidazole-6-carbonitrile as an yellow oil (109 mg, 5% yield). MS (m/z) 363 (M+H+).

Intermediate 8

1-{[(5S,7S)-7-Methyl-2-oxo-1-oxa-3-azaspiro[4.5]dec-7-yl]methyl}-1H-benzimidazole-6-carbonitrile

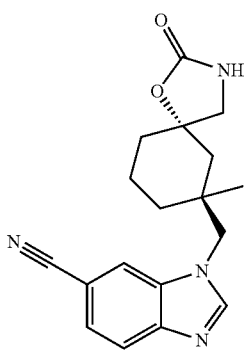 [SMILES: C[C@]1(Cn2cnc3ccc(C#N)cc32)CCC[C@@]2(CNC(=O)O2)C1]

Route 1

1-(((5S,7S)-3-(4-methoxybenzyl)-7-methyl-2-oxo-1-oxa-3-azaspiro[4.5]decan-7-ylmethyl)-1H-benzo[d]imidazole-6-carbonitrile may be prepared using procedures analogous to Example 4 using 4-methoxybenzylamine as an amine to react with 1-{[(3S,5S)-5-methyl-1-oxaspiro[2.5]oct-5-yl]methyl}-1H-benzimidazole-6-carbonitrile.

Alternatively, 1-(((5S,7S)-3-(4-methoxybenzyl)-7-methyl-2-oxo-1-oxa-3-azaspiro[4.5]decan-7-yl)methyl)-1H-benzo[d]imidazole-6-carbonitrile may also be prepared using procedures analogous to Example 12 using methyl iodide as an alkylating agent instead of benzyl chloromethyl ether in reaction with the enolate of 3-{[4-(methyloxy)phenyl]methyl}-2-oxo-1-oxa-3-azaspiro[4.5]decane-7-carboxylate (see Scheme 8). The modification to Scheme 8 required to prepare enantiomerically pure material is at the intermediate trans-(3-(4-methoxybenzyl)-7-methyl-2-oxo-1-oxa-3-azaspiro[4.5]decan-7-yl)methyl methanesulfonate stage. This racemic mixture (10 g) was separated into the enantiomers using SFC chiral chromatography (Chiralpak AS-H, Co-solvent: EtOH (35% Isocratic), 4 mL/min, 8 min/per injection, Column Temp.=40.1° C., Front Pressure=133 bar, Back Pressure=100 bar). Peak 2 gave the desired enantiomer, ((5S,7S)-3-(4-methoxybenzyl)-7-methyl-2-oxo-1-oxa-3-azaspiro[4.5]decan-7-yl)methyl methanesulfonate (4.25 g, 42.5%), as a white solid.

A yellow solution of 1-(((5S,7S)-3-(4-methoxybenzyl)-7-methyl-2-oxo-1-oxa-3-azaspiro[4.5]decan-7-yl)methyl)-1H-benzo[d]imidazole-6-carbonitrile (2.012 g, 4.53 mmol) in TFA (20.12 ml) was heated at 70° C. The reaction mixture turned dark brown overnight. Additional TFA (5 mL) was then added to the reaction mixture. After 21 h, additional TFA (5 mL) was added. After 23 h, reaction was completed as indicated by LCMS. The reaction mixture was then cooled to RT and concentrated. 2N NaOH (40 mL) and DCM (50 mL) were added to the mixture (aqueous layer was pH 13). The layers were separated and the aqueous layer was extracted with DCM (2×25 mL). Combined organic layers were dried over Na2SO4, filtered, and concentrated. The compound was loaded onto florisil and purified using silica gel chromatography CISCO): 1-5% MeOH/DCM (30 min), 5% (15 min), 40 g silica. Product began eluting at 22 minutes. The product was dried under high vacuum at 40° C. overnight to yield 1-{[(5S,7S)-7-methyl-2-oxo-1-oxa-3-azaspiro[4.5]dec-7-yl]methyl}-1H-benzimidazole-6-carbonitrile as a yellow solid (729 mg, 47.2% yield). MS (m/z) 325 (M+H+).

Route 2

A mixture of ethyl carbamate (0.237 g, 2.67 mmol) and KOtBu (0.259 g, 2.310 mmol) in NMP (8.89 mL) was heated at 100° C. for 15 min. 1-(((3S,5S)-5-methyl-1-oxaspiro[2.5]octan-5-ylmethyl)-1H-benzo[d]imidazole-6-carbonitrile (0.500 g, 1.777 mmol) was then added. The reaction mixture was stirred overnight (stopped heating at some point because of storm power outage). The reaction mixture was heated at 100° C. and stirred for an additional 6 h. Additional ethyl carbamate (0.237 g, 2.67 mmol) and KOtBu (0.065 g, 0.578 mmol) were added and stirred for 16 h. Additional ethyl carbamate (0.237 g, 2.67 mmol) and KOtBu (0.130 g, 1.156 mmol) were then added and heated at 110° C. for 16 h. The reaction mixture was heated at 130° C. for 2 days. Additional ethyl carbamate (0.237 g, 2.67 mmol) and KOtBu (0.065 g, 0.578 mmol) were added and mixture stirred for additional 3 h. The reaction mixture was heated at 110° C. for an additional 3 days, followed by the addition of 2N NaOH (30 mL) and EtOAc (75 mL). The layers were then separated and the organic layer washed with water (3×50 mL). The organic layer was dried over Na2SO4, filtered, and concentrated. The compound was loaded onto florisil and purified using silica gel chromatography CISCO): 1-3.5% MeOH/DCM (18 min), 3.5% (7 min), 25 g silica. Product eluted at 13 min. The product was dried under high vacuum at 40° C. overnight. 1-{[(5S,7S)-7-methyl-2-oxo-1-oxa-3-azaspiro[4.5]dec-7-yl]methyl}-1H-benzimidazole-6-carbonitrile was obtained as a white solid (336 mg, 55.4% yield). MS (m/z) 325 (M+H+).

Intermediate 9

1-{[(5S,7S)-7-Methyl-2-oxo-1-oxa-3-azasbiro[4.5]dec-7-yl]methyl}-1H-benzimidazole-6-carbonitrile

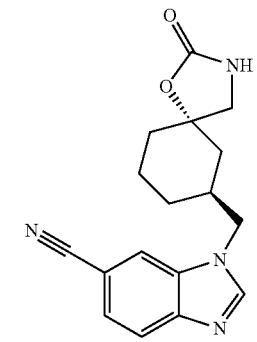 [SMILES: N#Cc1ccc2ncn(C[C@H]3CCC[C@@]4(CNC(=O)O4)C3)c2c1]

A suspension of 1-[(3S,5S)-1-oxaspiro[2.5]oct-5-ylmethyl]-1H-benzimidazole-6-carbonitrile (760 mg, 2.84 mmol) in MeOH (8 mL) was treated with 7M ammonia in MeOH (1.429 mL, 10.00 mmol) in a 20 mL microwave vial. The vial was sealed and heated in a microwave at 100° C. for 3 h. The reaction mixture was cooled to RT and blown down to dryness with nitrogen for 24 h to give crude 1-{[(1S,3S)-3-(aminomethyl)-3-hydroxycyclohexaneyl]methyl}-1H-benzimidazole-6-carbonitrile which was used without further purification. A solution of 1-{[(1S,3S)-3-(aminomethyl)-3-hydroxycyclohexaneyl]methyl}-1H-benzimidazole-6-carbonitrile (808 mg, 2.84 mmol) in THF (24 mL) was sealed under nitrogen in three 20 mL microwave vials and heated with microwave at 160° C. for 3 h. The combined reaction mixture was then concentrated to dryness and 50 mL of water was added. The solid was then filtered and washed with 2×10 mL of water. The solid was air-dried under house vacuum overnight. The compound was purified under normal phase flash column chromatography (ISCO CombiFlash Rf, 120 g silica column, MeOH/DCM 0-10%) to give 1-{[(5S,7S)-2-oxo-1-oxa-3-azaspiro[4.5]dec-7-yl]methyl}-1H-benzimidazole-6-carbonitrile as an off-white solid (856 mg, 97% yield). The aromatic region of the NMR spectra showed that the product contained less than 8% of the cis-diastereomer. MS (m/z) 311.1 (M+H$^+$).

Intermediate 10

1-((3S,5S)-1-Oxaspiro[2.5]octan-5-ylmethyl)-5-fluoro-1H-benzo[d]imidazole-6-carbonitrile

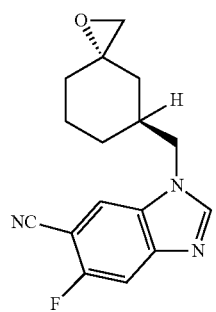 [SMILES: N#Cc1cc2c(cc1F)ncn2C[C@H]1CCC[C@@]2(CO2)C1]

1-Bromo-2,5-difluoro-4-nitrobenzene

To a stirred solution of 2-bromo-1,4-difluoro-benzene (98.6 g, 510.88 mmol) in 1.2 L of concentrated H$_2$SO$_4$ was added KNO$_3$ by portions at 0° C. After this addition, the mixture was allowed to warm to RT and stirred for additional 16 h. The mixture was poured onto ice-cold water and extracted with DCM. The combined organic layers were washed with brine, dried over Na$_2$SO$_4$ and concentrated to give 1-bromo-2,5-difluoro-4-nitro-benzene (95 g, 78.1% yield) as a yellow solid. $^1$H NMR (400 MHz, CDCl$_3$) δ 7.91-7.87 (dd, 1H), 7.52-7.57 (dd, 1H).

2,5-Difluoro-4-nitrobenzonitrile

A mixture of 1-bromo-2,5-difluoro-4-nitro-benzene (95 g, 399 mmol) and CuCN (71.8 g, 798 mmol) in NMP (700 mL) was set to a pre-heated 160° C. oil-base and stirred at 160° C. under N$_2$ over 450 min. The mixture was cooled to RT, charged with Na$_2$SO$_4$ (300 g) and MTBE (1 L), and stirred for an additional 15 min. The resulting mixture was filtered and the filtrate was charged with 800 mL of water, then the separated aqueous layer was extracted with MTBE. The combined organic layers were washed with water and brine, dried over Na$_2$SO$_4$ and concentrated. The material was recrystallized from EtOH/water (2/1) to yield 2,5-Difluoro-4-nitro-benzonitrile (50 g, 68% yield) as a pale brown solid. $^1$H NMR (400 MHz, CDCl$_3$) δ 7.96-7.95 (dd, 1H), 7.67-7.64 (dd, 1H).

1-((3S,5S)-1-oxasbiro[2.5]octan-5-ylmethyl)-5-fluoro-1H-benzo[d]imidazole-6-carbonitrile 1-((3S,5S)-1-oxaspiro[2.5]octan-5-ylmethyl)-5-fluoro-1H-benzo[d]imidazole-6-carbonitrile may be prepared using procedures analogous to those described for Intermediate 4. MS (m/z) 286 (M+H$^+$).

Intermediate 11

4-Chloro-1-[(3S,5S)-1-oxaspiro[2.5]oct-5-ylmethyl]-1H-benzimidazole-6-carbonitrile

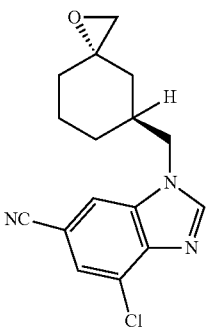 [SMILES: N#Cc1cc(Cl)c2ncn(C[C@H]3CCC[C@@]4(CO4)C3)c2c1]

4-Amino-3-chloro-5-fluorobenzonitrile

A solution of 4-amino-3-fluorobenzonitrile (25.13 g, 185 mmol) and NCS (24.65 g, 185 mmol) in acetonitrile (500 mL) was stirred at 86° C. (reflux) for 5 h. LCMS showed ~17% of starting material remained. Additional NCS (0.2 eq) was added and the reaction was stirred for 1 h. The reaction was partly concentrated and the residue was partitioned between 5% NaOH (100 mL) and EtOAc. The aqueous layer was back extracted with EtOAc. The organic extracts were dried over Na$_2$SO$_4$ and concentrated to a pink solid. The NMR spectrum showed some of the succinimate side product still remained. The crude product was washed with H$_2$O and air dried to give the desired product as a beige solid. This product was used in the next step without any further purification. MS (m/z) 171.1 (M+H$^+$).

3-Chloro-5-fluoro-4-nitrobenzonitrile

Sodium perborate tetrahydrate (131 g, 851 mmol) in acetic acid (200 mL) was heated to 60° C. A solution of 4-amino-3-chloro-5-fluorobenzonitrile (29.02 g, 170 mmol) in acetic acid (500 mL) was added dropwise and the reaction was stirred at 60° C. for 16 h. The LCMS the indicated the reaction showed ~50% conversion. Additional sodium perborate tetrahydrate (14.4 g) was added and the reaction stirred at 70° C. for 2 h. Then additional sodium perborate tetrahydrate (70 g) was added and the reaction was stirred at 80° C. for 5 h, followed by RT for 2 days. The reaction was then poured into ice water and extracted with EtOAc (3×). The combined organic extracts were washed with H$_2$O (2×), brine, dried over MgSO$_4$ and concentrated. When most of the acetic acid was evaporated, water was added to the residue. The orange precipitate was collected by filtration, washed with H$_2$O and air dried to give the crude product as an orange solid. NMR showed the product contaminated with ~10% of starting material. This product was used without any further purification.

4-Chloro-1-[(3S,5S)-1-oxaspiro[2.5]oct-5-ylmethyl]-1H-benzimidazole-6-carbonitrile 4-Chloro-1-[(3S,5S)-1-oxaspiro[2.5]oct-5-ylmethyl]-1H-benzimidazole-6-carbonitrile may be prepared using procedures analogous to those described for Intermediate 4. MS (m/z) 302.1 (M+H$^+$).

Intermediate 12

1-{[(3S,7R)-7-(Hydroxymethyl)-2-oxo-1-oxa-3-azaspiro[4.5]dec-7-yl]methyl}-1H-benzimidazole-6-carbonitrile

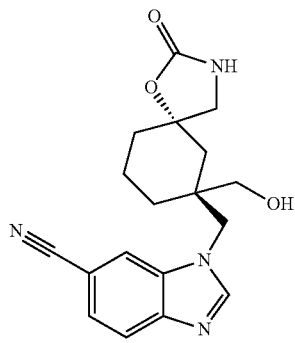 [SMILES: N#Cc1ccc2ncn(C[C@@]3(CO)CCC[C@@]4(CNC(=O)O4)C3)c2c1]

Methyl 3-hydroxycyclohexanecarboxylate

Methyl 3-hydroxycyclohexanecarboxylate (70.0 g, 460 mmol) and rhodium on alumina (7.5 g, 460 mmol) were added to a nitrogen purged 2 L Parr flask. Ethanol (300 mL) was carefully added and the flask was then shaken under hydrogen pressure (55 psi) on the Parr hydrogenator for 18 h. The Parr flask was carefully purged with N$_2$. The reaction mixture was filtered through a plug of Celite©, and the eluent was evaporated to provide the crude title compound which was used without further purification. $^1$H NMR (400 MHz, CDCl$_3$) δ 3.66 (s, 3H), 2.64-2.74 (m, 2H), 1.97-2.05 (m, 2H), 1.64-1.83 (m, 3H), 1.46-1.54 (m, 2H), 1.22-1.30 (m, 1H).

Methyl 3-oxocyclohexanecarboxylate

Ruthenium (IV) oxide hydrate (1.47 g, 11.1 mmol) and sodium bromate (100 g, 664 mmol) were combined in diethyl ether (600 mL) and water (300 mL). The resulting black mixture was stirred for 10 min and then cooled in an ice bath. Methyl 3-hydroxycyclohexanecarboxylate (35 g, 221 mmol) was dissolved in ether (to bring total volume to 100 mL) and was added dropwise to the ice cold reaction mixture. The temperature was not allowed to go above 30° C. The reaction mixture was stirred for 1 h with the reaction temperature at ~15° C. Isopropanol was carefully added to the reaction mixture at a rate necessary to keep the reaction temperature at ~27° C. The layers were separated and the organic layers were washed with ether. The combined organics were washed with saturated aqueous NaHCO$_3$ solution and brine. The organics were then dried over MgSO$_4$, filtered, and concentrated to provide methyl 3-oxocyclohexanecarboxylate (34.5 g, 100% yield) which was used without further purification. $^1$H NMR (400 MHz, CDCl$_3$) δ 3.68 (s, 3H), 2.79 (m, 1H), 2.52 (d, J=7.78 Hz, 2H), 2.23-2.42 (m, 2H), 1.98-2.15 (m, 2H), 1.82 (d, J=10.29 Hz, 1H), 1.61-1.77 (m, 1H).

Methyl 1-oxaspiro[2.5]octane-5-carboxylate

To a solution of trimethylsulfoxonium iodide (53.3 g, 242 mmol) in dry DMSO (300 mL) under N$_2$, was added sodium hydride (9.69 g, 242 mmol) portionwise over 30 min. This light yellow mixture was stirred at RT for 1 h. The reaction mixture was then cooled in an ice bath and treated with methyl 3-oxocyclohexanecarboxylate (29.0 g, 186 mmol) dropwise while maintaining a temperature at or below 27° C. The resulting reaction mixture was allowed to warm slowly to RT and stir overnight. The reaction was diluted with water and extracted with DCM. The combined organics were washed with water, dried over MgSO$_4$, filtered, and concentrated to provide methyl 1-oxaspiro[2.5]octane-5-carboxylate (31.8 g, 85% yield) which was used without further purification. $^1$H NMR (400 MHz, CDCl$_3$) δ 3.66 (s, 3H), 2.71 (m, 1H), 2.65 (d, J=1.76 Hz, 2H), 2.00 (dd J=11.8, 13.6 Hz, 2H), 1.74-1.85 (m, 2H), 1.60-1.74 (m, 1H), 1.40-1.56 (m, 2H), 1.17-1.32 (m, 1H).

Methyl 3-{[4-(methyloxy)phenyl]methyl}-2-oxo-1-oxa-3-azaspiro[4.5]decane-7-carboxylate To methyl 1-oxaspiro[2.5]octane-5-carboxylate (5 g, 29.4 mmol) (about 6:1 trans:cis) dissolved in MeOH (8.39 mL) was added 4-methoxybenzylamine (4.03 g, 29.4 mmol). This reaction mixture was heated at 110° C. behind a blast shield for 18 h. The reaction was then cooled to RT and concentrated. The compound was loaded onto florisil and purified using silica gel chromatography CISCO): 0-10% MeOH/DCM (35 min), 10% (20 min), 120 g silica. The product began eluting at 41 minutes and pure fractions were concentrated to yield an orange oil (5.693 g). The oil was dissolved in 1,4-dioxane (50.4 mL), and CDI (9.53 g, 58.8 mmol) was added. The reaction mixture was heated at 110° C. for 16 h. The reaction was then concentrated to an orange solid and EtOAc (150 mL) and 1N HCl (100 mL) were added. The layers were separated and the organic layer was washed with 1N HCl (50 mL). The organic layer was then dried over Na$_2$SO$_4$, filtered, and concentrated. The compound was loaded onto florisil and purified using silica gel chromatography CISCO): 5-35% ethyl acetate/hexanes (30 min), 80 g silica to obtain methyl 3-{[4-(methyloxy)phenyl]methyl}-2-oxo-1-oxa-3-azaspiro[4.5]decane-7-carboxylate as a light yellow solid (5.05 g, 49% yield). MS (m/z) 334.0 (M+H$^+$).

Methyl 3-{[4-(methyloxy)phenyl]methyl}-2-oxo-7-{[(phenylmethyl)oxy]methyl}-1-oxa-3-azaspiro[4.5]decane-7-carboxylate To a solution of methyl 3-{[4-(methyloxy)phenyl]methyl}-2-oxo-1-oxa-3-azaspiro[4.5]decane-7-carboxylate (5.05 g, 15.15 mmol) in THF (38.7 mL) under nitrogen at −78° C. was added sodium bis(trimethylsilyl)amide, (1M in THF, 45.4 mL, 45.4 mmol) over 30 minutes. The reaction mixture was stirred at −78° C. for 1 h. Benzyl chloromethyl ether (7.12 g, 45.4 mmol) was then added. After 1 h, the reaction was quenched slowly with water (5 mL). Saturated aq NaCl (100 mL) was then added and the mixture was extracted with EtOAc (2×125 mL). The combined organic layers were dried over $Na_2SO_4$, filtered, and concentrated. The compound was then loaded onto florisil and purified using silica gel chromatography CISCO): 10-25% ethyl acetate/hexanes (30 min), 25% (5 min.), 25-45% (15 min), 45% (5 min), 120 g silica. The product eluted at 45 minutes. Methyl 3-{[4-(methyloxy)phenyl]methyl}-2-oxo-7-{[(phenylmethyl)oxy]methyl}-1-oxa-3-azaspiro[4.5]decane-7-carboxylate was obtained as a light yellow oil (4.62 g, 64% yield) and NMR and LCMS were 95% clean for trans product. MS (m/z) 454.0 (M+H$^+$).

7-(Hydroxymethyl)-3-{[4-(methyloxy)phenyl]methyl}-7-{[(phenylmethyl)oxy]methyl}-1-oxa-3-azaspiro[4.5]decan-2-one To a solution of methyl 3-{[4-(methyloxy)phenyl]methyl}-2-oxo-7-{[(phenylmethyl)oxy]methyl}-1-oxa-3-azaspiro[4.5]decane-7-carboxylate (6.523 g, 14.38 mmol) in THF (27.9 mL) under nitrogen at −78° C. was added lithium aluminum hydride (1M in THF, 71.9 mL, 71.9 mmol) over 10 minutes and stirred for 2 days. The reaction was then quenched slowly with water (5 mL), followed by the addition of 2N HCl (200 mL). The reaction mixture was then extracted with EtOAc (2×150 mL). The combined organic layers were dried over $Na_2SO_4$, filtered, and concentrated. To the solution in THF (27.9 mL) was added lithium borohydride (2N in THF, 10.79 mL, 21.57 mmol) and the mixture was stirred for 30 minutes, then heated at 50° C. The additional lithium borohydride (2N in THF, 3.6 mL, 7.19 mmol) was added. The reaction mixture was then cooled to RT and quenched slowly with 2N HCl (100 mL). The mixture was then extracted with EtOAc (2×100 mL) and the combined organic layers were dried over $Na_2SO_4$, filtered, and concentrated. The mixture was then loaded onto florisil and purified using silica gel chromatography CISCO): 10-80% ethyl acetate/hexanes (30 min), 80% (5 min), 80 g silica. The product eluted at 26 minutes to yield 7-(Hydroxymethyl)-3-{[4-(methyloxy)phenyl]methyl}-7-{[(phenylmethyl)oxy]methyl}-1-oxa-3-azaspiro[4.5]decan-2-one as a colorless oil (5.2 g, 81% yield). MS (m/z) 426.1 (M+H$^+$).

(3-{[4-(Methyloxy)phenyl]methyl}-2-oxo-7-{[(phenylmethyl)oxy]methyl}-1-oxa-3-azasbiro[4.5]dec-7-yl)methyl methanesulfonate To a solution of 7-((benzyloxy)methyl)-7-(hydroxymethyl)-3-(4-methoxybenzyl)-1-oxa-3-azaspiro[4.5]decan-2-one (5.26 g, 12.36 mmol) in DCM (56 mL) at RT was added DIEA (4.32 mL, 24.7 mmol) and methanesulfonyl chloride (1.25 mL, 16.1 mmol). After 1 h, 2N HCl (100 mL) was added to the reaction. The layers were separated, and the aqueous layer was washed with DCM (100 mL). The combined organics were dried over sodium sulfate, filtered, and concentrated. The crude product was purified on a 80 g silica gel column (10-70% EtOAc/hexanes, 30 min gradient; 70% EtOAc/hexanes, 5 min; 60 mL/min elution; 254 nm detection) to afford (3-{[4-(Methyloxy)phenyl]methyl}-2-oxo-7-{[(phenylmethyl)oxy]methyl}-1-oxa-3-azaspiro[4.5]dec-7-yl)methyl methanesulfonate (5.71 g, 87% yield). MS (m/z) 504.2 (M+H$^+$).

7-(Azidomethyl)-3-{[4-(methyloxy)phenyl]methyl}-7-{[(phenylmethyl)oxy]methyl}-1-oxa-3-azasbiro[4.5]decan-2-one To a light orange solution of (7-((benzyloxy)methyl)-3-(4-methoxybenzyl)-2-oxo-1-oxa-3-azaspiro[4.5]decan-7-yl) methyl methanesulfonate (5.71 g, 11.3 mmol) in DMSO (45.4 mL) was added sodium azide (2.21 g, 34.0 mmol). The reaction was heated at 120° C. behind a blast shield. After 4 days the reaction was cooled to RT and diluted with 1:1 EtOAc:Et$_2$O (150 mL). This mixture was washed with water (3×100 mL), and the resulting organic layer was dried over magnesium sulphate, filtered, and concentrated to provide 7-(azidomethyl)-3-{[4-(methyloxy)phenyl]methyl}-7-{[(phenylmethyl)oxy]methyl}-1-oxa-3-azaspiro[4.5]decan-2-one (4.78 g, 89% crude yield) which was used without further purification. MS (m/z) 451.0 (M+H$^+$).

7-(Aminomethyl)-3-{[4-(methyloxy)phenyl]methyl}-7-{[(phenylmethyl)oxy]methyl}-1-oxa-3-azasbiro[4.5]decan-2-one To an orange solution of 7-(azidomethyl)-7-((benzyloxy) methyl)-3-(4-methoxybenzyl)-1-oxa-3-azaspiro[4.5]decan-2-one (4.78 g, 10.6 mmol) in MeOH (141 mL) was added nickel (II) chloride hexahydrate (2.52 g, 10.6 mmol). The reaction mixture was cooled to 0° C., and with quick stirring, sodium borohydride (0.802 g, 21.2 mmol) was added in 4 portions. The reaction turned from green to black with significant gas evolution. After 1 h, the reaction mixture was filtered through a pad of Celite©. The filtrate was concentrated and treated with 1N NaOH (100 mL) and EtOAc (300 mL). A green suspension formed which was filtered through celite. The layers were separated, and the aqueous layer was washed with EtOAc (50 mL). The combined organic layers were dried over magnesium sulfate, filtered, and concentrated to the crude title compound (4.27 g, 90% crude yield) as an orange oil which was used without further purification. MS (m/z) 425.1 (M+H$^+$).

3-{[(3-{[4-(Methyloxy)phenyl]methyl}-2-oxo-7-{[(phenylmethyl)oxy]methyl}-1-oxa-3-azaspiro[4.5]dec-7-yl)methyl]amino}-4-nitrobenzonitrile To a light yellow solution of 7-(aminomethyl)-7-((benzyloxy)methyl)-3-(4-methoxybenzyl)-1-oxa-3-azaspiro[4.5] decan-2-one (4.27 g, 10.1 mmol) in acetonitrile (67.1 mL) was added potassium carbonate (2.78 g, 20.1 mmol) and 3-fluoro-4-nitrobenzonitrile (2.51 g, 15.1 mmol) and the reaction was stirred at RT. After stirring 15 h, the reaction was filtered through a frit. The collected inorganics were washed with DCM/EtOAc. The filtrate was concentrated onto florisil and purified on a 80 g silica gel column (20-55% EtOAc/hexanes, 30 min gradient; 55% EtOAc/hexanes, 5 min.; 60 mL/min elution; 254 nm detection) to provide 3-{[(3-{[4-(methyloxy)phenyl]methyl}-2-oxo-7-{[(phenylmethyl)oxy] methyl}-1-oxa-3-azaspiro[4.5]dec-7-ylmethyl]amino)-4-nitrobenzonitrile (5.02 g, 83% yield) as a reddish-orange oil. MS (m/z) 571.0 (M+H$^+$).

1-[(3-{[4-(Methyloxy)phenyl]methyl}-2-oxo-7-{[(phenylmethyl)oxy]methyl}-1-oxa-3-azaspiro[4.5]dec-7-ylmethyl]-1H-benzimidazole-6-carbonitrile To an orange suspension of 3-((7-((benzyloxy)methyl)-3-(4-methoxybenzyl)-2-oxo-1-oxa-3-azaspiro[4.5]decan-7-yl) methyl)amino)-4-nitrobenzonitrile (5.02 g, 8.80 mmol) in MeOH (74.9 mL) was added iron (4.91 g, 88.0 mmol), trimethyl orthoformate (9.72 mL, 88.0 mmol), and formic acid (3.37 mL, 88 mmol). The reaction was stirred at 65° C. for 17 h and found to have 90% conversion to product by LCMS. Additional iron (0.98 g, 17.6 mmol) and trimethyl orthoformate (1.94 mL, 17.6 mmol) were added to the reaction. After 2 h, the reaction was cooled to RT and diluted with EtOAc (50 mL) and DCM (50 mL). The mixture was filtered through Celite© and concentrated. The crude material was suspended in 2N NaOH (75 mL) and extracted into EtOAc (2×100 mL). The combined organics were dried over sodium sulfate, filtered, and concentrated onto florisil for purification on a 80 g silica gel column (25-100 EtOAc/hexanes, 25 min gradient; 100% EtOAc, 10 min; 60 mL/min elution; 254 nm detection) yielding 1-[(3-{[4-(methyloxy)phenyl]methyl}-2-oxo-7-{[(phenyl)methyl)oxy]methyl}-1-oxa-3-azaspiro[4.5]dec-7-yl)methyl]-1H-benzimidazole-6-carbonitrile (3.51 g, 70.3% yield) as a yellow foam. MS (m/z) 551.1 (M+H⁺).

1-[(2-Oxo-7-{[(phenylmethyl)oxy]methyl}-1-oxa-3-azaspiro[4.5]dec-7-yl)methyl]-1H-benzimidazole-6-carbonitrile To a colorless solution of 1-[(3-{[4-(methyloxy)phenyl]methyl}-2-oxo-7-{[(phenylmethyl)oxy]methyl}-1-oxa-3-azaspiro[4.5]dec-7-yl)methyl]-1H-benzimidazole-6-carbonitrile (1.55 g, 2.81 mmol) in acetonitrile (28.1 mL) was added ceric ammonium nitrate (3.09 g, 5.63 mmol) and the mixture was stirred at room temperature. The reaction was then heated to 60° C. and stirred for 22 h. The reaction was then cooled to RT and the orange suspension was filtered using Buchner vacuum filtration. The solid was rinsed with MeCN (3×20 mL) and the filtrate concentrated to yield a glassy orange oil. Ethyl acetate (75 mL) and 2 N NaOH (50 mL) were then added. The mixture was filtered using Buchner vacuum filtration. The filtrate layers were separated and the aqueous layer was washed with EtOAc (50 mL). The combined organic layers were dried over Na₂SO₄, filtered, and concentrated. The concentrated organic layer was loaded onto florisil and purified using silica gel chromatography CISCO): 1-4% methanol/dichloromethane (25 min), 40 g silica. The product eluted at 11 minutes to yield 1-[(2-oxo-7-{[(phenylmethyl)oxy]methyl}-1-oxa-3-azaspiro[4.5]dec-7-yl)methyl]-1H-benzimidazole-6-carbonitrile as a orange foam (653 mg, 51% yield). MS (m/z) 431.0 (M+H⁺).

1-{[(3S,7R)-7-(Hydroxymethyl)-2-oxo-1-oxa-3-azaspiro[4.5]dec-7-yl]methyl}-1H-benzimidazole-6-carbonitrile To a light orange suspension of 1-((7-((benzyloxy)methyl)-2-oxo-1-oxa-3-azaspiro[4.5]decan-7-yl)methyl)-1H-benzo[d]imidazole-6-carbonitrile (0.120 g, 0.279 mmol) in 1,4-dioxane (2.157 mL) was added concentrated hydrobromic acid (0.631 mL, 5.57 mmol). The reaction mixture was heated at 70° C. for 17 h. The reaction was then cooled to RT. Next, 6N NaOH was added till the pH was adjusted to 13 and then the mixture extracted with EtOAc (2×10 mL). The combined organic layers were dried over Na₂SO₄, filtered, and concentrated. The compound was loaded onto florisil and purified using silica gel chromatography: 1-5% methanol/dichloromethane (25 min), 4 g silica. The product eluted early from 2-10 minutes. Next, the compound was loaded onto florisil and purified using silica gel chromatography: 1-10% methanol/dichloromethane (30 min), 12 g silica. The product did not elute cleanly but did yield 1-{[(5S,7R)-7-(hydroxymethyl)-2-oxo-1-oxa-3-azaspiro[4.5]dec-7-yl]methyl}-1H-benzimidazole-6-carbonitrile (70% pure, 62 mg, 46% yield). MS (m/z) 341.0 (M+H⁺).

Example 1

1-({(5S,7S)-3-[3-(1,1-Dimethylethyl)-5-isoxazolyl]-7-methyl-2-oxo-1-oxa-3-azaspiro[4.5]dec-7-yl}methyl)-1H-benzimidazole-6-carbonitrile

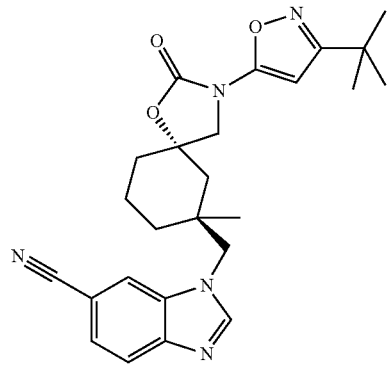 [SMILES: CC(C)(C)c1cc(N2C[C@@]3(CCC[C@](C)(Cn4cnc5ccc(C#N)cc54)C3)OC2=O)on1]

Bis(1,1-dimethylethyl)[3-(1,1-dimethylethyl)-5-isoxazolyl]imidodicarbonate

5-Amino-3-tert-butylisoxazole (50 g, 357 mmol) and Boc₂O (174 mL, 749 mmol) were dissolved in dichloromethane (DCM) (300 mL) in a 500 mL round bottom flask. TEA (54.7 mL, 392 mmol) and DMAP (0.436 g, 3.57 mmol) were added and the mixture stirred overnight. After 18 h stirring, additional Boc₂O (5 g, 35.7 mmol) was added and the reaction stirred overnight. Additional Boc₂O (2 g, 14.3 mmol) was added and the reaction was stirred for 5 h. The reaction mixture was poured into water (300 mL) and the layers separated. The organic layer was washed three times with water, dried over MgSO₄, filtered and concentrated under reduced pressure. The residue was dissolved and evaporated three times with toluene and the residue dried under high vacuum to obtain bis(1,1-dimethylethyl) [3-(1,1-dimethylethyl)-5-isoxazolyl]imidodicarbonate as a solid (116.6 g, 96% yield). MS (m/z) 341.2 (M+H⁺).

1-({(5S,7S)-3-[3-(1,1-Dimethylethyl)-5-isoxazolyl]-7-methyl-2-oxo-1-oxa-3-azaspiro[4.5]dec-7-yl}methyl)-1H-benzimidazole-6-carbonitrile To a 250 mL flask was added potassium tert-butoxide (7.18 g, 64.0 mmol), bis(1,1-dimethylethyl) [3-(1,1-dimethylethyl)-5-isoxazolyl]imidodicarbonate (21.78 g, 64.0 mmol) and 1-{[(3S,5S)-5-methyl-1-oxaspiro[2.5]oct-5-yl]methyl}-1H-benzimidazole-6-carbonitrile (15 g, 53.3 mmol) followed by NMP (142 mL). The reaction was stirred at 115° C. for 19 h and then cooled to RT, diluted with DCM and saturated aq NaHCO₃. The organic layer was separated, and the aqueous layer was extracted 2 more times with DCM. The combined DCM extracts were combined, washed with water, then brine, and dried over Na₂SO₄, filtered and concentrated to afford the crude residue which contained NMP. To the residue was added about 150 mL of ACN, then water was slowly added until the solution became cloudy. To the cloudy solution was added a small crystalline seed, and the volume of the solution was slowly increased by adding 1 L of water. The solution was stirred at RT for about 2 h and then filtered. The solids were added to a 1 L flask followed by 400 mL of IPA. The solution was heated to reflux, then cooled to RT, and water was added until a volume of ~900 mL. The solution was stirred for ~30 min, then the solids were filtered off. The filtrate was added to a separatory funnel and extracted with DCM to remove any remaining organics. The resulting tan solids were added to a 500 mL flask and slurried in 200 mL of IPA overnight. The next day, the slurry was filtered and concentrated. The filtrate was concentrated to give 2.5 g of residue that was purified by silica gel chromatography (ISCO) (Column 1): 120 g column, 0-10% MeOH/DCM over 30 min. The solid (12 g) was purified via ISCO (Column 2): 330 g column, 0-10% MeOH/DCM over 60 min. The mother liquor residue from the 2nd crystallization was purified via ISCO (Column 3) using a 330 g column using the same conditions as above. All fractions containing desired product were concentrated to give brown solid that contained impurities. Impure fractions from column 1 and 2 were combined and repurified on a 120 g column (Column 4). Impure fractions were purified on another 120 g column (Column 5). All fractions containing product from column 5 and 3 were combined and purified by SFC. All isolated pure fractions from columns 1, 2 and 4 were combined and concentrated. To the residue was added ~250 mL of IPA, and the mixture was heated to 80° C. and then slowly cooled to RT. The product formed white crystals. The solution stirred at RT for 1 h, then cooled to 5° C. with an ice/water bath. The mixture was stirred at 5° C. for 1 h, then the solid was filtered off, washed with IPA and dried under reduced pressure to give the desired product as an off white solid (11 g). The filtrate was concentrated to give a brown residue. All fractions containing desired product from columns 5 and 3 were combined along with the filtrate and purified by SFC. Concentration of the MeOH from the SFC gave the product as an off white residue. This residue was dissolved in IPA and added to the 11 g of solids collected above. The material was slurried in IPA for ~2 h, then filtered, and the solids were washed with IPA. The solids were then dried under reduced pressure to give 1-({(5S,7S)-3-[3-(1,1-dimethylethyl)-5-isoxazolyl]-7-methyl-2-oxo-1-oxa-3-azaspiro[4.5]dec-7-yl}methyl)-1H-benzimidazole-6-carbonitrile as a white solid (14.58 g, 60.5% yield). $^1$H NMR (400 MHz, CDCl$_3$) δ 8.25 (br. s., 1H), 7.92 (d, J=8.28 Hz, 1H), 7.76 (s, 1H), 7.59 (dd, J=1.25, 8.28 Hz, 1H), 6.17 (s, 1H), 4.04 (s, 2H), 3.83 (q, 2H), 2.09 (br. s., 1H), 1.93 (d, J=14.05 Hz, 1H), 1.70-1.80 (m, 1H), 1.64 (d, J=12.80 Hz, 1H), 1.57 (d, J=14.05 Hz, 1H), 1.36-1.49 (m, 3H), 1.32 (s, 9H), 1.28 (s, 3H). MS (m/z) 448.2 (M+H$^+$).

Example 2

1-(((5S,7S)-3-(3-(2-Cyanopropan-2-yl)isoxazol-5-yl)-7-methyl-2-oxo-1-oxa-3-azaspiro[4.5]decan-7-ylmethyl)-1H-benzo[d]imidazole-6-carbonitrile 1,1-Dimethylethyl [3-(1-cyano-1-methylethyl)-5-isoxazolyl]carbamate 2-(5-Amino-3-isoxazolyl)-2-methylpropanenitrile (1.5 g, 9.92 mmol) and Boc$_2$O (2.304 mL, 9.92 mmol) were dissolved in DCM (25 mL). Triethylamine (1.383 mL, 9.92 mmol) and DMAP (0.012 g, 0.099 mmol) were added and the mixture stirred at RT for 16 h. The mixture was then concentrated, chased with DCM and concentrated. The product (2.4 g) was used without further purification. MS (m/z) 252.2 (M+H$^+$).

1-(((5S,7S)-3-(3-(2-Cyanopropan-2-yl)isoxazol-5-yl)-7-methyl-2-oxo-1-oxa-3-azaspiro[4.5]decan-7-ylmethyl)-1H-benzo[d]imidazole-6-carbonitrile 1-{[(3S,5S)-5-methyl-1-oxaspiro[2.5]oct-5-yl]methyl}-1H-benzimidazole-6-carbonitrile (100 mg, 0.355 mmol) and potassium tert-butoxide (51.8 mg, 0.462 mmol) were added to a 20 mL microwave vial with nitrogen purging. 1,1-Dimethylethyl [3-(1-cyano-1-methylethyl)-5-isoxazolyl]carbamate (357 mg, 1.422 mmol) dissolved in NMP (3 mL) was then added. The vial was capped and heated to 125° C. for 16 h. The reaction mixture was purified by RP Gilson HPLC; 10-90% MeCN/H$_2$O, 0.1% TFA to yield 10.9 mg of product. The reaction was repeated using similar procedures as above using 150 mg of 1-{[(3S,5S)-5-methyl-1-oxaspiro[2.5]oct-5-yl]methyl}-1H-benzimidazole-6-carbonitrile and 3 equivalents of 1,1-dimethylethyl [3-(1-cyano-1-methylethyl)-5-isoxazolyl]carbamate. The reaction was heated for 3 h. The mixture was filtered and purified by RP Gilson HPLC; 10-90% MeCN/H$_2$O, 0.1% TFA 30×150 mm Waters Sunfire, 40 mL/min, 14 min. Fractions were concentrated and the TFA salt of 1-(((5S,7S)-3-(3-(2-cyanopropan-2-yl)isoxazol-5-yl)-7-methyl-2-oxo-1-oxa-3-azaspiro[4.5]decan-7-yl)methyl)-1H-benzo[d]imidazole-6-carbonitrile was isolated (55 mg, 25.7% yield). $^1$H NMR (400 MHz, CDCl$_3$) δ 10.60 (br. s., 1H), 9.14 (s, 1H), 8.07 (d, J=8.53 Hz, 1H), 8.01 (s, 1H), 7.78 (dd, J=1.25, 8.53 Hz, 1H), 6.29 (s, 1H), 4.25 (d, 2H), 3.92 (s, 2H), 2.08-2.17 (m, 1H), 1.98-2.05 (m, 1H), 1.87-1.98 (m, 1H), 1.75-1.85 (m, 2H), 1.73 (s, 6H), 1.60-1.68 (m, 1H), 1.53-1.61 (m, 1H), 1.42-1.53 (m, 1H), 1.28 (s, 3H). MS (m/z) 459.3 (M+H$^+$).

Example 3

1-({(5S,7S)-3-[5-(1,1-Dimethylethyl)-3-isoxazolyl]-7-methyl-2-oxo-1-oxa-3-azaspiro[4.5]dec-7-yl}methyl)-1H-benzimidazole-6-carbonitrile

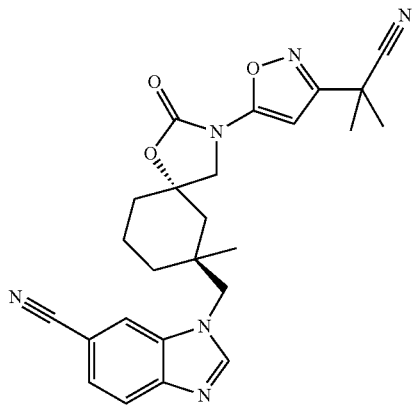 [SMILES: CC(C)(C#N)c1cc(N2C[C@@]3(CCC[C@](C)(Cn4cnc5ccc(C#N)cc54)C3)OC2=O)on1]

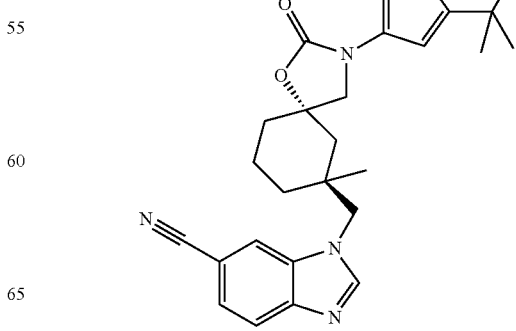

1,1-Dimethylethyl [5-(1,1-dimethylethyl)-3-isoxazolyl]carbamate 5-(1,1-Dimethylethyl)-3-isoxazolamine (500 mg, 3.57 mmol), Boc$_2$O (0.828 mL, 3.57 mmol), DMAP (4.36 mg, 0.036 mmol) and TEA (0.497 mL, 3.57 mmol) were dissolved in DCM (8 mL) in a 50 mL round bottom flask. The mixture was stirred over night. The mixture was evaporated, and crude 1,1-dimethylethyl [5-(1,1-dimethylethyl)-3-isoxazolyl]carbamate used without purification. MS (m/z) 241.2 (M+H$^+$).

1-({(5S,7S)-3-[5-(1,1-Dimethylethyl)-3-isoxazolyl]-7-methyl-2-oxo-1-oxa-3-azaspiro[4.5]dec-7-yl}methyl)-1H-benzimidazole-6-carbonitrile 1-{[(3S,5S)-5-methyl-1-oxaspiro[2.5]oct-5-yl]methyl}-1H-benzimidazole-6-carbonitrile (150 mg, 0.533 mmol), 1,1-dimethylethyl [5-(1,1-dimethylethyl)-3-isoxazolyl]carbamate (320 mg, 1.333 mmol) and potassium tert-butoxide (78 mg, 0.693 mmol) were added to a 10 mL microwave vial while nitrogen purging. Then, NMP (3 mL) was added and the vial was capped and heated to 125° C. for 16 h. The reaction was filtered and purified to give 42 mg (13.3%) of 1-({(5S,7S)-3-[5-(1,1-dimethylethyl)-3-isoxazolyl]-7-methyl-2-oxo-1-oxa-3-azaspiro[4.5]dec-7-yl}methyl)-1H-benzimidazole-6-carbonitrile. $^1$H NMR (400 MHz, MeOH-d$_4$) δ 8.43 (br. s., 1H), 8.19 (s, 1H), 7.82 (d, J=8.28 Hz, 1H), 7.58 (d, J=8.28 Hz, 1H), 6.56 (s, 1H), 4.19 (s, 2H), 3.66-3.79 (m, 2H), 2.04 (d, J=5.77 Hz, 1H), 1.95 (d, J=14.05 Hz, 1H), 1.78-1.90 (m, 1H), 1.65-1.78 (m, 2H), 1.40-1.63 (m, 3H), 1.32 (s, 9H), 1.18 (s, 3H). MS (m/z) 448.3 (M+H$^+$).

Example 4

1-{[(5S,7S)-7-Methyl-2-oxo-3-(2-pyridinylmethyl)-1-oxa-3-azaspiro[4.5]dec-7-yl]methyl}-1H-benzimidazole-6-carbonitrile

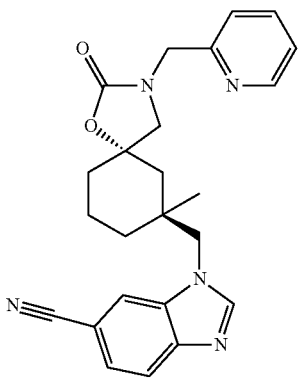 [SMILES: C[C@]1(Cn2cnc3ccc(C#N)cc32)CCC[C@@]2(CN(Cc3ccccn3)C(=O)O2)C1]

A 5 mL microsome vial was charged with 1-{[(3S,5S)-5-methyl-1-oxaspiro[2.5]oct-5-yl]methyl}-1H-benzimidazole-6-carbonitrile (100 mg, 0.355 mmol), (2-pyridinylmethyl)amine (38.4 mg, 0.355 mmol) and MeOH (4 mL). The tube was sealed and heated to 120° C. for 18 h. The reaction was then cooled, concentrated and azetroped with DCM (3×). The crude aminoalcohol was dissolved in 1,4-dioxane (4.00 mL) and CDI (288 mg, 1.777 mmol) was added, and the reaction were heated to 120° C. in sealed tubes for 24 h. Dioxane was then removed and the product was isolated by waters HPLC (10-30% MeCN/H$_2$O for B and 10-50% MeCN/H$_2$O for A, 16 min, 0.1% TFA, Sunfire column) to afford TFA salt of 1-{[(5S,7S)-7-methyl-2-oxo-3-(2-pyridinylmethyl)-1-oxa-3-azaspiro[4.5]dec-7-yl]methyl}-1H-benzimidazole-6-carbonitrile (37 mg, 15.37% yield) as a yellow solid. $^1$H NMR (400 MHz, CDCl$_3$) δ 8.83 (d, J=5.52 Hz, 1H), 8.80 (s, 1H), 8.22-8.29 (td, J=7.8, 1.6 Hz, 1H), 8.04 (d, J=8.53 Hz, 1H), 7.89 (s, 1H), 7.82 (d, J=7.78 Hz, 1H), 7.73-7.80 (m, 1H), 7.71 (dd, J=1.25, 8.53 Hz, 1H), 4.84 (d, J=15.8 Hz, 1H), 4.72 (d, J=15.8 Hz, 1H), 4.10 (s, 2H), 3.42 (s, 2H), 2.04 (d, J=15.31 Hz, 1H), 1.81-1.99 (m, 2H), 1.66-1.77 (m, 1H), 1.59 (d, J=12.80 Hz, 1H), 1.46 (d, J=14.05 Hz, 1H), 1.28-1.43 (m, 2H), 1.19 (s, 3H). MS (m/z) 416.0 (M+H$^+$).

Example 5

1-({(5S,7S)-3-[2-Methyl-2-(5-phenyl-1,3,4-oxadiazol-2-yl)propyl]-2-oxo-1-oxa-3-azaspiro[4.5]dec-7-yl}methyl)-1H-benzimidazole-6-carbonitrile

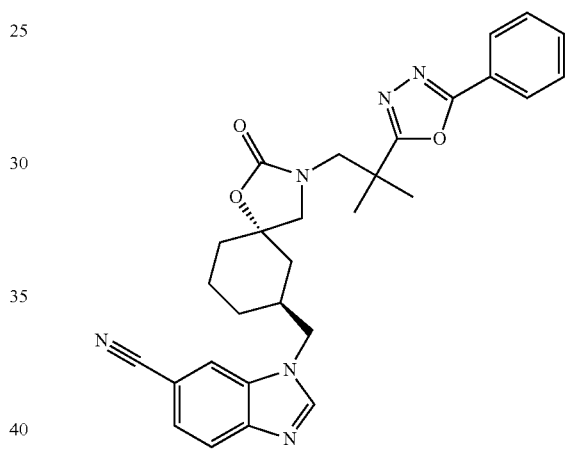

To a solution of 3-{(5S,7S)-7-[(6-cyano-1H-benzimidazol-1-yl)methyl]-2-oxo-1-oxa-3-azaspiro[4.5]dec-3-yl}-2,2-dimethylpropanoic acid (150 mg, 0.334 mmol) in DCM (4 mL) was added benzoyl hydrazine (45.4 mg, 0.334 mmol) and 2-chloro-1,3-dimethylimidazolium chloride (113 mg, 0.667 mmol). After stirring for 15 min at RT, TEA (0.233 mL, 1.668 mmol) was added over a period of 2 min, and the reaction mixture was stirred for 18 h at RT. Next, NaHCO$_3$ was added and the reaction was extracted with DCM. The organic layer was dried over Na$_2$SO$_4$ and concentrated. The residue was purified via HPLC (Waters, Sunfire C-18 column, OBD, 20-60% MeCN in water (0.1% TFA), 16 min, with at-column dilution, flow rate=45 mL/min). Fractions containing desired product were concentrated to give TFA salt of 1-({(5S,7S)-3-[2-methyl-2-(5-phenyl-1,3,4-oxadiazol-2-yl)propyl]-2-oxo-1-oxa-3-azaspiro[4.5]dec-7-yl}methyl)-1H-benzimidazole-6-carbonitrile as a white solid (21 mg, 10% yield). $^1$H NMR (400 MHz, CDCl$_3$) δ 9.03 (s, 1H), 8.00-8.12 (m, 3H), 7.94 (s, 1H), 7.78 (dd, J=1.25, 8.53 Hz, 1H), 7.49-7.64 (m, 3H), 4.22 (ddd, 2H), 3.60-3.70 (m, 1H), 3.47-3.57 (m, 1H), 3.09-3.21 (m, 2H), 2.41 (m, 1H), 1.93-2.01 (m, 2H), 1.60-1.76 (m, 3H), 1.53 (d, J=6.78 Hz, 6H), 1.13-1.40 (m, 2H), 1.03 (m, 1H). MS (m/z) 511.3 (M+H$^+$).

Example 6

1-({(5S,7S)-3-[2-(3-Ethyl-1,2,4-oxadiazol-5-yl)-2-methylpropyl]-2-oxo-1-oxa-3-azaspiro[4.5]dec-7-yl}methyl)-1H-benzimidazole-6-carbonitrile

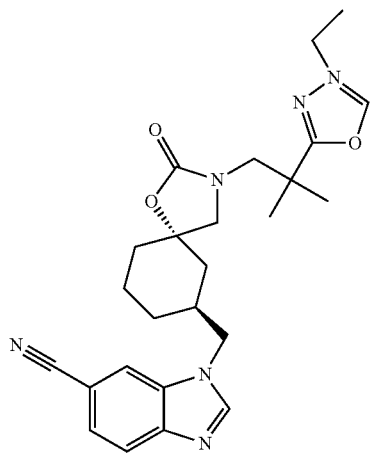

3-{(5S,7S)-7-[(6-cyano-1H-benzimidazol-1-yl)methyl]-2-oxo-1-oxa-3-azaspiro[4.5]dec-3-yl}-2,2-dimethylpropanoic acid (200 mg, 0.381 mmol), HATU (217 mg, 0.572 mmol) and DIEA (0.200 mL, 1.144 mmol) in DCM (4 mL) were stirred for 30 min at RT. N'-hydroxypropanimidamide (50.4 mg, 0.572 mmol) was added and the reaction mixture were stirred at RT for 18 h. The reaction mixture was then extracted with DCM. The organic layers was dried over Na$_2$SO$_4$ and filtered, and the filtrate was concentrated. The residues were dissolved in 1,4-dioxane (4 mL) and heated at 108° C. for 16 h. Reaction mixture was concentrated and purified via HPLC (Waters, Sunfire C-18 column, OBD, 20-60% MeCN in water (0.1% TFA), 16 min, with at-column dilution, flow rate 45 mL/min). Fractions containing desired products were concentrated to give TFA salt of 1-({(5S,7S)-3-[2-(3-ethyl-1,2,4-oxadiazol-5-yl)-2-methylpropyl]-2-oxo-1-oxa-3-azaspiro[4.5]dec-7-yl}methyl)-1H-benzimidazole-6-carbonitrile as a white solid (108 mg, 48.1% yield). MS (m/z) 463.3 (M+H$^+$).

Example 7

1-[((5S,7S)-3-{[3-Methyl-1-(2-pyrimidinyl)-3-pyrrolidinyl]methyl}-2-oxo-1-oxa-3-azaspiro[4.5]dec-7-yl)methyl]-1H-benzimidazole-6-carbonitrile

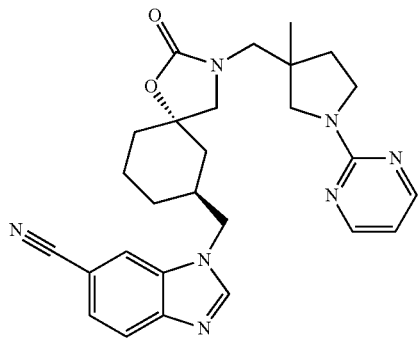 [SMILES: CC1(CN2C[C@@]3(CCC[C@H](Cn4cnc5ccc(C#N)cc54)C3)OC2=O)CCN(c2ncccn2)C1]

A suspension of 1-({(5S,7S)-3-[(3-methyl-3-pyrrolidinyl)methyl]-2-oxo-1-oxa-3-azaspiro[4.5]dec-7-yl}methyl)-1H-benzimidazole-6-carbonitrile (0.1 g, 0.208 mmol), 2-chloropyrimidine (0.026 g, 0.229 mmol), and cesium carbonate (0.203 g, 0.624 mmol) in NMP (1 mL) was subjected to microwave reactor for 1 h at 120° C. DIEA (0.5 mL) was then added, and the reaction mixture was microwaved for 30 min at 120° C. Next, the reaction mixture was extracted with DCM and concentrated. The residue was purified via HPLC to give TFA salt of 1-[((5S,7S)-3-{[3-methyl-1-(2-pyrimidinyl)-3-pyrrolidinyl]methyl}-2-oxo-1-oxa-3-azaspiro[4.5]dec-7-yl)methyl]-1H-benzimidazole-6-carbonitrile as a brown solid (55.6 mg, 44.5%). MS (m/z) 486.3 (M+H$^+$).

Example 8

1-({(5S,7S)-7-Methyl-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile

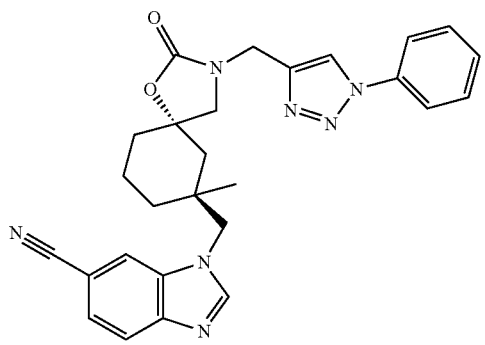 [SMILES: C[C@]1(Cn2cnc3ccc(C#N)cc32)CCC[C@@]2(CN(Cc3cn(-c4ccccc4)nn3)C(=O)O2)C1]

To a yellow solution of 1-{[(5S,7S)-7-methyl-2-oxo-3-(2-propyn-1-yl)-1-oxa-3-azaspiro[4.5]dec-7-yl]methyl}-1H-benzimidazole-6-carbonitrile (0.105 g, 0.232 mmol) in DMSO (2.086 mL) in a vial was added iodobenzene (0.047 g, 0.232 mmol), sodium azide (0.015 g, 0.232 mmol), D,L-proline (5.34 mg, 0.046 mmol), sodium carbonate (4.91 mg, 0.046 mmol), sodium L-ascorbate (4.59 mg, 0.023 mmol), copper(II) sulfate pentahydrate (5.79 mg, 0.023 mmol), and water (0.232 mL). The vial was capped and heated thermally at 65° C. After 2 h, the reaction mixture was dark brown solution. Next, the reaction mixture was cooled to RT and 1 mL of DMSO was added and then the mixture was filtered using Buchner funnel filtration. The filtrate was purified using Gilson prep HPLC: 30-40% CH$_3$CN/H$_2$O, 0.1% TFA, 30×150 mm Sunfire C18, 25 mL/min, 15 min to yield the TFA salt of 1-({(5S,7S)-7-methyl-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile was obtained as an orange foam (15.8 mg, 10.9% yield). $^1$H NMR (400 MHz, DMSO-d$_6$) δ 8.78 (s, 1H), 8.57 (br. s., 1H), 8.41 (br. s., 1H), 7.88-7.96 (m, 2H), 7.84 (d, J=7.78 Hz, 1H), 7.57-7.66 (m, 3H), 7.44-7.55 (m, 1H), 4.49 (m, 2H), 4.13 (s, 2H), 3.29 (dd, J=8.0, 16.0 Hz, 2H), 1.85 (m, 1H), 1.73 (m, 1H), 1.50-1.67 (m, 3H), 1.25-1.47 (m, 3H), 1.02 (s, 3H). MS (m/z) 482 (M+H$^+$).

Example 9

1-{[(5S,7S)-2-Oxo-3-({1-[5-(trifluoromethyl)-3-pyridinyl]-1H-1,2,3-triazol-4-yl}methyl)-1-oxa-3-azaspiro[4.5]dec-7-yl]methyl}-1H-benzimidazole-6-carbonitrile

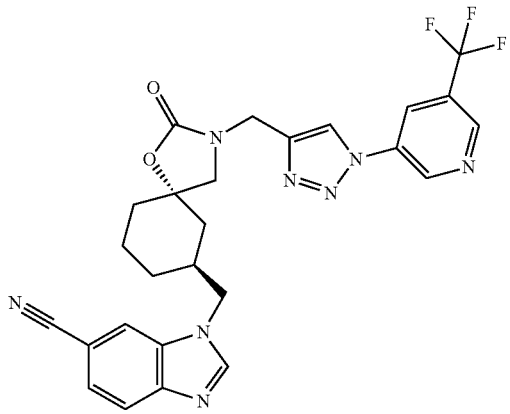 [SMILES: N#Cc1ccc2ncn(C[C@H]3CCC[C@]4(C3)CN(Cc3cn(-c5cncc(C(F)(F)F)c5)nn3)C(=O)O4)c2c1]

1-{[(5S,7S)-2-Oxo-3-(2-propyn-1-yl)-1-oxa-3-azaspiro[4.5]dec-7-yl]methyl}-1H-benzimidazole-6-carbonitrile To a solution of 5-(trifluoromethyl)-3-pyridinamine (0.150 g, 0.925 mmol) in EtOAc (3 mL) at 0° C. was added concentrated HCl (0.5 mL). The reaction mixture was stirred for 10 min, then a solution of sodium nitrite (0.192 g, 2.78 mmol, 3 eq; dissolved in 1 mL of water) was added over 2 min. The reaction mixture was then stirred for 30 min. A solution of sodium azide (0.180 g, 2.78 mmol) (3 eq; dissolved in 1 mL of water) was then added over 5 min. After 1 h, a solution of 10% $Na_2CO_3$ was added to the mixture to make the solution a pH 9-10. The mixture was then extracted with EtOAc (2×10 mL). Organic layers were dried over $MgSO_4$, filtered, and concentrated in vacuo. The product was placed in high vacuum for 30 min. 1-{[(5S,7S)-2-oxo-3-(2-propyn-1-yl)-1-oxa-3-azaspiro[4.5]dec-7-yl]methyl)-1H-benzimidazole-6-carbonitrile was obtained as a low viscosity dark orange oil (100 mg, 57% yield).

1-{[(5S,7S)-2-Oxo-3-({1-[5-(trifluoromethyl)-3-pyridinyl]-1H-1,2,3-triazol-4-yl}methyl)-1-oxa-3-azaspiro[4.5]dec-7-yl]methyl}-1H-benzimidazole-6-carbonitrile To a light orange solution of 1-{[(5S,7S)-2-oxo-3-(2-propyn-1-yl)-1-oxa-3-azaspiro[4.5]dec-7-yl]methyl}-1H-benzimidazole-6-carbonitrile (0.100 g, 0.287 mmol) (93:7 trans:cis) in tert-butanol (1.435 mL) and water (1.435 mL) in a vial was added 3-azido-5-(trifluoromethyl)pyridine (0.054 g, 0.287 mmol), sodium L-ascorbate (0.011 g, 0.057 mmol), copper(II) sulfate pentahydrate (0.014 g, 0.057 mmol), and water (1.435 mL). After 18 h, 1 mL of MeOH was added and the mixture was vacuum filtered using a small Buchner funnel. The filtrate was filtered through Acrodisc CR 25 mm syringe filter with 0.2 um PTFE membrane and purified by Gilson prep HPLC: 25-45% $CH_3CN/H_2O$, 0.1% TFA, 30×150 mm Sunfire C18, 25 mL/min, 15 min to yield the TFA salt of 1-{[(5S,7S)-2-oxo-3-({1-[5-(trifluoromethyl)-3-pyridinyl]-1H-1,2,3-triazol-4-yl}methyl)-1-oxa-3-azaspiro[4.5]dec-7-yl]methyl}-1H-benzimidazole-6-carbonitrile as an orange foam (18.1 mg, 9.2% yield). MS (m/z) 537 (M+H$^+$).

Example 10

1-({(5S,7S)-3-[4-Chloro-3-(1,1-dimethylethyl)-5-isoxazolyl]-7-methyl-2-oxo-1-oxa-3-azaspiro[4.5]dec-7-yl}methyl)-1H-benzimidazole-6-carbonitrile

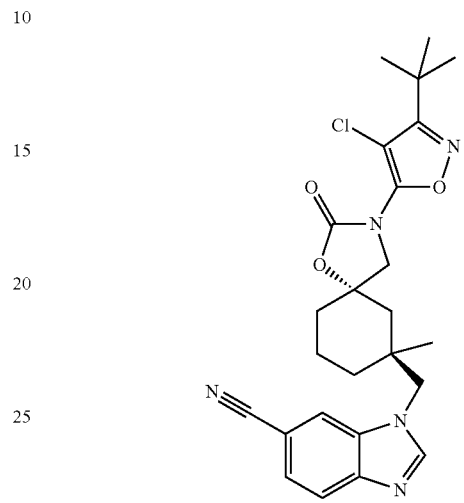

To a vial was added 1-({(5S,7S)-3-[3-(1,1-dimethylethyl)-5-isoxazolyl]-7-methyl-2-oxo-1-oxa-3-azaspiro[4.5]dec-7-yl}methyl)-1H-benzimidazole-6-carbonitrile (85 mg, 0.190 mmol) and chloroform (950 μL) at RT, followed by NCS (25.4 mg, 0.190 mmol). The reaction mixture was stirred at RT followed by 65° C. for 5 h. Ater 22 h reaction at 65° C. the crude mixture was purified by reverse phase HPLC (30-80% MeCN/H$_2$O, 0.1% TFA modifier, 30×150 mm Sunfire 18 column), and TFA salt of 1-({(5S,7S)-3-[4-chloro-3-(1,1-dimethylethyl)-5-isoxazolyl]-7-methyl-2-oxo-1-oxa-3-azaspiro[4.5]dec-7-yl}methyl)-1H-benzimidazole-6-carbonitrile was obtained (62.4 mg, 54% yield). MS (m/z) 482.2 (M+H$^+$).

Example 11

1-({(5S,7S)-7-Methyl-2-oxo-3-[5-(trifluoromethyl)-2-pyridinyl]-1-oxa-3-azaspiro[4.5]dec-7-yl}methyl)-1H-benzimidazole-6-carbonitrile

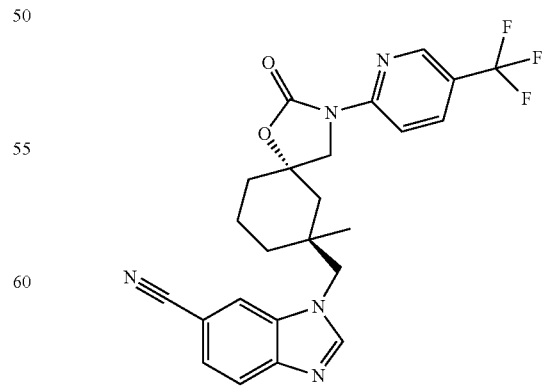

A 5 mL microwave vial was charged with 1-{[(3S,5S)-5-methyl-1-oxaspiro[2.5]oct-5-yl]methyl}-1H-benzimidazole-6-carbonitrile (150 mg, 0.533 mmol), ethyl [5-(trifluoromethyl)-2-pyridinyl]carbamate (137 mg, 0.586 mmol), KOtBu (90 mg, 0.800 mmol), and NMP (4 mL). The reaction mixture was heated to 100° C. for 3 h. The reaction mixture was partitioned between water and DCM, and the layers were separated. The aqueous layer was extracted with DCM (2×), and the combined organic extracts were washed with brine, eluted through a phase separator and concentrated to afford an oil. The oil was purified by MDAP HPLC (TFA 0.1%, 16 min, 30-70% MeCN/H$_2$O, Sunfire column) to afford TFA salt of 1-({(5S,7S)-7-methyl-2-oxo-3-[5-(trifluoromethyl)-2-pyridinyl]-1-oxa-3-azaspiro[4.5]dec-7-yl}methyl)-1H-benzimidazole-6-carbonitrile as a white solid (75 mg, 22.9% yield). $^1$H NMR (400 MHz, CDCl$_3$) δ 9.17 (br. s., 1H), 8.57 (s, 1H), 8.35 (d, J=9.03 Hz, 1H), 8.09 (d, J=8.53 Hz, 1H), 7.89-7.95 (m, 2H), 7.78 (dd, J=1.13, 8.41 Hz, 1H), 4.22 (s, 2H), 3.92-4.05 (m, 2H), 2.15 (m, 1H), 1.97 (d, J=13.55 Hz, 2H), 1.79 (m, 1H), 1.64-1.69 (m, 2H), 1.38-1.56 (m, 2H), 1.31 (s, 3H). MS (m/z) 470 (M+H$^+$).

Example 12

'1-({(5S,7S)-3-[6-(Ethyloxy)-3-pyridinyl]-7-methyl-2-oxo-1-oxa-3-azaspiro[4.5]dec-7-yl}methyl)-1H-benzimidazole-6-carbonitrile

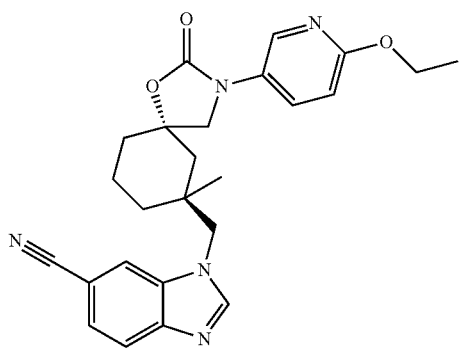 [SMILES: CCOc1ccc(N2C[C@@]3(CCC[C@](C)(Cn4cnc5ccc(C#N)cc54)C3)OC2=O)cn1]

1-{[(1S,3S)-3-({[6-(Ethyloxy)-3-pyridinyl]amino}methyl)-3-hydroxy-1-methylcyclohexaneyl]methyl}-1H-benzimidazole-6-carbonitrile A 5 mL microwave vial was charged with 1-{[(3S,5S)-5-methyl-1-oxaspiro[2.5]oct-5-yl]methyl}-1H-benzimidazole-6-carbonitrile (150 mg, 0.533 mmol),6-(ethyloxy)-3-pyridinamine (221 mg, 1.599 mmol) and MeOH (4 mL). The reaction mixture was stirred and heated to 120° C. for 24 h. The reaction mixture was concentrated down to afford an oil. The oil was purified by silica gel (40 g) loading and initially elluting in DCM through to 6% MeOH/DCM over 18 column volumes to afford 1-{[(1S,3S)-3-({[6-(ethyloxy)-3-pyridinyl]amino}methyl)-3-hydroxy-1-methylcyclohexaneyl]methyl}-1H-benzimidazole-6-carbonitrile as an colorless oil. MS (m/z) 420 (M+H$^+$).

1-({(5S,7S)-3-[6-(Ethyloxy)-3-pyridinyl]-7-methyl-2-oxo-1-oxa-3-azaspiro[4.5]dec-7-yl}methyl)-1H-benzimidazole-6-carbonitrile A 5 mL microwave vial was charged with 1-{[(1S,3S)-3-({[6-(ethyloxy)-3-pyridinyl]amino}methyl)-3-hydroxy-1-methylcyclohexaneyl]methyl}-1H-benzimidazole-6-carbonitrile (78 mg, 0.186 mmol), DCA (151 mg, 0.930 mmol) and 1,4-dioxane (4 mL) to give a yellow solution. Reaction mixture was stirred and heated at 120° C. for 24 h and then the reaction mixture was concentrated to afford an oil. The oil was purified by MDAP HPLC (TFA 0.1%, 16 min, 10-50% MeCN/H$_2$O, Sunfire column) to afford TFA salt of 1-({(5S,7S)-3-[6-(ethyloxy)-3-pyridinyl]-7-methyl-2-oxo-1-oxa-3-azaspiro[4.5]dec-7-yl}methyl)-1H-benzimidazole-6-carbonitrile as a cream solid (31 mg, 28.3% yield). $^1$H NMR (400 MHz, CDCl$_3$) δ 9.48 (br. s., 1H), 8.64 (dd, J=1.76, 9.29 Hz, 1H), 8.17 (d, J=2.01 Hz, 1H), 8.13 (d, J=8.53 Hz, 1H), 7.98 (s, 1H), 7.79 (d, J=8.78 Hz, 1H), 6.98 (d, J=9.29 Hz, 1H), 4.43 (q, J=6.86 Hz, 2H), 4.29 (dd, J=12.0, 20.0 Hz, 2H), 3.93 (d, J=8.0 Hz, 1H), 3.76 (d, J=8.0 Hz, 1H), 2.13 (d, J=5.27 Hz, 1H), 1.94-2.04 (m, 2H), 1.75-1.87 (m, 2H), 1.67 (m, 1H), 1.56 (dd, J=4.0, 16.0 Hz, 1H), 1.48 (t, J=7.03 Hz, 3H), 1.41 (dd, J=4.0, 12.0 Hz, 1H), 1.29 (s, 3H). MS (m/z) 446 (M+H$^+$).

Example 13

1-(((5S,7S)-3-(6-Methoxypyridin-3-yl)-7-methyl-2-oxo-1-oxa-3-azaspiro[4.5]decan-7-ylmethyl)-1H-benzo[d]imidazole-6-carbonitrile

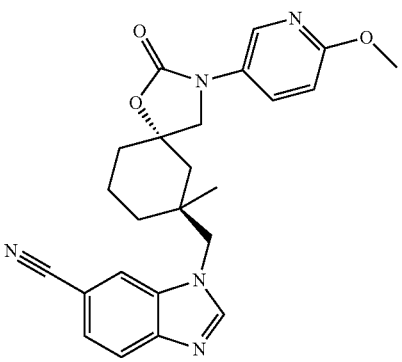 [SMILES: COc1ccc(N2C[C@@]3(CCC[C@](C)(Cn4cnc5ccc(C#N)cc54)C3)OC2=O)cn1]

Route 1

Tert-butyl (6-methoxypyridin-3-yl)carbamate

To a 500 mL flask was added THF (206 mL), 6-methoxypyridin-3-amine (25 g, 191 mmol) and Boc$_2$O (48.9 mL, 210 mmol). The dark solution was heated to reflux for 18 h, then cooled to RT and concentrated. The residue was purified via silica gel chromatography on the ISCO-RF: liquid load, 330 g column, 0-10% EtOAc/Hexane over 30 min. Concentration of fractions containing product afforded tert-butyl (6-methoxypyridin-3-yl)carbamate as a slightly yellow oil. This was used without further purification.

1-(((5S,7S)-3-(6-Methoxypyridin-3-yl)-7-methyl-2-oxo-1-oxa-3-azasbiro[4.5]decan-7-yl)methyl)-1H-benzo[d]imidazole-6-carbonitrile To a 4 mL vial was added NMP (1997 μL), tert-butyl (6-methoxypyridin-3-yl)carbamate (448 mg, 1.997 mmol) and potassium tert-butoxide (213 mg, 1.898 mmol) at RT. After stirring for ~1 min at RT, 1-{[(3S,5S)-5-methyl-1-oxaspiro[2.5]oct-5-yl]methyl}-1H-benzimidazole-6-carbonitrile (281 mg, 0.999 mmol) was added. The solution was then heated to 55° C. and stirred for 17 h. The resulting solution was cooled to RT, diluted with 2 mL of MeCN, then purified on HPLC: 20-60% MeCN/Water over 14 min, Sunfire C-18 column, 0.1% TFA. Fractions containing product were added to a separatory funnel, diluted with DCM and saturated NaHCO$_3$. DCM layer was separated, passed over a phase separator and concentrated to give 1-(((5S,7S)-3-(6-methoxypyridin-3-yl)-7-methyl-2-oxo-1-oxa-3-azaspiro[4.5]decan-7-yl)methyl)-1H-benzo[d]imidazole-6-carbonitrile (145 mg, 34% yield). $^1$H NMR (400 MHz, CDCl$_3$) δ 8.08 (dd, J=4, 12 Hz, 2H), 8.06 (s, 1H), 7.91 (d, J=4 Hz, 1H), 7.76 (s, 1H), 7.58 (dd, J=4 Hz, 1H), 6.80 (d, J=12 Hz, 1H), 4.02 (s, 2H), 3.94 (s, 3H), 3.66 (q, J=8 Hz, 2H), 2.14-2.18 (m, 1H), 1.94-2.00 (m, 2H), 1.66-1.77 (m, 2H), 1.51 (d, J=16 Hz, 1H), 1.36-1.44 (m, 2H), 1.33 (s, 3H). MS (m/z) 432.2 (M+H$^+$).

Alternatively, 1-(((5S,7S)-3-(6-methoxypyridin-3-yl)-7-methyl-2-oxo-1-oxa-3-azaspiro[4.5]decan-7-yl)methyl)-1H-benzo[d]imidazole-6-carbonitrile can be obtained using similar procedures as described above except using 1.0 eq KOtBu and 1.25 eq Boc amine, and heat the reaction mixture at 80° C. for 6 h.

Route 2

1-(((5S,7S)-3-(6-Methoxypyridin-3-yl)-7-methyl-2-oxo-1-oxa-3-azasbiro[4.5]decan-7-yl)methyl)-1H-benzo[d]imidazole-6-carbonitrile To a solution of tert-butyl (6-methoxypyridin-3-yl)carbamate (5.98 g, 26.7 mmol) in tetrahydrofuran (THF) (20 mL) at −78° C. under N$_2$ was added n-BuLi (2.5M in hexanes) (10.66 mL, 26.7 mmol). The mixture was allowed to warm up to RT and stirred for 20 min, to the mixture was added 1-{[(3S,5S)-5-methyl-1-oxaspiro[2.5]oct-5-yl]methyl}-1H-benzimidazole-6-carbonitrile (6.0 g, 21.33 mmol) followed by N-methyl-2-pyrrolidone (NMP) (20.00 mL). The mixture was heated at 75° C. for 2 days and then cooled to RT. The reaction mixture was diluted with EtOAc/H$_2$O and extracted with 3×EtOAc. The organic layers were washed with 2× brine, dried over Na$_2$SO$_4$, filtered and concentrated. To the residue was added 250 mL of i-PrOH, heated to reflux for 2 hours, and then cooled to RT for 2 days. The solid was filtered and air dried to afford 1-(((5S,7S)-3-(6-methoxypyridin-3-yl)-7-methyl-2-oxo-1-oxa-3-azaspiro[4.5]decan-7-yl)methyl)-1H-benzo[d]imidazole-6-carbonitrile as a white solid (7.43 g, 79% yield).

Example 14

1-(((5S,7S)-3-(5-Ethoxypyrazin-2-yl)-7-methyl-2-oxo-1-oxa-3-azaspiro[4.5]decan-7-yl)methyl)-1H-benzo[d]imidazole-6-carbonitrile

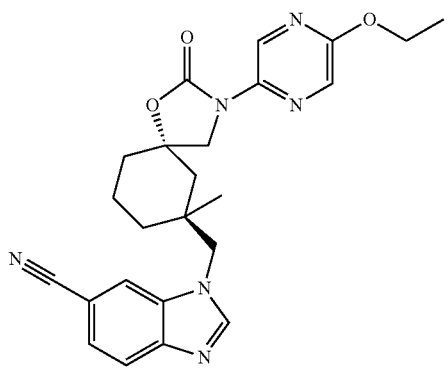 [SMILES: CCOc1cnc(N2C[C@@]3(CCC[C@](C)(Cn4cnc5ccc(C#N)cc54)C3)OC2=O)cn1]

Route 1

1,1-Dimethylethyl (5-chloro-2-pyrazinyl)carbamate

To a 500 mL flask was added THF (83 mL), 5-chloropyrazin-2-amine (10 g, 77 mmol) and Boc$_2$O (19.71 mL, 85 mmol). The dark solution was heated to reflux for 48 h, then cooled to RT, concentrated, and the residue purified via silica gel chromatography on the ISCO RF (liquid load, 330 g column, 0-10% EtOAc/Hexane over 30 min). Concentration of fractions containing product afforded 1,1-dimethylethyl (5-chloro-2-pyrazinyl)carbamate as a slightly yellow oil. This was used without further purification. Approximately 5 g of starting material was recovered. The rest of the material was a mixture of products.

Ethyl (5-ethoxypyrazin-2-yl)carbamate

The mixed products from 1,1-dimethylethyl (5-chloro-2-pyrazinyl)carbamate were combined and refluxed in 24% sodium ethoxide for 5 days, then cooled to RT, neutralized with HCl, and the product extracted out with DCM. The DCM was washed with saturated NaHCO$_3$, then concentrated to afford a black residue. Addition of EtOAc afforded solids that were filtered off, washed with EtOAc to give ethyl (5-ethoxypyrazin-2-yl)carbamate as a brown solid (3.5 g, 42.9%).

1-(((5S,7S)-3-(5-Ethoxypyrazin-2-yl)-7-methyl-2-oxo-1-oxa-3-azaspiro[4.5]decan-7-ylmethyl)-1H-benzo[d]imidazole-6-carbonitrile To a 10 mL flask was added NMP (7.11 mL), ethyl (5-ethoxypyrazin-2-yl)carbamate (0.863 g, 4.09 mmol) and potassium tert-butoxide (0.399 g, 3.55 mmol) at RT. After stirring for ~5 min at RT, 1-{[(3S,5S)-5-methyl-1-oxaspiro[2.5]oct-5-yl]methyl}-1H-benzimidazole-6-carbonitrile (1 g, 3.55 mmol) was added. The solution was then heated to 70° C. (oil bath) and stirred for 7 h. At 7 h, the temperature was taken to 80° C., then at 8 h, it was taken to 90° C. The mixture was allowed to stir at 90° C. for 16 h. The resulting solution was cooled to RT and added dropwise to a 50 mL solution of IPA/Water (1:1) that contained a small crystalline seed. The mixture was allowed to stir at RT overnight. The next day, the slurry was filtered, and the solids slurried in MeCN overnight. The next day, the solids were filtered off, dried under reduced pressure to give 1-(((5S,7S)-3-(5-ethoxypyrazin-2-yl)-7-methyl-2-oxo-1-oxa-3-azaspiro[4.5]decan-7-yl)methyl)-1H-benzo[d]imidazole-6-carbonitrile as a very light yellow solid (968 mg, 61% yield). $^1$H NMR (400 MHz, DMSO-d$_6$) δ 8.80 (d, J=1.25 Hz, 1H), 8.48 (s, 1H), 8.38 (s, 1H), 8.10 (d, J=1.51 Hz, 1H), 7.83 (d, J=8.53 Hz, 1H), 7.59 (dd, J=1.25, 8.28 Hz, 1H), 4.32 (q, J=7.03 Hz, 2H), 4.16 (s, 2H), 3.80-3.88 (m, 2H), 1.98 (d, J=13.80 Hz, 1H), 1.88 (d, J=14.31 Hz, 1H), 1.64-1.73 (m, 3H), 1.49-1.53 (m, 2H), 1.34-1.38 (m, 2H), 1.32-1.38 (t, J=8.0 Hz, 2H), 1.07 (s, 3H). MS (m/z) 447.2 (M+H$^+$).

Route 2

1-(((5S,7S)-3-(5-Ethoxypyrazin-2-yl)-7-methyl-2-oxo-1-oxa-3-azaspiro[4.5]decan-7-ylmethyl)-1H-benzo[d]imidazole-6-carbonitrile A suspension of ethyl (5-ethoxypyrazin-2-yl)carbamate (2.102 g, 9.95 mmol) in THF (7 mL) was cooled to −78° C. and 2.5N n-butyllithium in hexanes (3.84 mL, 9.60 mmol) was added dropwise over 2 minutes. The resulting mixture was stirred for 15 minutes and then allowed to warm to RT. 1-(((3S,5S)-5-methyl-1-oxaspiro[2.5]octan-5-yl)methyl)-1H-benzo[d]imidazole-6-carbonitrile (2 g, 7.11 mmol) was added as the solid followed by NMP (7.00 mL). The resultant was heated to 75° C. at which point it became a solution. The reaction contained a vent and no condenser to allow the removal of THF and hexanes in order to increase the reaction rate. The reaction mixture was stirred for two days. The reaction was cooled and diluted with 20 mL of IPA and was poured into 40 mL of stirred water. Additional water was added until a solid precipitated from solution (an oil also formed). The oily mixture was stirred overnight. Ethyl acetate was added to dissolve the product and the resultant liquors were separated. The aqueous layer was extracted twice with EtOAc and the combined organics washed with water (2×), brine, dried over sodium sulfate and concentrated to afford a brown solid 3.2 g. The solid was crystallized from hot MeCN (40 mL) to afford 1-(((5S,7S)-3-(5-ethoxypyrazin-2-yl)-7-methyl-2-oxo-1-oxa-3-azaspiro[4.5]decan-7-yl)methyl)-1H-benzo[d]imidazole-6-carbonitrile (1.1 g, 2.340 mmol, 32.9% yield) as a light brown solid.

Example 15

1-(((5S,7S)-3-(6-Methoxy-4-methylpyridin-3-yl)-7-methyl-2-oxo-1-oxa-3-azasbiro[4.5]decan-7-yl)methyl)-1H-benzo[d]imidazole-6-carbonitrile

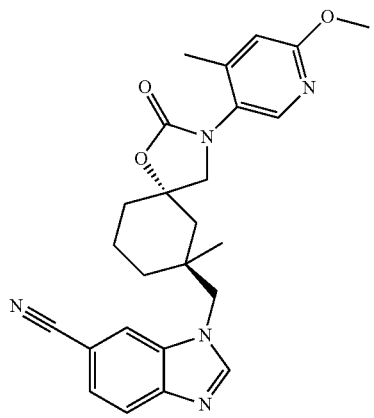 [SMILES: COc1cc(C)c(N2C[C@@]3(CCC[C@](C)(Cn4cnc5ccc(C#N)cc54)C3)OC2=O)cn1]

Route 1

Ethyl [4-methyl-6-(methyloxy)-3-pyridinyl]carbamate

To a 100 mL flask was added 4-methyl-6-(methyloxy)-3-pyridinamine (850 mg, 6.15 mmol), pyridine (10 mL) and then ethyl chloroformate (0.650 mL, 6.77 mmol) portionwise. The reaction mixture was stirred for 1 h at 0° C. The reaction mixture was then concentrated and partitioned between ammonium chloride and DCM, and the aqueous layer was extracted with DCM (2×). The combined organics layers were washed with brine (1×), eluted through a phase separator then concentrated to afford ethyl [4-methyl-6-(methyloxy)-3-pyridinyl]carbamate (1.223 g, 90% yield).

1-(((5S,7S)-3-(6-Methoxy-4-methylpyridin-3-yl)-7-methyl-2-oxo-1-oxa-3-azasbiro[4.5]decan-7-yl)methyl)-1H-benzo[d]imidazole-6-carbonitrile A mixture of ethyl (6-methoxy-4-methylpyridin-3-yl)carbamate (0.593 g, 2.82 mmol) and potassium tert-butoxide (0.275 g, 2.452 mmol) in NMP (4.90 mL) was stirred at RT for 5 min before 1-(((3S,5S)-5-methyl-1-oxaspiro[2.5]octan-5-yl)methyl)-1H-benzo[d]imidazole-6-carbonitrile (0.69 g, 2.452 mmol) was added. The reaction mixture was stirred at 55° C. for 16 h, then at 70° C. for 2.5 h and then at 85° C. for 16 h. Saturated aq NaHCO₃ was added and the mixture was extracted with EtOAc. The organic layer was concentrated and purified via HPLC (Waters, Sunfire C-18 column, OBD, 20-60% MeCN in water (0.1% TFA), 16 min, with at-column dilution, flow rate 45 mL/min). Fractions contained desired products were free based with NaHCO₃, extracted with DCM, dried over Na₂SO₄ and concentrated. The resulted foam was crystallized by stirring with a solution of 1/3 DCM/isopropanol (4 mL total) in an uncapped vial overnight. The resulted cloudy mix was concentrated to ~2 mL volume and then stirred for 1 h. The resulted light pink solids were collected by filtration and dried on high vacuum for 2 h to yield 1-(((5S,7S)-3-(6-methoxy-4-methylpyridin-3-yl)-7-methyl-2-oxo-1-oxa-3-azaspiro[4.5]decan-7-yl)methyl)-1H-benzo[d]imidazole-6-carbonitrile. $^1$H NMR (400 MHz, CDCl₃) δ 8.07 (s, 1H), 8.01 (s, 1H), 7.92 (d, J=8.53 Hz, 1H), 7.78 (s, 1H), 7.59 (dd, J=1.25, 8.28 Hz, 1H), 6.66 (s, 1H), 4.04 (s, 2H), 3.93 (s, 3H), 3.52-3.58 (m, 2H), 2.25 (s, 4H), 2.01 (d, J=13.80 Hz, 2H), 1.63-1.77 (m, 2H), 1.60 (s, 1H), 1.50 (d, J=13.80 Hz, 1H), 1.37-1.42 (m, 4H). MS (m/z) 446.2 (M+H⁺).

Route 2

1-(((5S,7S)-3-(6-Methoxy-4-methylpyridin-3-yl)-7-methyl-2-oxo-1-oxa-3-azaspiro[4.5]decan-7-yl)methyl)-1H-benzo[d]imidazole-6-carbonitrile To a 3 neck, 250 mL round bottom flask under N₂ equipped with thermometer and septa, was added tert-butyl (6-methoxy-4-methylpyridin-3-yl)carbamate (1.059 g, 4.44 mmol) and THF (3.55 mL). This mixture was stirred and brought to −78° C. while n-butyllithium (1.777 mL, 4.44 mmol) was added slowly via small additions keeping the reaction temperature below −70° C. The light brown solution was allowed to stir 10 min at this temperature, then the ice bath was removed and when temperature reached 5° C., 1-(((3S,5S)-5-methyl-1-oxaspiro[2.5]octan-5-yl)methyl)-1H-benzo[d]imidazole-6-carbonitrile (1 g, 3.55 mmol) followed by NMP (3.55 mL) was added. This new light brown mixture was heated using an oil bath to internal temperature of 75° C. for 16 h. To a 50 mL, 3 neck flask equipped with N₂ was added tert-butyl (6-methoxy-4-methylpyridin-3-yl)carbamate (350 mg, 1.5 mmol) in THF (1 mL), at −78° C. and 2.5M n-butyllithium (0.6 mL) while keeping the reaction temperature below −70° C. Upon completion of addition, the mixture was allowed to warm to 5° C. and was added to original reaction via syringe. This was heated to 75° C. using an oil bath and monitored. Ethyl acetate (15 mL) and H₂O (10 mL) were added, and the mixture was sonicated until all residue dissolved. The layers were separated, and the water layer was extracted with EtOAc (2×). The organic layers were combined and washed with water, dried over MgSO₄ and then concentrated to give a light brown film. This was dissolved in 27 mL of IPA, transferred to a 100 mL round bottom flask and brought to reflux for 2 h, then allowed to cool and stir at room temp for 20 h. The solid was then filtered, washed with IPA (2×5 mL) and dried on house vacuum to yield 1.2 g off-white solid. The solid was taken up in IPA (30 mL) and 3 mL DCM (for solubility) and refluxed for 2 h. The mixture was allowed to cool to RT and stir for 3 days. The solid was filtered and washed with IPA to yield 1-(((5S,7S)-3-(6-methoxy-4-methylpyridin-3-yl)-7-methyl-2-oxo-1-oxa-3-azaspiro[4.5]decan-7-yl)methyl)-1H-benzo[d]imidazole-6-carbonitrile (784 mg, 47% yield).

Example 16

1-(((5S,7S)-3-(1-Ethyl-5-methyl-1H-pyrazol-4-yl)-7-methyl-2-oxo-1-oxa-3-azaspiro[4.5]decan-7-yl)methyl)-1H-benzo[d]imidazole-6-carbonitrile

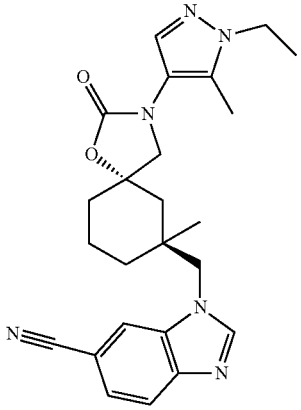 [SMILES: CCn1ncc(N2C[C@@]3(CCC[C@](C)(Cn4cnc5ccc(C#N)cc54)C3)OC2=O)c1C]

A solution of 1-ethyl-5-methyl-1H-pyrazol-4-amine, 2 hydrochloride (0.5 g, 2.52 mmol), Boc$_2$O (0.703 ml, 3.03 mmol), TEA (1.055 mL, 7.57 mmol) and DMAP (10 mg, 0.082 mmol) in DCM (18.74 mL) was stirred at RT for 16 h. The mixture was then extracted with DCM, dried over Na$_2$SO$_4$ and filtered. The filtrate was concentrated and purified via silica gel chromatography (ISCO, 40 g column; 0-5% MeOH/DCM) to give tert-butyl (1-ethyl-5-methyl-1H-pyrazol-4-yl)carbamate as brown oil (300 mg, 52.8% yield). To a solution of tert-butyl (1-ethyl-5-methyl-1H-pyrazol-4-yl)carbamate (0.162 g, 0.719 mmol) in THF (1 mL) at −78° C. under N$_2$ was added n-BuLi (2.5M in hexane) (0.27 ml, 0.675 mmol) dropwise. The mixture was allowed to warm up to RT and stirred for 20 min. 1-{[(3S,5S)-5-methyl-1-oxaspiro[2.5]oct-5-yl]methyl}-1H-benzimidazole-6-carbonitrile (0.15 g, 0.533 mmol) was then added followed by NMP (0.5 mL). The solution was then heated at 70° C. for 16 h. Water was then added to the reaction mixture and extracted with EtOAc. The organic layer was concentrated and purified via HPLC to give 1-(((5S,7S)-3-(1-ethyl-5-methyl-1H-pyrazol-4-yl)-7-methyl-2-oxo-1-oxa-3-azaspiro[4.5]decan-7-yl)methyl)-1H-benzo[d]imidazole-6-carbonitrile as a white solid (89.6 mg, 38.9% yield). $^1$H NMR (400 MHz, DMSO-d$_6$) δ 8.47 (s, 1H), 8.38 (s, 1H), 7.83 (d, J=8.28 Hz, 1H), 7.59 (dd, J=1.51, 8.28 Hz, 1H), 7.41 (s, 1H), 4.16 (br. s., 2H), 4.03 (q, J=7.03 Hz, 2H), 3.54 (s, 2H), 2.14 (s, 3H), 1.95 (d, J=14.0 Hz, 1H), 1.86 (d, J=14.31 Hz, 1H), 1.61 (d, J=13.55 Hz, 3H), 1.31-1.51 (m, 3H), 1.28 (t, 3H), 1.06 (s, 3H). MS (m/z) 433.3 (M+H$^+$).

Example 17

1-(((7S)-3-(5-Methoxypyrazin-2-yl)-7-methyl-2-oxo-1-oxa-3-azaspiro[4.5]decan-7-yl)methyl)-1H-benzo[d]imidazole-6-carbonitrile

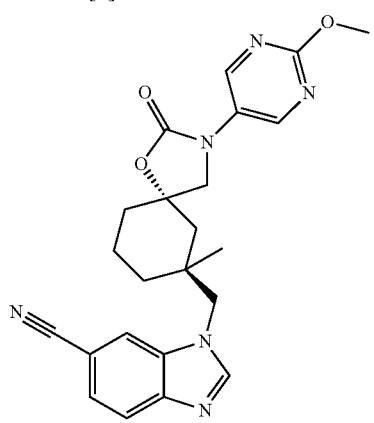

Methyl (5-methoxypyrazin-2-yl)carbamate

A 20 mL microwave vial was charged with ethyl (5-chloropyrazin-2-yl)carbamate (500 mg, 2.480 mmol) and 22% sodium methoxide in MeOH (10 mL). The tube was sealed and heated to 100° C. for 6 h. The reaction mixture was then concentrated, diluted between DCM and 2N HCl. The layers were separated and the aqueous layer was extracted with DCM (2×). The combined organic layers were washed with 2N HCl, brine, eluted through a phase separator and concentrated to afford methyl (5-methoxypyrazin-2-yl)carbamate as a brown oil (100 mg, 22.01% yield). MS (m/z) 184 (M+H$^+$).

1-(((7S)-3-(5-Methoxypyrazin-2-yl)-7-methyl-2-oxo-1-oxa-3-azaspiro[4.5]decan-7-yl)methyl)-1H-benzo[d]imidazole-6-carbonitrile A 5 mL microwave vial was charged with 1-(((3S,5S)-5-methyl-1-oxaspiro[2.5]octan-5-yl)methyl)-1H-benzo[d]imidazole-6-carbonitrile (125 mg, 0.444 mmol), methyl (5-methoxypyrazin-2-yl)carbamate (106 mg, 0.578 mmol), potassium tert-butoxide (54.8 mg, 0.489 mmol) and DMF (3 mL). The tube was sealed and heated to 70° C. for 16 h. The reaction mixture was loaded onto a 10 g SCX column and eluted with 3 volumes of MeOH followed by 3 volumes of 2N ammonia in MeOH. The fractions were combined and concentrated. Crude product was purified by Waters reverse phase HPLC (20% to 60% MeCN, 0.1% TFA, 16 min, 50 mL/min, Sunfire column) to afford TFA salt of 1-(((5S,7S)-3-(5-methoxypyrazin-2-yl)-7-methyl-2-oxo-1-oxa-3-azaspiro[4.5]decan-7-yl)methyl)-1H-benzo[d]imidazole-6-carbonitrile as a yellow solid (30 mg, 11.74% yield). $^1$H NMR (400 MHz, CDCl$_3$) δ 11.81 (br. s., 1H), 8.90-9.00 (m, 2H), 8.07 (d, J=8.53 Hz, 1H), 7.89-7.98 (m, 2H), 7.76 (d, J=8.53 Hz, 1H), 4.17 (s, 2H), 3.97 (s, 3H), 3.91 (d, J=12.0 Hz, 1H), 3.83 (d, J=8.0 Hz, 1H), 2.17 (br. s., 1H), 1.99 (d, J=13.8 Hz, 2H), 1.77 (m, 1H), 1.64 (d, J=12.55 Hz, 1H), 1.56 (d, J=13.80 Hz, 1H), 1.35-1.52 (m, 2H), 1.31 (s, 3H). MS (m/z) 433 (M+H$^+$).

Example 18

1-(((5S,7S)-3-(6-Chloropyridin-3-yl)-7-methyl-2-oxo-1-oxa-3-azaspiro[4.5]decan-7-ylmethyl)-1H-benzo[d]imidazole-6-carbonitrile

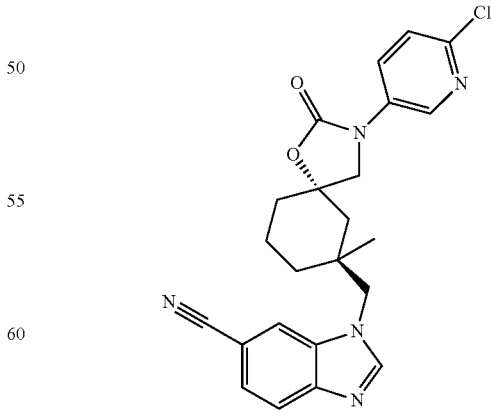

A 5 mL microwave vial was charged with 1-(((3S,5S)-5-methyl-1-oxaspiro[2.5]octan-5-ylmethyl)-1H-benzo[d]imidazole-6-carbonitrile (200 mg, 0.711 mmol), tert-butyl (6-chloropyridin-3-yl)carbamate (195 mg, 0.853 mmol), potassium tert-butoxide (96 mg, 0.853 mmol) and DMF. The tube was sealed and heated to 70° C. for 16 h. The reaction mixture was loaded onto a 10 g SCX SPE and eluted with 3 volumes of MeOH followed by 3 volumes of 2N ammonia in MeOH. The ammonia fractions were combined and concentrated and the crude product then purified by Waters reverse phase HPLC (20% to 60% MeCN, 0.1% TFA, 16 min, 50 mL/min, Sunfire column) to afford the TFA salt of 1-(((5S,7S)-3-(6-chloropyridin-3-yl)-7-methyl-2-oxo-1-oxa-3-azaspiro[4.5]decan-7-yl)methyl)-1H-benzo[d]imidazole-6-carbonitrile as a cream solid (55 mg, 12.67% yield). MS (m/z) 435.9 (M+H$^+$).

Example 19

1-(((5S,7S)-3-(6-(Dimethylamino)pyridin-3-yl)-7-methyl-2-oxo-1-oxa-3-azaspiro[4.5]decan-7-yl)methyl)-1H-benzo[d]imidazole-6-carbonitrile

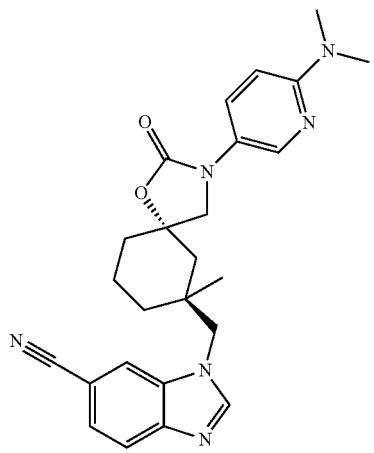 [SMILES: CN(C)c1ccc(N2C[C@@]3(CCC[C@](C)(Cn4cnc5ccc(C#N)cc54)C3)OC2=O)cn1]

A 5 mL microwave vial was charged with a solution of 1-(((5S,7S)-3-(6-chloropyridin-3-yl)-7-methyl-2-oxo-1-oxa-3-azaspiro[4.5]decan-7-yl)methyl)-1H-benzo[d]imidazole-6-carbonitrile (50 mg, 0.115 mmol) in 2N dimethylamine in MeOH (4 mL, 8.00 mmol). The tube was sealed and heated for 24 h at 120° C. The reaction mixture was then concentrated, dissolved in MeOH and purified by Waters reverse phase HPLC (10% to 40% MeCN, 0.1% TFA, 16 min, 50 mL/min, Sunfire column) to afford the TFA salt of 1-(((5S,7S)-3-(6-(dimethylamino)pyridin-3-yl)-7-methyl-2-oxo-1-oxa-3-azaspiro[4.5]decan-7-yl)methyl)-1H-benzo[d]imidazole-6-carbonitrile as a cream solid (5 mg, 7.4% yield). MS (m/z) 445 (M+H$^+$).

Example 20

Tert-butyl (2-(5-((5S,7S)-7-((6-cyano-1H-benzo[d]imidazol-1-yl)methyl)-7-methyl-2-oxo-1-oxa-3-azaspiro[4.5]decan-3-yl)isoxazol-3-yl)-2-methylpropyl) carbonate

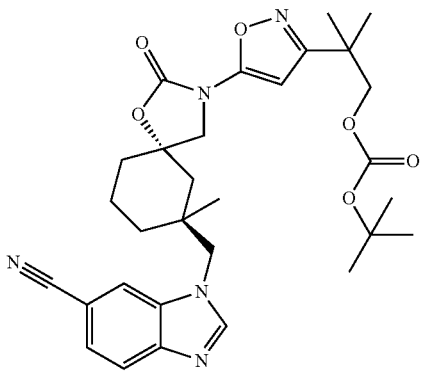 [SMILES: CC(C)(C)OC(=O)OCC(C)(C)c1cc(N2C[C@@]3(CCC[C@](C)(Cn4cnc5ccc(C#N)cc54)C3)OC2=O)on1]

Tert-butyl (2-(5-((5S,7S)-7-((6-cyano-1H-benzo[d]imidazol-1-yl)methyl)-7-methyl-2-oxo-1-oxa-3-azaspiro[4.5]decan-3-yl)isoxazol-3-yl)-2-methylpropyl) carbonate To a 2 mL nitrogen purged microwave vial was added 1-(((3S,5S)-5-methyl-1-oxaspiro[2.5]octan-5-yl)methyl)-1H-benzo[d]imidazole-6-carbonitrile (100 mg, 0.355 mmol), potassium tert-butoxide (51.8 mg, 0.462 mmol), bis(1,1-dimethylethyl) {3-[2-({[(1,1-dimethylethyhoxy]carbonyl}oxy)-1,1-dimethylethyl]-5-isoxazolyl}imidodicarbonate (325 mg, 0.355 mmol) and NMP (1.5 mL). This mixture was heated to 120° C. for 2 h. The mixture was then heated for an additional 5 h. The mixture was then filtered through paper, and the paper washed with MeOH (2 mL), then concentrated. The mixture was purified on reverse phase Gilson HPLC: 30 mm×150 mm Waters Sunfire column, neutral conditions 10-100% MeCN/H$_2$O, 14 min, 40 mL/min to give tert-butyl (2-(5-((5S,7S)-7-((6-cyano-1H-benzo[d]imidazol-1-yl)methyl)-7-methyl-2-oxo-1-oxa-3-azaspiro[4.5]decan-3-yl)isoxazol-3-yl)-2-methylpropyl) carbonate as a clear light brown film (33 mg, 14.8% yield). MS (m/z) 564.3 (M+H$^+$).

Example 21

1-(((5S,7S)-3-(3-(1-Hydroxy-2-methylpropan-2-yl)isoxazol-5-yl)-7-methyl-2-oxo-1-oxa-3-azaspiro[4.5]decan-7-yl)methyl)-1H-benzo[d]imidazole-6-carbonitrile

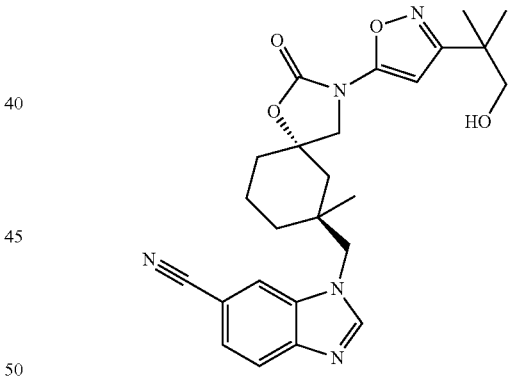

To a 2 mL microwave vial was added tert-butyl (2-(5-((5S,7S)-7-((6-cyano-1H-benzo[d]imidazol-1-yl)methyl)-7-methyl-2-oxo-1-oxa-3-azaspiro[4.5]decan-3-yl)isoxazol-3-yl)-2-methylpropyl) carbonate (30 mg, 0.053 mmol), K$_2$CO$_3$ (5.15 µg, 0.037 µmol), water (0.500 mL) and MeOH (0.5 mL). The vial was capped and heated to 110° C. for 3 h. The mixture was then filtered through paper, and the paper washed with MeOH (2 mL), then concentrated. This mixture was purified on reverse phase Gilson HPLC: 30 mm×150 mm Waters Sunfire column, neutral conditions 10-100% MeCN/H$_2$O, 14 min, 40 mL/min to give 1-(((5S,7S)-3-(3-(1-hydroxy-2-methylpropan-2-yl)isoxazol-5-yl)-7-methyl-2-oxo-1-oxa-3-azaspiro[4.5]decan-7-yl)methyl)-1H-benzo[d]imidazole-6-carbonitrile as a white solid (6.2 mg, 24% yield). MS (m/z) 464.3 (M+H$^+$).

Example 22

1-(((5S,7S)-3-(4,6-Dimethoxyipyridin-3-yl)-7-methyl-2-oxo-1-oxa-3-azasbiro[4.5]decan-7-yl)methyl)-1H-benzo[d]imidazole-6-carbonitrile

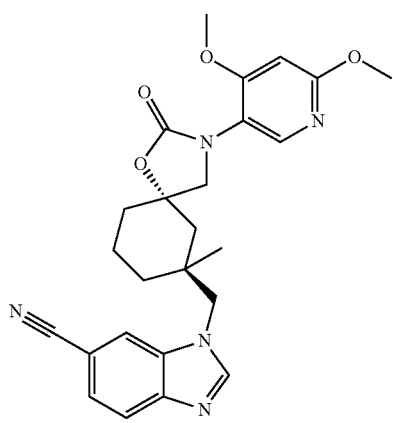 [SMILES: COc1cc(OC)c(N2C[C@@]3(CCC[C@](C)(Cn4cnc5ccc(C#N)cc54)C3)OC2=O)cn1]

1-(((1S,3S)-3-(((4,6-Dimethoxyipyridin-3-yl)amino)methyl)-3-hydroxy-1-methylcyclohexaneyl)methyl)-1H-benzo[d]imidazole-6-carbonitrile A mixture of 1-(((3S,5S)-5-methyl-1-oxaspiro[2.5]octan-5-yl)methyl)-1H-benzo[d]imidazole-6-carbonitrile (100 mg, 0.355 mmol) and 4,6-bis(methyloxy)-3-pyridinamine (110 mg, 0.711 mmol) in isopropanol (10 mL) was heated to reflux overnight. The reaction mixture was cooled to RT, and solvent was removed. The residue was redissolved in DCM and hexane was added. The solvent was removed, and the residue was purified via silica gel chromatography (ISCO, 40 g Silica, 40 mL/min, 0%-10% MeOH/CH$_2$Cl$_2$). Fractions with product were collected and concentrated to afford 1-(((1S,3S)-3-(((4,6-dimethoxypyridin-3-yl)amino)methyl)-3-hydroxy-1-methylcyclohexaneyl)methyl)-1H-benzo[d]imidazole-6-carbonitrile (100 mg, 64.6% yield). MS (m/z) 436 (M+H$^+$).

1-(((5S,7S)-3-(4,6-Dimethoxypyridin-3-yl)-7-methyl-2-oxo-1-oxa-3-azasbiro[4.5]decan-7-yl)methyl)-1H-benzo[d]imidazole-6-carbonitrile A mixture of 1-(((1S,3S)-3-(((4,6-dimethoxypyridin-3-yl)amino)methyl)-3-hydroxy-1-methylcyclohexaneyl)methyl)-1H-benzo[d]imidazole-6-carbonitrile (100 mg, 0.230 mmol) and CDI (372 mg, 2.296 mmol) in 1,4-dioxane (10 mL) was heated to reflux for 16 h. The reaction mixture was evaporated and diluted with DCM and saturated aq NaHCO$_3$ and extracted with DCM (3×). The organic layers were washed brine (2×), dried over Na$_2$SO$_4$, filtered and concentrated. The residue was purified via reverse phase HPLC to afford the TFA salt of 1-(((5S,7S)-3-(4,6-dimethoxypyridin-3-yl)-7-methyl-2-oxo-1-oxa-3-azasbiro[4.5]decan-7-yl)methyl)-1H-benzo[d]imidazole-6-carbonitrile (19.7 mg, 14.9% yield). $^1$H NMR (400 MHz, DMSO-d$_6$) δ 8.63 (s, 1H), 8.45 (s, 1H), 7.98 (s, 1H), 7.87 (d, J=8.53 Hz, 1H), 7.64 (d, J=8.53 Hz, 1H), 6.51 (s, 1H), 4.19 (s, 2H), 3.84 (s, 3H), 3.82 (s, 3H), 3.50 (s, 2H), 1.99 (d, J=12.0 Hz, 1H), 1.86 (d, J=14.31 Hz, 1H), 1.58-1.73 (m, 3H), 1.42-1.52 (m, 2H), 1.28-1.41 (m, 1H), 1.07 (s, 3H). MS (m/z) 462.3 (M+H$^+$).

Example 23

1-(((5S,7S)-3-(6-Ethoxy-4-methylpyridin-3-yl)-2-oxo-1-oxa-3-azasbiro[4.5]decan-7-yl)methyl)-1H-benzo[d]imidazole-6-carbonitrile

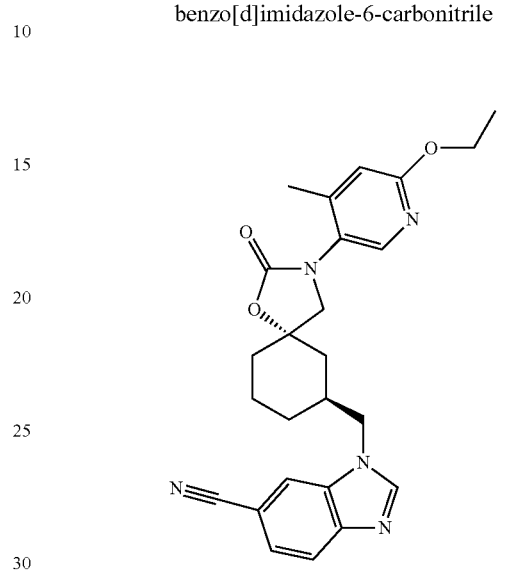

Tert-butyl (6-ethoxy-4-methylpyridin-3-yl)carbamate

A solution of 6-ethoxy-4-methylpyridin-3-amine (2.2 g, 14.46 mmol) and di-tert-butyl dicarbonate (3.47 g, 15.90 mmol) in THF (30 mL) was heated slowly to reflux for 3 h. After cooling to RT, the reaction mixture was concentrated, and the residue purified via silica gel chromatography ISCO (80 g Silica, 60 mL/min, 0%-20% Hexanes/EA). Fractions containing products were collected and concentrated to afford tert-butyl (6-ethoxy-4-methylpyridin-3-yl)carbamate (3 g, 82% yield).

1-(((5S,7S)-3-(6-Ethoxy-4-methylpyridin-3-yl)-2-oxo-1-oxa-3-azaspiro[4.5]decan-7-ylmethyl)-1H-benzo[d]imidazole-6-carbonitrile A solution of potassium tert-butoxide (63.0 mg, 0.561 mmol), 1-((3S,5S)-1-oxaspiro[2.5]octan-5-ylmethyl)-1H-benzo[d]imidazole-6-carbonitrile (100 mg, 0.374 mmol), tert-butyl (6-ethoxy-4-methylpyridin-3-yl)carbamate (236 mg, 0.935 mmol) in NMP (1 mL) was stirred and heated at 80° C. for 8 h. The reaction mixture was cooled to RT, and diluted with acetonitrile. The crude product was purified via reverse phase HPLC to afford the TFA salt of 1-(((5S,7S)-3-(6-ethoxy-4-methylpyridin-3-yl)-2-oxo-1-oxa-3-azaspiro[4.5]decan-7-yl)methyl)-1H-benzo[d]imidazole-6-carbonitrile (45.4 mg, 19.5% yield). $^1$H NMR (400 MHz, DMSO-d$_6$) δ 8.70 (d, J=7.03 Hz, 1H), 8.46 (s, 1H), 8.07 (s, 1H), 7.87 (d, J=8.28 Hz, 1H), 7.65 (d, J=8.28 Hz, 1H), 6.73 (s, 1H), 4.18-4.37 (m, 6H), 2.17-2.32 (m, 1H), 2.11 (s, 3H), 2.04 (d, J=8.0 Hz, 1H), 1.97 (d, J=12.0 Hz, 1H), 1.67 (br. s., 1H), 1.34-1.62 (m, 4H), 1.29 (t, J=7.03 Hz, 3H), 1.08 (m, 1H). MS (m/z) 446.3 (M+H$^+$).

Example 24

1-(((5S,7S)-3-(6-Ethoxy-4-methylpyridazin-3-yl)-7-methyl-2-oxo-1-oxa-3-azaspiro[4.5]decan-7-yl)methyl)-1H-benzo[d]imidazole-6-carbonitrile

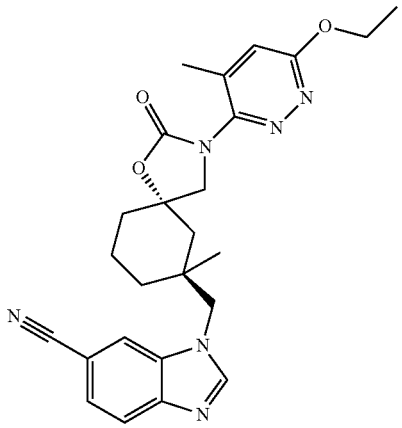 [SMILES: CCOc1cc(C)c(N2C[C@@]3(CCC[C@](C)(Cn4cnc5ccc(C#N)cc54)C3)OC2=O)nn1]

6-Chloro-4-methylpyridazin-3-amine

A 100 mL flask was charged with 4-bromo-6-chloropyridazin-3-amine (1 g, 4.80 mmol), dimethylzinc (9.59 mL, 9.59 mmol), Pd(PPh$_3$)$_4$ (0.277 g, 0.240 mmol) and DMF (10 mL). The reaction mixture was stirred at RT. Then the reaction mixture was quenched with MeOH and concentrated. The crude product was loaded onto a 10 g SCX SPE, and 3 volumes of MeOH followed by 3 volumes of 2N ammonia in MeOH were added. The fractions were combined and concentrated to afford 6-chloro-4-methylpyridazin-3-amine (693 mg, 80% yield).

Ethyl (6-chloro-4-methylpyridazin-3-yl)carbamate

A 100 mL flask was charged with 6-chloro-4-methylpyridazin-3-amine (700 mg, 4.88 mmol) and pyridine (20 mL) then ethyl chloroformate (0.421 mL, 4.39 mmol) was added portionwise. The reaction mixture was stirred for 1 h at 0° C. The reaction mixture was then concentrated and partitioned between ammonium chloride and DCM. The aqueous layer was extracted with DCM (2×). The organic layers were combined and washed with brine (1×), eluted through a phase separator and concentrated to afford ethyl (6-chloro-4-methylpyridazin-3-yl)carbamate (549 mg, 49.6% yield).

Ethyl (6-ethoxy-4-methylpyridazin-3-yl)carbamate

A 20 mL microwavable vial was charged with ethyl (6-chloro-4-methylpyridazin-3-yl)carbamate (550 mg, 2.55 mmol) and sodium ethoxide (3.11 mL, 17.85 mmol), then stirred and heated at 110° C. for 12 h. The reaction mixture was then concentrated and partitioned between ammonium chloride and DCM. The layers were separated and the aqueous layers were washed with DCM (2×). The combined organic layers were washed with water, brine, and eluted through a phase separator. The organic layers were concentrated to afford ethyl (6-ethoxy-4-methylpyridazin-3-yl)carbamate (398 mg, 65.8% yield).

1-(((5S,7S)-3-(6-Ethoxy-4-methylpyridazin-3-yl)-7-methyl-2-oxo-1-oxa-3-azaspiro[4.5]decan-7-yl)methyl)-1H-benzo[d]imidazole-6-carbonitrile A 5 mL microwave vial was charged with 1-(((3S,5S)-5-methyl-1-oxaspiro[2.5]octan-5-ylmethyl)-1H-benzo[d]imidazole-6-carbonitrile (200 mg, 0.711 mmol), ethyl (6-ethoxy-4-methylpyridazin-3-yl)carbamate (208 mg, 0.924 mmol), KOtBu (104 mg, 0.924 mmol) and NMP (4 mL). The reaction mixture was stirred and heated to 80° C. for 20 h. Then the reaction mixture was loaded onto a 10 g SCX SPE, and eluted with 3 volumes of MeOH followed by 3 volumes of 2N ammonia in MeOH. The fractions were combined and concentrated and purified by MDAP HPLC (TFA 0.1%, 16 min, 20-60% MeCN/Water, Sunfire column) to afford TFA salt of 1-(((5S,7S)-3-(6-ethoxy-4-methylpyridazin-3-yl)-7-methyl-2-oxo-1-oxa-3-azaspiro[4.5]decan-7-ylmethyl)-1H-benzo[d]imidazole-6-carbonitrile as an oil (20 mg, 4.65% yield). $^1$H NMR (400 MHz, CDCl$_3$) δ 8.65 (s, 1H), 8.04 (d, J=8.53 Hz, 1H), 7.88 (s, 1H), 7.71 (d, J=8.53 Hz, 1H), 6.88 (s, 1H), 6.56 (br. s., 1H), 4.53 (d, J=7.03 Hz, 2H), 4.13 (s, 2H), 4.05 (d, J=9.54 Hz, 1H), 3.94 (d, J=9.29 Hz, 1H), 2.35 (s, 3H), 2.27 (d, J=16.0 Hz, 1H), 2.05 (d, J=14.05 Hz, 1H), 1.97 (m, 1H), 1.78 (m, 1H), 1.52-1.69 (m, 2H), 1.35-1.51 (m, 1H), 1.44 (t, J=7.03 Hz, 3H), 1.31 (s, 3H). MS (m/z) 461 (M+H$^+$).

Example 25

1-(((5S,7S)-7-Methyl-2-oxo-3-(2-(trifluoromethyl)pyrimidin-5-yl)-1-oxa-3-azaspiro[4.5]decan-7-yl)methyl)-1H-benzo[d]imidazole-6-carbonitrile

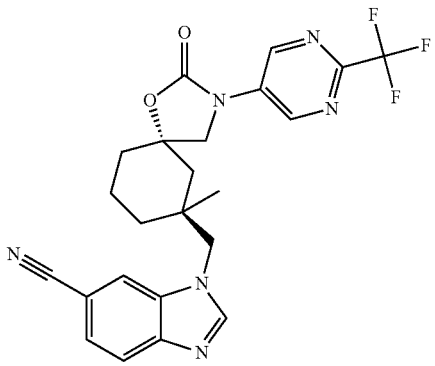 [SMILES: C[C@]1(Cn2cnc3ccc(C#N)cc32)CCC[C@@]2(CN(c3cnc(C(F)(F)F)nc3)C(=O)O2)C1]

A 5 mL microwave vial was charged with 1-(((3S,5S)-5-methyl-1-oxaspiro[2.5]octan-5-ylmethyl)-1H-benzo[d]imidazole-6-carbonitrile (160 mg, 0.570 mmol), tert-butyl (2-(trifluoromethyl)pyrimidin-5-yl)carbamate (300 mg, 1.140 mmol), KOtBu (121 mg, 1.083 mmol), and NMP (4 mL). The reaction mixture was stirred and heated to 80° C. for 20 h then 2 h at 100° C. The reaction mixture was then loaded onto a 10 g SCX SPE and eluted with 3 volumes of MeOH followed by 3 volumes of 2N ammonia in MeOH. The fractions were combined and concentrated and purified by MDAP HPLC (TFA 0.1%, 16 min, 30-70% MeCN/Water, Sunfire column) to afford TFA salt of 1-(((5S,7S)-7-methyl-2-oxo-3-(2-(trifluoromethyl)pyrimidin-5-yl)-1-oxa-3-azaspiro[4.5]decan-7-yl)methyl)-1H-benzo[d]imidazole-6-carbonitrile as a white solid (77 mg, 11% yield). $^1$H NMR (400 MHz, CDCl$_3$) δ 9.12 (s, 2H), 8.46 (s, 1H), 8.01 (d, J=8.28 Hz, 1H), 7.83 (s, 1H), 7.68 (dd, J=1.25, 8.53 Hz, 1H), 4.10 (s, 2H), 3.78 (dd, J=8.78, 14.05 Hz, 2H), 2.18 (d, J=13.05 Hz, 1H), 1.92-2.06 (m, 2H), 1.82 (m, 1H), 1.70 (d, J=12.3 Hz, 1H), 1.58 (d, J=14.05 Hz, 1H), 1.37-1.54 (m, 2H), 1.34 (s, 3H). MS (m/z) 471 (M+H$^+$).

Example 26

1-(((5S,7S)-7-Methyl-2-oxo-3-(3-(trifluoromethyl)pyridin-2-yl)-1-oxa-3-azaspiro[4.5]decan-7-yl)methyl)-1H-benzo[d]imidazole-6-carbonitrile

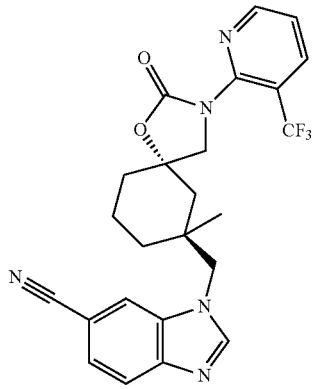 [SMILES: C[C@]1(Cn2cnc3ccc(C#N)cc32)CCC[C@@]2(CN(c3ncccc3C(F)(F)F)C(=O)O2)C1]

To a light yellow suspension of 1-(((5S,7S)-7-methyl-2-oxo-1-oxa-3-azaspiro[4.5]decan-7-yl)methyl)-1H-benzo[d]imidazole-6-carbonitrile (0.050 g, 0.154 mmol) in 1,4-dioxane (2.052 mL) was added copper(I) iodide (2.94 mg, 0.015 mmol), potassium phosphate tribasic (0.065 g, 0.308 mmol), trans-1,2-diaminocyclohexane (3.71 µL, 0.031 mmol), and 2-bromo-3-(trifluoromethyl)pyridine (0.042 g, 0.185 mmol). The reaction mixture was heated at 100° C. for 20 h. Additional 2-bromo-3-(trifluoromethyl)pyridine (0.042 g, 0.185 mmol), copper(I) iodide (2.94 mg, 0.015 mmol), and trans-1,2-diaminocyclohexane (3.71 µL, 0.031 mmol) was added to the reaction mixture. The mixture was stirred for an additional 49 h. Additional 2-bromo-3-(trifluoromethyl)pyridine (0.6 eq, 0.021 g, 0.093 mmol), copper(I) iodide (2.94 mg, 0.015 mmol), and trans-1,2-diaminocyclohexane (3.71 µL, 0.031 mmol) was added. The reaction was stirred for 18 h and then cooled to RT and MeCN (3 mL) was added and the mixture was vacuum filtered using a Hirsch funnel. The filtrate was filtered through Acrodisc CR 25 mm syringe filter with 0.2 um PTFE membrane. The mixture was then purified by Waters prep HPLC: 20-60% CH$_3$CN/H$_2$O, 0.1% TFA, 30×150 mm Sunfire C18, 25 mL/min, 15 min. The product eluted at 12 minutes yielding the TFA salt of 1-(((5S,7S)-7-methyl-2-oxo-3-(3-(trifluoromethyl)pyridin-2-yl)-1-oxa-3-azaspiro[4.5]decan-7-yl)methyl)-1H-benzo[d]imidazole-6-carbonitrile as an orange foam (53 mg, 56% yield). MS (m/z) 470 (M+H$^+$).

Example 27

1-({(5S,7S)-3-[(5-Chloro-1-benzothien-3-yl)methyl]-2-oxo-1-oxa-3-azaspiro[4.5]dec-7-yl}methyl)-1H-benzimidazole-6-carbonitrile

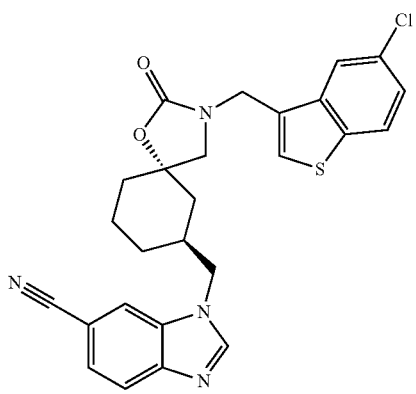 [SMILES: N#Cc1ccc2ncn(C[C@H]3CCC[C@]4(C3)CN(Cc3csc5ccc(Cl)cc35)C(=O)O4)c2c1]

A solution of 1-{[(5S,7S)-2-oxo-1-oxa-3-azaspiro[4.5]dec-7-yl]methyl}-1H-benzimidazole-6-carbonitrile (350 mg, 1.128 mmol) in DMF (20 mL) was treated with sodium hydride (45.1 mg, 1.128 mmol) in one portion under nitrogen at RT. After 20 min of stirring, 3-(bromomethyl)-5-chloro-1-benzothiophene (324 mg, 1.241 mmol) was added in one portion into the pale brown suspension. The resulting mixture was stirred at RT under nitrogen for 5 h. The reaction mixture was quenched with water (1 mL) and the resulting solution was poured into a 50 mL saturated aq NH$_4$Cl solution. The precipitation was filtered, washed with distilled water (2×20 mL) and air-dried under house vacuum. The product was purified through reverse phase HPLC (Waters, Sunfire 30×100 C-18 prep column, CH$_3$CN/Water w/0.1% TFA 30-80% over 14 min) to yield the TFA salt of 1-({(5S,7S)-3-[(5-chloro-1-benzothien-3-yl)methyl]-2-oxo-1-oxa-3-azaspiro[4.5]dec-7-yl}methyl)-1H-benzimidazole-6-carbonitrile as a white solid (253 mg, 36.3% yield). MS (m/z) 491.1 (M+H$^+$).

Example 28

1-{[(5S,7S)-3-(2-{3-[1-(Ethyloxy)ethyl]-1,2,4-oxadiazol-5-yl}-2-methylpropyl)-2-oxo-1-oxa-3-azaspiro[4.5]dec-7-yl]methyl}-1H-benzimidazole-6-carbonitrile

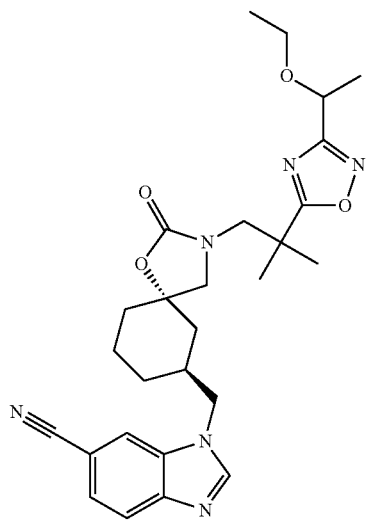 [SMILES: CCOC(C)c1noc(C(C)(C)CN2C[C@@]3(CCC[C@H](Cn4cnc5ccc(C#N)cc54)C3)OC2=O)n1]

1-[((5S,7S)-3-{2-[3-(1-Hydroxyethyl)-1,2,4-oxadiazol-5-yl]-2-methyloropyl}-2-oxo-1-oxa-3-azasbiro[4.5]dec-7-yl)methyl]-1H-benzimidazole-6-carbonitrile A suspension of 3-{(5S,7S)-7-[(6-cyano-1H-benzimidazol-1-yl)methyl]-2-oxo-1-oxa-3-azaspiro[4.5]dec-3-yl}-2,2-dimethylpropanoic acid (1.2 g, 2.67 mmol), DIEA (1.399 mL, 8.01 mmol), HATU (1.522 g, 4.00 mmol), and 2,N-dihydroxy-propionamidedine (0.417 g, 4.00 mmol) in DCM (10 mL) was stirred at RT for 18 h. The reaction mixture was extracted with DCM (2×), dried over Na$_2$SO$_4$ and concentrated. The residue was taken up in 1,4-dioxane (3 mL) and stirred at 105° C. for 16 h. The reaction mixture was concentrated and purified via silica gel column chromatography (ISCO, 80 g silica gel column. Solvent A=DCM; B=MeOH; 0-5% B: 10 min; 5% B: 10 min; 5-15% B: 10 min) to yield 1-[((5S,7S)-3-{2-[3-(1-hydroxyethyl)-1,2,4-oxadiazol-5-yl]-2-methylpropyl}-2-oxo-1-oxa-3-azaspiro[4.5]dec-7-yl)methyl]-1H-benzimidazole-6-carbonitrile as a white crispy foam (0.4 g, 31.3% yield).

1-{[(5S,7S)-3-(2-{3-[1-(Ethyloxy)ethyl]-1,2,4-oxadiazol-5-yl}-2-methylpropyl)-2-oxo-1-oxa-3-azasbiro[4.5]dec-7-yl]methyl}-1H-benzimidazole-6-carbonitrile A solution of 1-[((5S,7S)-3-{2-[3-(1-hydroxyethyl)-1,2,4-oxadiazol-5-yl]-2-methylpropyl}-2-oxo-1-oxa-3-azaspiro[4.5]dec-7-yl)methyl]-1H-benzimidazole-6-carbonitrile (0.07 g, 0.146 mmol) in DMF (0.704 mL) was cooled to 0° C. and sodium hydride (7.61 mg, 0.190 mmol) was added. The reaction mixture was stirred for 30 min. Iodoethane (0.015 ml, 0.190 mmol) was then added, and the reaction mixture was stirred at RT for 16 h. The reaction mixture was heated to 40° C. for 3 h. The mixture was quenched with saturated aq NH₄Cl and extracted with EtOAc. The organic layer was concentrated, and the residue was purified via HPLC to yield the TFA salt of 1-{[(5S,7S)-3-(2-{3-[1-(ethyloxy)ethyl]-1,2,4-oxadiazol-5-yl}-2-methylpropyl)-2-oxo-1-oxa-3-azaspiro[4.5]dec-7-yl]methyl}-1H-benzimidazole-6-carbonitrile as a white solid. MS (m/z) 507.3 (M+H$^+$).

The following compounds were prepared using procedures analogous to those described in Example 1, 2, 3 using appropriately substituted starting materials. As is appreciated by those skilled in the art, these analogous examples may involve variations in general reaction conditions.

| Ex | Name | Structure | M + H (m/z) |
|---|---|---|---|
| 29 | 1-{[(5S,7S)-7-methyl-3-(5-methyl-2-pyridinyl)-2-oxo-1-oxa-3-azaspiro[4.5]dec-7-yl]methyl}-1H-benzimidazole-6-carbonitrile | 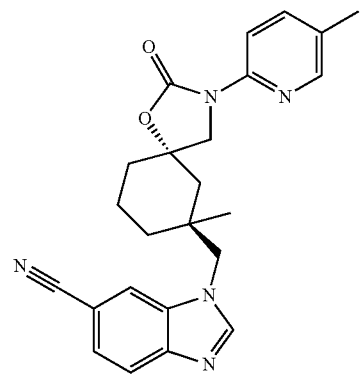 [SMILES: Cc1ccc(N2C[C@@]3(CCC[C@](C)(Cn4cnc5ccc(C#N)cc54)C3)OC2=O)nc1] | 416 |
| 30 | 1-({(5S,7S)-7-methyl-3-[3-(1-methylethyl)-5-isoxazolyl]-2-oxo-1-oxa-3-azaspiro[4.5]dec-7-yl}methyl)-1H-benzimidazole-6-carbonitrile | 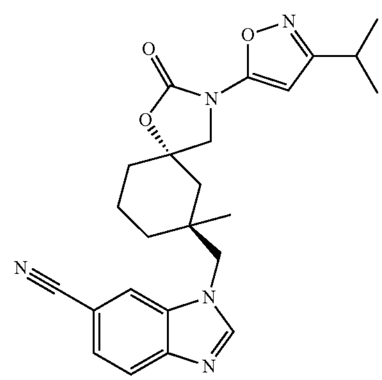 [SMILES: CC(C)c1cc(N2C[C@@]3(CCC[C@](C)(Cn4cnc5ccc(C#N)cc54)C3)OC2=O)on1] | 434.2 |
| 31 | 1-({(5S,7S)-7-methyl-3-[3-(2-methylpropyl)-5-isoxazolyl]-2-oxo-1-oxa-3-azaspiro[4.5]dec-7-yl}methyl)-1H-benzimidazole-6-carbonitrile | 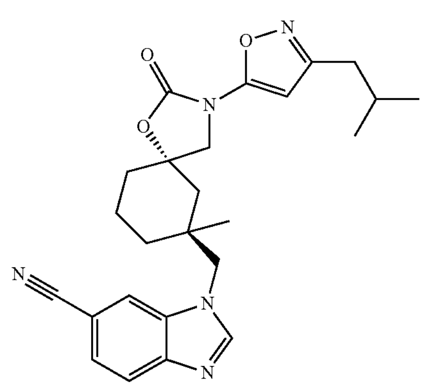 [SMILES: CC(C)Cc1cc(N2C[C@@]3(CCC[C@](C)(Cn4cnc5ccc(C#N)cc54)C3)OC2=O)on1] | 448.3 |

-continued

| Ex | Name | Structure | M + H (m/z) |
|---|---|---|---|
| 32 | 1-{[(5S,7S)-3-(1-tert-butyl-1H-pyrazol-4-yl)-7-methyl-2-oxo-1-oxa-3-azaspiro[4.5]dec-7-yl]methyl}-1H-benzimidazole-6-carbonitrile | 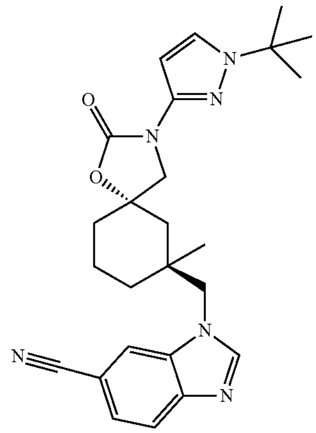 [SMILES: CC(C)(C)n1ccc(N2C[C@@]3(CCC[C@](C)(Cn4cnc5ccc(C#N)cc54)C3)OC2=O)n1] | 447.3 |
| 33 | 1-{[(5S,7S)-3-(3-ethyl-5-isoxazolyl)-7-methyl-2-oxo-1-oxa-3-azaspiro[4.5]dec-7-yl]methyl}-1H-benzimidazole-6-carbonitrile | 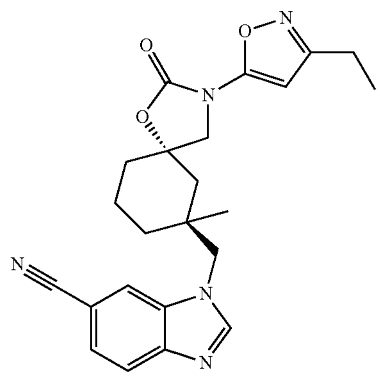 [SMILES: CCc1cc(N2C[C@@]3(CCC[C@](C)(Cn4cnc5ccc(C#N)cc54)C3)OC2=O)on1] | 420.3 |
| 34 | 1-{[(5S,7S)-3-(3-cyclopropyl-5-isoxazolyl)-7-methyl-2-oxo-1-oxa-3-azaspiro[4.5]dec-7-yl]methyl}-1H-benzimidazole-6-carbonitrile | 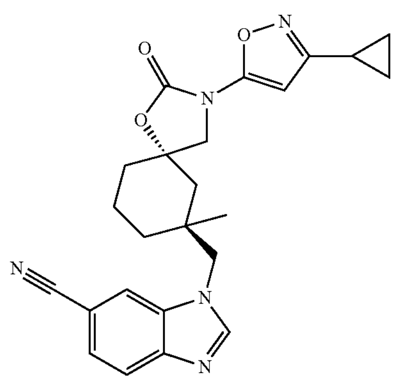 [SMILES: C[C@]1(Cn2cnc3ccc(C#N)cc32)CCC[C@@]2(CN(c3cc(C4CC4)no3)C(=O)O2)C1] | 432 |
| 35 | 1-{[(5S,7S)-7-methyl-2-oxo-3-(3-phenyl-5-isoxazolyl)-1-oxa-3-azaspiro[4.5]dec-7-yl]methyl}-1H-benzimidazole-6-carbonitrile | 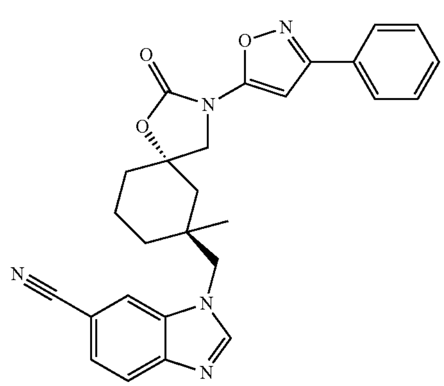 [SMILES: C[C@]1(Cn2cnc3ccc(C#N)cc32)CCC[C@@]2(CN(c3cc(-c4ccccc4)no3)C(=O)O2)C1] | 468.2 |

| Ex | Name | Structure | M + H (m/z) |
|---|---|---|---|
| 36 | 1-({(5S,7S)-3-[3-(1,1-dimethylethyl)-1-methyl-1H-pyrazol-5-yl]-7-methyl-2-oxo-1-oxa-3-azaspiro[4.5]dec-7-yl}methyl)-1H-benzimidazole-6-carbonitrile | 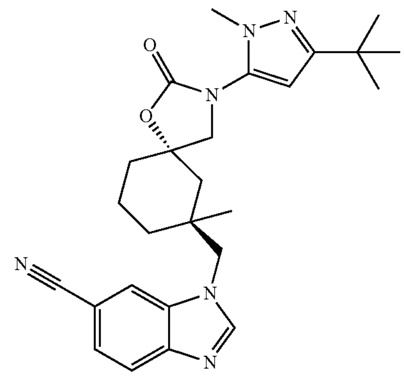 [SMILES: Cn1nc(C(C)(C)C)cc1N1C[C@@]2(CCC[C@](C)(Cn3cnc4ccc(C#N)cc43)C2)OC1=O] | 461.3 |
| 37 | 1-({(5S,7S)-7-methyl-2-oxo-3-[3-(trifluoromethyl)-5-isoxazolyl]-1-oxa-3-azaspiro[4.5]dec-7-yl}methyl)-1H-benzimidazole-6-carbonitrile | 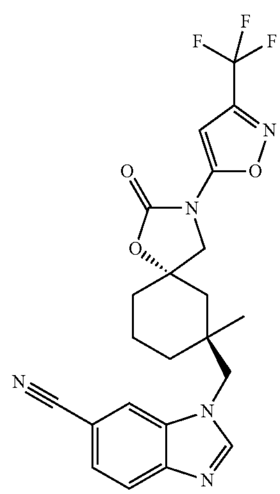 [SMILES: C[C@]1(Cn2cnc3ccc(C#N)cc32)CCC[C@@]2(CN(c3cc(C(F)(F)F)no3)C(=O)O2)C1] | 460 |
| 38 | 1-({(5S,7S)-3-[3-(1-cyanocyclopropyl)-5-isoxazolyl]-7-methyl-2-oxo-1-oxa-3-azaspiro[4.5]dec-7-yl}methyl)-1H-benzimidazole-6-carbonitrile | 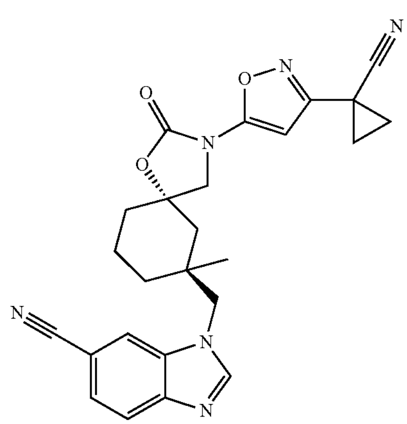 [SMILES: C[C@]1(Cn2cnc3ccc(C#N)cc32)CCC[C@@]2(CN(c3cc(C4(C#N)CC4)no3)C(=O)O2)C1] | 457.1 |

| Ex | Name | Structure | M + H (m/z) |
|---|---|---|---|
| 39 | 1-(((5S,7S)-3-(3-(2-fluoropropan-2-yl)isoxazol-5-yl)-7-methyl-2-oxo-1-oxa-3-azaspiro[4.5]decan-7-yl)methyl)-1H-benzo[d]imidazole-6-carbonitrile | 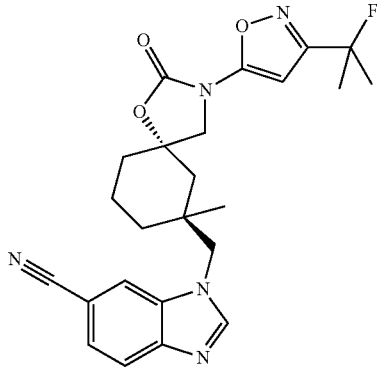 [SMILES: CC(C)(F)c1cc(N2C[C@@]3(CCC[C@](C)(Cn4cnc5ccc(C#N)cc54)C3)OC2=O)on1] | 452.2 |
| 40 | 1-(((5S,7S)-3-(3-cyclobutylisoxazol-5-yl)-7-methyl-2-oxo-1-oxa-3-azaspiro[4.5]decan-7-yl)methyl)-1H-benzo[d]imidazole-6-carbonitrile | 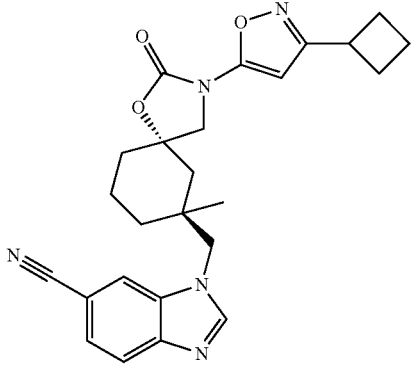 [SMILES: C[C@]1(Cn2cnc3ccc(C#N)cc32)CCC[C@@]2(CN(c3cc(C4CCC4)no3)C(=O)O2)C1] | 446.3 |
| 41 | 1-(((5S,7S)-3-(3-(tert-butyl)-4-methylisoxazol-5-yl)-7-methyl-2-oxo-1-oxa-3-azaspiro[4.5]decan-7-yl)methyl)-1H-benzo[d]imidazole-6-carbonitrile | 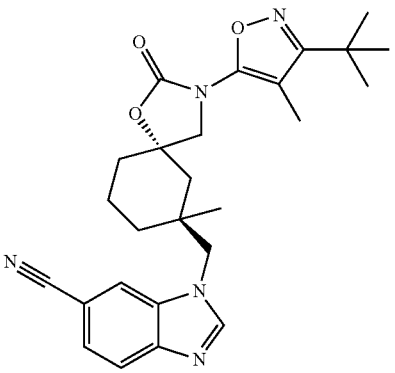 [SMILES: Cc1c(C(C)(C)C)noc1N1C[C@@]2(CCC[C@](C)(Cn3cnc4ccc(C#N)cc43)C2)OC1=O] | 462 |
| 42 | 1-(((5S,7S)-3-(4-(tert-butyl)oxazol-2-yl)-7-methyl-2-oxo-1-oxa-3-azaspiro[4.5]decan-7-yl)methyl)-1H-benzo[d]imidazole-6-carbonitrile | 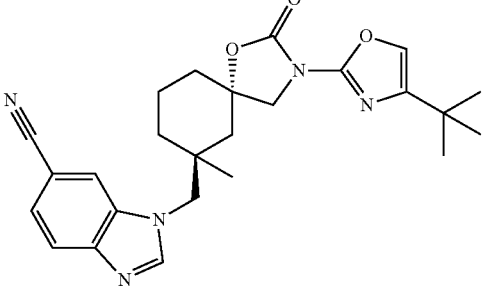 | 448.3 |

-continued

| Ex | Name | Structure | M + H (m/z) |
|---|---|---|---|
| 43 | 1-(((5S,7S)-3-(1-(tert-butyl)-1H-pyrazol-4-yl)-7-methyl-2-oxo-1-oxa-3-azaspiro[4.5]decan-7-yl)methyl)-1H-benzo[d]imidazole-6-carbonitrile | 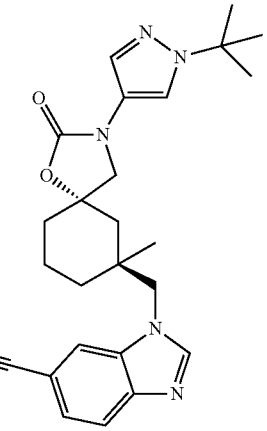 | 447.3 |
| 44 | 1-(((5S,7S)-3-(3-(tert-butyl)-4-fluoroisoxazol-5-yl)-7-methyl-2-oxo-1-oxa-3-azaspiro[4.5]decan-7-yl)methyl)-1H-benzo[d]imidazole-6-carbonitrile | 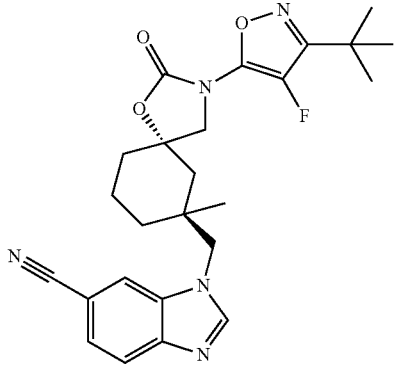 [SMILES: CC(C)(C)c1noc(N2C[C@@]3(CCC[C@](C)(Cn4cnc5ccc(C#N)cc54)C3)OC2=O)c1F] | 466.2 |
| 45 | 1-(((5S,7S)-3-(3-(1,1-difluoroethyl)isoxazol-5-yl)-7-methyl-2-oxo-1-oxa-3-azaspiro[4.5]decan-7-yl)methyl)-1H-benzo[d]imidazole-6-carbonitrile | 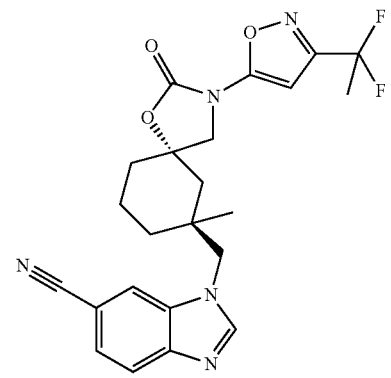 [SMILES: CC(F)(F)c1cc(N2C[C@@]3(CCC[C@](C)(Cn4cnc5ccc(C#N)cc54)C3)OC2=O)on1] | 456.2 |
| 46 | 1-(((5S,7S)-3-(3-(tert-butyl)-4-methylisoxazol-5-yl)-2-oxo-1-oxa-3-azaspiro[4.5]decan-7-yl)methyl)-1H-benzo[d]imidazole-6-carbonitrile | 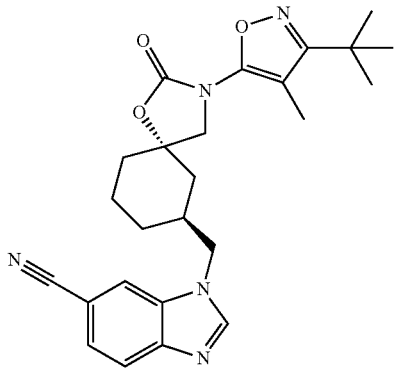 [SMILES: Cc1c(C(C)(C)C)noc1N1C[C@@]2(CCC[C@H](Cn3cnc4ccc(C#N)cc43)C2)OC1=O] | 448.3 |

| Ex | Name | Structure | M + H (m/z) |
|---|---|---|---|
| 47 | 1-(((5S,7S)-3-(3-(tert-butyl)-4-fluoroisoxazol-5-yl)-2-oxo-1-oxa-3-azaspiro[4.5]decan-7-yl)methyl)-1H-benzo[d]imidazole-6-carbonitrile | 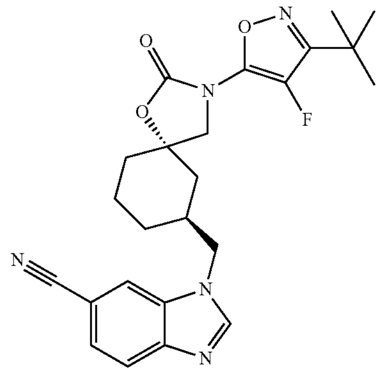 [SMILES: CC(C)(C)c1noc(N2C[C@@]3(CCC[C@H](Cn4cnc5ccc(C#N)cc54)C3)OC2=O)c1F] | 452.2 |
| 48 | 1-(((5S,7S)-3-(6-(tert-butyl)pyridazin-3-yl)-7-methyl-2-oxo-1-oxa-3-azaspiro[4.5]decan-7-yl)methyl)-1H-benzo[d]imidazole-6-carbonitrile | 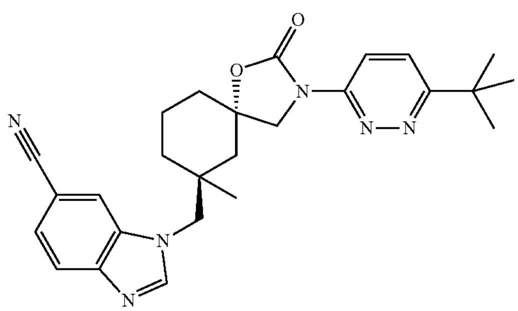 [SMILES: CC(C)(C)c1ccc(N2C[C@@]3(CCC[C@](C)(Cn4cnc5ccc(C#N)cc54)C3)OC2=O)nn1] | 459.3 |
| 49 | 1-(((5S,7S)-3-(5-(tert-butyl)pyrimidin-2-yl)-7-methyl-2-oxo-1-oxa-3-azaspiro[4.5]decan-7-yl)methyl)-1H-benzo[d]imidazole-6-carbonitrile | 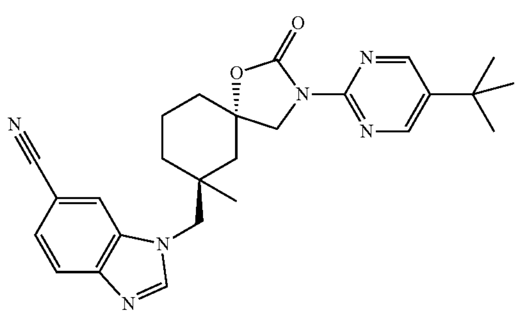 [SMILES: CC(C)(C)c1cnc(N2C[C@@]3(CCC[C@](C)(Cn4cnc5ccc(C#N)cc54)C3)OC2=O)nc1] | 459.3 |
| 50 | 1-(((5S,7S)-3-(2-(tert-butyl)-2H-1,2,3-triazol-4-yl)-7-methyl-2-oxo-1-oxa-3-azaspiro[4.5]decan-7-yl)methyl)-1H-benzo[d]imidazole-6-carbonitrile | 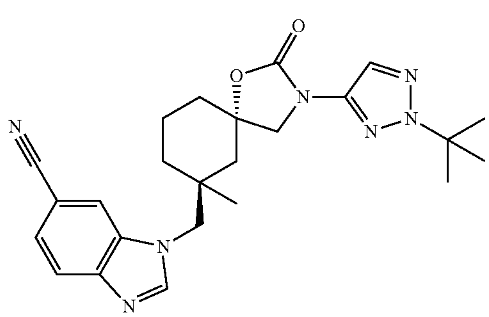 [SMILES: CC(C)(C)n1ncc(N2C[C@@]3(CCC[C@](C)(Cn4cnc5ccc(C#N)cc54)C3)OC2=O)n1] | 448.3 |

-continued

| Ex | Name | Structure | M + H (m/z) |
|---|---|---|---|
| 51 | 1-(((5S,7S)-7-methyl-3-(3-(1-methyl-1H-pyrazol-3-yl)isoxazol-5-yl)-2-oxo-1-oxa-3-azaspiro[4.5]decan-7-yl)methyl)-1H-benzo[d]imidazole-6-carbonitrile | 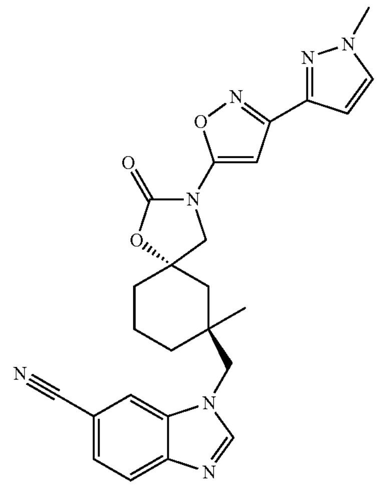 [SMILES: Cn1ccc(-c2cc(N3C[C@@]4(CCC[C@](C)(Cn5cnc6ccc(C#N)cc65)C4)OC3=O)on2)n1] | 472.2 |
| 52 | 1-(((5S,7S)-3-(1-(tert-butyl)-1H-1,2,3-triazol-4-yl)-7-methyl-2-oxo-1-oxa-3-azaspiro[4.5]decan-7-yl)methyl)-1H-benzo[d]imidazole-6-carbonitrile | 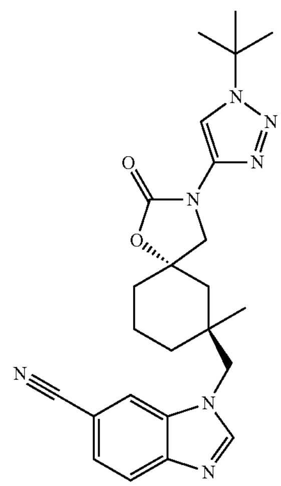 [SMILES: CC(C)(C)n1cc(N2C[C@@]3(CCC[C@](C)(Cn4cnc5ccc(C#N)cc54)C3)OC2=O)nn1] | 448.3 |
| 53 | 1-(((5S,7S)-3-(5-(tert-butyl)pyrazin-2-yl)-7-methyl-2-oxo-1-oxa-3-azaspiro[4.5]decan-7-yl)methyl)-1H-benzo[d]imidazole-6-carbonitrile | 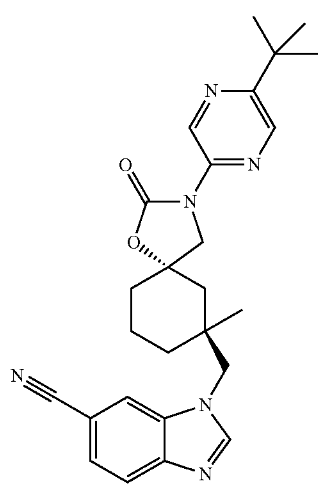 [SMILES: CC(C)(C)c1cnc(N2C[C@@]3(CCC[C@](C)(Cn4cnc5ccc(C#N)cc54)C3)OC2=O)cn1] | 459.2 |

-continued

| Ex | Name | Structure | M + H (m/z) |
|---|---|---|---|
| 54 | 1-(((5S,7S)-7-methyl-2-oxo-3-(5-(trifluoromethyl)pyrimidin-2-yl)-1-oxa-3-azaspiro[4.5]decan-7-yl)methyl)-1H-benzo[d]imidazole-6-carbonitrile | 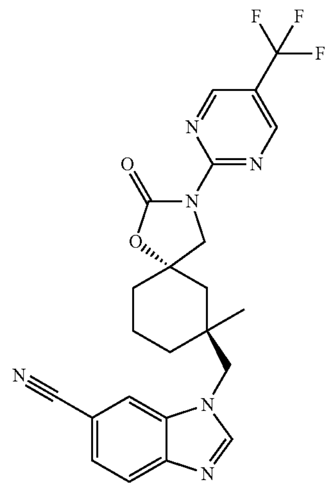 [SMILES: C[C@]1(Cn2cnc3ccc(C#N)cc32)CCC[C@@]2(CN(c3ncc(C(F)(F)F)cn3)C(=O)O2)C1] | 471.2 |
| 55 | 1-(((5S,7S)-3-(6-(2-methoxypropan-2-yl)pyridin-3-yl)-7-methyl-2-oxo-1-oxa-3-azaspiro[4.5]decan-7-yl)methyl)-1H-benzo[d]imidazole-6-carbonitrile | 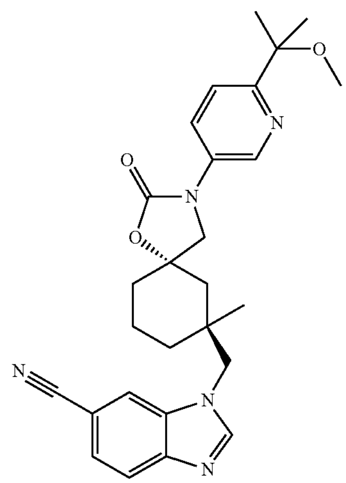 [SMILES: COC(C)(C)c1ccc(N2C[C@@]3(CCC[C@](C)(Cn4cnc5ccc(C#N)cc54)C3)OC2=O)cn1] | 474.2 |
| 56 | 1-(((5S,7S)-7-methyl-2-oxo-3-(3-(prop-1-en-2-yl)isoxazol-5-yl)-1-oxa-3-azaspiro[4.5]decan-7-yl)methyl)-1H-benzo[d]imidazole-6-carbonitrile | 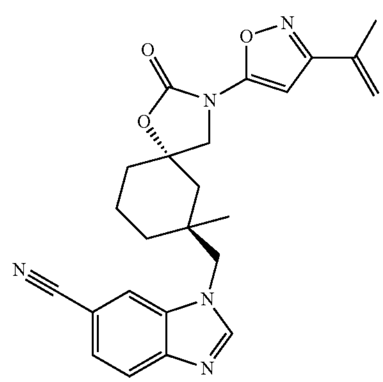 [SMILES: C=C(C)c1cc(N2C[C@@]3(CCC[C@](C)(Cn4cnc5ccc(C#N)cc54)C3)OC2=O)on1] | 432.2 |

Example 57

1-(((5S,7S)-3-(3,4-Dimethylisoxazol-5-yl)-7-methyl-2-oxo-1-oxa-3-azaspiro[4.5]decan-7-yl)methyl)-1H-benzo[d]imidazole-6-carbonitrile

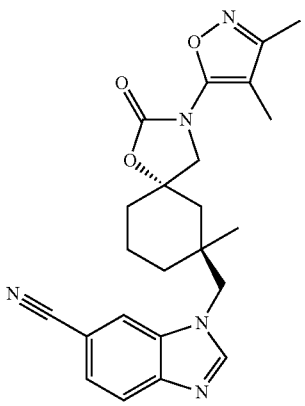 [SMILES: Cc1noc(N2C[C@@]3(CCC[C@](C)(Cn4cnc5ccc(C#N)cc54)C3)OC2=O)c1C]

1-(((5S,7S)-3-(3,4-Dimethylisoxazol-5-yl)-7-methyl-2-oxo-1-oxa-3-azasbiro[4.5]decan-7-yl)methyl)-1H-benzo[d]imidazole-6-carbonitrile To a microwave vial was added (bis-N,N-(tert-butoxycarbonyl)-5-amino-3,4-dimethylisoxazole (175 mg, 0.561 mmol) and 1-(((3S,5S)-5-methyl-1-oxaspiro[2.5]octan-5-yl)methyl)-1H-benzo[d]imidazole-6-carbonitrile (105 mg, 0.374 mmol) in NMP (1870 µL). To this solution was added potassium tert-butoxide (50.4 mg, 0.449 mmol), and the vial was capped and heated at 80° C. for 16 h. The reaction was then diluted with 10% $Na_2CO_3$, extracted with DCM (3×), washed with brine, dried and evaporated to a dark oil. This oil was purified by reverse phase HPLC purification (20-60% MeCN/Water w/0.1% TFA, 30 mm×150 mm Sunfire column) to yield 1-(((5S,7S)-3-(3,4-dimethylisoxazol-5-yl)-7-methyl-2-oxo-1-oxa-3-azaspiro[4.5]decan-7-yl)methyl)-1H-benzo[d]imidazole-6-carbonitrile (29.5 mg, 14.6% yield). $^1$H NMR (500 MHz, DMSO-$d_6$) δ 8.53 (s, 1H), 8.39 (s, 1H), 7.84 (d, J=8.30 Hz, 1H), 7.61 (d, J=8.55 Hz, 1H), 4.17 (s, 2H), 3.70-3.80 (m, 2H), 2.16 (s, 3H), 2.00 (d, J=12.0 Hz, 1H), 1.92 (d, J=14.16 Hz, 1H), 1.86 (s, 3H), 1.68 (d, J=14.40 Hz, 1H), 1.59-1.68 (m, 2H), 1.41-1.54 (m, 2H), 1.34 (m, 1H), 1.05 (s, 3H). MS (m/z) 420.2 (M+H$^+$).

The following compound was prepared using procedures analogous to those described in Example 57 using appropriate substituted starting materials. As is appreciated by those skilled in the art, this analogous example may involve variations in general reaction conditions.

| Ex | Name | Structure | M + H (m/z) |
|---|---|---|---|
| 58 | 1-(((5S,7S)-3-(3,4-dimethylisoxazol-5-yl)-2-oxo-1-oxa-3-azaspiro[4.5]decan-7-yl)methyl)-1H-benzo[d]imidazole-6-carbonitrile | 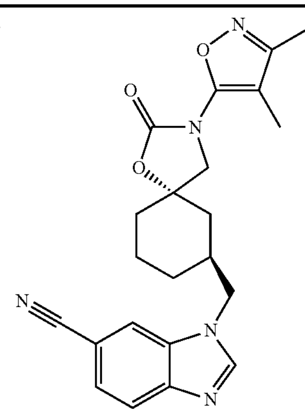 | 406.2 |

The following compounds were prepared using procedures analogous to those described in Example 4 using appropriate substituted starting materials. As is appreciated by those skilled in the art, these analogous examples may involve variations in general reaction conditions.

| Ex | Name | Structure | M + H (m/z) |
|---|---|---|---|
| 59 | 1-({3-[(5-chloro-1-benzothien-3-yl)methyl]-2-oxo-1-oxa-3-azaspiro[4.5]dec-7-yl}methyl)-1H-indole-6-carbonitrile | 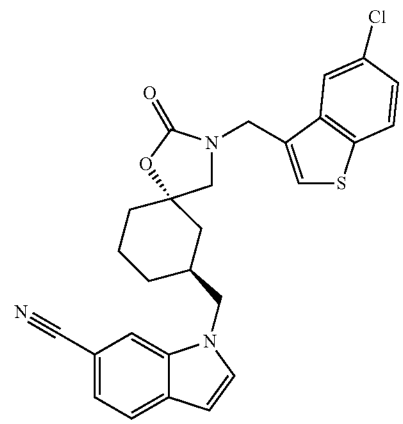 [SMILES: N#Cc1ccc2ccn(C[C@H]3CCC[C@]4(C3)CN(Cc3csc5ccc(Cl)cc35)C(=O)O4)c2c1] | 490.1 |
| 60 | 1-({3-[(5-chloro-1-benzothien-3-yl)methyl]-2-oxo-1-oxa-3-azaspiro[4.5]dec-7-yl}methyl)-2-(trifluoromethyl)-1H-benzimidazole-6-carbonitrile | 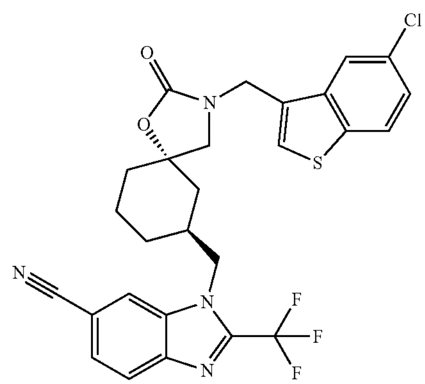 [SMILES: N#Cc1ccc2nc(C(F)(F)F)n(C[C@H]3CCC[C@]4(C3)CN(Cc3csc5ccc(Cl)cc35)C(=O)O4)c2c1] | 559.1 |
| 61 | 1-({3-[(5-chloro-1-benzothien-3-yl)methyl]-2-oxo-1-oxa-3-azaspiro[4.5]dec-7-yl}methyl)-1H-benzimidazole-6-carbonitrile | 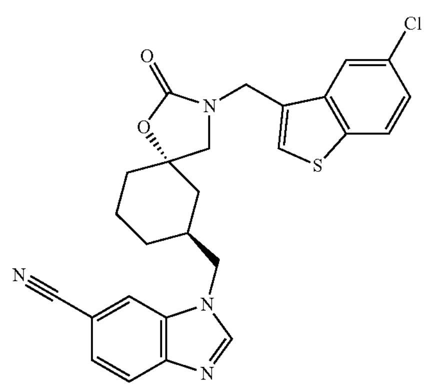 [SMILES: N#Cc1ccc2ncn(C[C@H]3CCC[C@]4(C3)CN(Cc3csc5ccc(Cl)cc35)C(=O)O4)c2c1] | 491.1 |
| 62 | 1-{[3-(1-benzothien-3-ylmethyl)-2-oxo-1-oxa-3-azaspiro[4.5]dec-7-yl]methyl}-1H-benzimidazole-6-carbonitrile | 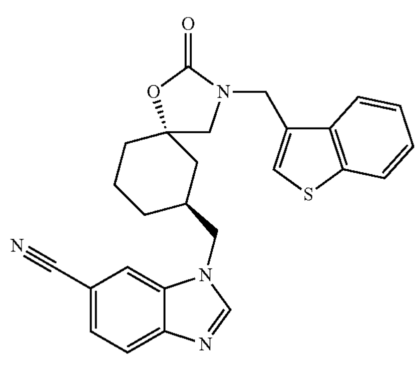 [SMILES: N#Cc1ccc2ncn(C[C@H]3CCC[C@]4(C3)CN(Cc3csc5ccccc35)C(=O)O4)c2c1] | 457.2 |

-continued

| Ex | Name | Structure | M + H (m/z) |
|---|---|---|---|
| 63 | 1-({(5S,7S)-2-oxo-3-[(2-phenyl-1,3-thiazol-4-yl)methyl]-1-oxa-3-azaspiro[4.5]dec-7-yl}methyl)-1H-benzimidazole-6-carbonitrile | 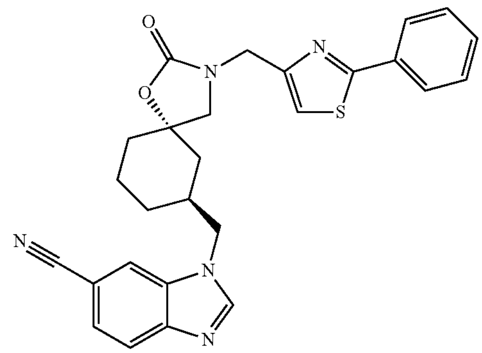 [SMILES: N#Cc1ccc2ncn(C[C@H]3CCC[C@]4(C3)CN(Cc3csc(-c5ccccc5)n3)C(=O)O4)c2c1] | 484.2 |
| 64 | 1-({(5S,7S)-2-oxo-3-[(6-phenyl-2-pyridinyl)methyl]-1-oxa-3-azaspiro[4.5]dec-7-yl}methyl)-1H-benzimidazole-6-carbonitrile | 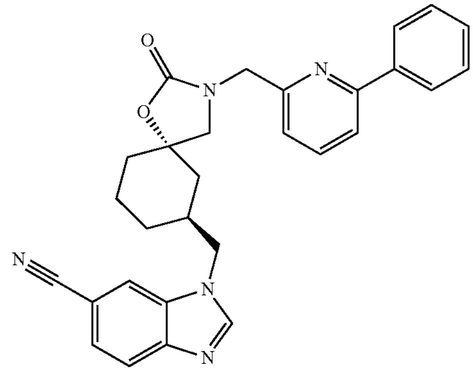 [SMILES: N#Cc1ccc2ncn(C[C@H]3CCC[C@]4(C3)CN(Cc3cccc(-c5ccccc5)n3)C(=O)O4)c2c1] | 478.3 |
| 65 | 1-[((5S,7S)-3-{2-methyl-2-[3-(tetrahydro-2H-pyran-4-yl)-1,2,4-oxadiazol-5-yl]propyl}-2-oxo-1-oxa-3-azaspiro[4.5]dec-7-yl)methyl]-1H-benzimidazole-6-carbonitrile | 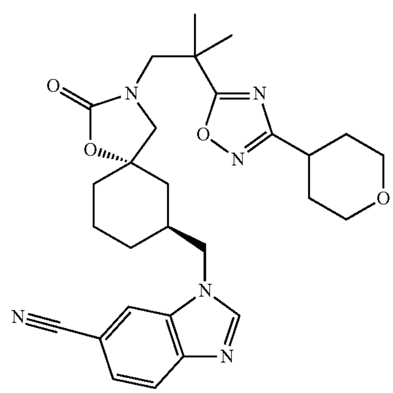 [SMILES: CC(C)(CN1C[C@@]2(CCC[C@H](Cn3cnc4ccc(C#N)cc43)C2)OC1=O)c1nc(C2CCOCC2)no1] | 519.3 |
| 66 | 1-({(5S,7S)-2-oxo-3-[(4-phenyl-1,3-thiazol-2-yl)methyl]-1-oxa-3-azaspiro[4.5]dec-7-yl}methyl)-1H-benzimidazole-6-carbonitrile | 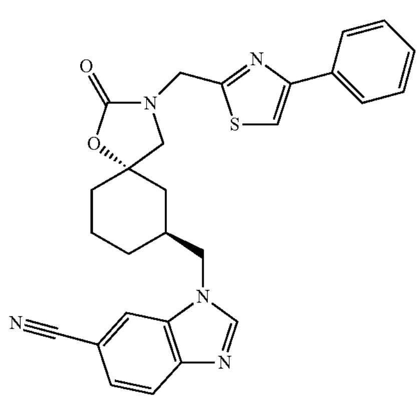 [SMILES: N#Cc1ccc2ncn(C[C@H]3CCC[C@]4(C3)CN(Cc3nc(-c5ccccc5)cs3)C(=O)O4)c2c1] | 483.9 |

-continued

| Ex | Name | Structure | M + H (m/z) |
|---|---|---|---|
| 67 | 1-[((5S,7S)-3-{[3-(4-chlorophenyl)-5-isoxazolyl]methyl}-2-oxo-1-oxa-3-azaspiro[4.5]dec-7-yl)methyl]-1H-benzimidazole-6-carbonitrile | 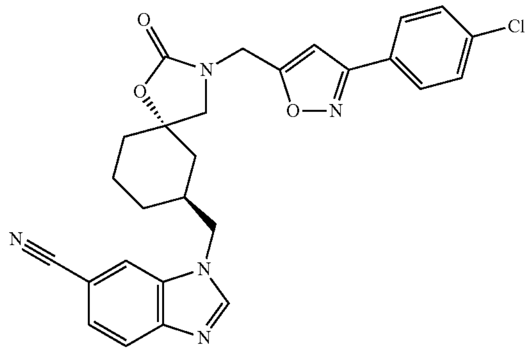 [SMILES: N#Cc1ccc2ncn(C[C@H]3CCC[C@]4(C3)CN(Cc3cc(-c5ccc(Cl)cc5)no3)C(=O)O4)c2c1] | 501.9 |
| 68 | 1-({(5S,7S)-2-oxo-3-[(3-phenyl-5-isoxazolyl)methyl]-1-oxa-3-azaspiro[4.5]dec-7-yl}methyl)-1H-benzimidazole-6-carbonitrile | 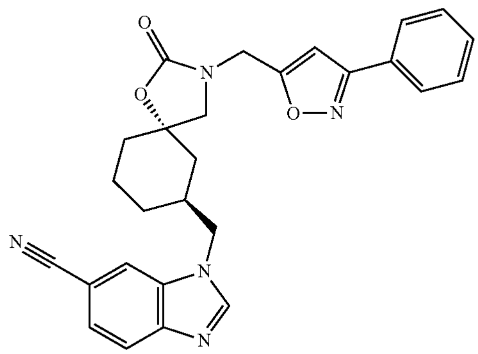 [SMILES: N#Cc1ccc2ncn(C[C@H]3CCC[C@]4(C3)CN(Cc3cc(-c5ccccc5)no3)C(=O)O4)c2c1] | 468 |
| 69 | 1-({(5S,7S)-3-[(1-methyl-5-phenyl-1H-pyrazol-3-yl)methyl]-2-oxo-1-oxa-3-azaspiro[4.5]dec-7-yl}methyl)-1H-benzimidazole-6-carbonitrile | 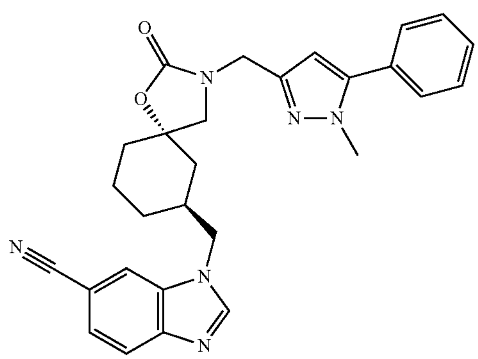 [SMILES: Cn1nc(CN2C[C@@]3(CCC[C@H](Cn4cnc5ccc(C#N)cc54)C3)OC2=O)cc1-c1ccccc1] | 481 |
| 70 | 1-{[(5S,7S)-3-({4-[3-methyl-4-(methyloxy)phenyl]-1,3-thiazol-2-yl}methyl)-2-oxo-1-oxa-3-azaspiro[4.5]dec-7-yl]methyl}-1H-benzimidazole-6-carbonitrile | 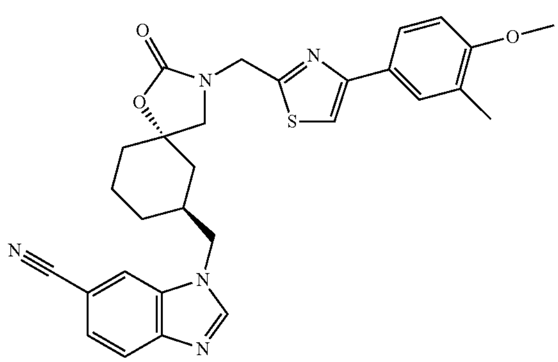 [SMILES: COc1ccc(-c2csc(CN3C[C@@]4(CCC[C@H](Cn5cnc6ccc(C#N)cc65)C4)OC3=O)n2)cc1C] | 528 |

| Ex | Name | Structure | M + H (m/z) |
|----|------|-----------|-------------|
| 71 | 1-({(5S,7S)-2-oxo-3-[(3-phenyl-1H-1,2,4-triazol-5-yl)methyl]-1-oxa-3-azaspiro[4.5]dec-7-yl}methyl)-1H-benzimidazole-6-carbonitrile | 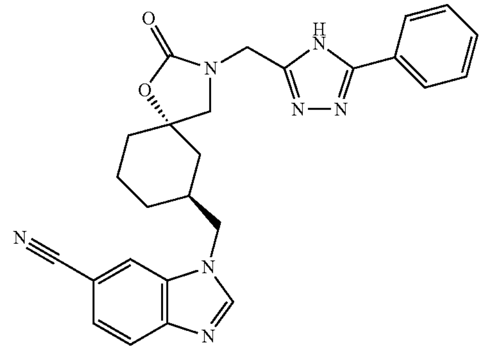 [SMILES: N#Cc1ccc2ncn(C[C@H]3CCC[C@]4(C3)CN(Cc3nnc(-c5ccccc5)[nH]3)C(=O)O4)c2c1] | 468 |
| 72 | 1-({(5S,7S)-2-oxo-3-[(5-phenyl-3-pyridinyl)methyl]-1-oxa-3-azaspiro[4.5]dec-7-yl}methyl)-1H-benzimidazole-6-carbonitrile trifluoroacetate | 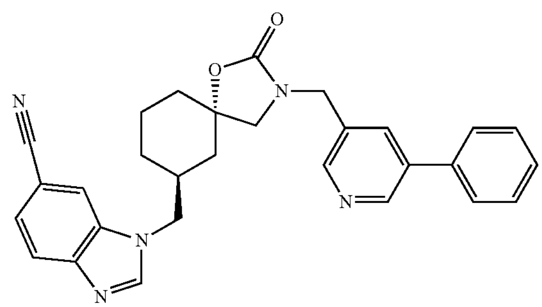 [SMILES: N#Cc1ccc2ncn(C[C@H]3CCC[C@]4(C3)CN(Cc3cncc(-c5ccccc5)c3)C(=O)O4)c2c1] | 478.2 |
| 73 | 4-chloro-1-({(5S,7S)-3-[2-methyl-2-(3-phenyl-1,2,4-oxadiazol-5-yl)propyl]-2-oxo-1-oxa-3-azaspiro[4.5]dec-7-yl}methyl)-1H-benzimidazole-6-carbonitrile | 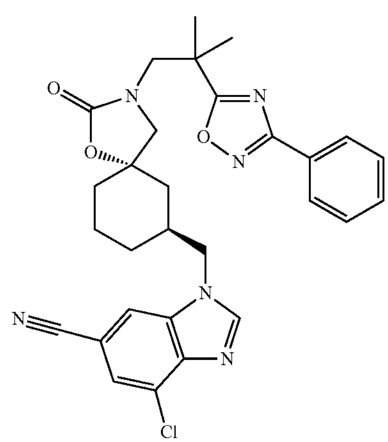 [SMILES: CC(C)(CN1C[C@@]2(CCC[C@H](Cn3cnc4c(Cl)cc(C#N)cc43)C2)OC1=O)c1nc(-c2ccccc2)no1] | 545.2 |

The following compounds were prepared using procedures analogous to those described in Example 6 using appropriately substituted starting materials. As is appreciated by those skilled in the art, these analogous examples may involve variations in general reaction conditions.

| Ex | Name | Structure | M + H (m/z) |
|---|---|---|---|
| 74 | 1-({(5S,7S)-3-[2-methyl-2-(3-methyl-1,2,4-oxadiazol-5-yl)propyl]-2-oxo-1-oxa-3-azaspiro[4.5]dec-7-yl}methyl)-1H-benzimidazole-6-carbonitrile | 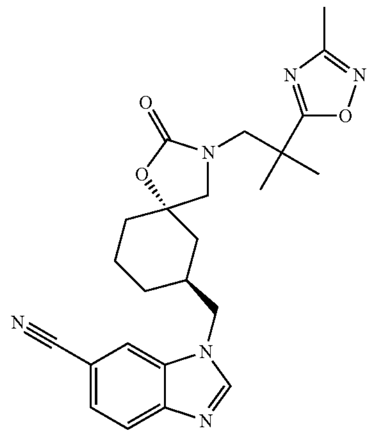 [SMILES: Cc1noc(C(C)(C)CN2C[C@@]3(CCC[C@H](Cn4cnc5ccc(C#N)cc54)C3)OC2=O)n1] | 449.2 |
| 75 | 1-({(5S,7S)-3-[2-methyl-2-(3-phenyl-1,2,4-oxadiazol-5-yl)propyl]-2-oxo-1-oxa-3-azaspiro[4.5]dec-7-yl}methyl)-1H-benzimidazole-6-carbonitrile | 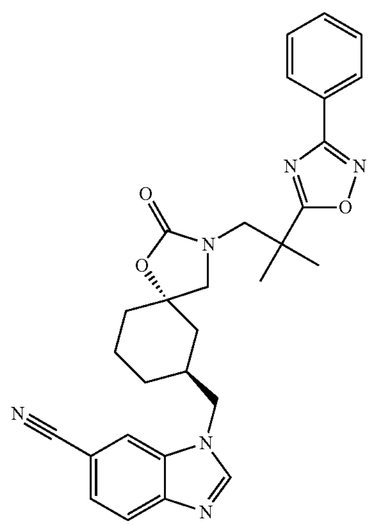 [SMILES: CC(C)(CN1C[C@@]2(CCC[C@H](Cn3cnc4ccc(C#N)cc43)C2)OC1=O)c1nc(-c2ccccc2)no1] | 511.3 |
| 76 | 1-[((5S,7S)-3-{2-methyl-2-[3-(1-methylethyl)-1,2,4-oxadiazol-5-yl]propyl}-2-oxo-1-oxa-3-azaspiro[4.5]dec-7-yl)methyl]-1H-benzimidazole-6-carbonitrile | 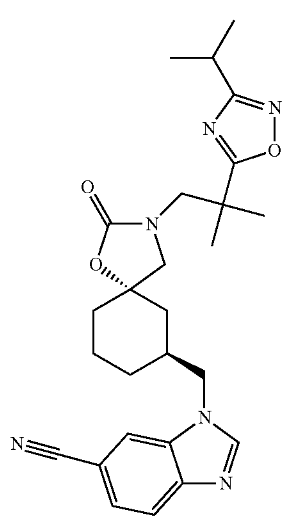 [SMILES: CC(C)c1noc(C(C)(C)CN2C[C@@]3(CCC[C@H](Cn4cnc5ccc(C#N)cc54)C3)OC2=O)n1] | 477.2 |

-continued

| Ex | Name | Structure | M + H (m/z) |
|----|------|-----------|-------------|
| 77 | 1-({(5S,7S)-3-[2-(3-cyclopentyl-1,2,4-oxadiazol-5-yl)-2-methylpropyl]-2-oxo-1-oxa-3-azaspiro[4.5]dec-7-yl}methyl)-1H-benzimidazole-6-carbonitrile | 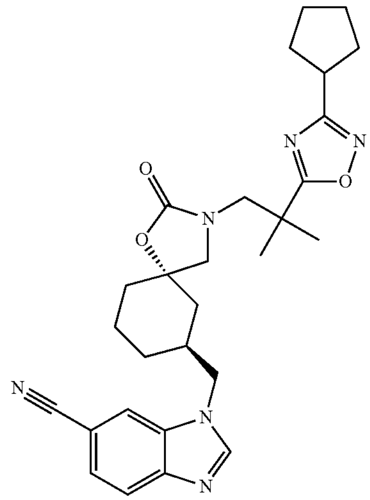 [SMILES: CC(C)(CN1C[C@@]2(CCC[C@H](Cn3cnc4ccc(C#N)cc43)C2)OC1=O)c1nc(C2CCCC2)no1] | 503.3 |
| 78 | 1-[((5S,7S)-3-{2-methyl-2-[3-(5-pyrimidinyl)-1,2,4-oxadiazol-5-yl]propyl}-2-oxo-1-oxa-3-azaspiro[4.5]dec-7-yl)methyl]-1H-benzimidazole-6-carbonitrile | 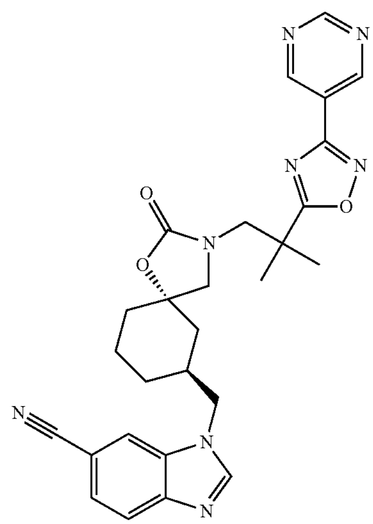 [SMILES: CC(C)(CN1C[C@@]2(CCC[C@H](Cn3cnc4ccc(C#N)cc43)C2)OC1=O)c1nc(-c2cncnc2)no1] | 513.3 |
| 79 | 1-[((5S,7S)-3-{2-[3-(1,1-dimethylethyl)-1,2,4-oxadiazol-5-yl]-2-methylpropyl}-2-oxo-1-oxa-3-azaspiro[4.5]dec-7-yl)methyl]-1H-benzimidazole-6-carbonitrile | 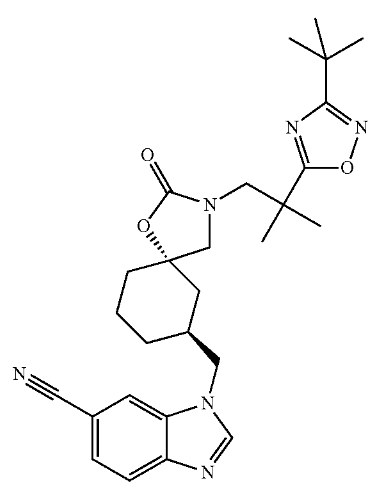 [SMILES: CC(C)(C)c1noc(C(C)(C)CN2C[C@@]3(CCC[C@H](Cn4cnc5ccc(C#N)cc54)C3)OC2=O)n1] | 491.3 |

| Ex | Name | Structure | M + H (m/z) |
|---|---|---|---|
| 80 | 1-[((5S,7S)-3-{2-methyl-2-[3-(trifluoromethyl)-1,2,4-oxadiazol-5-yl]propyl}-2-oxo-1-oxa-3-azaspiro[4.5]dec-7-yl)methyl]-1H-benzimidazole-6-carbonitrile | 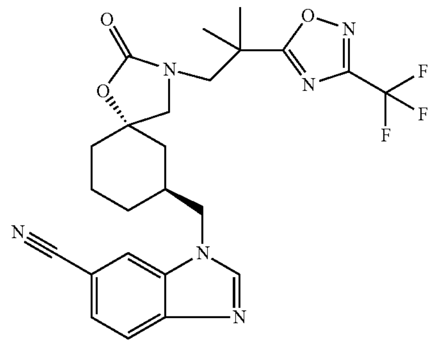 [SMILES: CC(C)(CN1C[C@@]2(CCC[C@H](Cn3cnc4ccc(C#N)cc43)C2)OC1=O)c1nc(C(F)(F)F)no1] | 503.2 |
| 81 | 1-{[(5S,7S)-3-(2-methyl-2-{3-[(methyloxy)methyl]-1,2,4-oxadiazol-5-yl}propyl)-2-oxo-1-oxa-3-azaspiro[4.5]dec-7-yl]methyl}-1H-benzimidazole-6-carbonitrile | 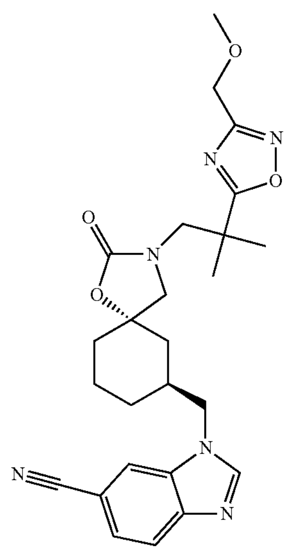 [SMILES: COCc1noc(C(C)(C)CN2C[C@@]3(CCC[C@H](Cn4cnc5ccc(C#N)cc54)C3)OC2=O)n1] | 479.3 |
| 82 | 1-[((5S,7S)-3-{2-methyl-2-[3-(2-methylpropyl)-1,2,4-oxadiazol-5-yl]propyl}-2-oxo-1-oxa-3-azaspiro[4.5]dec-7-yl)methyl]-1H-benzimidazole-6-carbonitrile | 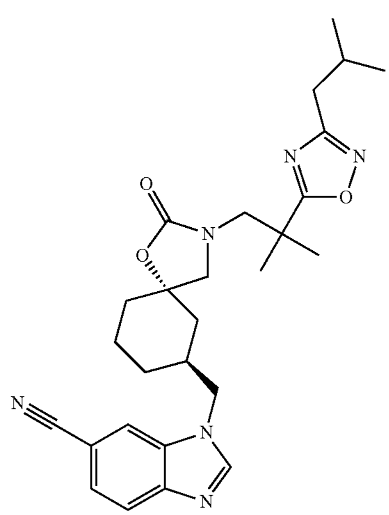 [SMILES: CC(C)Cc1noc(C(C)(C)CN2C[C@@]3(CCC[C@H](Cn4cnc5ccc(C#N)cc54)C3)OC2=O)n1] | 491.3 |

-continued

| Ex | Name | Structure | M + H (m/z) |
|---|---|---|---|
| 83 | 1-({(5S,7S)-3-[2-methyl-2-(3-{[(1-methylethyl)oxy]methyl}-1,2,4-oxadiazol-5-yl)propyl]-2-oxo-1-oxa-3-azaspiro[4.5]dec-7-yl}methyl)-1H-benzimidazole-6-carbonitrile | 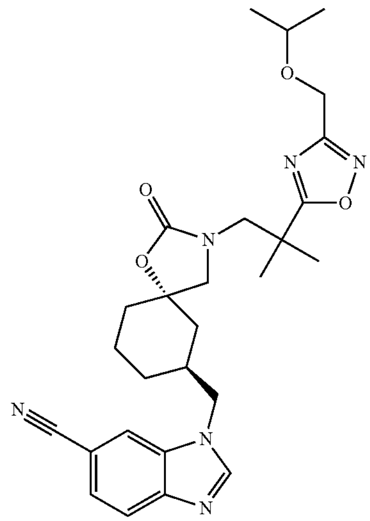 [SMILES: CC(C)OCc1noc(C(C)(C)CN2C[C@@]3(CCC[C@H](Cn4cnc5ccc(C#N)cc54)C3)OC2=O)n1] | 507.3 |
| 84 | 4-chloro-1-[((5S,7S)-2-oxo-3-{[4-(3-phenyl-1,2,4-oxadiazol-5-yl)tetrahydro-2H-pyran-4-yl]methyl}-1-oxa-3-azaspiro[4.5]dec-7-yl)methyl]-1H-benzimidazole-6-carbonitrile | 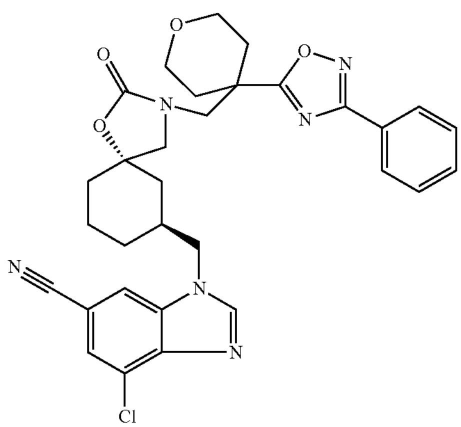 [SMILES: N#Cc1cc(Cl)c2ncn(C[C@H]3CCC[C@]4(C3)CN(CC3(c5nc(-c6ccccc6)no5)CCOCC3)C(=O)O4)c2c1] | 587.2 |
| 85 | 4-chloro-1-[((5S,7S)-3-{[4-(3-cyclopentyl-1,2,4-oxadiazol-5-yl)tetrahydro-2H-pyran-4-yl]methyl}-2-oxo-1-oxa-3-azaspiro[4.5]dec-7-yl)methyl]-1H-benzimidazole-6-carbonitrile | 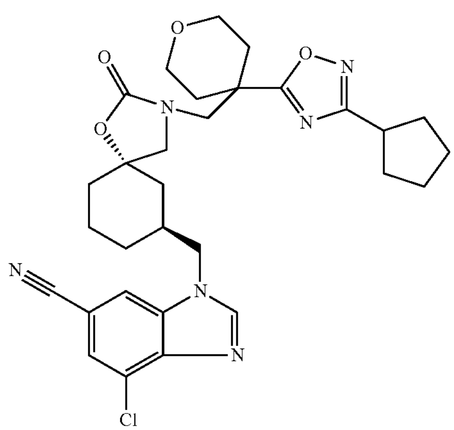 [SMILES: N#Cc1cc(Cl)c2ncn(C[C@H]3CCC[C@]4(C3)CN(CC3(c5nc(C6CCCC6)no5)CCOCC3)C(=O)O4)c2c1] | 579.3 |

The following compound was prepared using procedures analogous to those described in Example 7 using appropriately substituted starting materials. As is appreciated by those skilled in the art, this analogous example may involve variations in general reaction conditions.

| Ex | Name | Structure | M + H (m/z) |
|---|---|---|---|
| 86 | 1-[((5S,7S)-2-oxo-3-{[1-(2-pyridinyl)-3-pyrrolidinyl]methyl}-1-oxa-3-azaspiro[4.5]dec-7-yl)methyl]-1H-benzimidazole-6-carbonitrile | 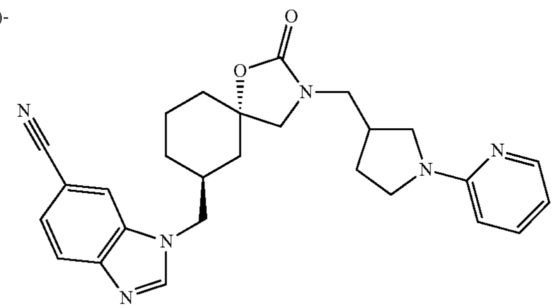 | 471.3 |

The following compounds were prepared using procedures analogous to those described in Example 8 using appropriately substituted starting materials. As is appreciated by those skilled in the art, these analogous examples may involve variations in general reaction conditions.

| Ex | Name | Structure | M + H (m/z) |
|---|---|---|---|
| 87 | 1-({(5S,7S)-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile | 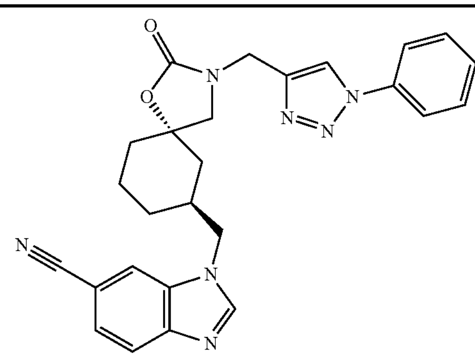 | 468 |
| 88 | 1-[((5S,7S)-3-{[1-(4-cyanophenyl)-1H-1,2,3-triazol-4-yl]methyl}-2-oxo-1-oxa-3-azaspiro[4.5]dec-7-yl)methyl]-1H-benzimidazole-6-carbonitrile | 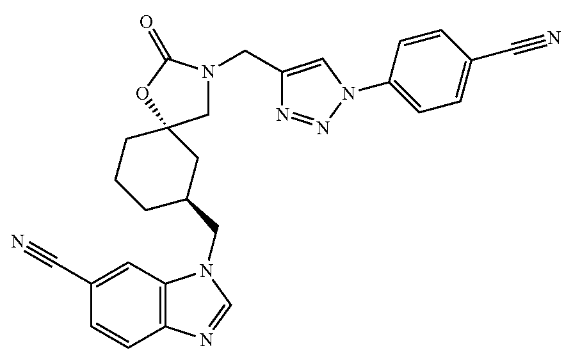 [SMILES: N#Cc1ccc(-n2cc(CN3C[C@@]4(CCC[C@H](Cn5cnc6ccc(C#N)cc65)C4)OC3=O)nn2)cc1] | 493 |
| 89 | 1-[((5S(7S)-3-{[1-(4-chlorophenyl)-1H-1,2,3-triazol-4-yl]methyl}-2-oxo-1-oxa-3-azaspiro[4.5]dec-7-yl)methyl]-1H-benzimidazole-6-carbonitrile | 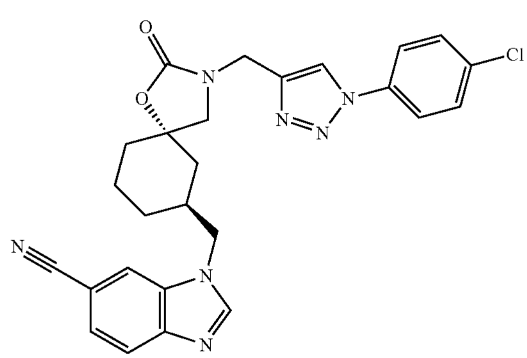 [SMILES: N#Cc1ccc2ncn(C[C@H]3CCC[C@]4(C3)CN(Cc3cn(-c5ccc(Cl)cc5)nn3)C(=O)O4)c2c1] | 5028 |

-continued

| Ex | Name | Structure | M + H (m/z) |
|---|---|---|---|
| 90 | 1-[((5S,7S)-3-{[1-(3-chlorophenyl)-1H-1,2,3-triazol-4-yl]methyl}-2-oxo-1-oxa-3-azaspiro[4.5]dec-7-yl)methyl]-1H-benzimidazole-6-carbonitrile | 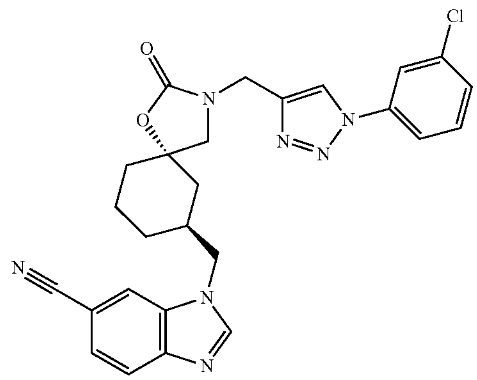 [SMILES: N#Cc1ccc2ncn(C[C@H]3CCC[C@]4(C3)CN(Cc3cn(-c5cccc(Cl)c5)nn3)C(=O)O4)c2c1] | 502 |
| 91 | 1-[((5S,7S)-3-{[1-(4-methylphenyl)-1H-1,2,3-triazol-4-yl]methyl}-2-oxo-1-oxa-3-azaspiro[4.5]dec-7-yl)methyl]-1H-benzimidazole-6-carbonitrile | 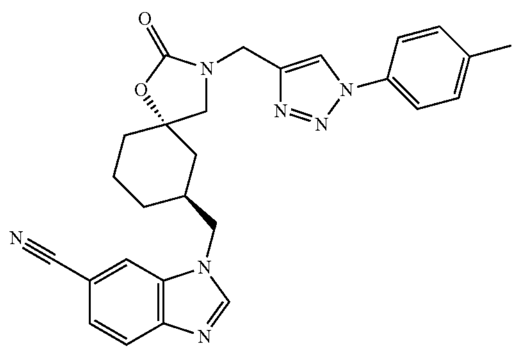 [SMILES: Cc1ccc(-n2cc(CN3C[C@@]4(CCC[C@H](Cn5cnc6ccc(C#N)cc65)C4)OC3=O)nn2)cc1] | 482 |
| 92 | 1-[((5S,7S)-3-{[1-(3-cyanophenyl)-1H-1,2,3-triazol-4-yl]methyl}-2-oxo-1-oxa-3-azaspiro[4.5]dec-7-yl)methyl]-1H-benzimidazole-6-carbonitrile | 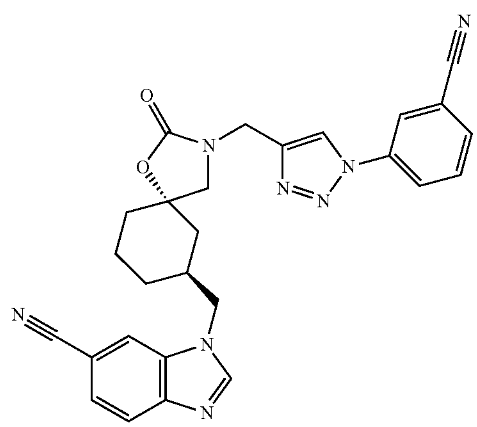 [SMILES: N#Cc1cccc(-n2cc(CN3C[C@@]4(CCC[C@H](Cn5cnc6ccc(C#N)cc65)C4)OC3=O)nn2)c1] | 493 |
| 93 | 1-{[(5S,7S)-2-oxo-3-({1-[3-(trifluoromethyl)phenyl]-1H-1,2,3-triazol-4-yl}methyl)-1-oxa-3-azaspiro[4.5]dec-7-yl]methyl}-1H-benzimidazole-6-carbonitrile | 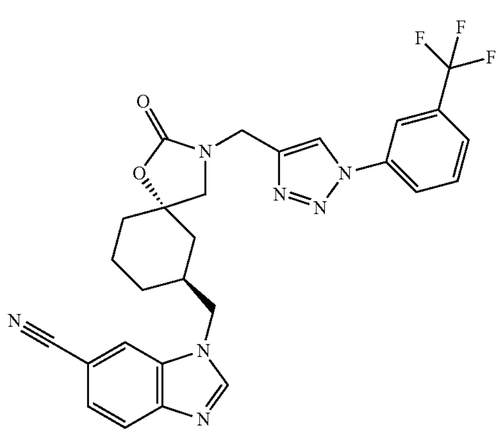 [SMILES: N#Cc1ccc2ncn(C[C@H]3CCC[C@]4(C3)CN(Cc3cn(-c5cccc(C(F)(F)F)c5)nn3)C(=O)O4)c2c1] | 536 |

| Ex | Name | Structure | M + H (m/z) |
|---|---|---|---|
| 94 | 1-[((5S,7S)-3-{[1-(3-fluorophenyl)-1H-1,2,3-triazol-4-yl]methyl}-2-oxo-1-oxa-3-azaspiro[4.5]dec-7-yl)methyl]-1H-benzimidazole-6-carbonitrile | 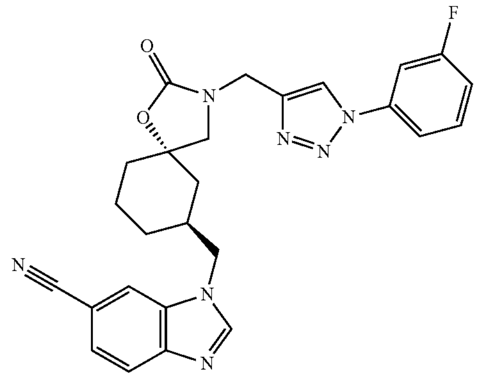 [SMILES: N#Cc1ccc2ncn(C[C@H]3CCC[C@]4(C3)CN(Cc3cn(-c5cccc(F)c5)nn3)C(=O)O4)c2c1] | 486 |
| 95 | 1-{[(5S,7S)-3-({1-[3-(methyloxy)phenyl]-1H-1,2,3-triazol-4-yl}methyl)-2-oxo-1-oxa-3-azaspiro[4.5]dec-7-yl]methyl}-1H-benzimidazole-6-carbonitrile | 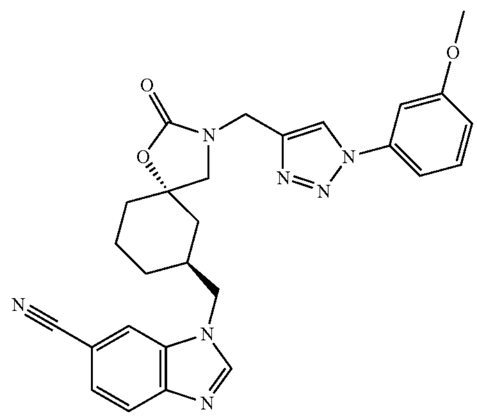 [SMILES: COc1cccc(-n2cc(CN3C[C@@]4(CCC[C@H](Cn5cnc6ccc(C#N)cc65)C4)OC3=O)nn2)c1] | 498 |
| 96 | 1-[((5S,7S)-3-{[1-(3-methylphenyl)-1H-1,2,3-triazol-4-yl]methyl}-2-oxo-1-oxa-3-azaspiro[4.5]dec-7-yl)methyl]-1H-benzimidazole-6-carbonitrile | 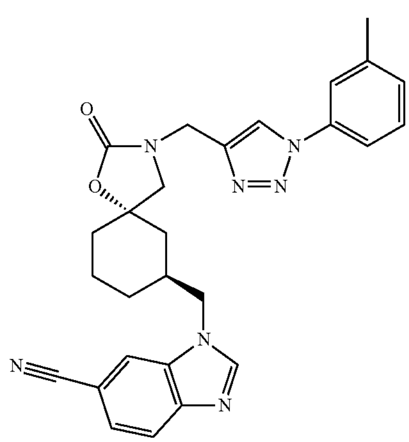 [SMILES: Cc1cccc(-n2cc(CN3C[C@@]4(CCC[C@H](Cn5cnc6ccc(C#N)cc65)C4)OC3=O)nn2)c1] | 482 |

| Ex | Name | Structure | M + H (m/z) |
|---|---|---|---|
| 97 | 1-({(5S,7S)-3-[(1-cyclohexaneyl-1H-1,2,3-triazol-4-yl)methyl]-2-oxo-1-oxa-3-azaspiro[4.5]dec-7-yl}methyl)-1H-benzimidazole-6-carbonitrile | 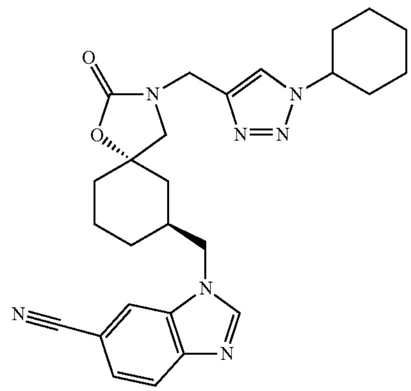 [SMILES: N#Cc1ccc2ncn(C[C@H]3CCC[C@]4(C3)CN(Cc3cn(C5CCCCC5)nn3)C(=O)O4)c2c1] | 474 |
| 98 | 1-{[(5S,7S)-3-({1-[4-cyano-3-(trifluoromethyl)phenyl]-1H-1,2,3-triazol-4-yl}methyl)-2-oxo-1-oxa-C azaspiro[4.5]dec-7-yl]methyl}-1H benzimidazole-6-carbonitrile | 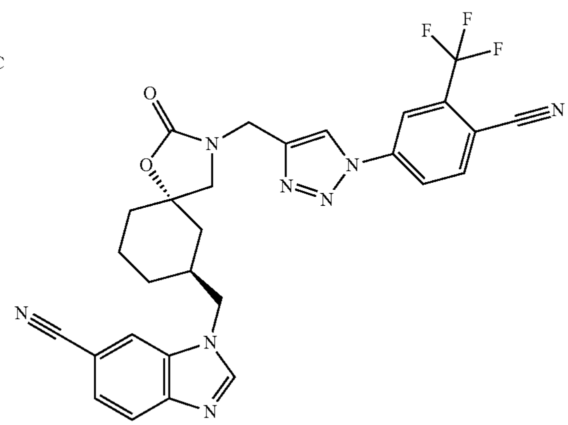 | 561 |
| 99 | 1-[((5S,7S)-3-{[1-(3-chloro-5-cyanophenyl)-1H-1,2,3-triazol-4-yl]methyl}-2-oxo-1-oxa-3-azaspiro[4.5]dec-7-yl)methyl]-1H-benzimidazole-6-carbonitrile | 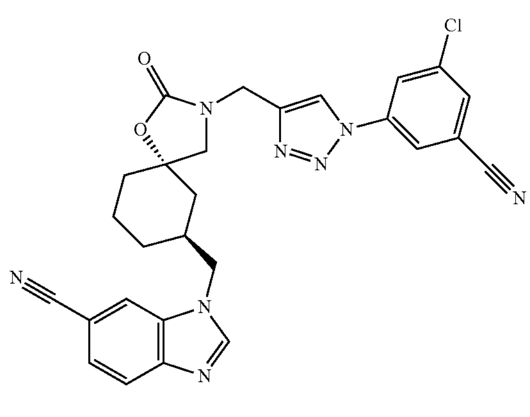 [SMILES: N#Cc1cc(Cl)cc(-n2cc(CN3C[C@@]4(CCC[C@H](Cn5cnc6ccc(C#N)cc65)C4)OC3=O)nn2)c1] | 527 |

| Ex | Name | Structure | M + H (m/z) |
|---|---|---|---|
| 100 | 1-{[(5S,7S)-2-oxo-3-({1-[2-(trifluoromethyl)-4-pyridinyl]-1H-1,2,3-triazol-4-yl}methyl)-1-oxa-3-azaspiro[4.5]dec-7-yl]methyl}-1H-benzimidazole-6-carbonitrile | 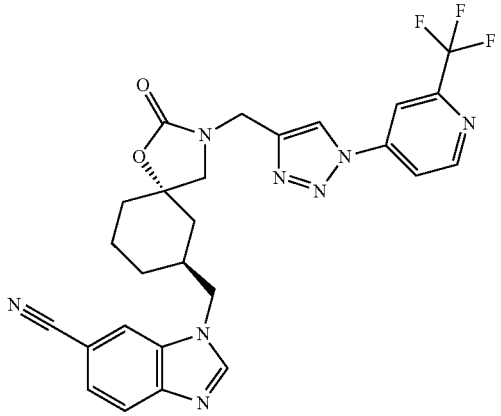 [SMILES: N#Cc1ccc2ncn(C[C@H]3CCC[C@]4(C3)CN(Cc3cn(-c5ccnc(C(F)(F)F)c5)nn3)C(=O)O4)c2c1] | 537 |
| 101 | 1-[((5S,7S)-3-{[1-(3,5-difluorophenyl)-1H-1,2,3-triazol-4-yl]methyl}-2-oxo-1-oxa-3-azaspiro[4.5]dec-7-yl)methyl]-1H-benzimidazole-6-carbonitrile | 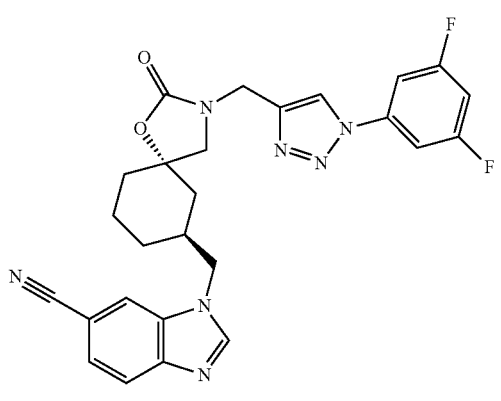 [SMILES: N#Cc1ccc2ncn(C[C@H]3CCC[C@]4(C3)CN(Cc3cn(-c5cc(F)cc(F)c5)nn3)C(=O)O4)c2c1] | 504 |
| 102 | 1-{[(5S,7S)-2-oxo-3-({1-[4-(trifluoromethyl)phenyl]-1H-1,2,3-triazol-4-yl}methyl)-1-oxa-3-azaspiro[4.5]dec-7-yl]methyl}-1H-benzimidazole-6-carbonitrile | 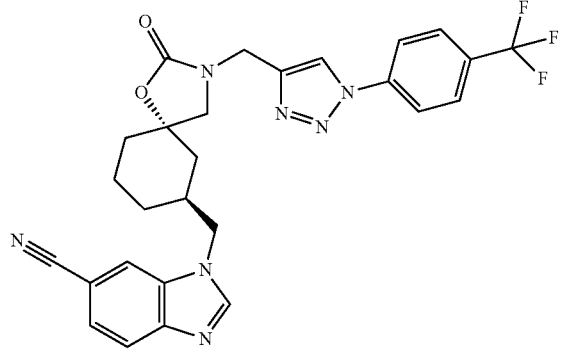 [SMILES: N#Cc1ccc2ncn(C[C@H]3CCC[C@]4(C3)CN(Cc3cn(-c5ccc(C(F)(F)F)cc5)nn3)C(=O)O4)c2c1] | 536 |
| 103 | 1-[((5S,7S)-3-{[1-(3-cyano-5-fluorophenyl)-1H-1,2,3-triazol-4-yl]methyl}-2-oxo-1-oxa-3-azaspiro[4.5]dec-7-yl)methyl]-1H-benzimidazole-6-carbonitrile | 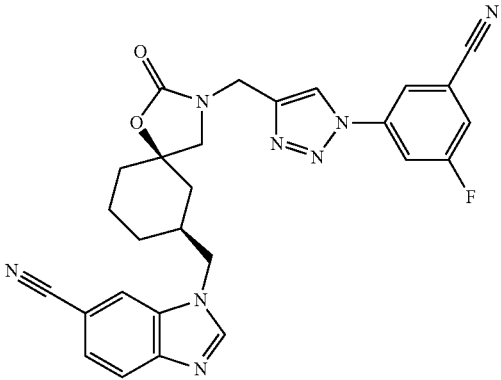 [SMILES: N#Cc1cc(F)cc(-n2cc(CN3C[C@]4(CCC[C@H](Cn5cnc6ccc(C#N)cc65)C4)OC3=O)nn2)c1] | 511 |

-continued

| Ex | Name | Structure | M + H (m/z) |
|---|---|---|---|
| 104 | 1-[((5S,7S)-7-methyl-3-{[1-(1-methylethyl)-1H-1,2,3-triazol-4-yl]methyl}-2-oxo-1-oxa-3-azaspiro[4.5]dec-7-yl)methyl]-1H-benzimidazole-6-carbonitrile | 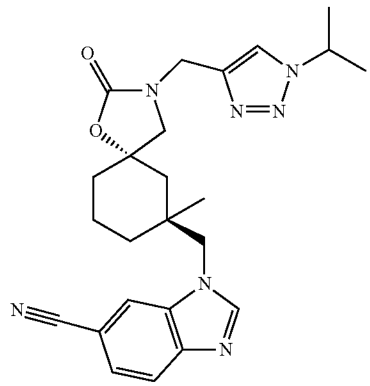 [SMILES: CC(C)n1cc(CN2C[C@@]3(CCC[C@](C)(Cn4cnc5ccc(C#N)cc54)C3)OC2=O)nn1] | 448 |
| 105 | 1-({(5R,7S)-7-methyl-2-oxo-3-[(1-phenyl-1H-1,2,3-triazol-4-yl)methyl]-1-oxa-3-azaspiro[4.5]dec-7-yl}methyl)-1H benzimidazole-6-carbonitrile | 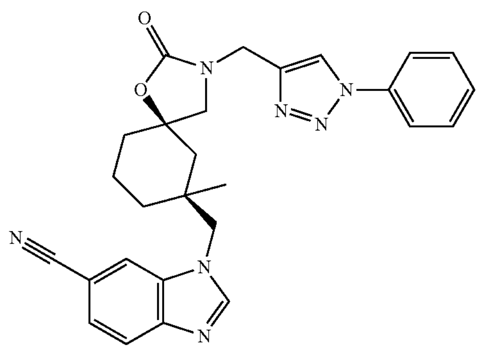 [SMILES: C[C@]1(Cn2cnc3ccc(C#N)cc32)CCC[C@]2(CN(Cc3cn(-c4ccccc4)nn3)C(=O)O2)C1] | 482 |

The following compound was prepared using procedures analogous to those described in Example 9 using appropriately substituted starting materials. As is appreciated by those skilled in the art, this analogous example may involve variations in general reaction conditions.

| Ex | Name | Structure | M + H (m/z) |
|---|---|---|---|
| 106 | 1-[((5S,7S)-3-{[1-(5-chloro-3-pyridinyl)-1H-1,2,3-triazol-4-yl]methyl}-2-oxo-1-oxa-3-azaspiro[4.5]dec-7-yl)methyl]-1H-benzimidazole-6-carbonitrile | 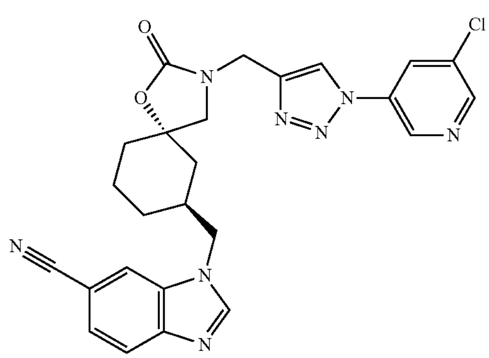 [SMILES: N#Cc1ccc2ncn(C[C@H]3CCC[C@]4(C3)CN(Cc3cn(-c5cncc(Cl)c5)nn3)C(=O)O4)c2c1] | 503 |

The following compounds were prepared using procedures analogous to those described in Example 10 using appropriately substituted starting materials. NCS was used for chlorination while NBS was used for bromination. As is appreciated by those skilled in the art, these analogous examples may involve variations in general reaction conditions.

| Ex | Name | Structure | M + H (m/z) |
|---|---|---|---|
| 107 | 1-(((5S,7S)-3-(4-chloro-3-(2-cyanopropan-2-yl)isoxazol-5-yl)-7-methyl-2-oxo-1-oxa-3-azaspiro[4.5]decan-7-yl)methyl)-1H-benzo[d]imidazole-6-carbonitrile | 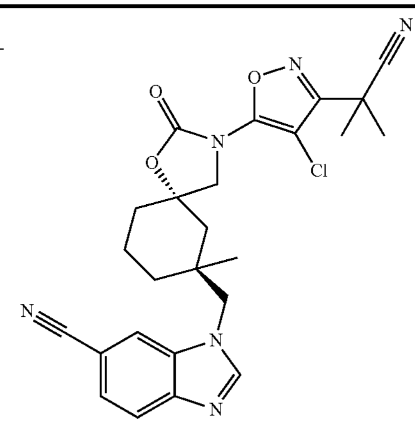 | 492.9 |
| 108 | 1-({(5S,7S)-3-[4-bromo-3-(1,1-dimethylethyl)-5-isoxazolyl]-7-methyl-2-oxo-1-oxa-3-azaspiro[4.5]dec-7-yl}methyl)-1H-benzimidazole-6-carbonitrile | 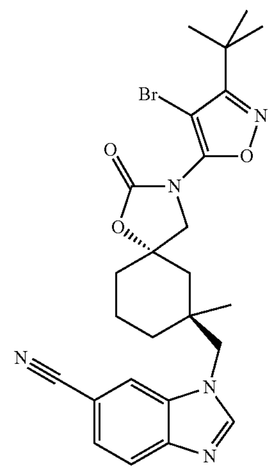 [SMILES: CC(C)(C)c1noc(N2C[C@@]3(CCC[C@](C)(Cn4cnc5ccc(C#N)cc54)C3)OC2=O)c1Br] | 526 |

The following compounds were prepared using procedures analogous to those described in Example 11 using appropriately substituted starting materials. As is appreciated by those skilled in the art, these analogous examples may involve variations in general reaction conditions.

| Ex | Name | Structure | M + H (m/z) |
|---|---|---|---|
| 109 | 1-[{(5S,7S)-7-methyl-3-[2-(methyloxy)-3-pyridinyl]-2-oxo-1-oxa-3-azaspiro[4.5]dec-7-yl}methyl]-1H-benzimidazole-6-carbonitrile | 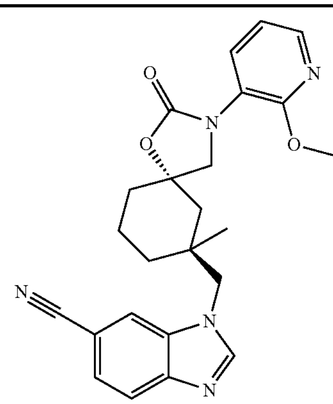 | 432 |

-continued

| Ex | Name | Structure | M + H (m/z) |
|---|---|---|---|
| 110 | 1-({(5S,7S)-3-[2,6-bis(methyloxy)-3-pyridinyl]-7-methyl-2-oxo-1-oxa-3-azaspiro[4.5]dec-7-yl}methyl)-1H-benzimidazole-6-carbonitrile | 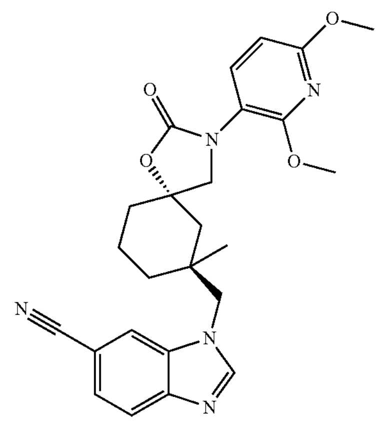 [SMILES: COc1ccc(N2C[C@@]3(CCC[C@](C)(Cn4cnc5ccc(C#N)cc54)C3)OC2=O)c(OC)n1] | 462 |
| 111 | 1-({(5S,7S)-3-[4-methyl-6-(methyloxy)-3-pyridinyl]-2-oxo-1-oxa-3-azaspiro[4.5]dec-7-yl}methyl)-1H-benzimidazole-6-carbonitrile | 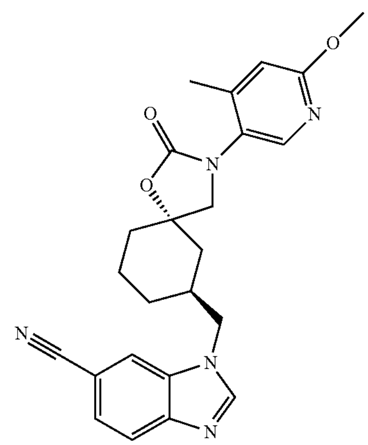 [SMILES: COc1cc(C)c(N2C[C@@]3(CCC[C@H](Cn4cnc5ccc(C#N)cc54)C3)OC2=O)cn1] | 432 |
| 112 | 1-(((7S)-3-(3,5-dichloropyridin-2-yl)-7-methyl-2-oxo-1-oxa-3-azaspiro[4.5]decan-7-yl)methyl)-1H-benzo[d]imidazole-6-carbonitrile | 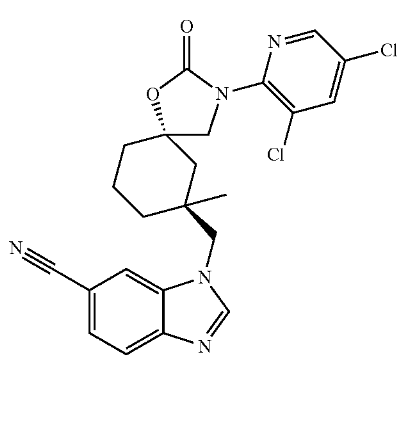 [SMILES: C[C@]1(Cn2cnc3ccc(C#N)cc32)CCC[C@@]2(CN(c3ncc(Cl)cc3Cl)C(=O)O2)C1] | 469.9 |

-continued

| Ex | Name | Structure | M + H (m/z) |
|---|---|---|---|
| 113 | 1-(((5S,7S)-3-(2-ethoxypyrimidin-5-yl)-7-methyl-2-oxo-1-oxa-3-azaspiro[4.5]decan-7-yl)methyl)-1H-benzo[d]imidazole-6-carbonitrile | 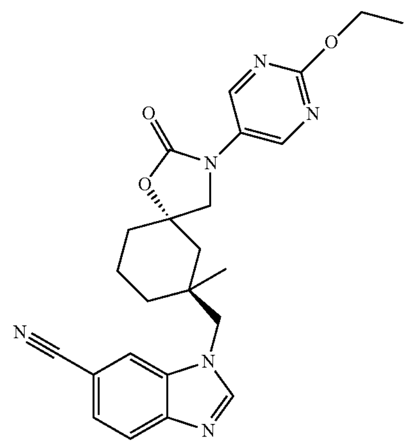 [SMILES: CCOc1ncc(N2C[C@@]3(CCC[C@](C)(Cn4cnc5ccc(C#N)cc54)C3)OC2=O)cn1] | 447 |
| 114 | 1-(((5S,7S)-3-(5-chloro-3-fluoropyridin-2-yl)-7-methyl-2-oxo-1-oxa-3-azaspiro[4.5]decan-7-yl)methyl)-1H-benzo[d]imidazole-6-carbonitrile | 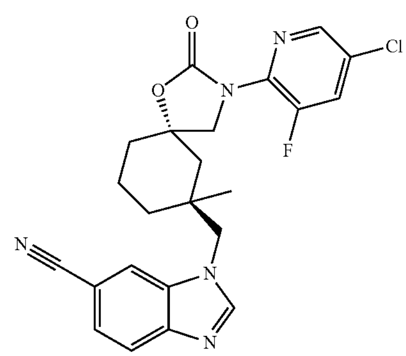 [SMILES: C[C@]1(Cn2cnc3ccc(C#N)cc32)CCC[C@@]2(CN(c3ncc(Cl)cc3F)C(=O)O2)C1] | 454 |
| 115 | 1-(((5S,7S)-7-methyl-2-oxo-3-(5-(trifluoromethyl)pyrazin-2-yl)-1-oxa-3-azaspiro[4.5]decan-7-yl)methyl)-1H-benzo[d]imidazole-6-carbonitrile | 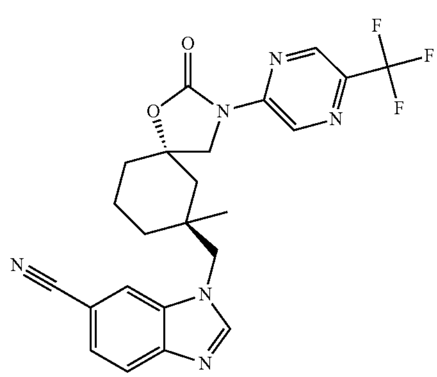 [SMILES: C[C@]1(Cn2cnc3ccc(C#N)cc32)CCC[C@@]2(CN(c3cnc(C(F)(F)F)cn3)C(=O)O2)C1] | 471 |

| Ex | Name | Structure | M + H (m/z) |
|---|---|---|---|
| 116 | 1-(((5S,7S)-3-(2-(tert-butyl)pyrimidin-5-yl)-2-oxo-1-oxa-3-azaspiro[4.5]decan-7-yl)methyl)-1H-benzo[d]imidazole-6-carbonitrile | 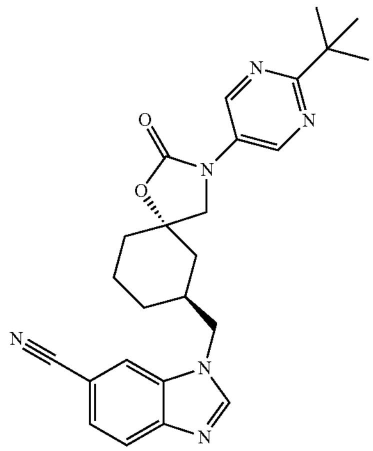 [SMILES: CC(C)(C)c1ncc(N2C[C@@]3(CCC[C@H](Cn4cnc5ccc(C#N)cc54)C3)OC2=O)cn1] | 445.3 |
| 117 | 1-(((5S,7S)-7-methyl-3-(5-methylpyrazin-2-yl)-2-oxo-1-oxa-3-azaspiro[4.5]decan-7-yl)methyl)-1H-benzo[d]imidazole-6-carbonitrile | 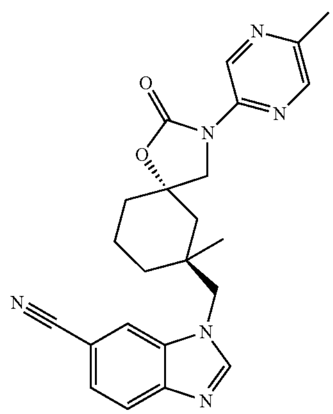 [SMILES: Cc1cnc(N2C[C@@]3(CCC[C@](C)(Cn4cnc5ccc(C#N)cc54)C3)OC2=O)cn1] | 417 |
| 118 | 1-(((5S,7S)-3-(6-ethoxy-4-methylpyridin-3-yl)-7-methyl-2-oxo-1-oxa-3-azaspiro[4.5]decan-7-yl)methyl)-1H-benzo[d]imidazole-6-carbonitrile | 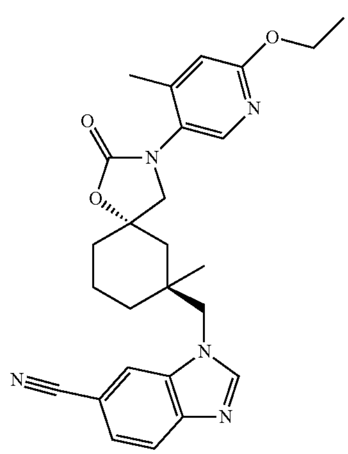 [SMILES: CCOc1cc(C)c(N2C[C@@]3(CCC[C@](C)(Cn4cnc5ccc(C#N)cc54)C3)OC2=O)cn1] | 460.3 |

-continued

| Ex | Name | Structure | M + H (m/z) |
|---|---|---|---|
| 119 | 1-((((5S,7S)-3-(6-chloro-4-methylpyridin-3-yl)-7-methyl-2-oxo-1-oxa-3-azaspiro[4.5]decan-7-yl)methyl)-1H-benzo[d]imidazole-6-carbonitrile | 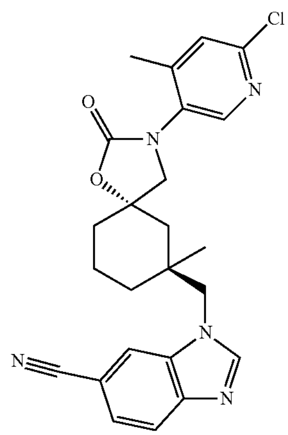 | 450.2 |
| 120 | 1-((((5S,7S)-3-(6-chloro-4-methylpyridin-3-yl)-2-oxo-1-oxa-3-azaspiro[4.5]decan-7-yl)methyl)-1H-benzo[d]imidazole-6-carbonitrile | 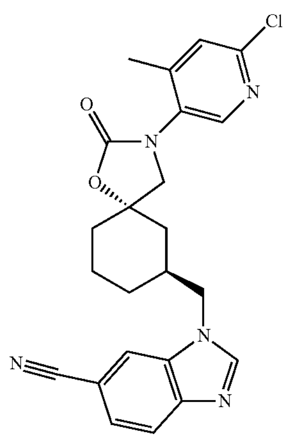 [SMILES: Cc1cc(Cl)ncc1N1C[C@@]2(CCC[C@H](Cn3cnc4ccc(C#N)cc43)C2)OC1=O] | 436.2 |
| 121 | 1-((((5S,7S)-3-(5-chloro-3-methylpyridin-2-yl)-7-methyl-2-oxo-1-oxa-3-azaspiro[4.5]decan-7-yl)methyl)-1H-benzo[d]imidazole-6-carbonitrile | 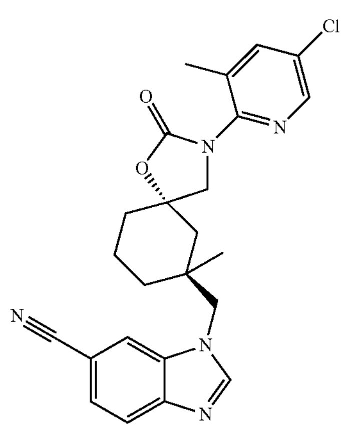 [SMILES: Cc1cc(Cl)cnc1N1C[C@@]2(CCC[C@](C)(Cn3cnc4ccc(C#N)cc43)C2)OC1=O] | 450 |

-continued

| Ex | Name | Structure | M + H (m/z) |
|---|---|---|---|
| 122 | 1-((((5S,7S)-3-(6-chloro-4-methoxypyridin-3-yl)-7-methyl-2-oxo-1-oxa-3-azaspiro[4.5]decan-7-yl)methyl)-1H-benzo[d]imidazole-6-carbonitrile | 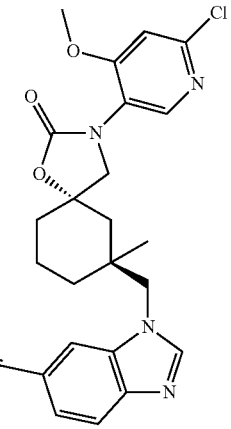 | 466.2 |
| 123 | 1-(((5S,7S)-3-(6-chloro-4-methoxypyridin-3-yl)-2-oxo-1-oxa-3-azaspiro[4.5]decan-7-yl)methyl)-1H-benzo[d]imidazole-6-carbonitrile | 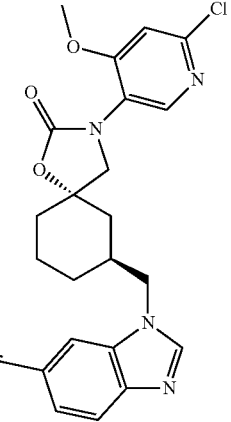 | 452.2 |
| 124 | 1-(((5S,7S)-3-(4-methyl-2-(trifluoromethyl)pyrimidin-5-yl)-2-oxo-1-oxa-3-azaspiro[4.5]decan-7-yl)methyl)-1H-benzo[d]imidazole-6-carbonitrile | 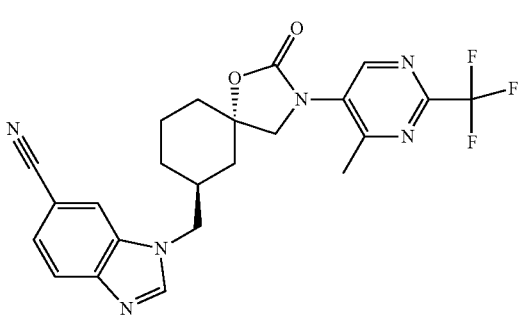 [SMILES: Cc1nc(C(F)(F)F)ncc1N1C[C@@]2(CCC[C@H](Cn3cnc4ccc(C#N)cc43)C2)OC1=O] | 471.1 |
| 125 | 1-(((5S,7S)-3-(6-ethoxy-4-methylpyridin-3-yl)-2-oxo-1-oxa-3-azaspiro[4.5]decan-7-yl)methyl)-5-fluoro-1H-benzo[d]imidazole-6-carbonitrile | 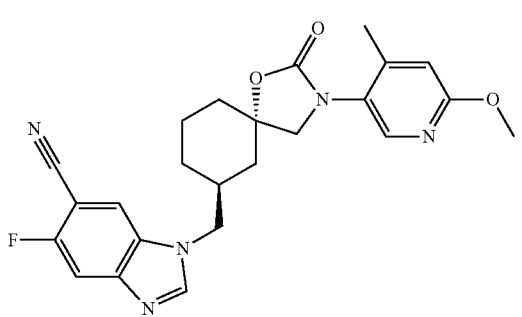 [SMILES: COc1cc(C)c(N2C[C@@]3(CCC[C@H](Cn4cnc5cc(F)c(C#N)cc54)C3)OC2=O)cn1] | 464.2 |

-continued

| Ex | Name | Structure | M + H (m/z) |
|---|---|---|---|
| 126 | 1-(((5S,7S)-3-(2-methoxy-6-methylpyridin-3-yl)-7-methyl-2-oxo-1-oxa-3-azaspiro[4.5]decan-7-yl)methyl)-1H-benzo[d]imidazole-6-carbonitrile | 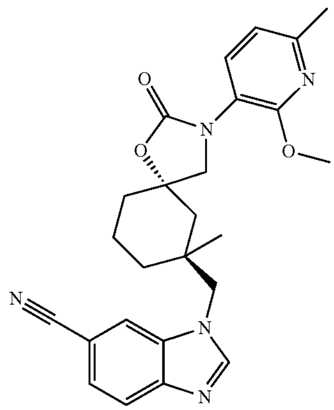 [SMILES: COc1nc(C)ccc1N1C[C@@]2(CCC[C@](C)(Cn3cnc4ccc(C#N)cc43)C2)OC1=O] | 446.2 |
| 127 | 1-(((5S,7S)-3-(3-methoxy-5-methylpyridin-2-yl)-7-methyl-2-oxo-1-oxa-3-azaspiro[4.5]decan-7-yl)methyl)-1H-benzo[d]imidazole-6-carbonitrile | 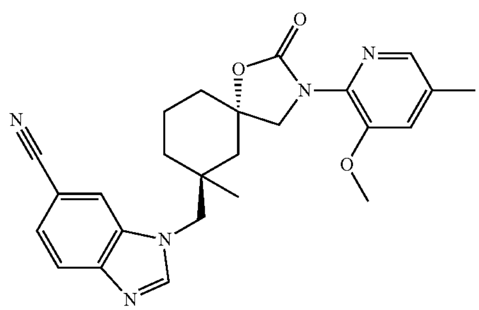 [SMILES: COc1cc(C)cnc1N1C[C@@]2(CCC[C@](C)(Cn3cnc4ccc(C#N)cc43)C2)OC1=O] | 446 |
| 128 | 1-(((5S,7S)-3-(3-chloro-5-methylpyridin-2-yl)-7-methyl-2-oxo-1-oxa-3-azaspiro[4.5]decan-7-yl)methyl)-1H-benzo[d]imidazole-6-carbonitrile | 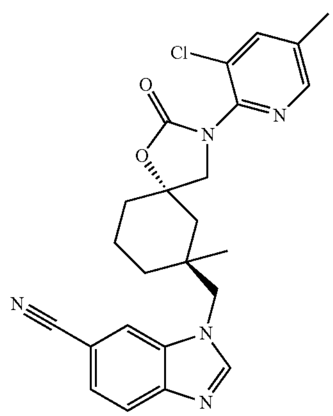 [SMILES: Cc1cnc(N2C[C@@]3(CCC[C@](C)(Cn4cnc5ccc(C#N)cc54)C3)OC2=O)c(Cl)c1] | 450.2 |
| 129 | 1-(((5S,7S)-3-(3-ethylpyridin-2-yl)-7-methyl-2-oxo-1-oxa-3-azaspiro[4.5]decan-7-yl)methyl)-1H-benzo[d]imidazole-6-carbonitrile | 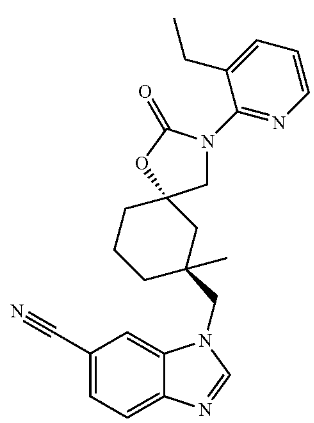 [SMILES: CCc1cccnc1N1C[C@@]2(CCC[C@](C)(Cn3cnc4ccc(C#N)cc43)C2)OC1=O] | 430 |

| Ex | Name | Structure | M + H (m/z) |
|---|---|---|---|
| 130 | 1-(((5S,7S)-3-(3,5-dimethylpyrazin-2-yl)-7-methyl-2-oxo-1-oxa-3-azaspiro[4.5]decan-7-yl)methyl)-1H-benzo[d]imidazole-6-carbonitrile | 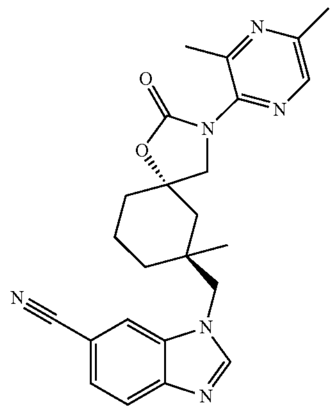 [SMILES: Cc1cnc(N2C[C@@]3(CCC[C@](C)(Cn4cnc5ccc(C#N)cc54)C3)OC2=O)c(C)n1] | 431 |
| 131 | 1-(((5S,7S)-3-(3-methyl-5-(trifluoromethyl)pyrazin-2-yl)-2-oxo-1-oxa-3-azaspiro[4.5]decan-7-yl)methyl)-1H-benzo[d]imidazole-6-carbonitrile | 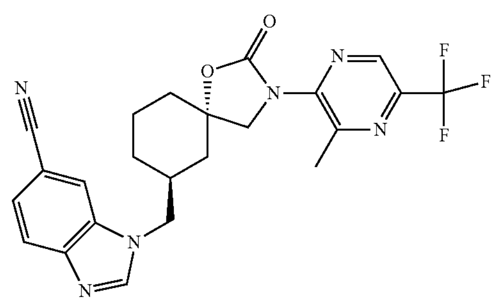 [SMILES: Cc1nc(C(F)(F)F)cnc1N1C[C@@]2(CCC[C@H](Cn3cnc4ccc(C#N)cc43)C2)OC1=O] | 471.2 |
| 132 | 1-(((5S,7S)-3-(6-methoxy-5-methylpyridin-3-yl)-7-methyl-2-oxo-1-oxa-3-azaspiro[4.5]decan-7-yl)methyl)-1H-benzo[d]imidazole-6-carbonitrile | 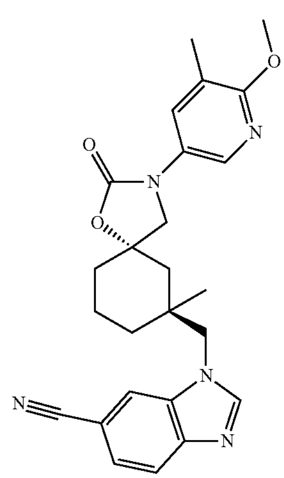 [SMILES: COc1ncc(N2C[C@@]3(CCC[C@](C)(Cn4cnc5ccc(C#N)cc54)C3)OC2=O)cc1C] | 446 |

The following compounds were prepared using procedures analogous to those described in Example 15 using appropriately substituted starting materials. As is appreciated by those skilled in the art, these analogous examples may involve variations in general reaction conditions.

| Ex | Name | Structure | M + H (m/z) |
|---|---|---|---|
| 133 | 1-(((5S,7S)-3-(6-(2-cyanopropan-2-yl)pyridin-3-yl)-7-methyl-2-oxo-1-oxa-3-azaspiro[4.5]decan-7-yl)methyl]-1H-benzo[d]imidazole-6-carbonitrile | 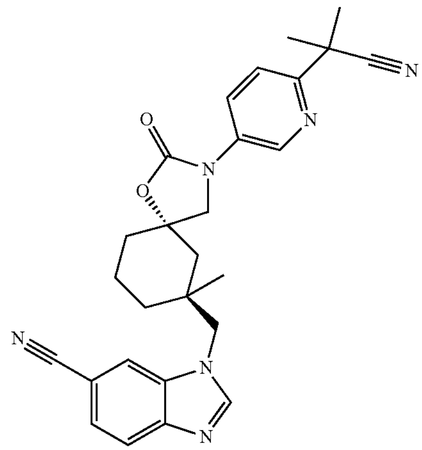 [SMILES: CC(C)(C#N)c1ccc(N2C[C@@]3(CCC[C@](C)(Cn4cnc5ccc(C#N)cc54)C3)OC2=O)cn1] | 469.3 |
| 134 | 1-(((5S,7S)-3-(2-(tert-butyl)pyrimidin-5-yl)-7-methyl-2-oxo-1-oxa-3-azaspiro[4.5]decan-7-yl)methyl)-1H-benzo[d]imidazole-6-carbonitrile | 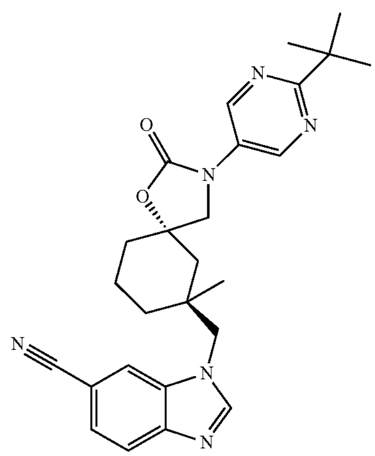 [SMILES: CC(C)(C)c1ncc(N2C[C@@]3(CCC[C@](C)(Cn4cnc5ccc(C#N)cc54)C3)OC2=O)cn1] | 459.3 |

The following compounds were prepared using procedures analogous to those described in Example 17 using appropriately substituted starting materials. As is appreciated by those skilled in the art, these analogous examples may involve variations in general reaction conditions.

| Ex | Name | Structure | M + H (m/z) |
|---|---|---|---|
| 135 | 1-({(5S,7S)-7-methyl-3-[5-(methyloxy)-2-pyridinyl]-2-oxo-1-oxa-3-azaspiro[4.5]dec-7-yl}methyl)-1H-benzimidazole-6-carbonitrile | 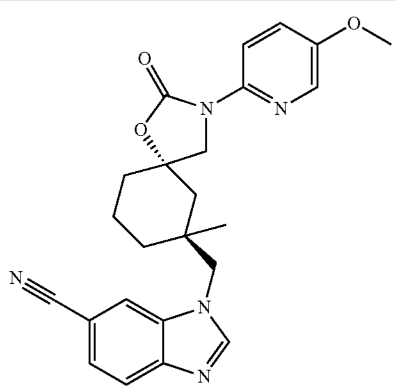 [SMILES: COc1ccc(N2C[C@@]3(CCC[C@](C)(Cn4cnc5ccc(C#N)cc54)C3)OC2=O)nc1] | 432 |

-continued

| Ex | Name | Structure | M + H (m/z) |
|---|---|---|---|
| 136 | 1-({(5S,7S)-3-[6-(ethyloxy)-3-pyridazinyl]-7-methyl-2-oxo-1-oxa-3-azaspiro[4.5]dec-7-yl}methyl)-1H-benzimidazole-6-carbonitrile | 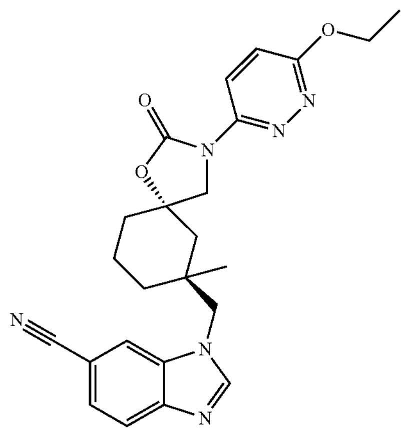 [SMILES: CCOc1ccc(N2C[C@@]3(CCC[C@](C)(Cn4cnc5ccc(C#N)cc54)C3)OC2=O)nn1] | 447 |
| 137 | 1-{[(5S,7S)-3-(3-chloro-2-pyridinyl)-7-methyl-2-oxo-1-oxa-3-azaspiro[4.5]dec-7-yl]methyl}-1H-benzimidazole-6-carbonitrile | 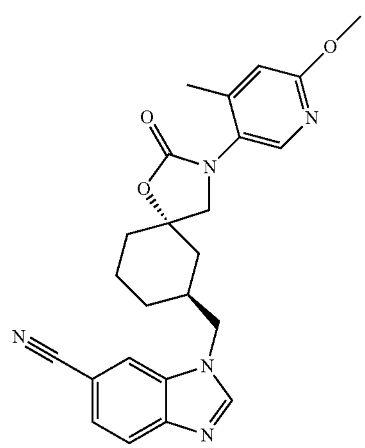 [SMILES: COc1cc(C)c(N2C[C@@]3(CCC[C@H](Cn4cnc5ccc(C#N)cc54)C3)OC2=O)cn1] | 436 |
| 138 | 1-({(5S,7S)-7-methyl-3-[3-(methyloxy)-2-pyridinyl]-2-oxo-1-oxa-3-azaspiro[4.5]dec-7-yl}methyl)-1H-benzimidazole-6-carbonitrile | 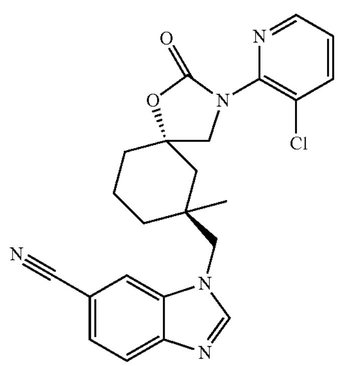 [SMILES: C[C@]1(Cn2cnc3ccc(C#N)cc32)CCC[C@@]2(CN(c3ncccc3Cl)C(=O)O2)C1] | 432 |

| Ex | Name | Structure | M + H (m/z) |
|---|---|---|---|
| 139 | 1-({(5S,7S)-7-methyl-2-oxo-3-[6-(trifluoromethyl)-3-pyridinyl]-1-oxa-3-azaspiro[4.5]dec-7-yl}methyl)-1H-benzimidazole-6-carbonitrile | 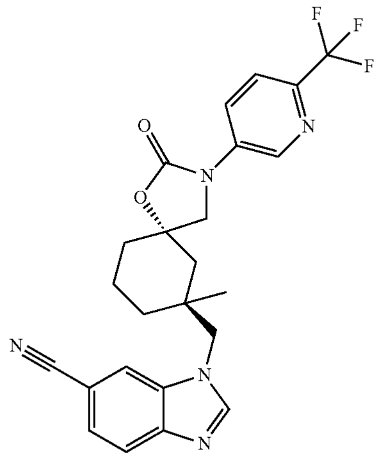 [SMILES: C[C@]1(Cn2cnc3ccc(C#N)cc32)CCC[C@@]2(CN(c3ccc(C(F)(F)F)nc3)C(=O)O2)C1] | 470 |
| 140 | 1-(((5S,7S)-7-methyl-3-(6-methylpyridin-3-yl)-2-oxo-1-oxa-3-azaspiro[4.5]decan-7-yl)methyl)-1H-benzo[d]imidazole-6-carbonitrile | 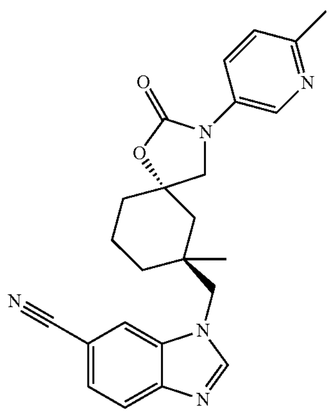 [SMILES: Cc1ccc(N2C[C@@]3(CCC[C@](C)(Cn4cnc5ccc(C#N)cc54)C3)OC2=O)cn1] | 416.2 |

The following compounds were prepared using procedures analogous to those described in Example 22 using appropriately substituted starting materials. As is appreciated by those skilled in the art, these analogous examples may involve variations in general reaction conditions.

| Ex | Name | Structure | M + H (m/z) |
|---|---|---|---|
| 141 | 1-({(5S,7S)-3-[4,6-bis(methyloxy)-3-pyridinyl]-2-oxo-1-oxa-3-azaspiro[4.5]dec-7-yl}methyl)-1H-benzimidazole-6-carbonitrile | 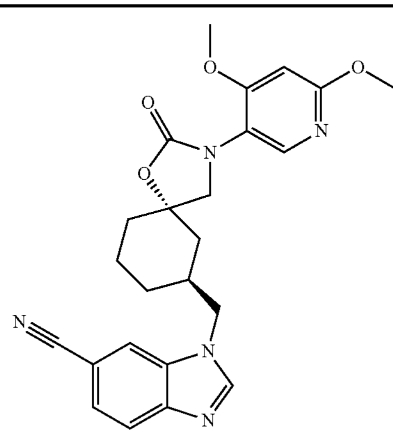 | 448.2 |

| Ex | Name | Structure | M + H (m/z) |
|---|---|---|---|
| 142 | 1-({(5S,7S)-3-[6-(1-methylethyl)-3-pyridinyl]-2-oxo-1-oxa-3-azaspiro[4.5]dec-7-yl}methyl)-1H-benzimidazole-6-carbonitrile | 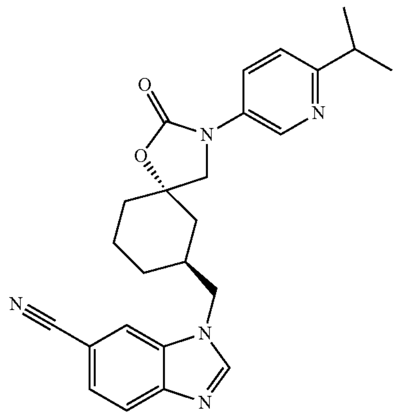 [SMILES: CC(C)c1ccc(N2C[C@@]3(CCC[C@H](Cn4cnc5ccc(C#N)cc54)C3)OC2=O)cn1] | 430.3 |

The following compounds were prepared using procedures analogous to those described in Example 26 using appropriately substituted starting materials. As is appreciated by those skilled in the art, these analogous examples may involve variations in general reaction conditions.

| Ex | Name | Structure | M + H (m/z) |
|---|---|---|---|
| 143 | 1-((7-(hydroxymethyl)-3-(6-methoxy-4-methylpyridin-3-yl)-2-oxo-1-oxa-3-azaspiro[4.5]decan-7-yl)methyl)-1H-benzo[d]imidazole-6-carbonitrile | 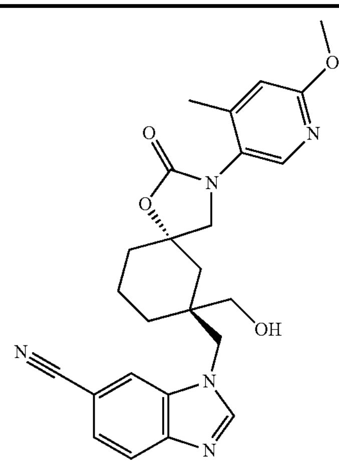 | 462 |
| 144 | 1-(((5S,7S)-7-methyl-2-oxo-3-(4-(trifluoromethyl)pyridin-3-yl)-1-oxa-3-azaspiro[4.5]decan-7-yl)methyl)-1H-benzo[d]imidazole-6-carbonitrile | 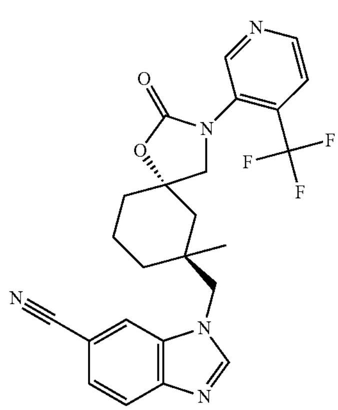 [SMILES: C[C@]1(Cn2cnc3ccc(C#N)cc32)CCC[C@@]2(CN(c3cnccc3C(F)(F)F)C(=O)O2)C1] | 470 |

| Ex | Name | Structure | M + H (m/z) |
|---|---|---|---|
| 145 | 1-(((5S,7S)-3-(2-(dimethylamino)pyrimidin-5-yl)-7-methyl-2-oxo-1-oxa-3-azaspiro[4.5]decan-7-yl)methyl)-1H-benzo[d]imidazole-6-carbonitrile | 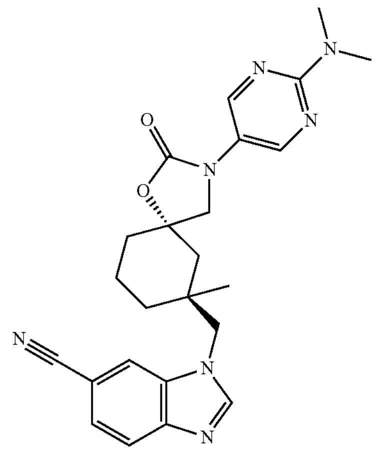 [SMILES: CN(C)c1ncc(N2C[C@@]3(CCC[C@](C)(Cn4cnc5ccc(C#N)cc54)C3)OC2=O)cn1] | 446 |
| 146 | 1-(((5S,7S)-7-methyl-3-(4-methylpyridin-3-yl)-2-oxo-1-oxa-3-azaspiro[4.5]decan-7-yl)methyl)-1H-benzo[d]imidazole-6-carbonitrile | 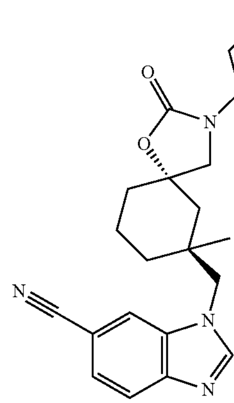 | 416 |

Example 147

1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

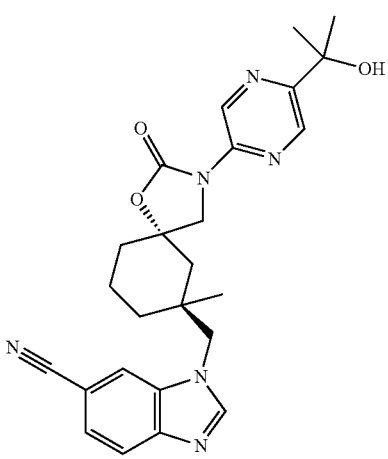 [SMILES: CC(C)(O)c1cnc(N2C[C@@]3(CCC[C@](C)(Cn4cnc5ccc(C#N)cc54)C3)OC2=O)cn1]

Route 1

2-(5-bromopyrazin-2-yl)propan-2-ol

To a solution of methyl 5-bromopyrazine-2-carboxylate (0.250 g, 1.152 mmol) in Tetrahydrofuran (THF) (6.53 ml) at 0° C. under nitrogen was added methylmagnesium bromide, 3 M in diethyl ether (1.152 ml, 3.46 mmol) slowly. After 1 hour at 0° C., 2N HCl (15 mL) was added slowly. The mixture was extracted with ethyl acetate (2×15 mL). The combined organic extracts were dried ($Na_2SO_4$), filtered, and concentrated. The residue was purified using silica gel chromatography CISCO): 10-30% ethyl acetate/hexanes (20 min), 12 gram silica gel column. Obtained 2-(5-bromopyrazin-2-yl)propan-2-ol as an orange oil (71 mg, 24%). MS (m/z) 216.9 (M+).

1-(((5S,7S)-3-(5-(2-Hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile To a light yellow solution of 1-(((5S,7S)-7-methyl-2-oxo-1-oxa-3-azaspiro[4.5]decan-7-yl)methyl)-1H-benzo[d]imidazole-6-carbonitrile (0.050 g, 0.154 mmol) in 1,4-dioxane (2.052 mL) was added copper(I) iodide (2.94 mg, 0.015 mmol), potassium phosphate tribasic (0.065 g, 0.308 mmol), trans-1,2-diaminocyclohexane (3.71 µL, 0.031 mmol), and 2-(5-bromopyrazin-2-yl)propan-2-ol (0.040 g, 0.185 mmol). The reaction mixture was heated at 100° C. for 15 h. Then, additional copper(I) iodide (2.94 mg, 0.015 mmol) and trans- 1,2-diaminocyclohexane (3.71 μL, 0.031 mmol) were added and stirred for an additional hour at 100° C. Additional copper (I) iodide (2.94 mg, 0.015 mmol) and trans-1,2-diaminocyclohexane (3.71 μL, 0.031 mmol) were then added and stirred for an additional 3 h at 100° C. The reaction was then cooled to RT and CH$_3$CN (5 mL) was added and the mixture vacuum filtered using a Hirsch funnel. The solid was rinsed with CH$_3$CN (3×2 mL) and the filtrate was loaded onto florisil and purified using silica gel chromatography CISCO): 0.5-2% MeOH/DCM (30 min), 12 g silica gel column. The product eluted at 19 minutes to obtain 1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile as an orange foam (43 mg, 38% yield). $^1$H NMR (400 MHz, DMSO-d$_6$) δ 9.18 (s, 1H), 8.59 (s, 1H), 8.47 (s, 1H), 8.37 (s, 1H), 7.82 (d, J=8.28 Hz, 1H), 7.58 (d, J=8.28 Hz, 1H), 5.41 (s, 1H), 4.16 (br. s., 2H), 3.77-3.96 (m, 2H), 1.98 (d, J=7.03 Hz, 1H), 1.82-1.93 (m, 1H), 1.72 (d, J=14.56 Hz, 2H), 1.58-1.67 (m, 2H), 1.28-1.57 (m, 8H), 1.06 (s, 3H). MS (m/z) 461.0 (M+H$^+$).

Route 2

2-(5-chloropyrazin-2-yl)propan-2-ol

A well-stirring solution of methyl 5-chloropyrazine-2-carboxylate (23.5 g, 136 mmol) in Tetrahydrofuran (THF) (172 ml) under nitrogen was cooled to −10° C. and became a thick tan suspension. Added methylmagnesium bromide, 3M in diethyl ether (100 ml, 300 mmol) slowly making sure the temperature did not rise above 0° C. After 1 hour, the reaction now at 0° C. was quenched with saturated NH$_4$Cl (100 mL) slowly, followed by EtOAc (100 mL), and the dark mixture was stirred overnight. The mixture was diluted with 400 mL water and 100 mL EtOAc, and the layers were separated. The aqueous layer was extracted with EtOAc (2×300 mL). The combined EtOAc extracts were dried over MgSO$_4$, filtered, and concentrated to give a dark residue, which was divided into two batches. Each batch was loaded (with 10% CH$_2$Cl$_2$/cyclohexane) onto a pre-equilibrated (with hexanes) 330 g silica cartridge and purified using normal phase chromatography CISCO): 0-25% ethyl acetate/hexanes (30 min), 25% (15 min). Product began eluting at 33 minutes. Product fractions were concentrated to afford 2-(5-chloropyrazin-2-yl)propan-2-ol (6.232 g, 25%) as a low viscosity orange oil. MS (m/z) 173.1 (M+H$^+$).

1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile Two identical reactions were set up: To a 1 L flask containing 2-(5-chloropyrazin-2-yl)propan-2-ol (18.29 g, 106 mmol) was added reagents in the following order: first potassium phosphate tribasic (36.0 g, 170 mmol), followed by 1-(((5S,7S)-7-methyl-2-oxo-1-oxa-3-azaspiro[4.5]decan-7-yl)methyl)-1H-benzo[d]imidazole-6-carbonitrile (27.5 g, 85 mmol). Next 1,4-dioxane (424 mL) was added followed by N1,N2-dimethylethane-1,2-diamine (7.47 g, 85 mmol). To the resulting white slurry was added copper(I) iodide (8.07 g, 42.4 mmol). The slurry was put under nitrogen and heated to 100° C. (Reaction 1=44 h, Reaction 2=68 h). After completion, the mixture was cooled to RT, diluted with DCM and water and 7N NH$_3$ in MeOH and allowed to stir for 10 min. The layers were separated and the aqueous layer was extracted with DCM (2×). The combined DCM extracts were diluted with 7N NH$_3$ in MeOH (300 mL) (to remove residual copper ions), and then washed with water (2×500 mL), and dried over Na$_2$SO$_4$, filtered, and concentrated. Each residue was purified on the ISCO: 4×330 g silica, 0-10% MeOH/DCM over 10 CV. Fractions containing product were concentrated, dissolved in DCM, and washed one final time with water/7N NH$_3$ in MeOH to remove any leftover copper. The resulting layers were separated, the aqueous layer extracted with DCM (2×), and the combined DCM extracts were dried over Na$_2$SO$_4$, filtered, and concentrated. The residue was then azeotroped with MeCN (300 mL) and then diluted to a volume of ~650 mL. The solution was heated to 70° C. (all solids went into solution affording a yellow solution), then allowed to cool to RT with stirring and crystals started to form. After stirring at RT for ~2 h, the slurry was diluted with 2 L water. Stirring was continued overnight before the slurry was filtered and the solids dried under reduced pressure to 1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (71.3 g, 91%) as a white solid. MS (m/z) 461.2 (M+H$^+$) $^1$H NMR (400 MHz, DMSO-d$_6$) δ 9.18 (s, 1H), 8.59 (s, 1H), 8.47 (s, 1H), 8.37 (s, 1H), 7.82 (d, J=8.28 Hz, 1H), 7.58 (d, J=8.28 Hz, 1H), 5.41 (s, 1H), 4.16 (br. s., 2H), 3.77-3.96 (m, 2H), 1.98 (d, J=7.03 Hz, 1H), 1.82-1.93 (m, 1H), 1.72 (d, J=14.56 Hz, 2H), 1.58-1.67 (m, 2H), 1.28-1.57 (m, 8H), 1.06 (s, 3H). MS (m/z) 461.0 (M+H$^+$).

The following compounds were prepared using procedures analogous to those described in Example 26 using appropriately substituted starting materials. As is appreciated by those skilled in the art, these analogous examples may involve variations in general reaction conditions.

| Ex | Name | Structure | M + H (m/z) |
|---|---|---|---|
| 148 | 1-(((5S,7S)-3-(2-(2-hydroxypropan-2-yl)pyrimidin-5-yl)-7-methyl-2-oxo-1-oxa-3-azaspiro[4.5]decan-7-yl)methyl)-1H-benzo[d]imidazole-6-carbonitrile | 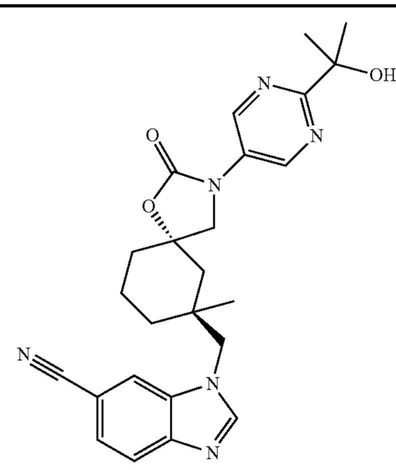 | 461 |

-continued

| Ex | Name | Structure | M + H (m/z) |
|---|---|---|---|
| 149 | 1-(((5S,7S)-3-(4-methoxypyridin-3-yl)-7-methyl-2-oxo-1-oxa-3-azaspiro[4.5]decan-7-yl)methyl)-1H-benzo[d]imidazole-6-carbonitrile | 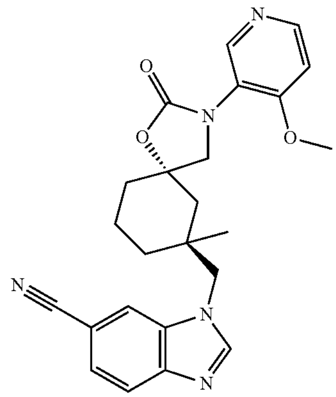 [SMILES: COc1ccncc1N1C[C@@]2(CCC[C@](C)(Cn3cnc4ccc(C#N)cc43)C2)OC1=O] | 432 |
| 150 | 1-(((5S,7S)-3-(5-(dimethylamino)pyrazin-2-yl)-7-methyl-2-oxo-1-oxa-3-azaspiro[4.5]decan-7-yl)methyl)-1H-benzo[d]imidazole-6-carbonitrile | 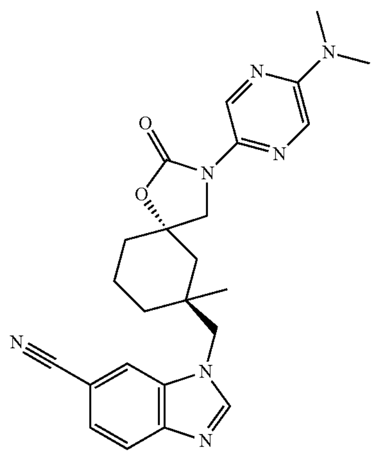 [SMILES: CN(C)c1cnc(N2C[C@@]3(CCC[C@](C)(Cn4cnc5ccc(C#N)cc54)C3)OC2=O)cn1] | 446 |

The following compounds were prepared using procedures analogous to those described in Example 27 using appropriately substituted starting materials. As is appreciated by those skilled in the art, these analogous examples may involve variations in general reaction conditions.

| Ex | Name | Structure | M + H (m/z) |
|---|---|---|---|
| 151 | 1-{[(5S,7S)-2-oxo-3-(thieno[2,3-b]pyridin-3-ylmethyl)-1-oxa-3-azaspiro[4.5]dec-7-yl]methyl}-1H-benzimidazole-6-carbonitrile | 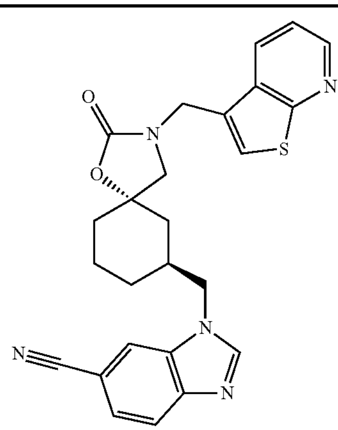 | 458.2 |

| Ex | Name | Structure | M + H (m/z) |
|---|---|---|---|
| 152 | 1-{[(trans)-7-methyl-2-oxo-3-(thieno[2,3-b]pyridin-3-ylmethyl)-1-oxa-3-azaspiro[4.5]dec-7-yl]methyl}-1H-benzimidazole-6-carbonitrile | 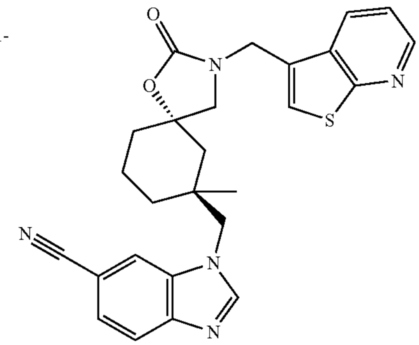 | 472.2 |
| 153 | 1-({(5S,7S)-3-[(3-bromothieno[2(3-b]pyridin-2-yl)methyl]-2-oxo-1-oxa-3-azaspiro[4.5]dec-7-yl}methyl)-1H-benzimidazole-6-carbonitrile | 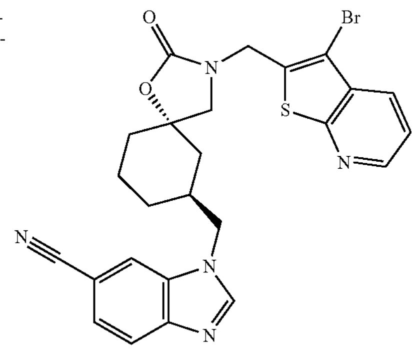 | 536.1 |

35

The following compound was prepared using procedures analogous to those described in Example 28 using appropriately substituted starting materials. As is appreciated by those skilled in the art, these analogous examples may involve variations in general reaction conditions.

| Ex | Name | Structure | M + H (m/z) |
|---|---|---|---|
| 154 | 1-{[(5S,7S)-3-(2-methyl-2-{3-[1-(methyloxy)ethyl]-1,2,4-oxadiazol-5-yl}propyl)-2-oxo-1-oxa-3-azaspiro[4.5]dec-7-yl]methyl}-1H-benzimidazole-6-carbonitrile | 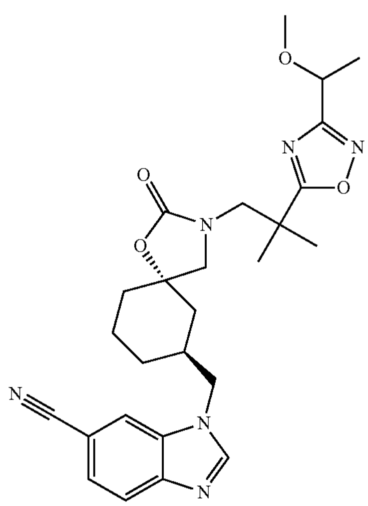 [SMILES: COC(C)c1noc(C(C)(C)CN2C[C@@]3(CCC[C@H](Cn4cnc5ccc(C#N)cc54)C3)OC2=O)n1] | 493.2 |

Example 155

1-(((5S,7S)-3-((5-ethoxypyrazin-2-ylmethyl)-7-methyl-2-oxo-1-oxa-3-azaspiro[4.5]decan-7-yl)methyl)-1H-benzo[d]imidazole-6-carbonitrile

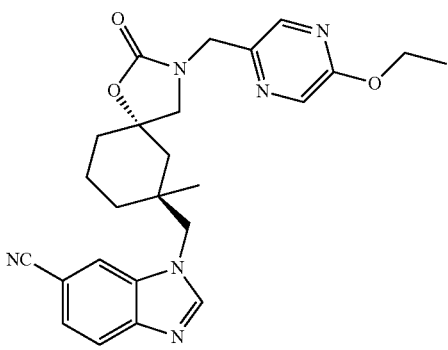 [SMILES: CCOc1cnc(CN2C[C@@]3(CCC[C@](C)(Cn4cnc5ccc(C#N)cc54)C3)OC2=O)cn1]

2-(bromomethyl)-5-ethoxypyrazine

A mixture of 2-ethoxy-5-methylpyrazine (0.86 g, 6.22 mmol), NBS (1.440 g, 8.09 mmol), and diphenylperoxyanhydride (0.151 g, 0.622 mmol) in carbon tetrachloride (20 mL) was heated to 80° C. overnight. Cooled to RT, diluted with saturated NaHCO$_3$, and extracted with ethyl acetate (3×). The combined organic extracts were washed with saturated NaCl (2×), dried over Na$_2$SO$_4$, filtered, and concentrated. The residue was purified via ISCO (40 g silica, 40 mL/min, 0-30% EtOAc/Hexanes over 25 min) to afford 2-(bromomethyl)-5-ethoxypyrazine (430 mg, 32%). MS (m/z) 217.0 (M+).

1-(((5S,7S)-3-((5-ethoxypyrazin-2-yl)methyl)-7-methyl-2-oxo-1-oxa-3-azaspiro[4.5]decan-7-yl)methyl)-1H-benzo[d]imidazole-6-carbonitrile To a solution of 1-{[(5S,7S)-7-methyl-2-oxo-1-oxa-3-azaspiro[4.5]dec-7-yl]methyl}-1H-benzimidazole-6-carbonitrile (150 mg, 0.462 mmol) in N,N-Dimethylformamide (DMF) (2 mL) was added 60% sodium hydride in mineral oil (24.04 mg, 0.601 mmol) and stirred for 30 minutes. To the mixture was added 2-(bromomethyl)-5-ethoxypyrazine (120 mg, 0.555 mmol) and stirred overnight. The reaction was diluted with saturated NH$_4$Cl and extracted with ethyl acetate (3×). The combined organic extracts were washed with saturated NaCl (2×), dried over Na$_2$SO$_4$, filtered, and concentrated. The residue was purified via silica gel ISCO chromatography (40 g silica gel, 40 mL/min, 0-10% MeOH/CH$_2$Cl$_2$ over 25 min) to afford 1-(((5S,7S)-3-((5-ethoxypyrazin-2-yl)methyl)-7-methyl-2-oxo-1-oxa-3-azaspiro[4.5]decan-7-yl)methyl)-1H-benzo[d]imidazole-6-carbonitrile (125 mg, 56%). $^1$H NMR (400 MHz, DMSO-d$_6$) δ 8.45 (s, 1H), 8.35 (d, J=0.75 Hz, 1H), 8.21 (d, J=1.25 Hz, 1H), 8.13 (d, J=1.51 Hz, 1H), 7.83 (d, J=8.28 Hz, 1H), 7.59 (dd, J=8.28, 1.51 Hz, 1H), 4.31-4.41 (m, 4H), 4.12 (s, 2H), 3.21 (dd, J=23.09, 9.03 Hz, 2H), 1.81 (d, J=13.30 Hz, 1H), 1.49-1.74 (m, 4H), 1.22-1.46 (m, 6H), 1.02 (s, 3H). MS (m/z) 461.2 (M+H$^+$).

The following compounds were prepared using procedures analogous to those described in Example 155 using appropriately substituted starting materials. As is appreciated by those skilled in the art, these analogous examples may involve variations in general reaction conditions.

| Ex | Name | Structure | M + H (m/z) |
|---|---|---|---|
| 156 | 1-(((5S,7S)-3-((4-ethoxypyridin-2-yl)methyl)-7-methyl-2-oxo-1-oxa-3-azaspiro[4.5]decan-7-yl)methyl)-1H-benzo[d]imidazole-6-carbonitrile | 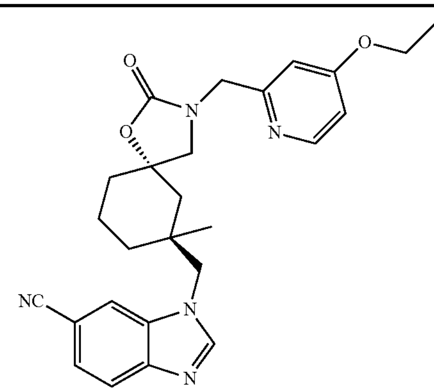 | 460.2 |
| 157 | 1-(((5S,7S)-3-((5-ethoxypyridin-2-yl)methyl)-7-methyl-2-oxo-1-oxa-3-azaspiro[4.5]decan-7-yl)methyl)-1H-benzo[d]imidazole-6-carbonitrile | 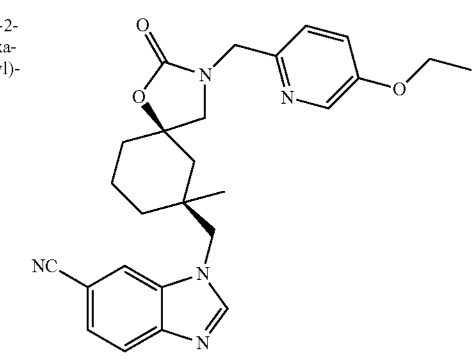 | 460.2 |

-continued

| Ex | Name | Structure | M + H (m/z) |
|---|---|---|---|
| 158 | 1-(((5S,7S)-3-((4-fluoropyridin-2-yl)methyl)-7-methyl-2-oxo-1-oxa-3-azaspiro[4.5]decan-7-yl)methyl)-1H-benzo[d]imidazole-6-carbonitrile | 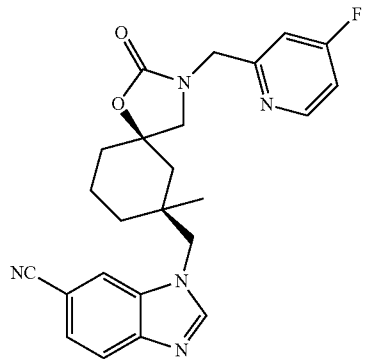 [SMILES: C[C@]1(Cn2cnc3ccc(C#N)cc32)CCC[C@]2(CN(Cc3cc(F)ccn3)C(=O)O2)C1] | 434.2 |
| 159 | 1-(((5S,7S)-3-((5-fluoropyridin-2-yl)methyl)-7-methyl-2-oxo-1-oxa-3-azaspiro[4.5]decan-7-yl)methyl)-1H-benzo[d]imidazole-6-carbonitrile | 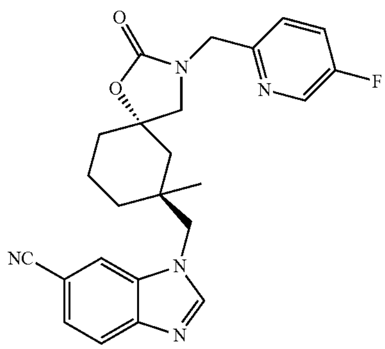 [SMILES: C[C@]1(Cn2cnc3ccc(C#N)cc32)CCC[C@@]2(CN(Cc3ccc(F)cn3)C(=O)O2)C1] | 434.2 |

Example 160

1-(((5S,7S)-7-methyl-3-((4-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile

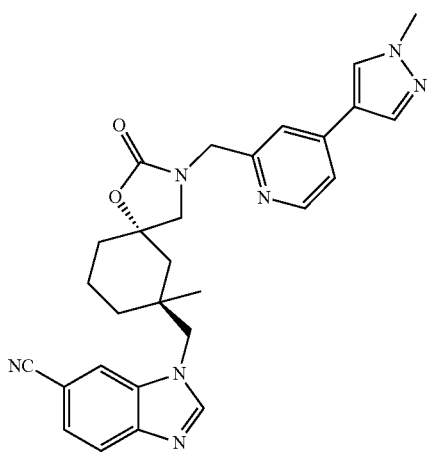 [SMILES: Cn1cc(-c2ccnc(CN3C[C@@]4(CCC[C@](C)(Cn5cnc6ccc(C#N)cc65)C4)OC3=O)c2)cn1]

4-bromo-2-(bromomethyl)pyridine

A mixture of 4-bromo-2-methylpyridine (2.0 g, 11.63 mmol), NBS (2.69 g, 15.11 mmol), and diphenylperoxyanhydride (0.282 g, 1.163 mmol) in carbon tetrachloride (50 mL) was heated to 100° C. overnight. Cooled to RT, diluted with saturated NaHCO$_3$, and extracted with ethyl acetate (3×). The combined organic extracts were washed with saturated NaCl (2×), dried over Na$_2$SO$_4$, filtered, and concentrated. The residue was purified via silica gel chromatography (ISCO, 120 g silica, 60 mL/min, 0-80% EtOAc/Hexanes over 45 min) to afford 4-bromo-2-(bromomethyl)pyridine (1.05 g, 36%). MS (m/z) 251.9.

1-(((5S,7S)-3-((4-bromopyridin-2-yl)methyl)-7-methyl-2-oxo-1-oxa-3-azasbiro[4.5]decan-7-yl)methyl)-1H-benzo[d]imidazole-6-carbonitrile To a solution of 1-{[(5S,7S)-7-methyl-2-oxo-1-oxa-3-azaspiro[4.5]dec-7-yl]methyl}-1H-benzimidazole-6-carbonitrile (1.0 g, 3.08 mmol) in N,N-Dimethylformamide (DMF) (7 mL) was added 60% sodium hydride in mineral oil (0.160 g, 4.01 mmol) and stirred for 30 minutes. To the mixture was added 4-bromo-2-(bromomethyl)pyridine (0.928 g, 3.70 mmol) and stirred overnight. The reaction was diluted with saturated NH$_4$Cl and extracted with ethyl acetate (3×). The combined organic extracts were washed with saturated NaCl (2×), dried over Na$_2$SO$_4$, filtered, and concentrated. The residue was purified via silica gel chromatography (ISCO, 120 g silica, 60 mL/min, 0-10% MeOH/CH$_2$Cl$_2$ over 45 min) to afford 1-(((5S,7S)-3-((4-bromopyridin-2-yl)methyl)-7-methyl-2-oxo-1-oxa-3-azaspiro[4.5]decan-7-yl)methyl)-1H-benzo[d]imidazole-6-carbonitrile (1.41 g, 93%). MS (m/z) 494.1 (M+).

1-(((5S,7S)-7-methyl-3-((4-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile To a microwave vial was added 1-(((5S,7S)-3-((4-bromopyridin-2-yl)methyl)-7-methyl-2-oxo-1-oxa-3-azaspiro[4.5]decan-7-yl)methyl)-1H-benzo[d]imidazole-6-carbonitrile (100 mg, 0.202 mmol), sodium carbonate (64.3 mg, 0.607 mmol), 1-methyl-4-(4,4,5,5-tetramethyl-1,3,2-dioxaborolan-2-yl)-1H-pyrazole (63.1 mg, 0.303 mmol), and $PdCl_2(dpV)$ (14.80 mg, 0.020 mmol) in 1,4-Dioxane (3.0 mL) and Water (1.000 mL). The mixture was subjected to the microwave at 120° C. for 20 minutes. The mixture was diluted with saturated $NaHCO_3$ and extracted with DCM (3×). The combined DCM extracts were passed through a phase separator and concentrated. The residue was purified via reverse HPLC (Waters Sunfire 30×150 mm Acetonitrile:Water TFA 20-60%, 50 mL/min, 15 min). The product was free based with $PL-HCO_3$ resin SPE to yield 1-(((5S,7S)-7-methyl-3-((4-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile (99 mg, 94%). $^1H$ NMR (400 MHz, DMSO-$d_6$) δ 8.50-8.61 (m, 3H), 8.38 (s, 1H), 8.22 (s, 1H), 7.85 (d, J=8.28 Hz, 1H), 7.73-7.82 (m, 2H), 7.61 (dd, J=8.28, 1.25 Hz, 1H), 4.53 (dd, J=21.83, 16.31 Hz, 2H), 4.07-4.20 (m, 2H), 3.93 (s, 3H), 3.28 (dd, J=19.07, 8.78 Hz, 2H), 1.97 (d, J=13.30 Hz, 1H), 1.79 (d, J=14.56 Hz, 1H), 1.52-1.73 (m, 3H), 1.25-1.49 (m, 3H), 1.05 (s, 3H). MS (m/z) 496.3 (M+H$^+$).

The following compounds were prepared using procedures analogous to those described in Example 160 using appropriately substituted starting materials. As is appreciated by those skilled in the art, these analogous examples may involve variations in general reaction conditions.

Example 162

1-(((5S,7S)-3-(5-(2-methoxypropan-2-yl)pyrazin-2-yl)-7-methyl-2-oxo-1-oxa-3-azaspiro[4.5]decan-7-yl)methyl)-1H-benzo[d]imidazole-6-carbonitrile

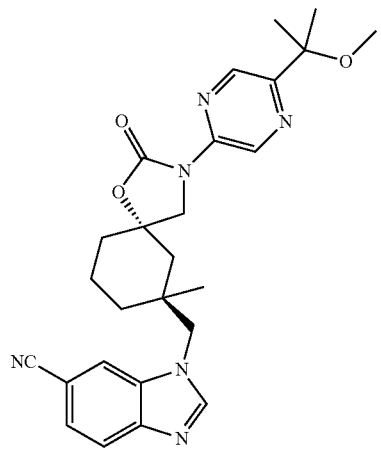 [SMILES: COC(C)(C)c1cnc(N2C[C@@]3(CCC[C@](C)(Cn4cnc5ccc(C#N)cc54)C3)OC2=O)cn1]

To a solution of 1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (75 mg, 0.163 mmol) in N,N-Dimethylformamide (DMF) (1 mL) was added sodium hydride (9.77 mg, 0.244 mmol) at RT. After 10 minutes, MeI (0.020 mL, 0.326 mmol) was added. The mixture stirred for an hour and was purified by reverse phase HPLC (Waters Sunfire 30×150 mm Acetonitrile:Water 0.1% TFA 30-70%, 50 mL/min, 15 min). The product was free based with $PL-HCO_3$ resin SPE to yield 1-(((5S,7S)-3-(5-(2-methoxypropan-2-yl)pyrazin-2-yl)-7-methyl-2-oxo-1-oxa-3-azaspiro[4.5]decan-7-yl)methyl)-1H-benzo[d]imidazole-6-carbonitrile as a white powder (45 mg, 58%). $^1H$ NMR (400 MHz, DMSO-$d_6$) δ 9.25 (d, J=1.51 Hz, 1H), 8.47-8.53 (m,

| Ex | Name | Structure | M + H (m/z) |
|---|---|---|---|
| 161 | 1-(((5S,7S)-7-methyl-3-((6-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile | 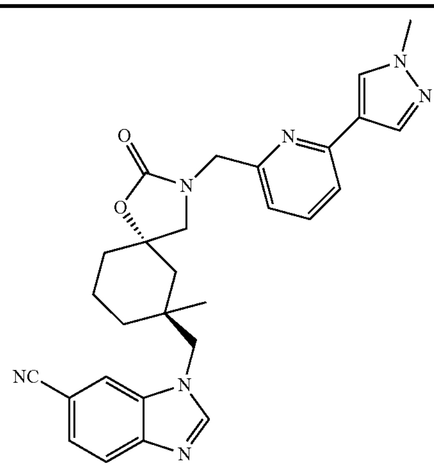 | 496.3 |

2H), 8.39 (d, J=1.00 Hz, 1H), 7.84 (d, J=8.78 Hz, 1H), 7.60 (dd, J=8.53, 1.51 Hz, 1H), 4.17 (s, 2H), 3.88 (dd, J=23.09, 10.29 Hz, 2H), 3.09 (s, 3H), 2.00 (d, J=14.05 Hz, 1H), 1.89 (d, J=14.56 Hz, 1H), 1.59-1.78 (m, 3H), 1.30-1.56 (m, 9H), 1.08 (s, 3H). MS (m/z) 443.2 (M-OMe).

Example 163

1-(((5S,7S)-3-(5-(2-(2-methoxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile

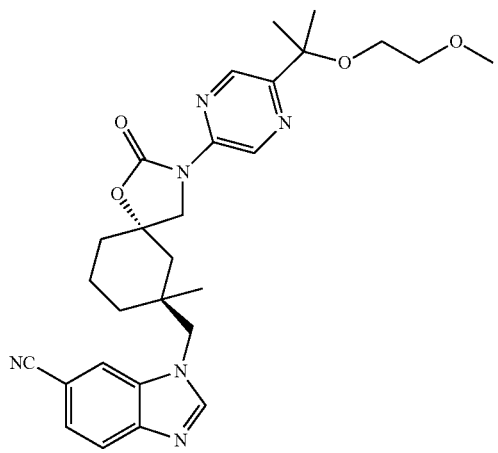 [SMILES: COCCOC(C)(C)c1cnc(N2C[C@@]3(CCC[C@](C)(Cn4cnc5ccc(C#N)cc54)C3)OC2=O)cn1]

1-(((5S,7S)-3-(5-(2-(2-hydroxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile To a solution of 1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (500 mg, 1.086 mmol, example 147) in ethylene glycol (4.93 mL) was added concentrated H$_2$SO$_4$ (0.5 mL, 9.38 mmol) at RT and heated at 60° C. overnight. The reaction mixture was cooled to RT, diluted with water, and extracted 5×DCM. The combined DCM layers were washed with brine, concentrated, and purified by reverse phase HPLC (Waters Sunfire 30×150 mm column, acetonitrile:water 0.1% TFA long 20-60%, 50 mL/min, 15 min). The product was free based with PL-HCO$_3$ resin SPE to yield 1-(((5S,7S)-3-(5-(2-(2-hydroxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile as a white solid (121 mg, 21%). MS (m/z) 505.3 (M+H$^+$).

1-(((5S,7S)-3-(5-(2-(2-methoxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile To a solution of 1-(((5S,7S)-3-(5-(2-(2-hydroxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile (40 mg, 0.079 mmol) in N,N-Dimethylformamide (DMF) (1 mL) was added sodium hydride (4.76 mg, 0.119 mmol) at RT. After 10 minutes, MeI (0.020 mL, 0.317 mmol) was added and stirred for an hour. To the mixture was added 0.5 mL MeOH and 2 drops 5% AcOH to buffer to pH 10, then filtered and purified by reverse phase HPLC (Waters Sunfire 30×150 mm Acetonitrile:Water 0.1% TFA 50-100%, 50 mL/min, 15 min). The product was free based with PL-HCO$_3$ resin SPE to yield 1-(((5S,7S)-3-(5-(2-(2-methoxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile as a white solid (16.5 mg, 39%). $^1$H NMR (400 MHz, DMSO-d$_6$) δ 9.23 (d, J=1.51 Hz, 1H), 8.57 (d, J=1.51 Hz, 1H), 8.50 (s, 1H), 8.39 (d, J=0.75 Hz, 1H), 7.84 (d, J=8.53 Hz, 1H), 7.60 (dd, J=8.41, 1.38 Hz, 1H), 4.12-4.23 (m, 2H), 3.88 (dd, J=23.09, 10.29 Hz, 2H), 3.43-3.48 (m, 2H), 3.34-3.39 (m, 2H), 3.26 (s, 3H), 2.00 (d, J=13.30 Hz, 1H), 1.89 (d, J=14.31 Hz, 1H), 1.58-1.77 (m, 3H), 1.43-1.56 (m, 8H), 1.30-1.41 (m, 1H), 1.07 (s, 3H). MS (m/z) 519.3 (M+H$^+$).

Example 164

2-((2-(5-((5S,7S)-7-((6-cyano-1H-benzo[d]imidazol-1-yl)methyl)-7-methyl-2-oxo-1-oxa-3-azaspiro[4.5]decan-3-yl)pyrazin-2-yl)propan-2-yl)oxy)ethyl dimethylphosphinate

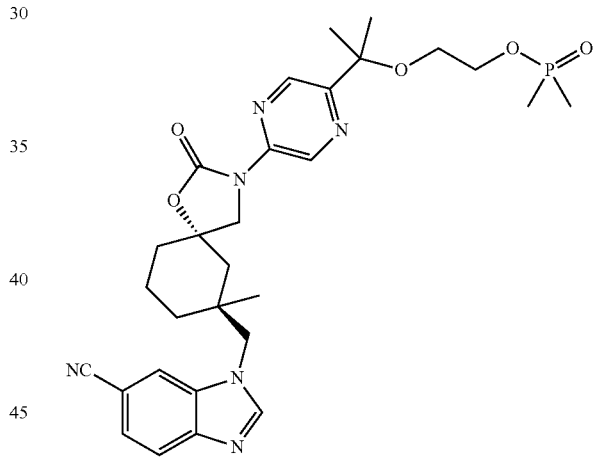

To a solution of 1-(((5S,7S)-3-(5-(2-(2-hydroxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile (60 mg, 0.119 mmol) in dichloromethane (DCM) (1127 μl) was added DIEA (62.3 μl, 0.357 mmol) and dimethylphosphinic chloride (40.1 mg, 0.357 mmol) at RT. The mixture was stirred for 2 hours, concentrated and reconstituted in DMSO/MeOH and filtered. The solution was purified by reverse phase HPLC (Waters Sunfire 30×150 mm Acetonitrile: Water TFA 30-70%, 50 mL/min, 15 min.). The product was free based with PL-HCO$_3$ resin SPE to yield 2-((2-(5-((5S,7S)-7-((6-cyano-1H-benzo[d]imidazol-1-yl)methyl)-7-methyl-2-oxo-1-oxa-3-azaspiro[4.5]decan-3-yl)pyrazin-2-yl)propan-2-yl)oxy)ethyl dimethylphosphinate as a white solid (5.8 mg, 8%). $^1$H NMR (400 MHz, DMSO-d$_6$) δ 9.24 (d, J=1.51 Hz, 1H), 8.60 (d, J=1.26 Hz, 1H), 8.48 (s, 1H), 8.38 (s, 1H), 7.83 (d, J=8.53 Hz, 1H), 4.12-4.21 (m, 2H), 3.94-4.03 (m, 2H), 3.88 (dd, J=23.09, 10.04 Hz, 2H), 3.42 (t, J=4.77 Hz, 2H), 2.00 (d, J=13.30 Hz, 1H), 1.88 (d, J=14.05 Hz, 1H), 1.59-1.78 (m, 3H), 1.30-1.56 (m, 15H), 1.07 (s, 3H). MS (m/z) 581.3 (M+H⁺).

Example 165

1-(((5S,7S)-3-(5'-fluoro-4-methyl-[2,2'-bipyridin]-5-yl)-7-methyl-2-oxo-1-oxa-3-azaspiro[4.5]decan-7-yl)methyl)-1H-benzo[d]imidazole-6-carbonitrile

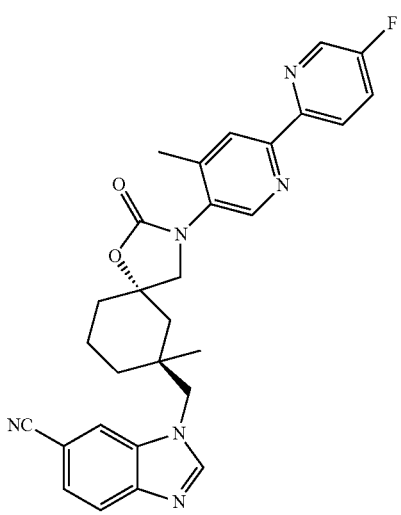 [SMILES: Cc1cc(-c2ccc(F)cn2)ncc1N1C[C@@]2(CCC[C@](C)(Cn3cnc4ccc(C#N)cc43)C2)OC1=O]

1-(((5S,7S)-7-methyl-3-(4-methyl-6-oxo-1,6-dihydropyridin-3-yl)-2-oxo-1-oxa-3-azaspiro[4.5]decan-7-yl)methyl)-1H-benzo[d]imidazole-6-carbonitrile To a suspension of 1-(((5S,7S)-3-(6-methoxy-4-methylpyridin-3-yl)-7-methyl-2-oxo-1-oxa-3-azaspiro[4.5]decan-7-yl)methyl)-1H-benzo[d]imidazole-6-carbonitrile (5000 mg, 11.22 mmol) and sodium iodide (5047 mg, 33.7 mmol) in Acetonitrile (42.900 mL) was added TMSCl (4.30 mL, 33.7 mmol). The reaction was stirred at room temperature overnight. More sodium iodide (5047 mg, 33.7 mmol) and TMSCl (4.30 mL, 33.7 mmol) were added and stirred overnight at room temperature. The reaction mixture was concentrated to remove MeCN, and the residue was partitioned between saturated aqueous sodium metabisulfite (30 mL) and 10% MeOH/DCM (50 mL). The layers were separated, and the aqueous layer was extracted with 2×DCM. The combined organic extracts were dried over sodium sulfate, filtered, and concentrated. The material was purified by ISCO Rf chromatography (220 g column, silica load): 0-20% MeOH/DCM (20 min), 20% MeOH/DCM (20 min). Obtained 1-(((5S,7S)-7-methyl-3-(4-methyl-6-oxo-1,6-dihydropyridin-3-yl)-2-oxo-1-oxa-3-azaspiro[4.5]decan-7-yl)methyl)-1H-benzo[d]imidazole-6-carbonitrile as a white foam (3.35 g, 69%). MS (m/z) 432.2 (M+H⁺).

5-((5S,7S)-7-((6-cyano-1H-benzo[d]imidazol-1-yl)methyl)-7-methyl-2-oxo-1-oxa-3-azasbiro[4.5]decan-3-yl)-4-methylpyridin-2-yl trifluoromethanesulfonate To a solution of 1-(((5S,7S)-7-methyl-3-(4-methyl-6-oxo-1,6-dihydropyridin-3-yl)-2-oxo-1-oxa-3-azaspiro[4.5]decan-7-yl)methyl)-1H-benzo[d]imidazole-6-carbonitrile (2.25 g, 5.21 mmol) and pyridine (4.22 ml, 52.1 mmol) in Dichloromethane (DCM) (38.9 ml) cooled to 0° C. under nitrogen was added triflic anhydride (2.202 ml, 13.04 mmol). After 1 hour, the reaction mixture was diluted with water and extracted with 3×DCM. The combined organic extracts were washed with 0.5 M HCl, dried over sodium sulfate, filtered, and concentrated. The material was purified by ISCO Rf chromatography (220 g silica): 0-10% MeOH/DCM (20 min), 10% MeOH/DCM (20 min). Obtained 5-((5S,7S)-7-((6-cyano-1H-benzo[d]imidazol-1-yl)methyl)-7-methyl-2-oxo-1-oxa-3-azaspiro[4.5]decan-3-yl)-4-methylpyridin-2-yl trifluoromethanesulfonate as a yellow foam (2.79 g, 95%). MS (m/z) 564.1 (M+H⁺).

1-(((5S,7S)-3-(5-fluoro-4-methyl-[2,2'-bipyridin]-5-yl)-7-methyl-2-oxo-1-oxa-3-azaspiro[4.5]decan-7-yl)methyl)-1H-benzo[d]imidazole-6-carbonitrile A mixture of 5-((5S,7S)-7-((6-cyano-1H-benzo[d]imidazol-1-yl)methyl)-7-methyl-2-oxo-1-oxa-3-azaspiro[4.5]decan-3-yl)-4-methylpyridin-2-yl trifluoromethanesulfonate (120 mg, 0.213 mmol) and Pd(PPh₃)₄ (12.30 mg, 10.65 μmol) in Tetrahydrofuran (THF) (4 mL) was treated with (5-fluoropyridin-2-yl)zinc(II) bromide (0.5M in THF) (4.26 mL, 2.129 mmol) under nitrogen and stirred at room temperature overnight. The reaction was concentrated and purified by normal phase chromatography (ISCO Rf, 80 g silica, 0-5% MeOH/DCM). Obtained desired product containing 10% triphenylphosphine oxide, which was dissolved in 1 mL of MeOH and recrystallized to afford 1-(((5S,7S)-3-(5'-fluoro-4-methyl-[2,2'-bipyridin]-5-yl)-7-methyl-2-oxo-1-oxa-3-azaspiro[4.5]decan-7-yl)methyl)-1H-benzo[d]imidazole-6-carbonitrile (50.5 mg, 44%). ¹H NMR (400 MHz, DMSO-d₆) δ 8.69 (d, J=2.76 Hz, 1H), 8.63 (s, 1H), 8.50 (s, 1H), 8.39-8.46 (m, 2H), 8.27 (s, 1H), 7.82-7.92 (m, 2H), 7.61 (dd, J=8.28, 1.51 Hz, 1H), 4.15-4.24 (m, 2H), 3.78 (dd, J=13.80, 8.78 Hz, 2H), 2.33 (s, 3H), 2.10 (d, J=13.55 Hz, 1H), 1.97 (d, J=14.31 Hz, 1H), 1.59-1.80 (m, 3H), 1.44-1.56 (m, 2H), 1.32-1.43 (m, 1H), 1.10 (s, 3H). MS (m/z) 511.2 (M+H⁺).

Example 166

1-(((5S,7S)-7-methyl-3-(4-methyl-6-morpholinopyridin-3-yl)-2-oxo-1-oxa-3-azaspiro[4.5]decan-7-yl)methyl)-1H-benzo[d]imidazole-6-carbonitrile

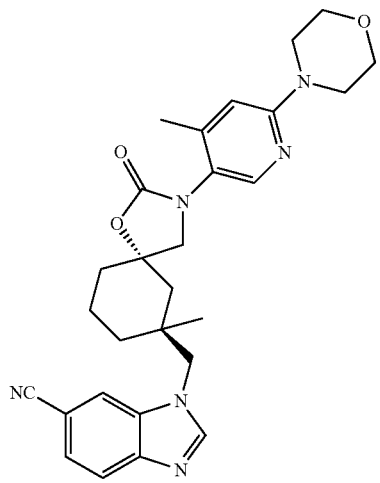 [SMILES: Cc1cc(N2CCOCC2)ncc1N1C[C@@]2(CCC[C@](C)(Cn3cnc4ccc(C#N)cc43)C2)OC1=O]

A mixture of 5-(((5S,7S)-7-((6-cyano-1H-benzo[d]imidazol-1-yl)methyl)-7-methyl-2-oxo-1-oxa-3-azaspiro[4.5]decan-3-yl)-4-methylpyridin-2-yl trifluoromethanesulfonate (100 mg, 0.177 mmol) and morpholine (0.077 mL, 0.887 mmol) in Dimethyl Sulfoxide (DMSO) (1.5 mL) was heated in the microwave for 35 minutes at 100° C. The solution was purified by reverse phase HPLC (Waters Sunfire 30×150 mm Acetonitrile: Water 0.1% TFA 10-50%, 50 mL/min, 15 min) to afford the bis-TFA salt of 1-(((5S,7S)-7-methyl-3-(4-methyl-6-morpholinopyridin-3-yl)-2-oxo-1-oxa-3-azaspiro[4.5]decan-7-yl)methyl)-1H-benzo[d]imidazole-6-carbonitrile (60 mg, 46%). $^1$H NMR (400 MHz, DMSO-d$_6$) δ 8.65 (s, 1H), 8.46 (s, 1H), 8.08 (s, 1H), 7.88 (d, J=8.28 Hz, 1H), 7.65 (dd, J=8.28, 1.25 Hz, 1H), 6.94 (s, 1H), 4.15-4.25 (m, 2H), 3.67-3.74 (m, 4H), 3.59 (s, 2H), 3.45-3.52 (m, 4H), 2.17 (s, 3H), 2.04 (d, J=13.55 Hz, 1H), 1.92 (d, J=14.56 Hz, 1H), 1.58-1.77 (m, 3H), 1.30-1.52 (m, 3H), 1.08 (s, 3H). MS (m/z) 501.3 (M+H$^+$).

The following compounds were prepared using procedures analogous to those described in Example 26 using appropriately substituted starting materials. As is appreciated by those skilled in the art, these analogous examples may involve variations in general reaction conditions.

Example 169

1-(((5S,7S)-3-(6-cyclopropyl-4-methoxypyridin-3-yl)-7-methyl-2-oxo-1-oxa-3-azaspiro[4.5]decan-7-yl)methyl)-1H-benzo[d]imidazole-6-carbonitrile

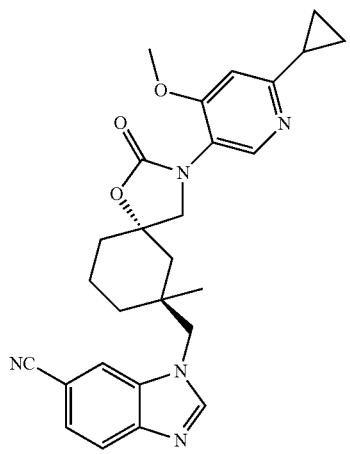

| Ex | Name | Structure | M + H (m/z) |
|---|---|---|---|
| 167 | 1-(((5S,7S)-3-(5-(2-hydroxypropan-2-yl)pyridin-2-yl)-7-methyl-2-oxo-1-oxa-3-azaspiro[4.5]decan-7-yl)methyl)-1H-benzo[d]imidazole-6-carbonitrile | 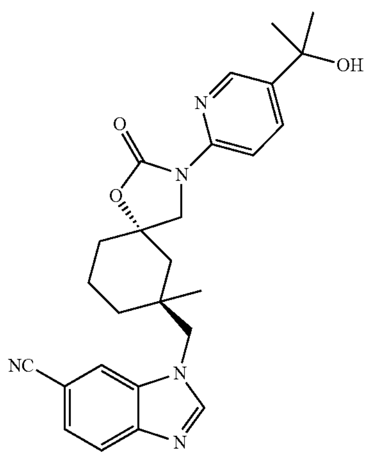 [SMILES: CC(C)(O)c1ccc(N2C[C@@]3(CCC[C@](C)(Cn4cnc5ccc(C#N)cc54)C3)OC2=O)nc1] | 460 |
| 168 | 1-(((5S,7S)-3-(5-(1-hydroxy-2-methylpropan-2-yl)pyrazin-2-yl)-7-methyl-2-oxo-1-oxa-3-azaspiro[4.5]decan-7-yl)methyl)-1H-benzo[d]imidazole-6-carbonitrile | 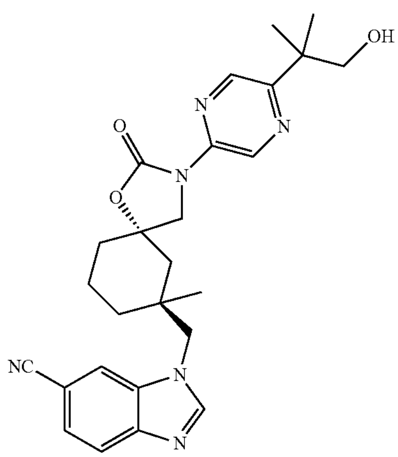 [SMILES: CC(C)(CO)c1cnc(N2C[C@@]3(CCC[C@](C)(Cn4cnc5ccc(C#N)cc54)C3)OC2=O)cn1] | 475 |

2-cyclopropyl-4-methoxy-5-nitropyridine

A mixture of 2-chloro-4-methoxy-5-nitropyridine (1.6 g, 8.48 mmol), cyclopropylboronic acid (1.458 g, 16.97 mmol), PdCl$_2$(dppf)-CH$_2$Cl$_2$ adduct (1.386 g, 1.697 mmol), cesium carbonate (8.29 g, 25.5 mmol), and 1,4-Dioxane (15 mL) were heated using the microwave at 140° C. for 10 minutes. The reaction mixture was purified by normal phase chromatography (ISCO, 120 g silica, 0-3% methanol/DCM) to afford 2-cyclopropyl-4-methoxy-5-nitropyridine as a red solid (492 mg, 28%). MS (m/z) 195.0 (M+H$^+$).

6-cyclopropyl-4-methoxypyridin-3-amine

To a mixture of 2-cyclopropyl-4-methoxy-5-nitropyridine (805 mg, 4.15 mmol), nickel(II) chloride, 6H$_2$O (2956 mg, 12.44 mmol), and methanol (25 mL), cooled to 0° C., was added sodium borohydride (941 mg, 24.87 mmol) portion wise over 1 minute. After 5 minutes, the reaction was diluted with DCM (50 mL), saturated sodium bicarbonate (50 mL), and water (50 mL), and filtered through Celite©. The layers of the filtrate were separated and the aqueous layer was further extracted with DCM (50 mL). The combined organic extracts were washed with water (50 mL), brine (50 mL), eluted through a phase separator, and concentrated to afford 6-cyclopropyl-4-methoxypyridin-3-amine (448 mg, 63%) as a yellow oil. MS (m/z) 165.1 (M+H$^+$).

tert-butyl (6-cyclopropyl-4-methoxypyridin-3-yl)carbamate

A solution of 6-cyclopropyl-4-methoxypyridin-3-amine (448 mg, 2.73 mmol), di-tert-butyl dicarbonate (655 mg, 3.00 mmol), and tetrahydrofuran (THF) (20 mL) was stirred at 60° C. overnight. The reaction was diluted with DCM (50 mL) and water (50 mL), and the layers were separated. The aqueous layer was further extracted with DCM (25 mL), and the combined organic extracts were washed with water (50 ml), brine (50 mL), eluted through a phase separator, and concentrated. The resultant oil was purified by normal phase chromatography (ISCO, 120 g silica, 0-4% methanol/DCM) to afford tert-butyl (6-cyclopropyl-4-methoxypyridin-3-yl)carbamate (500 mg, 66%) as a red solid. MS (m/z) 265.1 (M+H$^+$).

The invention claimed is:

1. A compound of Formula (I):

Wherein:

R$_1$ is hydrogen, C$_{1-3}$alkyl, CH$_2$OH, CH$_2$—O—CH$_3$, CH$_2$OCH$_2$Ph, CH$_2$CN, CN, halo or C(O)OCH$_3$;

R$_2$ is independently hydrogen, CN, CF$_3$, halo, SO$_2$C$_{1-3}$alkyl, C$_{1-3}$alkyl or C≡CH;

R$_3$ is hydrogen, C$_{1-2}$alkyl, CF$_3$ or OH;

R$_4$ is hydrogen, halo or C$_{1-3}$alkyl;

X is CR$_4$ or N;

A is (CH$_2$)$_n$-Het;

or A is (CH$_2$)$_n$—(CR$_a$R$_b$)—(C$_{1-2}$)$_m$-Het;

R$_a$ is hydrogen or C$_{1-3}$alkyl, wherein the C$_{1-3}$alkyl may be further substituted with one or more halos;

R$_b$ is C$_{1-3}$alkyl;

or R$_a$ and R$_b$ together with the carbon atom they are attached form a C$_{3-6}$cycloalkyl group;

or one of the carbon atoms in the C$_{3-6}$cycloalkyl group formed by R$_a$ and R$_b$ may be replaced with oxygen to form an oxetane, tetrahydrofuryl or tetrahydropyranyl group;

or one of the carbon atoms in the C$_{3-6}$cycloalkyl group formed by R$_a$ and R$_b$ may be replaced with nitrogen to form a pyrrolidinyl or piperidinyl group;

Het is:

wherein Het may be substituted by one, two or three substituents chosen from: halo, C$_{1-5}$alkyl, CN, CH$_2$F, CHF$_2$, CF$_3$, C$_{3-6}$cycloalkyl, (CH$_2$)$_n$—O—C$_{1-3}$alkyl, (CH$_2$)$_n$-phenyl, (CH$_2$)$_n$-pyridyl, pyrimidinyl, pyrazinyl, CH(CH$_3$)—O—C$_{1-3}$alkyl, CH(OH)—C$_{1-5}$alkyl, C(CH$_3$)$_2$—R$_5$, C(O)N(CH$_3$)$_p$, N(C$_{1-3}$alkYl)$_p$, NH$_2$, C(O)NH$_2$, oxetane, oxetane-CH$_3$, tetrahydrofuryl, tetrahydropyranyl, morpholinyl, or pyrazolyl;

wherein the phenyl, pyrazolyl, and pyridyl substituent on the Het may be further substituted by one or two substituents chosen from: halo, CN, OCH$_3$, C$_{1-3}$alkyl or CF$_3$;

and the C$_{1-5}$alkyl and C$_{3-6}$cycloalkyl substituent on the Het may be further substituted by CN or OH;

R$_5$ is CN, O—C$_{1-4}$alkyl, (CH$_2$)$_m$—OH, (CH$_2$)$_p$—O—C(O)—O—C$_{1-5}$alkyl, or O—(CH$_2$)$_p$O—R$_6$;

R$_6$ is C$_{1-4}$alkyl or P(O)$_2$(CH$_3$)$_2$;

n is independently 0, 1 or 2;

m is independently 0, 1 or 2;

p is independently 1 or 2; and y is 1, 2 or 3;

or a pharmaceutically acceptable salt thereof.

2. A compound of Formula (I):

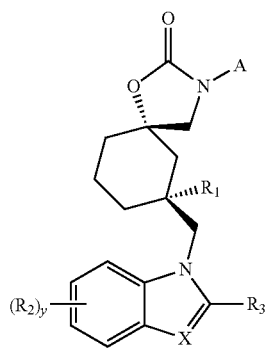

Wherein:
R₁ is hydrogen, $C_{1-3}$alkyl, $CH_2OH$, $CH_2$—O—$CH_3$, $CH_2OCH_2Ph$, $CH_2CN$, CN, halo or $C(O)OCH_3$;
R₂ is independently hydrogen, CN, $CF_3$, halo, $SO_2C_{1-3}$alkyl, $C_{1-3}$alkyl or C≡CH;
R₃ is hydrogen, $C_{1-2}$alkyl, $CF_3$ or OH;
R₄ is hydrogen, halo or $C_{1-3}$alkyl;
X is $CR_4$ or N;
A is $(CH_2)_n$-Het;
or A is $(CH_2)_n$—$(CR_aR_b)$—$(CH_2)_m$-Het;
$R_a$ is hydrogen or $C_{1-3}$alkyl, wherein the $C_{1-3}$alkyl may be further substituted with one or more halos;
$R_b$ is $C_{1-3}$alkyl;
or $R_a$ and $R_b$ together with the carbon atom they are attached form a $C_{3-6}$cycloalkyl group;
or one of the carbon atoms in the $C_{3-6}$cycloalkyl group formed by $R_a$ and $R_b$ may be replaced with oxygen to form an oxetane, tetrahydrofuryl or tetrahydropyranyl group;
or one of the carbon atoms in the $C_{3-6}$cycloalkyl group formed by $R_a$ and $R_b$ may be replaced with nitrogen to form a pyrrolidinyl or piperidinyl group;
Het is

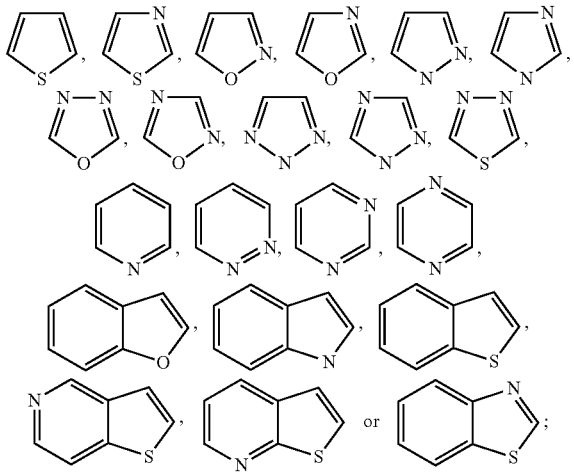

Wherein Het may be substituted by one, two or three substituents chosen from: halo, $C_{1-5}$alkyl, CN, $CH_2F$, $CHF_2$, $CF_3$, $C_{3-6}$cycloalkyl, $(CH_2)_n$—O—alkyl, $(CH)_n$-phenyl, $(CH_2)_n$-pyridyl, pyrimidinyl, pyrazinyl, $CH(CH_3)$—O—$C_{1-3}$alkyl, $C(CH_3)_2$—OH, $C(CH_3)_2$—O—$CH_3$, $C(CH_3)_2$—CN, $C(CH_3)_2$—$CH_2OH$, $C(CH_3)_2$—$CH_2$—O—$C(O)$—O—$C_{1-5}$alkyl, $C(O)N(CH_3)_p$, $N(C_{1-3}alkyl)_p$, $NH_2$, $C(O)NH_2$, oxetane, oxetane-$CH_3$, tetrahydrofuryl or tetrahydropyranyl;
wherein the phenyl and pyridyl substituent on the Het may be further substituted by one or two substituents chosen from: halo, CN, $OCH_3$, $C_{1-3}$alkyl or $CF_3$;
and the $C_{1-6}$alkyl and $C_{3-6}$cycloalkyl substituent on the Het may be further substituted by CN or OH;
n is independently 0, 1 or 2;
m is independently 0, 1 or 2;
p is independently 1 or 2;
y is 1, 2 or 3;
or a pharmaceutically acceptable salt thereof.

3. A compound of claim 2 wherein:
R₁ is hydrogen, $C_{1-3}$ alkyl or $CH_2OH$;
R₂ is CN;
R₃ is hydrogen;
X is N;
A is $(CH_2)_n$-Het;
or A is $(CH_2)_n$—$(CR_aR_b)$—$(CH_2)_m$-Het;
$R_a$ is hydrogen or $C_{1-3}$alkyl, wherein the $C_{1-3}$alkyl may be further substituted with one or more halos;
$R_b$ is $C_{1-3}$alkyl;
or $R_a$ and $R_b$ together with the carbon atom they are attached to form a $C_{3-6}$ cycloalkyl group;
or one of the carbon atoms in the $C_{3-6}$cycloalkyl group formed by $R_a$ and $R_b$ may be replaced with oxygen to form an oxetane, tetrahydrofuryl or tetrahydropyranyl group;
or one of the carbon atoms in the $C_{3-6}$cycloalkyl group formed by $R_a$ and $R_b$ may be replaced with nitrogen to form a pyrrolidinyl or piperidinyl group;
Het is

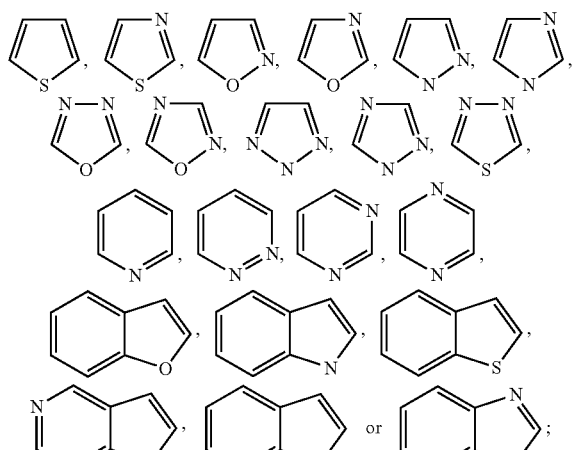

Wherein Het may be substituted by one, two or three substituents chosen from: halo, $C_{1-5}$alkyl, CN, $CH_2F$, $CHF_2$, $CF_3$, $C_{3-6}$cycloalkyl, $(CH_2)_n$—O—$C_{1-3}$alkyl, $(CH_2)_n$-phenyl, $(CH_2)_n$-pyridyl, pyrimidinyl, pyrazinyl, $CH(CH_3)$—O—$C_{1-3}$alkyl, $C(CH_3)_2$—OH, $C(CH_3)_2$—O—$CH_3$, $C(CH_3)_2$—CN, $C(CH_3)_2$—$CH_2OH$, $C(CH_3)_2$—$CH_2$—O—$C(O)$—O—$C_{1-5}$alkyl, $C(O)N(CH_3)_p$, $N(C_{1-3}alkyl)_p$, $NH_2$, $C(O)NH_2$, oxetane, oxetane-$CH_3$, tetrahydrofuryl or tetrahydropyranyl;

wherein the phenyl and pyridyl substituent on the Het may be further substituted by one or two substituents chosen from: halo, CN, OCH$_3$, C$_{1-3}$ alkyl or CF$_3$;

and the C$_{1-5}$ alkyl and C$_{3-6}$cycloalkyl substituent on the Het may be further substituted by CN or OH;

n is independently 0 or 1;
m is independently 0 or 1;
p is independently 1 or 2; and
y is 1 or 2;
or a pharmaceutically acceptable salt thereof.

4. A compound of claim 2 wherein:
R$_1$ is hydrogen, C$_{1-3}$alkyl or CH$_2$OH;
R$_2$ is CN;
R$_3$ is hydrogen;
X is N;
A is (CH$_2$)$_n$-Het;
or A is (CH$_2$)$_n$—(CR$_a$R$_b$)—(CH$_2$)$_m$-Het;
R$_a$ is hydrogen or C$_{1-3}$alkyl, wherein the C$_{1-3}$alkyl may be further substituted with one or more halos;
R$_b$ is C$_{1-3}$alkyl;
or R$_a$ and R$_b$ together with the carbon atom they are attached to form a C$_{3-6}$ cycloalkyl group;
or one of the carbon atoms in the C$_{3-6}$cycloalkyl group formed by R$_a$ and R$_b$ may be replaced with oxygen to form an oxetane, tetrahydrofuryl or tetrahydropyranyl group;
or one of the carbon atoms in the C$_{3-6}$cycloalkyl group formed by R$_a$ and R$_b$ may be replaced with nitrogen to form a pyrrolidinyl or piperidinyl group;
Het is

[structures of Het rings]

wherein Het may be substituted by one, two or three substituents chosen from: halo, C$_{1-5}$alkyl, CN, CH$_2$F, CHF$_2$, CF$_3$, C$_{3-6}$cycloalkyl, (CH$_2$)$_n$—O—C$_{1-3}$alkyl, (CH$_2$)$_n$-phenyl, (CH$_2$)$_n$-pyridyl, pyrimidinyl, pyrazinyl, CH(CH$_3$)—O—C$_{1-3}$alkyl, C(CH$_3$)$_2$—OH, C(CH$_3$)$_2$—O—CH$_3$, C(CH$_3$)$_2$—CN, C(CH$_3$)$_2$—CH$_2$OH, C(CH$_3$)$_2$—CH$_2$—O—C(O)—O—C$_{1-5}$alkyl, C(O)N(CH$_3$)$_p$, N(C$_{1-3}$alkyl)$_p$, NH$_2$, C(O)NH$_2$, oxetane, oxetane-CH$_3$, tetrahydrofuryl or tetrahydropyranyl;
wherein the phenyl and pyridyl substituent on the Het may be further substituted by one or two substituents chosen from: halo, CN, OCH$_3$, C$_{1-3}$alkyl, or CF$_3$;
and the C$_{1-5}$alkyl and C$_{3-6}$cycloalkyl substituent on the Het may be further substituted by CN or OH;
n is independently 0 or 1;
m is independently 0 or 1;
p is independently 1 or 2; and
y is 1 or 2;
or a pharmaceutically acceptable salt thereof.

5. A compound of claim 2 wherein:
R$_1$ is hydrogen, C$_{1-3}$alkyl or CH$_2$OH;
R$_2$ is CN;
R$_3$ is hydrogen;
X is N;
A is (CH$_2$)$_n$-Het;
Het is

[structures of Het rings]

wherein Het may be substituted by one, two or three substituents chosen from: halo, C$_{1-5}$alkyl, CN, CH$_2$F, CHF$_2$, CF$_3$, C$_{3-6}$cycloalkyl, (CH$_2$)$_n$—O—C$_{1-3}$alkyl, (CH$_2$)$_n$-phenyl, (CH$_2$)$_n$-pyridyl, pyrimidinyl, pyrazinyl, CH(CH$_3$)—O—C$_{1-3}$alkyl, C(CH$_3$)$_2$—OH, C(CH$_3$)$_2$—O—CH$_3$, C(CH$_3$)$_2$—CN, C(CH$_3$)$_2$—CH$_2$OH, C(CH$_3$)$_2$—CH$_2$—O—C(O)—O—C$_{1-5}$alkyl, C(O)N(CH$_3$)$_p$, N(C$_{1-3}$alkyl)$_p$, NH$_2$, C(O)NH$_2$, oxetane, oxetane-CH$_3$, tetrahydrofuryl or tetrahydropyranyl;
wherein the phenyl and pyridyl substituent on the Het may be further substituted by one or two substituents chosen from: halo, CN, OCH$_3$, C$_{1-3}$alkyl, or CF$_3$;
and the C$_{1-5}$alkyl and C$_{3-6}$cycloalkyl substituent on the Het may be further substituted by CN or OH;
n is independently 0 or 1;
p is independently 1 or 2; and
y is 1 or 2;
or a pharmaceutically acceptable salt thereof.

6. A compound of claim 2 wherein:
R$_1$ is hydrogen, C$_{1-3}$alkyl or CH$_2$OH;
R$_2$ is CN;
R$_3$ is hydrogen;
X is N;
A is (CH$_2$)$_n$-Het;
Het is

[structures of Het rings]

Wherein Het may be substituted by one, two or three substituents chosen from: Halo, C$_{1-5}$alkyl, CN, CH$_2$F, CHF$_2$, CF$_3$, C$_{3-6}$cycloalkyl, (CH$_2$)$_n$—O—C$_{1-3}$alkyl, (CH$_2$)$_n$-phenyl, (CH$_2$)$_n$-pyridyl, pyrimidinyl, pyrazinyl, CH(CH$_3$)—O—C$_{1-3}$alkyl, C(CH$_3$)$_2$—OH, C(CH$_3$)$_2$—O—CH$_3$, C(CH$_3$)$_2$—CN, C(CH$_3$)$_2$—CH$_2$OH, C(CH$_3$)$_2$—CH$_2$—O—C(O)—O—C$_{1-5}$alkyl, C(O)N(CH$_3$)$_p$, N(C$_{1-3}$alkyl)$_p$, N H$_2$, C(O)NH$_2$, oxetane, oxetane-CH$_3$, tetrahydrofuryl or tetrahydropyranyl;
wherein the phenyl and pyridyl substituent on the Het may be further substituted by one or two substituents chosen from: halo, CN, OCH$_3$, C$_{1-3}$alkyl, or CF$_3$;

and the $C_{1-5}$alkyl and $C_{3-6}$cycloalkyl substituent on the Het may be further substituted by CN or OH;

n is 0;

p is independently 1 or 2; and y is 1 or 2;

or a pharmaceutically acceptable salt thereof.

7. A compound of claim 1 chosen from:

1-({(5S,7S)-3-[3-(1,1-dimethylethyl)-5-isoxazolyl]-7-methyl-2-oxo-1-oxa-3-azaspiro[4.5]dec-7-yl}methyl)-1H-benzimidazole-6-carbonitrile;

1-(((5S,7S)-3-(3-(2-cyanopropan-2-yl)isoxazol-5-yl)-7-methyl-2-oxo-1-oxa-3-azaspiro[4.5]decan-7-yl)methyl)-1H-benzo[d]imidazole-6-carbonitrile;

1-({(5S,7S)-3-[5-(1,1-dimethylethyl)-3-isoxazolyl]-7-methyl-2-oxo-1-oxa-3-azaspiro[4.5]dec-7-yl}methyl)-1H-benzimidazole-6-carbonitrile;

1-{[(5S,7S)-7-methyl-2-oxo-3-(2-pyridinylmethyl)-1-oxa-3-azaspiro[4.5]dec-7-yl]methyl}-1H-benzimidazole-6-carbonitrile;

1-({(5S,7S)-3-[2-methyl-2-(5-phenyl-1,3,4-oxadiazol-2-yl)propyl]-2-oxo-1-oxa-3-azaspiro[4.5]dec-7-yl}methyl)-1H-benzimidazole-6-carbonitrile;

1-({(5S,7S)-3-[2-(3-ethyl-1,2,4-oxadiazol-5-yl)-2-methylpropyl]-2-oxo-1-oxa-3-azaspiro[4.5]dec-7-yl}methyl)-1H-benzimidazole-6-carbonitrile;

1-[((5S,7S)-3-{[3-methyl-1-(2-pyrimidinyl)-3-pyrrolidinyl]methyl}-2-oxo-1-oxa-3-azaspiro[4.5]dec-7-yl)methyl]-1H-benzimidazole-6-carbonitrile;

1-({(5S,7S)-7-methyl-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile;

1-{[(5S,7S)-2-oxo-3-({1-[5-(trifluoromethyl)-3-pyridinyl]-1H-1,2,3-triazol-4-yl}methyl)-1-oxa-3-azaspiro[4.5]dec-7-yl]methyl}-1H-benzimidazole-6-carbonitrile;

1-({(5S,7S)-3-[4-chloro-3-(1,1-dimethylethyl)-5-isoxazolyl]-7-methyl-2-oxo-1-oxa-3-azaspiro[4.5]dec-7-yl}methyl)-1H-benzimidazole-6-carbonitrile;

1-({(5S,7S)-7-methyl-2-oxo-3-[5-(trifluoromethyl)-2-pyridinyl]-1-oxa-3-azaspiro[4.5]dec-7-yl}methyl)-1H-benzimidazole-6-carbonitrile;

1-({(5S,7S)-3-[6-(ethyloxy)-3-pyridinyl]-7-methyl-2-oxo-1-oxa-3-azaspiro[4.5]dec-7-yl}methyl)-1H-benzimidazole-6-carbonitrile;

1-(((5S,7S)-3-(6-methoxypyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(5-ethoxypyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(6-methoxy-4-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(1-ethyl-5-methyl-1H-pyrazol-4-yl)-7-methyl-2-oxo-1-oxa-3-azaspiro[4.5]decan-7-yl)methyl)-1H-benzo[d]imidazole-6-carbonitrile;

1-(((7S)-3-(5-methoxypyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloropyridin-3-yl)-7-methyl-2-oxo-1-oxa-3-azaspiro[4.5]decan-7-yl)methyly)-1H-benzo[d]imidazole-6-carbonitrile;

1-(((5S,7S)-3-(6-(dimethylamino)pyridin-3-yl)-7-methyl-2-oxo-1-oxa-3-azaspiro[4.5]decan-7-yl)methyl)-1H-benzo[d]imidazole-6-carbonitrile;

tert-butyl (2-(5-((5S,7S)-7-((6-cyano-1H-benzo[d]imidazol-1-yl)methyl)-7-methyl-2-oxo-1-oxa-3-azaspiro[4.5]decan-3-yl)isoxazol-3-yl)-2-methylpropyl) carbonate;

1-(((5S,7S)-3-(3-(1-hydroxy-2-methylpropan-2-yl)isoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(4,6-dimethoxypyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-ethoxy-4-methylpyridin-3-yl)-2-oxo-1-oxa-3-azaspiro[4.5]decan-7-yl)methyl)-1H-benzo[d]imidazole-6-carbonitrile;

1-(((5S,7S)-3-(6-ethoxy-4-methylpyridazin-3-yl)-7-methyl-2-oxo-1-oxa-3-azaspiro[4.5]decan-7-yl)methyl)-1H-benzo[d]imidazole-6-carbonitrile;

1-(((5S,7S)-7-methyl-2-oxo-3-(2-(trifluoromethyl)pyrimidin-5-yl)-1-oxa-3-azaspiro[4.5]decan-7-yl)methyl)-1H-benzo[d]imidazole-6-carbonitrile;

1-(((5S,7S)-7-methyl-2-oxo-3-(3-(trifluoromethyl)pyridin-2-yl)-1-oxa-3-azaspiro[4.5]decan-7-yl)methyl)-1H-benzo[d]imidazole-6-carbonitrile;

1-({(5S,7S)-3-[(5-chloro-1-benzothien-3-yl)methyl]-2-oxo-1-oxa-3-azaspiro[4.5]dec-7-yl}methyl)-1H-benzimidazole-6-carbonitrile;

1-{[(5S,7S)-3-(2-{3-[1-(ethyloxy)ethyl]-1,2,4-oxadiazol-5-yl}-2-methylpropyl)-2-oxo-1-oxa-3-azaspiro[4.5]dec-7-yl]methyl}-1H-benzimidazole-6-carbonitrile;

1-{[(5S,7S)-7-methyl-3-(5-methyl-2-pyridinyl)-2-oxo-1-oxa-3-azaspiro[4.5]dec-7-yl]methyl}-1H-benzimidazole-6-carbonitrile;

1-({(5S,7S)-7-methyl-3-[3-(1-methylethyl)-5-isoxazolyl]-2-oxo-1-oxa-3-azaspiro[4.5]dec-7-yl}methyl)-1H-benzimidazole-6-carbonitrile;

1-({(5S,7S)-7-methyl-3-[3-(2-methylpropyl)-5-isoxazolyl]-2-oxo-1-oxa-3-azaspiro[4.5]dec-7-yl}methyl)-1H-benzimidazole-6-carbonitrile;

1-{[(5S,7S)-3-(1-tert-butyl-1H-pyrazol-4-yl)-7-methyl-2-oxo-1-oxa-3-azaspiro[4.5]dec-7-yl]methyl}-1H-benzimidazole-6-carbonitrile;

1-{[(5S,7S)-3-(3-ethyl-5-isoxazolyl)-7-methyl-2-oxo-1-oxa-3-azaspiro[4.5]dec-7-yl]methyl}-1H-benzimidazole-6-carbonitrile;

1-{[(5S,7S)-3-(3-cyclopropyl-5-isoxazolyl)-7-methyl-2-oxo-1-oxa-3-azaspiro[4.5]dec-7-yl]methyl}-1H-benzimidazole-6-carbonitrile;

1-{[(5S,7S)-7-methyl-2-oxo-3-(3-phenyl-5-isoxazolyl)-1-oxa-3-azaspiro[4.5]dec-7-yl]methyl}-1H-benzimidazole-6-carbonitrile;

1-({(5S,7S)-3-[3-(1,1-dimethylethyl)-1-methyl-1H-pyrazol-5-yl]-7-methyl-2-oxo-1-oxa-3-azaspiro[4.5]dec-7-yl}methyl)-1H-benzimidazole-6-carbonitrile;

1-({(5S,7S)-7-methyl-2-oxo-3-[(trifluoromethyl)-5-isoxazolyl]-1-oxa-3-azaspiro[4.5]dec-7-yl}methyl)-1H-benzimidazole-6-carbonitrile;

1-({(5S,7S)-3-[3-(1-cyanocyclopropyl)-5-isoxazolyl]-7-methyl-2-oxo-1-oxa-3-azaspiro[4.5]dec-7-yl}methyl)-1H-benzimidazole-6-carbonitrile;

1-(((5S,7S)-3-(3-(2-fluoropropan-2-yl)isoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3-cyclobutylisoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3-(tert-butyl)-4-methylisoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(4-(tert-butyl)oxazol-2-yl)-7-methyl-2-oxo-1-oxa-3-azaspiro[4.5]decan-7-yl)methyl)-1H-benzo[d]imidazole-6-carbonitrile;

1-(((5S,7S)-3-(1-(tert-butyl)-1H-pyrazol-4-yl)-7-methyl-2-oxo-1-oxa-3-azaspiro[4.5]decan-7-yl)methyl)-1H-benzo[d]imidazole-6-carbonitrile;

1-(((5S,7S)-3-(3-(tert-butyl)-4-fluoroisoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3-(1,1-difluoroethyl)isoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3-(tert-butyl)-4-methylisoxazol-5-yl)-2-oxo-1-oxa-3-azaspiro[4.5]decan-7-yl)methyl)-1H-benzo[d]imidazole-6-carbonitrile;

1-(((5S,7S)-3-(3-(tert-butyl)-4-fluoroisoxazol-5-yl)-2-oxo-1-oxa-3-azaspiro[4.5]decan-7-yl)methyl)-1H-benzo[d]imidazole-6-carbonitrile;

1-(((5S,7S)-3-(6-(tert-butyl)pyridazin-3-yl)-7-methyl-2-oxo-1-oxa-3-azaspiro[4.5]decan-7-yl)methyl)-1H-benzo[d]imidazole-6-carbonitrile;

1-(((5S,7S)-3-(5-(tert-butyl)pyrimidin-2-yl)-7-methyl-2-oxo-1-oxa-3-azaspiro[4.5]decan-7-yl)methyl)-1H-benzo[d]imidazole-6-carbonitrile;

1-(((5S,7S)-3-(2-(tert-butyl)-2H-1,2,3-triazol-4-yl)-7-methyl-2-oxo-1-oxa-3-azaspiro[4.5]decan-7-yl)methyl)-1H-benzo[d]imidazole-6-carbonitrile;

1-(((5S,7S)-7-methyl-3-(3-(1-methyl-1H-pyrazol-3-yl)isoxazol-5-yl)-2-oxo-1-oxa-3-azaspiro[4.5]decan-7-yl)methyl)-1H-benzo[d]imidazole-6-carbonitrile;

1-(((5S,7S)-3-(1-(tert-butyl)-1H-1,2,3-triazol-4-yl)-7-methyl-2-oxo-1-oxa-3-azaspiro[4.5]decan-7-yl)methyl)-1H-benzo[d]imidazole-6-carbonitrile;

1-(((5S,7S)-3-(5-(tert-butyl)pyrazin-2-yl)-7-methyl-2-oxo-1-oxa-3-azaspiro[4.5]decan-7-yl)methyl)-1H-benzo[d]imidazole-6-carbonitrile;

1-(((5S,7S)-7-methyl-2-oxo-3-(5-(trifluoromethyl)pyrimidin-2-yl)-1-oxa-3-azaspiro[4.5]decan-7-yl)methyl)-1H-benzo[d]imidazole-6-carbonitrile;

1-(((5S,7S)-3-(6-(2-methoxypropan-2-yl)pyridin-3-yl)-7-methyl-2-oxo-1-oxa-3-azaspiro[4.5]decan-7-yl)methyl)-1H-benzo[d]imidazole-6-carbonitrile;

1-(((5S,7S)-7-methyl-2-oxo-3-(3-(prop-1-en-2-yl)isoxazol-5-yl)-1-oxa-3-azaspiro[4.5]decan-7-yl)methyl)-1H-benzo[d]imidazole-6-carbonitrile;

1-(((5S,7S)-3-(3,4-dimethylisoxazol-5-yl)-7-methyl-2-oxo-1-oxa-3-azaspiro[4.5]decan-7-yl)methyl)-1H-benzo[d]imidazole-6-carbonitrile;

1-(((5S,7S)-3-(3,4-dimethylisoxazol-5-yl)-2-oxo-1-oxa-3-azaspiro[4.5]decan-7-yl)methyl)-1H-benzo[d]imidazole-6-carbonitrile;

1-({3-[(5-chloro-1-benzothien-3-yl)methyl]-2-oxo-1-oxa-3-azaspiro[4.5]dec-7-yl}methyl)-1H-indole-6-carbonitrile;

1-({3-[(5-chloro-1-benzothien-3-yl)methyl]-2-oxo-1-oxa-3-azaspiro[4.5]dec-7-yl}methyl)-2-(trifluoromethyl)-1H-benzimidazole-6-carbonitrile;

1-({3-[(5-chloro-1-benzothien-3-yl)methyl]-2-oxo-1-oxa-3-azaspiro[4.5]dec-7-yl}methyl)-1H-benzimidazole-6-carbonitrile;

1-{[3-(1-benzothien-3-ylmethyl)-2-oxo-1-oxa-3-azaspiro[4.5]dec-7-yl]methyl}-1H-benzimidazole-6-carbonitrile;

1-({(5S,7S)-2-oxo-3-[(2-phenyl-1,3-thiazol-4-yl)methyl]-1-oxa-3-azaspiro[4.5]dec-7-yl}methyl)-1H-benzimidazole-6-carbonitrile;

1-({(5S,7S)-2-oxo-3-[(6-phenyl-2-pyridinyl)methyl]-1-oxa-3-azaspiro[4.5]dec-7-yl}methyl)-1H-benzimidazole-6-carbonitrile;

1-[(5S,7S)-3-{2-methyl-2-[3-(tetrahydro-2H-pyran-4-yl)-1,2,4-oxadiazol-5-yl]propyl}-2-oxo-1-oxa-3-azaspiro[4.5]dec-7-yl)methyl]-1H-benzimidazole-6-carbonitrile;

1-({(5S,7S)-2-oxo-3-[(4-phenyl-1,3-thiazol-2-yl)methyl]-1-oxa-3-azaspiro[4.5]dec-7-yl}methyl)-1H-benzimidazole-6-carbonitrile;

1-[(5S,7S)-3-{[3-(4-chlorophenyl)-5-isoxazolyl]methyl}-2-oxo-1-oxa-3-azaspiro[4.5]dec-7-yl)methyl]-1H-benzimidazole-6-carbonitrile;

1-({(5S,7S)-2-oxo-3-[(3-phenyl-5-isoxazolyl)methyl]-1-oxa-3-azaspiro[4.5]dec-7-yl}methyl)-1H-benzimidazole-6-carbonitrile;

1-({(5S,7S)-3-[(1-methyl-5-phenyl-1H-pyrazol-3-yl)methyl]-2-oxo-1-oxa-3-azaspiro[4.5]dec-7-yl}methyl)-1H-benzimidazole-6-carbonitrile;

1-{[(5S,7S)-3-({4-[3-methyl-4-(methyloxy)phenyl]-1,3-thiazol-2-yl}methyl)-2-oxo-1-oxa-3-azaspiro[4.5]dec-7-yl]methyl}-1H-benzimidazole-6-carbonitrile;

1-({(5S,7S)-2-oxo-3-[(3-phenyl-1H-1,2,4-triazol-5-yl)methyl]-1-oxa-3-azaspiro[4.5]dec-7-yl}methyl)-1H-benzimidazole-6-carbonitrile;

1-({(5S,7S)-2-oxo-3-[(5-phenyl-3-pyridinyl)methyl]-1-oxa-3-azaspiro[4.5]dec-7-yl}methyl)-1H-benzimidazole-6-carbonitrile trifluoroacetate;

4-chloro-1-({(5S,7S)-3-[2-methyl-2-(3-phenyl-1,2,4-oxadiazol-5-yl)propyl]-2-oxo-1-oxa-3-azaspiro[4.5]dec-7-yl}methyl)-1H-benzimidazole-6-carbonitrile;

1-({(5S,7S)-3-[2-methyl-2-(3-methyl-1,2,4-oxadiazol-5-yl)propyl]-2-oxo-1-oxa-3-azaspiro[4.5]dec-7-yl}methyl)-1H-benzimidazole-6-carbonitrile;

1-({(5S,7S)-3-[2-methyl-2-(3-phenyl-1,2,4-oxadiazol-5-yl)propyl]-2-oxo-1-oxa-3-azaspiro[4.5]dec-7-yl}methyl)-1H-benzimidazole-6-carbonitrile;

1-[(5S,7S)-3-{2-methyl-2-[3-(1-methylethyl)-1,2,4-oxadiazol-5-yl]propyl}-2-oxo-1-oxa-3-azaspiro[4.5]dec-7-yl)methyl]-1H-benzimidazole-6-carbonitrile;

1-({(5S,7S)-3-[2-(3-cyclopentyl-1,2,4-oxadiazol-5-yl)-2-methylpropyl]-2-oxo-1-oxa-3-azaspiro[4.5]dec-7-yl}methyl)-1H-benzimidazole-6-carbonitrile;

1-[(5S,7S)-3-{2-methyl-2-[3-(5-pyrimidinyl)-1,2,4-oxadiazol-5-yl]propyl}-2-oxo-1-oxa-3-azaspiro[4.5]dec-7-yl)methyl]-1H-benzimidazole-6-carbonitrile;

1-[(5S,7S)-3-{2-[3-(1,1-dimethylethyl)-1,2,4-oxadiazol-5-yl]-2-methylpropyl}-2-oxo-1-oxa-3-azaspiro[4.5]dec-7-yl)methyl]-1H-benzimidazole-6-carbonitrile;

1-[(5S,7S)-3-{2-methyl-2-[3-(trifluoromethyl)-1,2,4-oxadiazol-5-yl]propyl}-2-oxo-1-oxa-3-azaspiro[4.5]dec-7-yl)methyl]-1H-benzimidazole-6-carbonitrile;

1-{[(5S,7S)-3-(2-methyl-2-{3-[(methyloxy)methyl]-1,2,4-oxadiazol-5-yl}propyl)-2-oxo-1-oxa-3-azaspiro[4.5]dec-7-yl]methyl}-1H-benzimidazole-6-carbonitrile;

1-[(5S,7S)-3-{2-methyl-2-[3-(2-methylpropyl)-1,2,4-oxadiazol-5-yl]propyl}-2-oxo-1-oxa-3-azaspiro[4.5]dec-7-yl)methyl]-1H-benzimidazole-6-carbonitrile;

1-({(5S,7S)-3-[2-methyl-2-(3-{[(1-methylethyl)oxy]methyl}-1,2,4-oxadiazol-5-yl)propyl]-2-oxo-1-oxa-3-azaspiro[4.5]dec-7-yl}methyl)-1H-benzimidazole-6-carbonitrile;

4-chloro-1-[((5S,7S)-2-oxo-3-{[4-(3-phenyl-1,2,4-oxadiazol-5-yl)tetrahydro-2H-pyran-4-yl]methyl}-1-oxa-3-azaspiro[4.5]dec-7-yl)methyl]-1H-benzimidazole-6-carbonitrile;

4-chloro-1-[((5S,7S)-3-{[4-(3-cyclopentyl-1,2,4-oxadiazol-5-yl)tetrahydro-2H-pyran-4-yl]methyl}-2-oxo-1-oxa-3-azaspiro[4.5]dec-7-yl)methyl]-1H-benzimidazole-6-carbonitrile;

1-[(5S,7S)-2-oxo-3-{[1-(2-pyridinyl)-3-pyrrolidinyl]methyl}-1-oxa-3-azaspiro[4.5]dec-7-yl)methyl]-1H-benzimidazole-6-carbonitrile;

1-({(5S,7S)-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile;

1-[(5S,7S)-3-{[1-(4-cyanophenyl)-1H-1,2,3-triazol-4-yl]methyl}-2-oxo-1-oxa-3-azaspiro[4.5]dec-7-yl)methyl]-1H-benzimidazole-6-carbonitrile;

1-[(5S,7S)-3-{[1-(4-chlorophenyl)-1H-1,2,3-triazol-4-yl]methyl}-2-oxo-1-oxa-3-azaspiro[4.5]dec-7-yl)methyl]-1H-benzimidazole-6-carbonitrile;

1-[(5S,7S)-3-{[1-(3-chlorophenyl)-1H-1,2,3-triazol-4-yl]methyl}-2-oxo-1-oxa-3-azaspiro[4.5]dec-7-yl)methyl]-1H-benzimidazole-6-carbonitrile;

1-[(5S,7S)-3-{[1-(4-methylphenyl)-1H-1,2,3-triazol-4-yl]methyl}-2-oxo-1-oxa-3-azaspiro[4.5]dec-7-yl)methyl]-1H-benzimidazole-6-carbonitrile;

1-[(5S,7S)-3-{[1-(3-cyanophenyl)-1H-1,2,3-triazol-4-yl]methyl}-2-oxo-1-oxa-3-azaspiro[4.5]dec-7-yl)methyl]-1H-benzimidazole-6-carbonitrile;

1-{[(5S,7S)-2-oxo-3-({1-[3-(trifluoromethyl)phenyl]-1H-1,2,3-triazol-4-yl}methyl)-1-oxa-3-azaspiro[4.5]dec-7-yl]methyl}-1H-benzimidazole-6-carbonitrile;

1-[(5S,7S)-3-{[1-(3-fluorophenyl)-1H-1,2,3-triazol-4-yl]methyl}-2-oxo-1-oxa-3-azaspiro[4.5]dec-7-yl)methyl]-1H-benzimidazole-6-carbonitrile;

1-{[(5S,7S)-3-({1-[3-(methyloxy)phenyl]-1H-1,2,3-triazol-4-yl}methyl)-2-oxo-1-oxa-3-azaspiro[4.5]dec-7-yl]methyl}-1H-benzimidazole-6-carbonitrile;

1-[(5S,7S)-3-{[1-(3-methylphenyl)-1H-1,2,3-triazol-4-yl]methyl}-2-oxo-1-oxa-3-azaspiro[4.5]dec-7-yl)methyl]-1H-benzimidazole-6-carbonitrile;

1-({(5S,7S)-3-[(1-cyclohexaneyl-1H-1,2,3-triazol-4-yl)methyl]-2-oxo-1-oxa-3-azaspiro[4.5]dec-7-yl}methyl)-1H-benzimidazole-6-carbonitrile;

1-{[(5S,7S)-3-({1-[4-cyano-3-(trifluoromethyl)phenyl]-1H-1,2,3-triazol-4-yl}methyl)-2-oxo-1-oxa-3-azaspiro[4.5]dec-7-yl]methyl}-1H-benzimidazole-6-carbonitrile;

1-[(5S,7S)-3-{[1-(3-chloro-5-cyanophenyl)-1H-1,2,3-triazol-4-yl]methyl}-2-oxo-1-oxa-3-azaspiro[4.5]dec-7-yl)methyl]-1H-benzimidazole-6-carbonitrile;

1-{[(5S,7S)-2-oxo-3-({1-[2-(trifluoromethyl)-4-pyridinyl]-1H-1,2,3-triazol-4-yl}methyl)-1-oxa-3-azaspiro[4.5]dec-7-yl]methyl}-1H-benzimidazole-6-carbonitrile;

1-[(5S,7S)-3-{[1-(3,5-difluorophenyl)-1H-1,2,3-triazol-4-yl]methyl}-2-oxo-1-oxa-3-azaspiro[4.5]dec-7-yl)methyl]-1H-benzimidazole-6-carbonitrile;

1-{[(5S,7S)-2-oxo-3-({1-[4-(trifluoromethyl)phenyl]-1H-1,2,3-triazol-4-yl}methyl)-1-oxa-3-azaspiro[4.5]dec-7-yl]methyl}-1H-benzimidazole-6-carbonitrile;

1-[(5S,7S)-3-{[1-(3-cyano-5-fluorophenyl)-1H-1,2,3-triazol-4-yl]methyl}-2-oxo-1-oxa-3-azaspiro[4.5]dec-7-yl)methyl]-1H-benzimidazole-6-carbonitrile;

1-[(5S,7S)-7-methyl-3-{[1-(1-methylethyl)-1H-1,2,3-triazol-4-yl]methyl}-2-oxo-1-oxa-3-azaspiro[4.5]dec-7-yl)methyl]-1H-benzimidazole-6-carbonitrile;

1-({(5R,7S)-7-methyl-2-oxo-3-[(1-phenyl-1H-1,2,3-triazol-4-yl)methyl]-1-oxa-3-azaspiro[4.5]dec-7-yl}methyl)-1H-benzimidazole-6-carbonitrile;

1-[(5S,7S)-3-{[1-(5-chloro-3-pyridinyl)-1H-1,2,3-triazol-4-yl]methyl}-2-oxo-1-oxa-3-azaspiro[4.5]dec-7-yl)methyl]-1H-benzimidazole-6-carbonitrile;

1-(((5S,7S)-3-(4-chloro-3-(2-cyanopropan-2-yl)isoxazol-5-yl)-7-methyl-2-oxo-1-oxa-3-azaspiro[4.5]decan-7-yl)methyl)-1H-benzo[d]imidazole-6-carbonitrile;

1-({(5S,7S)-3-[4-bromo-3-(1,1-dimethylethyl)-5-isoxazolyl]-7-methyl-2-oxo-1-oxa-3-azaspiro[4.5]dec-7-yl}methyl)-1H-benzimidazole-6-carbonitrile;

1-({(5S,7S)-7-methyl-3-[2-(methyloxy)-3-pyridinyl]-2-oxo-1-oxa-3-azaspiro[4.5]dec-7-yl}methyl)-1H-benzimidazole-6-carbonitrile;

1-({(5S,7S)-3-[2,6-bis(methyloxy)-3-pyridinyl]-7-methyl-2-oxo-1-oxa-3-azaspiro[4.5]dec-7-yl}methyl)-1H-benzimidazole-6-carbonitrile;

1-({(5S,7S)-3-[4-methyl-6-(methyloxy)-3-pyridinyl]-2-oxo-1-oxa-3-azaspiro[4.5]dec-7-yl}methyl)-1H-benzimidazole-6-carbonitrile;

1-(((7S)-3-(3,5-dichloropyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(2-ethoxypyrimidin-5-yl)-7-methyl-2-oxo-1-oxa-3-azaspiro[4.5]decan-7-yl)methyl)-1H-benzo[d]imidazole-6-carbonitrile;

1-(((5S,7S)-3-(5-chloro-3-fluoropyridin-2-yl)-7-methyl-2-oxo-1-oxa-3-azaspiro[4.5]decan-7-yl)methyl)-1H-benzo[d]imidazole-6-carbonitrile;

1-(((5S,7S)-7-methyl-2-oxo-3-(5-(trifluoromethyl)pyrazin-2-yl)-1-oxa-3-azaspiro[4.5]decan-7-yl)methyl)-1H-benzo[d]imidazole-6-carbonitrile;

1-(((5S,7S)-3-(2-(tert-butyl)pyrimidin-5-yl)-2-oxo-1-oxa-3-azaspiro[4.5]decan-7-yl)methyl)-1H-benzo[d]imidazole-6-carbonitrile;

1-(((5S,7S)-7-methyl-3-(5-methylpyrazin-2-yl)-2-oxo-1-oxa-3-azaspiro[4.5]decan-7-yl)methyl)-1H-benzo[d]imidazole-6-carbonitrile;

1-(((5S,7S)-3-(6-ethoxy-4-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methylpyridin-3-yl)-2-oxo-1-oxa-3-azaspiro[4.5]decan-7-yl)methyl)-1H-benzo[d]imidazole-6-carbonitrile;

1-(((5S,7S)-3-(5-chloro-3-methylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methoxypyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-chloro-4-methoxypyridin-3-yl)-2-oxo-1-oxa-3-azaspiro[4.5]decan-7-yl)methyl)-1H-benzo[d]imidazole-6-carbonitrile;

1-(((5S,7S)-3-(4-methyl-2-(trifluoromethyl)pyrimidin-5-yl)-2-oxo-1-oxa-3-azaspiro[4.5]decan-7-yl)methyl)-1H-benzo[d]imidazole-6-carbonitrile;

1-(((5S,7S)-3-(6-ethoxy-4-methylpyridin-3-yl)-2-oxo-1-oxa-3-azaspiro[4.5]decan-7-yl)methyl)-5-fluoro-1H-benzo[d]imidazole-6-carbonitrile;

1-(((5S,7S)-3-(2-methoxy-6-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(3-methoxy-5-methylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3-chloro-5-methylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3-ethylpyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3,5-dimethylpyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(3-methyl-5-(trifluoromethyl)pyrazin-2-yl)-2-oxo-1-oxa-3-azaspiro[4.5]decan-7-yl)methyl)-1H-benzo[d]imidazole-6-carbonitrile;

1-(((5S,7S)-3-(6-methoxy-5-methylpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(6-(2-cyanopropan-2-yOpyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(2-(tert-butyl)pyrimidin-5-yl)-7-methyl-2-oxo-1-oxa-3-azaspiro[4.5]decan-7-yl)methyl)-1H-benzo[d]imidazole-6-carbonitrile;

1-({(5S,7S)-7-methyl-3-[5-(methyloxy)-2-pyridinyl]-2-oxo-1-oxa-3-azaspiro[4.5]dec-7-yl}methyl)-1H-benzimidazole-6-carbonitrile;

1-({(5S,7S)-3-[6-(ethyloxy)-3-pyridazinyl]-7-methyl-2-oxo-1-oxa-3-azaspiro[4.5]dec-7-yl}methyl)-1H-benzimidazole-6-carbonitrile;

1-{[(5S,7S)-3-(3-chloro-2-pyridinyl)-7-methyl-2-oxo-1-oxa-3-azaspiro[4.5]dec-7-yl]methyl}-1H-benzimidazole-6-carbonitrile;

1-({(5S,7S)-7-methyl-3-[3-(methyloxy)-2-pyridinyl]-2-oxo-1-oxa-3-azaspiro[4.5]dec-7-yl}methyl)-1H-benzimidazole-6-carbonitrile;

1-({(5S,7S)-7-methyl-2-oxo-3-[6-(trifluoromethyl)-3-pyridinyl]-1-oxa-3-azaspiro[4.5]dec-7-yl}methyl)-1H-benzimidazole-6-carbonitrile;

1-(((5S,7S)-7-methyl-3-(6-methylpyridin-3-yl)-2-oxo-1-oxa-3-azaspiro[4.5]decan-7-yl)methyl)-1H-benzo[d]imidazole-6-carbonitrile;

1-({(5S,7S)-3-[4,6-bis(methyloxy)-3-pyridinyl]-2-oxo-1-oxa-3-azaspiro[4.5]dec-7-yl}methyl)-1H-benzimidazole-6-carbonitrile;

1-({(5S,7S)-3-[6-(1-methylethyl)-3-pyridinyl]-2-oxo-1-oxa-3-azaspiro[4.5]dec-7-yl}methyl)-1H-benzimidazole-6-carbonitrile;

1-((7-(hydroxymethyl)-3-(6-methoxy-4-methylpyridin-3-yl)-2-oxo-1-oxa-3-azaspiro[4.5]decan-7-yl)methyl)-1H-benzo[d]imidazole-6-carbonitrile;

1-(((5S,7S)-7-methyl-2-oxo-3-(4-(trifluoromethyl)pyridin-3-yl)-1-oxa-3-azaspiro[4.5]decan-7-yl)methyl)-1H-benzo[d]imidazole-6-carbonitrile;

1-(((5S,7S)-3-(2-(dimethylamino)pyrimidin-5-yl)-7-methyl-2-oxo-1-oxa-3-azaspiro[4.5]decan-7-yl)methyl)-1H-benzo[d]imidazole-6-carbonitrile;

1-(((5S,7S)-7-methyl-3-(4-methylpyridin-3-yl)-2-oxo-1-oxa-3-azaspiro[4.5]decan-7-yl)methyl)-1H-benzo[d]imidazole-6-carbonitrile;

1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(2-(2-hydroxypropan-2-yl)pyrimidin-5-yl)-7-methyl-2-oxo-1-oxa-3-azaspiro[4.5]decan-7-yl)methyl)-1H-benzo[d]imidazole-6-carbonitrile;

1-(((5S,7S)-3-(4-methoxypyridin-3-yl)-7-methyl-2-oxo-1-oxa-3-azaspiro[4.5]decan-7-yl)methyl)-1H-benzo[d]imidazole-6-carbonitrile;

1-(((5S,7S)-3-(5-(dimethylamino)pyrazin-2-yl)-7-methyl-2-oxo-1-oxa-3-azaspiro[4.5]decan-7-yl)methyl)-1H-benzo[d]imidazole-6-carbonitrile;

1-{[(5S,7S)-2-oxo-3-(thieno[2,3-b]pyridin-3-ylmethyl)-1-oxa-3-azaspiro[4.5]dec-7-yl]methyl}-1H-benzimidazole-6-carbonitrile;

1-{[(trans)-7-methyl-2-oxo-3-(thieno[2,3-b]pyridin-3-ylmethyl)-1-oxa-3-azaspiro[4.5]dec-7-yl]methyl}-1H-benzimidazole-6-carbonitrile;

1-({(5S,7S)-3-[(3-bromothieno[2,3-b]pyridin-2-yl)methyl]-2-oxo-1-oxa-3-azaspiro[4.5]dec-7-yl}methyl)-1H-benzimidazole-6-carbonitrile; and 1-{[(5S,7S)-3-methyl-2-{3-[1-(methyloxy)ethyl]-1,2,4-oxadiazol-5-yl}propyl)-2-oxo-1-oxa-3-azaspiro[4.5]dec-7-yl]methyl}-1H-benzimidazole-6-carbonitrile;

1-(((5S,7S)-3-((5-ethoxypyrazin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((4-ethoxypyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((5-ethoxypyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((4-fluoropyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-3-((5-fluoropyridin-2-yl)methyl)-7-methyl-2-oxo-1-oxa-3-azaspiro[4.5]decan-7-yl)methyl)-1H-benzo[d]imidazole-6-carbonitrile;

1-(((5S,7S)-7-methyl-3-((4-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile;

1-(((5S,7S)-7-methyl-3-((6-(1-methyl-1H-pyrazol-4-yl)pyridin-2-yl)methyl)-2-oxo-1-oxa-3-azaspiro[4.5]decan-7-yl)methyl)-1H-benzo[d]imidazole-6-carbonitrile;

1-(((5S,7S)-3-(5-(2-methoxypropan-2-yl)pyrazin-2-yl)-7-methyl-2-oxo-1-oxa-3-azaspiro[4.5]decan-7-yl)methyl)-1H-benzo[d]imidazole-6-carbonitrile;

1-(((5S,7S)-3-(5-(2-(2-methoxyethoxy)propan-2-yl)pyrazin-2-yl)-7-methyl-2-oxo-1-oxa-3-azaspiro[4.5]decan-7-yl)methyl)-1H-benzo[d]imidazole-6-carbonitrile;

2-((2-(5-((5S,7S)-7-((6-cyano-1H-benzo[d]imidazol-1-yl)methyl)-7-methyl-2-oxo-1-oxa-3-azaspiro[4.5]decan-3-yl)pyrazin-2-yl)propan-2-yl)oxy)ethyl dimethylphosphinate;

1-(((5S,7S)-3-(5'-fluoro-4-methyl-[2,2'-bipyridin]-5-yl)-7-methyl-2-oxo-1-oxa-3-azaspiro[4.5]decan-7-yl)methyl)-1H-benzo[d]imidazole-6-carbonitrile;

1-(((5S,7S)-7-methyl-3-(4-methyl-6-morpholinopyridin-3-yl)-2-oxo-1-oxa-3-azaspiro[4.5]decan-7-yl)methyl)-1H-benzo[d]imidazole-6-carbonitrile;

1-(((5S,7S)-3-(5-(2-hydroxypropan-2-yl)pyridin-2-yl)-7-methyl-2-oxo-1-oxa-3-azaspiro[4.5]decan-7-yl)methyl)-1H-benzo[d]imidazole-6-carbonitrile;

1-(((5S,7S)-3-(5-(1-hydroxy-2-methylpropan-2-yl)pyrazin-2-yl)-7-methyl-2-oxo-1-oxa-3-azaspiro[4.5]decan-7-yl)methyl)-1H-benzo[d]imidazole-6-carbonitrile; or 1-(((5S,7S)-3-(6-cyclopropyl-4- methoxypyridin-3-yl)-7-methyl-2-oxo-1-oxa-3-azaspiro[4.5]decan-7-yl)methyl)-1H-benzo[d]imidazole-6-carbonitrile;

or a pharmaceutically acceptable salt thereof.

8. A compound which is 1-(((5S,7S)-3-(5-Ethoxypyrazin-2-yl)-7-methyl-2-oxo-1-oxa-3-azaspiro[4.5]decan-7-yl)methyl)-1H-benzo[d]imidazole-6-carbonitrile;

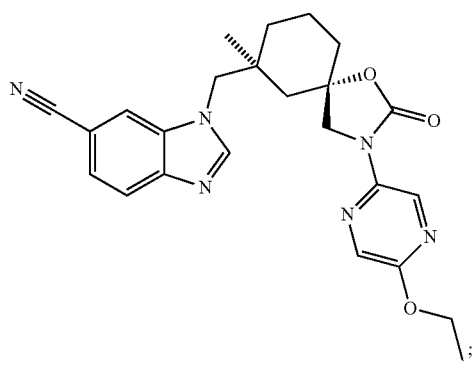 [SMILES: CCOc1cnc(N2C[C@@]3(CCC[C@](C)(Cn4cnc5ccc(C#N)cc54)C3)OC2=O)cn1]

or a pharmaceutically acceptable salt thereof.

9. A compound which is 1-(((5S,7S)-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile;

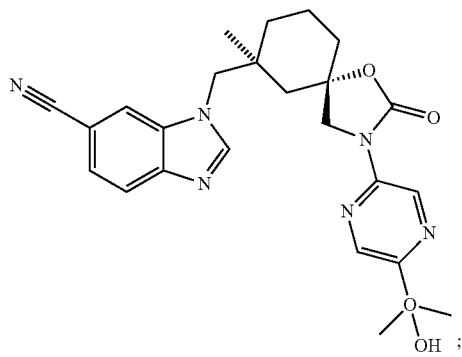

or a pharmaceutically acceptable salt thereof.

10. A pharmaceutical composition comprising a compound of claim 1 and a pharmaceutically acceptable carrier or excipient.

11. A method of treating atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, pain, motor neuron disorders, genetic gain of function disorders, renal dysfunction, osteoarthritis crohn's disease, colitis, intestinal irregularity (hyperreactivity/hyporeactivity), intestinal pain and cramping, which comprises administering to a human in need thereof, a compound of claim 1.

12. A method according to claim 11 wherein the compound is administered orally.

13. A method according to claim 11 wherein the compound is administered intravenously.

14. A method according to claim 11 wherein the disease is congestive heart failure.

15. A method according to claim 11 wherein the disease is acute lung injury.

16. A pharmaceutical composition comprising a compound of claim 8 and a pharmaceutically acceptable carrier or excipient.

17. A pharmaceutical composition comprising a compound of claim 9 and a pharmaceutically acceptable carrier or excipient.

18. A method of treating atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, pain, motor neuron disorders, genetic gain of function disorders, renal dysfunction, osteoarthritis crohn's disease, colitis, intestinal irregularity (hyperreactivity/hyporeactivity), intestinal pain and cramping, which comprises administering to a human in need thereof, a compound of claim 8.

19. A method of treating atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, pain, motor neuron disorders, genetic gain of function disorders, renal dysfunction, osteoarthritis crohn's disease, colitis, intestinal irregularity (hyperreactivity/hyporeactivity), intestinal pain and cramping, which comprises administering to a human in need thereof, a compound of claim 9.

20. A method according to claim 15 wherein the compound is administered by inhalation.

* * * * *

UNITED STATES PATENT AND TRADEMARK OFFICE
CERTIFICATE OF CORRECTION

PATENT NO. : 9,187,464 B2
APPLICATION NO. : 14/125378
DATED : November 17, 2015
INVENTOR(S) : Brooks et al.

It is certified that error appears in the above-identified patent and that said Letters Patent is hereby corrected as shown below:

In the claims

Column 191,
Line 5, Claim 8 After "A compound", insert --of claim 1--

Column 191,
Line 26, Claim 9 After "A compound", insert --of claim 1--

Signed and Sealed this
Seventh Day of June, 2016

Michelle K. Lee
*Director of the United States Patent and Trademark Office*